(12) United States Patent
Holland et al.

(10) Patent No.: US 11,859,000 B2
(45) Date of Patent: Jan. 2, 2024

(54) ANTI-CCR8 ANTIBODIES AND USES THEREOF

(71) Applicant: Vaccinex, Inc., Rochester, NY (US)

(72) Inventors: Pamela M. Holland, Cambridge, MA (US); Andrew Lake, Cambridge, MA (US); Austin Dulak, Cambridge, MA (US); Ernest Smith, Rochester, NY (US); Maria Scrivens, Cambridge, MA (US); Caroline Harvey, Rochester, NY (US); Renee Kirk, Rochester, NY (US); Leslie Balch, Rochester, NY (US); Sonia G. Das, Cambridge, MA (US); Christopher Converse Wells, Cambridge, MA (US)

(73) Assignee: Vaccinex Inc., Rochester, NY (US)

( * ) Notice: Subject to any disclaimer, the term of this patent is extended or adjusted under 35 U.S.C. 154(b) by 226 days.

(21) Appl. No.: 17/142,862

(22) Filed: Jan. 6, 2021

(65) Prior Publication Data

US 2021/0238292 A1 Aug. 5, 2021

Related U.S. Application Data

(60) Provisional application No. 63/198,803, filed on Nov. 13, 2020, provisional application No. 62/985,152, filed on Mar. 4, 2020, provisional application No. 62/957,758, filed on Jan. 6, 2020.

(51) Int. Cl.
*C07K 16/28* (2006.01)
*A61K 47/68* (2017.01)
*A61P 35/00* (2006.01)

(52) U.S. Cl.
CPC ...... *C07K 16/2866* (2013.01); *A61K 47/6803* (2017.08); *A61K 47/6849* (2017.08); *A61P 35/00* (2018.01); *C07K 2317/31* (2013.01); *C07K 2317/41* (2013.01); *C07K 2317/622* (2013.01); *C07K 2317/732* (2013.01); *C07K 2317/92* (2013.01)

(58) Field of Classification Search
CPC ................ C07K 16/18; C07K 16/2818; C07K 2317/24; C07K 2317/565; A61K 47/6843; A61K 47/6817; A61K 2039/505; A61K 2039/545; A61P 35/04; A61P 35/00
See application file for complete search history.

(56) References Cited

U.S. PATENT DOCUMENTS

| | | | |
|---|---|---|---|
| 3,773,919 A | 11/1973 | Boswell et al. |
| 4,676,980 A | 6/1987 | Segal et al. |
| 5,223,409 A | 6/1993 | Ladner et al. |
| 5,403,484 A | 4/1995 | Ladner et al. |
| 5,427,908 A | 6/1995 | Dower et al. |
| 5,500,362 A | 3/1996 | Robinson et al. |
| 5,516,637 A | 5/1996 | Huang et al. |
| 5,571,698 A | 11/1996 | Ladner et al. |
| 5,580,717 A | 12/1996 | Dower et al. |
| 5,624,821 A | 4/1997 | Winter et al. |
| 5,648,260 A | 7/1997 | Winter et al. |
| 5,658,727 A | 8/1997 | Barbas et al. |
| 5,698,426 A | 12/1997 | Huse |
| 5,733,743 A | 3/1998 | Johnson et al. |
| 5,750,753 A | 5/1998 | Kimae et al. |
| 5,780,225 A | 7/1998 | Wigler et al. |
| 5,821,047 A | 10/1998 | Garrard et al. |
| 5,821,337 A | 10/1998 | Carter et al. |
| 5,969,108 A | 10/1999 | McCafferty et al. |
| 6,001,329 A | 12/1999 | Buchsbaum et al. |
| 6,005,079 A | 12/1999 | Casterman et al. |
| 6,194,551 B1 | 2/2001 | Idusogie et al. |
| 6,300,064 B1 | 10/2001 | Knappik et al. |
| 6,737,056 B1 | 5/2004 | Presta |
| 6,933,368 B2 | 8/2005 | Co et al. |
| 6,995,259 B1 | 2/2006 | Vargeese et al. |
| 7,332,581 B2 | 2/2008 | Presta |
| 7,371,826 B2 | 5/2008 | Presta |
| 2005/0014934 A1 | 1/2005 | Hinton et al. |

FOREIGN PATENT DOCUMENTS

| | | | | |
|---|---|---|---|---|
| EP | 0058481 A1 | 8/1982 | | |
| EP | 0133988 A2 | 3/1985 | | |
| EP | 0088046 B1 | 12/1987 | | |
| EP | 0143949 B1 | 10/1988 | | |
| EP | 0036676 B2 | 9/1990 | | |
| EP | 3431105 A1 * | 1/2019 | ............ | A61K 35/17 |
| WO | WO-9002809 A1 | 3/1990 | | |
| WO | WO-9110737 A1 | 7/1991 | | |
| WO | WO-9201047 A1 | 1/1992 | | |

(Continued)

OTHER PUBLICATIONS

Mccarthy et al. (J. Immunol. Methods, 251(1-2): 137-149, 2001) (Year: 2001).*
Akdis, M., et al., "T regulatory cells in allergy: Novel concepts in the pathogenesis, prevention, and treatment of allergic diseases," J Allergy Clin Immunol 116(5):961-8, Elsevier, Netherlands (Nov. 2005).
Altschul, S.F., et al., "Basic Local Alignment Search Tool," Journal of Molecular Biology 215(3):403-410, Elsevier, United Kingdom (Oct. 1990).
Altschul, S.F., et al., "Gapped BLAST and PSI-BLAST: A New Generation of Protein Database Search Programs," Nucleic Acids Research 25(17):3389-3402, Oxford University Press, United Kingdom (Sep. 1997).

(Continued)

*Primary Examiner* — Adam Weidner
*Assistant Examiner* — Ashley H. Gao
(74) *Attorney, Agent, or Firm* — McNeill Baur PLLC

(57) ABSTRACT

The present disclosure is directed to antibodies or antigen-binding portions thereof that specifically bind human CCR8, polynucleotides and vectors encoding the same, and pharmaceutical compositions comprising the same. Some aspects of the disclosure are directed to methods of treating a disease or condition comprising administering the anti-CCR8 antibody to a subject in need thereof.

20 Claims, 30 Drawing Sheets
Specification includes a Sequence Listing.

(56) References Cited

FOREIGN PATENT DOCUMENTS

| | | |
|---|---|---|
| WO | WO-9218619 A1 | 10/1992 |
| WO | WO-9311236 A1 | 6/1993 |
| WO | WO-9315722 A1 | 8/1993 |
| WO | WO-9404678 A1 | 3/1994 |
| WO | WO-9420069 A1 | 9/1994 |
| WO | WO-9425591 A1 | 11/1994 |
| WO | WO-9429351 A2 | 12/1994 |
| WO | WO-9515982 A2 | 6/1995 |
| WO | WO-9520401 A1 | 8/1995 |
| WO | WO-9627011 A1 | 9/1996 |
| WO | WO-9951642 A1 | 10/1999 |
| WO | WO-2004056312 A2 | 7/2004 |
| WO | WO-2005100402 A1 | 10/2005 |
| WO | WO-2006029879 A2 | 3/2006 |
| WO | WO-2007024715 A2 | 3/2007 |
| WO | WO-2007044756 A2 | 4/2007 |
| WO | WO-2008024188 A2 | 2/2008 |
| WO | WO-2013131010 A2 | 9/2013 |
| WO | WO-2015063187 A1 | 5/2015 |
| WO | WO-2015103072 A1 | 7/2015 |
| WO | WO-2018112032 A1 | 6/2018 |
| WO | WO-2021142002 A1 | 7/2021 |

OTHER PUBLICATIONS

Ames, R.S., et al., "Conversion of Murine Fabs Isolated From a Combinatorial Phage Display Library to Full Length Immunoglobulins," Journal of Immunological Methods 184(2):177-186, Elsevier, Netherlands (1995).

Annunziato, F., et al., "Phenotype, Localization, and Mechanism of Suppression of CD4+ cd25+ Human Thymocytes," J Exp Med 196(3):379-87, Rockefeller University Press, United States (Aug. 2002).

Baldridge, J.R. and Crane, R.T., "Monophosphoryl Lipid A (MPL) Formulations for the Next Generation of Vaccines," Methods, 19(1):103-107, Academic Press, United States (Sep. 1999).

Barsheshet, Y., et al., "CCR8 + FOXp3 + T reg Cells as Master Drivers of Immune Regulation," Proceedings of the National Academy of Sciences of the United States of America, 114(23):6086-6091, National Academy of Sciences, United States (Jun. 2017).

Batzer, M.A., et al., "Enhanced evolutionary PCR using oligonucleotides with inosine at the 3'-terminus," Nucleic Acids Research 19(18):5081, Oxford University Press, United Kingdom (Sep. 1991).

Berge, S.M., et al., "Pharmaceutical Salts," Journal of Pharmaceutical Sciences 66(1):1-19, Elsevier, United States (Jan. 1977).

Bhatt, D., et al., "STARTRAC analyses of scRNAseq data from tumor models reveal T cell dynamics and therapeutic targets," J Exp Med 218(6):e20201329, Rockefeller University Press, United States (Jun. 2021).

Bieg, S., et al., "Gad65 and Insulin B Chain Peptide (9-23) Are Not Primary Autoantigens in the Type 1 Diabetes Syndrome of the Bb Rat," Autoimmunity 31(1):15-24, Taylor & Francis, United Kingdom (Jan. 1999).

Bird, R.E., et al., "Single-chain Antigen-binding Proteins," Science 242(4877):423-426, Association for the Advancement of Science, United States (Oct. 1988).

Boder, E,T. and Wittrup, K,D., "Yeast Surface Display for Directed Evolution of Protein Expression, Affinity, and Stability," Methods Enzymology, 328:430-444, Academic Press, United States (2000).

Bos, P., et al., "Transient regulatory T cell ablation deters oncogene-driven breast cancer and enhances radiotherapy," J Exp Med 210(11):2435-66, Rockefeller University Press, United States (Oct. 2013).

Bournazos, S., et al., "The Role and Function of Fcγ Receptors on Myeloid Cells," Microbiol Spectr 4(6):10, American Society for Microbiology, United States (Dec. 2016).

Boutros, C., et al., "Safety profiles of anti-CTLA-4 and anti-PD-1 antibodies alone and in combination," Nat Rev Clin Oncol 13(8):473-86, Springer, Germany (Aug. 2016).

Brahmer, J., et al., "Safety and Activity of Anti-PD-L1 Antibody in Patients with Advanced Cancer," N Engl J Med 366(26):2455-65, Massachusetts Medical Society, United States (Jun. 2012).

Brennan, M., et al., "Preparation of Bispecific Antibodies by Chemical Recombination of Monoclonal Immunoglobulin G1 Fragments," Science 229(4708):81-83, American Association for the Advancement of Science, United States (Jul. 1985).

Brinkmann, U., et al., "Phage Display of Disulfide-stabilized Fv Fragments," Journal of Immunological Methods 182(1):41-50, Elsevier, Netherlands (1995).

Bruggemann, M., et al., "Comparison of the Effector Functions of Human Immunoglobulins Using a Matched Set of Chimeric Antibodies," The Journal of Experimental Medicine, 166:1351-1361, Rockefeller University Press, United States (Nov. 1987).

Burton, D.R. and Barbas, C.F. 3rd., "Human Antibodies From Combinatorial Libraries," Advances in Immunology 57:191-280, Academic Press, United States (1994).

Cambay, F., et al., "Impact of IgG1 N-glycosylation on their interaction with Fc gamma receptors," Curr Res Immunol 1:23-37, Elsevier, Netherlands (Jun. 2020).

Campbell, J., et al., "Fc-optimized anti-CCR8 antibody depletes regulatory T cells in human tumor models," Cancer Res 81(11):2983-2994, American Association for Cancer Research, United States (Jun. 2021).

Canfield, S.M., et al., "The Binding Affinity of Human Igg for Its High Affinity Fc Receptor Is Determined by Multiple Amino Acids in the Ch2 Domain and Is Modulated by the Hinge Region," Journal of Experimental Medicine 173(6):1483-1491, Rockefeller University Press, United States (Jun. 1991).

Cao, W., et al., "CD83 is preformed inside monocytes, macrophages and dendritic cells, but it is only stably expressed on activated dendritic cells," Biochem J 385(Pt 1):85-93, Biochemical Society (Jan. 2005).

Caron, P.C., et al., "Engineered Humanized Dimeric Forms of Igg Are More Effective Antibodies," Journal of Experimental Medicine 176(4):1191-1195, Rockefeller University Press, United States (Oct. 1992).

Chasteen, L., et al.,, "Eliminating Helper Phage From Phage Display," Nucleic Acids Research, 34(21):e145, Oxford University Press, United Kingdom (2006).

Chensue, S.W., et al., "Aberrant In Vivo T Helper Type 2 Cell Response and Impaired Eosinophil Recruitment in CC Chemokine Receptor 8 Knockout Mice," J Exp Med 193(5):573-84, Rockefeller University Press, United States (Mar. 2001).

Cheung, R.C., et al., "Epitope-specific Antibody Response to the Surface Antigen of Duck Hepatitis B Virus in Infected Ducks," Virology 176(2):546-552, Academic Press, United States (1990).

Chung, C.D., et al., "CCR8 Is Not Essential for the Development of Inflammation in a Mouse Model of Allergic Airway Disease," J Immunol 170(1):581-7, American Association of Immunologists, United States (Jan. 2003).

Clynes, R., et al., "Fc Receptors Are Required in Passive and Active Immunity to Melanoma," Proceedings of the National Academy of Sciences of the USA 95(2):652-656, National Academy of Sciences, United States (1998).

Co, M.S., et al., "Genetically Engineered Deglycosylation of the Variable Domain Increases the Affinity of an Anti-CD33 Monoclonal Antibody," Molecular Immunology 30(15):1361-1367, Pergamon Press, United Kingdom (1993).

Cornelis, P., et al., "Expressing Genes in Different *Escherichia coli* Compartments", Current Opinion in Biotechnology 11(5):450-454, Elsevier, United Kingdom (Oct. 2000).

Cragg, M.S, and Glennie, M.J., "Antibody Specificity Controls in Vivo Effector Mechanisms of Anti-CD20 Reagents," Blood, 103:2738-2743, Elsevier, United States (Apr. 2004).

Cragg, M.S., et al., "Complement-mediated Lysis by Anti-CD20 mAb Correlates with Segregation into Lipid Rafts," Blood 101(3):1045-1052, American Society of Hematology, United States (Feb. 2003).

Das, S., et al., "Immune-related adverse events and antitumor efficacy of immune checkpoint inhibitors," J Immunother Cancer 7(1):306, BMJ Publishing Group Ltd and Society for Immunotherapy of Cancer, United Kingdom (Nov. 2019).

(56) References Cited

OTHER PUBLICATIONS

De Simone, M., et al., "Transcriptional Landscape of Human Tissue Lymphocytes Unveils Uniqueness of Tumor-Infiltrating T Regulatory Cells," Immunity 45(5):1135-1147, Cell Press, United States (Nov. 2016).
Deans, R.J., et al., "Expression of an Immunoglobulin Heavy Chain Gene Transfected Into Lymphocytes," Proceedings of the National Academy of Sciences of the United States of America, 81(5):1292-1296, National Academy of Sciences, United States (Mar. 1984).
Delacher, M., et al., : Single-cell chromatin accessibility landscape identifies tissue repair program in human regulatory T cells, Immunity 54(4):702-720, Cell Press, United States (Apr. 2021).
Demengeot, J., et al., "Regulatory T cells in microbial infection," Springer Semin Immunopathol 28(1):41-50, Springer, Germany (Aug. 2006).
Domingues-Villar, M., et al., "Regulatory T cells in autoimmune disease," Nat Immunol 19(7):665-673, Springer, Germany (Jul. 2018).
Duncan, A,R. and Winter, G., "The Binding Site for C1q on IgG," Nature, 332(6166):738-740, Nature Publishing Group, United Kingdom (Apr. 1988).
Ebert, L., et al., "Homing and Function of Human Skin gammadelta T Cells and NK Cells: Relevance for Tumor Surveillance," J Immunol 176(7):4331-6, American Association of Immunologists, United States (Apr. 2006).
Eisenhauer, E.A., et al., "New response evaluation criteria in solid tumours: Revised RECIST guideline (version 1.1)," Eur J Cancer 45(2):228-47, Elsevier, Netherlands (Jan. 2009).
Engberg, J., et al., "Phage-Display Libraries of Murine and Human Antibody Fab Fragments," Methods in Molecular Biology, 51:355-376, Humana Press, United States (1995).
Eppstein, D.A., et al., "Biological activity of liposome-encapsulated murine interferon gamma is mediated by a cell membrane receptor," Proceedings of the National Academy of Sciences 82(11):3688-3692, National Academy of Sciences, United States (1985).
Etz, H., et al., "Bacterial Phage Receptors, Versatile Tools for Display of Polypeptides on the Cell Surface," Journal of Bacteriology 183(23):6924-6935, American Society for Microbiology, United States (Dec. 2001).
Falconer, D., et al., "Antibody fucosylation lowers FcγRIIIa/CD16a affinity by limiting the conformations sampled by the N162-glycan," ACS Chem Biol 13(8):2179-2189, American Chemical Society, United States (Aug. 2018).
Fu., J., et al., "Increased Regulatory T Cells Correlate With CD8 T-Cell Impairment and Poor Survival in Hepatocellular Carcinoma Patients," Gastroenterology 132(7):2328-39, Elsevier, Netherlands (Jun. 2007).
Gazzano-Santoro, H., et al., "A Non-Radioactive Complement-dependent Cytotoxicity Assay for Anti-CD20 Monoclonal Antibody," Journal of Immunological Methods, 202:163-171, Elsevier, Netherlands (Mar. 1997).
Goldberg, B., et al., "Antibody-mediated complement activation in pathology and protection," Immunol Cell Biol 98(4):305-317, Wiley, United States (Apr. 2020).
Goya, I., et al., "Absence of CCR8 Does Not Impair the Response to Ovalbumin-Induced Allergic Airway Disease," J Immunol 170(4):2138-46, American Association of Immunologists, United States (Feb. 2003).
Grabherr, R and Ernst, W., "The Baculovirus Expression System as a Tool for Generating Diversity by Viral Surface Display," Combinatorial Chemistry & High Throughput Screening, 4(2):185-192, Bentham Science Publishers, United Arab Emirates (Apr. 2001).
Green, J., et al., "A nonimmune function of T cells in promoting lung tumor progression," J Exp Med 214(12):3565-3575, Rockefeller University Press, United States (Dec. 2017).
Gruber, M., et al., "Efficient Tumor Cell Lysis Mediated by a Bispecific Single Chain Antibody Expressed in *Escherichia coli*," The Journal of Immunology 152(11):5368-5374, The American Association of Immunologists, Inc., United States (Jun. 1994).
Gupta, R.K and Siber, G.R., "Adjuvants for Human Vaccines—current Status, Problems and Future Prospects," Vaccine, 13(14):1263-1276, Elsevier Science, Netherlands (Oct. 1995).
Guyer, R.L., et al., "Immunoglobulin Binding by Mouse Intestinal Epithelial Cell Receptors," Journal of Immunology, 117(2):587-93, American Association of Immunologists, United States (Aug. 1976).
Hanes, J., et al., "Picomolar Affinity Antibodies from a Fully Synthetic Naive Library Selected and Evolved by Ribosome Display," Nature Biotechnology 18(12):1287-1292, Nature America Publishing, United States (Dec. 2000).
Harding, F.A. and Lonberg, N., "Class Switching in Human Immunoglobulin Transgenic Mice," Annals of the New York Academy of Sciences 764:536-546, The Academy, United States (1995).
Hellstrom, I., et al., "Strong Antitumor Activities of IgG3 Antibodies to a Human Melanoma-Associated Ganglioside," Proceedings of the National Academy of Sciences of the United States of America, 82:1499-1502, National Academy of Sciences, United States (Mar. 1985).
Hellstrom, I., et al., "Antitumor Effects of L6, An IgG2a Antibody That Reacts With Most Human Carcinomas," Proceedings of the National Academy of Sciences of the United States of America, 83:7059-7063. National Academy of Sciences, United States (Sep. 1986).
Hodi, F., et al., "Improved Survival with Ipilimumab in Patients with Metastatic Melanoma," N Engl J Med 363(8):711-23, Massachusetts Medical Society, United States (Aug. 2010).
Hoelzinger, D.B., et al., Blockade of CCL1 Inhibits T Regulatory Cell Suppressive Function Enhancing Tumor Immunity without Affecting T Effector Responses, Journal of Immunology, 184(12):6833-6842, American Association of Immunologists, United States (Jun. 2010).
Holliger, P., et al., "Diabodies: Small Bivalent and Bispecific Antibody Fragments," Proceedings of the National Academy of Sciences of the United States of America 90(14):6444-6448, National Academy of Sciences, United States (Jul. 1993).
Hoogenboom, H.R., et al., "Designing and Optimizing Library Selection Strategies for Generating High-affinity Antibodies," Trends in Biotechnology 15(2):62-70, Elsevier Science, United Kingdom (1997).
Hou, J. and Zhan, H., "Expression of Active Thrombopoietin and Identification of Its Key Residues Responsible for Receptor Binding", Cytokine 10(5):319-330, Elsevier Science Ltd, United Kingdom (May 1998).
Houdebine, L.M., "Antibody Manufacture in Transgenic Animals and Comparisons With Other Systems", Current Opinion in Biotechnology 13(6):625-629, Elsevier, United Kingdom (Dec. 2002).
Huang, S., et al., "Development of Hybrid Viral Vectors for Gene Therapy," Biotechnology Advances, 31(2):208-223, Elsevier Science, United Kingdom (Mar.-Apr. 2013).
Hudson, P.J. and Kortt, A.A., "High Avidity scFv Multimers; Diabodies and Triabodies," Journal of Immunological Methods 231(1-2):177-189, Elsevier, Netherlands (Dec. 1999).
Huston, J.S., et al., "Protein Engineering of Antibody Binding Sites: Recovery of Specific Activity in an Anti-digoxin Single-chain Fv Analogue Produced in *Escherichia coli*," Proceedings of the National Academy of Sciences of the United States of America 85(16):5879-5883, National Academy of Sciences, United States (Aug. 1988).
Idusogie, E.E., et al., "Mapping of the C1q Binding Site on Rituxan, A Chimeric Antibody with a Human IgG1 Fc," The Journal of Immunology 164(8):4178-4184, American Association of Immunologists, United States (2000).
International Search Report and Written Opinion for International Application No. PCT/US2021/012329, European Patent Office, Netherlands, dated May 4, 2021, 12 pages.
Islam, S., et al., "Identification of human CCR8 as a CCL18 receptor," J Exp Med 210(10):1889-98, Rockefeller University Press, United States (Sep. 2013).
Jhunjhunwala, S., et al., "Antigen presentation in cancer: insights into tumour immunogenicity and immune evasion," Nat Rev Cancer 21(5):298-312, Springer, Germany (May 2021).
Jo, M., et al., "Engineering Therapeutic Antibodies Targeting G-protein-coupled Receptors," Experimental & Molecular Medicine, 48(2):e207, Nature Publishing Group, United States (Feb. 2016).

(56) References Cited

OTHER PUBLICATIONS

Johnson, D.A., "3-O-Desacyl monophosphoryl lipid A Derivatives: Synthesis and Immunostimulant Activities," Journal of Medicinal Chemistry 42(22):4640-4649, American Chemical Society, United States (Nov. 1999).
Kabat, E.A., et al., "Sequences of proteins of immunological interest," 5th Edition, NIH publication No. 91-3242, U.S. Department of Public Health and Human Services, National Institutes of Health, United States (1991).
Kang, L., et al., "CCR8 Signaling via CCL1 Regulates Responses of Intestinal IFN-g Producing Innate Lymphoid Cells and Protects From Experimental Colitis," Front Immunol 11:609400, Frontiers Media S.A., Switzerland (Feb. 2021).
Kaszubska, W., et al., "Expression, Purification, and Characterization of Human Recombinant Thrombopoietin in Chinese Hamster Ovary Cells," Protein Expression and Purification 18(2):213-220, Academic Press, United States (Mar. 2000).
Kettleborough, C.A., et al., "Isolation of Tumor Cell-specific Single-chain Fv From Immunized Mice Using Phage-antibody Libraries and the Re-construction of Whole Antibodies From These Antibody Fragments," European Journal of Immunology 24(4):952-958, Wiley-VCH, Germany (1994).
Kidani, Y., et al., "CCR8-targeted specific depletion of clonally expanded Treg cells in tumor tissues evokes potent tumor immunity with long-lasting memory," Proc Natl Acad Sci U S A 119(7):e2114282119, National Academy of Sciences (Feb. 2022).
Kieke, M.C., et al., "Isolation of Anti-T Cell Receptor ScFv Mutants by Yeast Surface Display", Protein Engineering, 10(11):1303-1310, Oxford University Press, United Kingdom (Nov. 1997).
Kim, J., et al., "Regulatory T cells prevent catastrophic autoimmunity throughout the lifespan of mice," Nat Immunol 8(2):191-7, Springer, Germany (Feb. 2007).
Kim, J.K., et al., "Identifying Amino Acid Residues that Influence Plasma Clearance of Murine IgG1 Fragments by Site-Directed Mutagenesis," European Journal of Immunology 24(3):542-548, Wiley-VCH, Germany (Mar. 1994).
Kinstler, O., et al., "Mono-N-terminal Poly(Ethylene Glycol)-protein Conjugates," Advanced Drug Delivery Reviews 54(4):477-485, Elsevier Science Publishers, Netherlands (Jun. 2002).
Kirkland, T.N., et al., "Analysis of the Fine Specificity and Cross-reactivity of Monoclonal Anti-lipid A Antibodies," Journal of Microbiology 137(11):3614-3619, Microbiological Society of Korea, Korea (1986).
Klemm, P. and Schembri, M, A., "Fimbrial Surface Display Systems in Bacteria: From Vaccines to Random Libraries," Microbiology (Reading), 146(12):3025-3032, Microbiology Society, United Kingdom (Dec. 2000).
Kostelny, S.A., et al., "Formation of a Bispecific Antibody by the Use of Leucine Zippers," The Journal of Immunology 148(5):1547-1553, American Association of Immunologists, United States (Mar. 1992).
Kuik-Romeijn, P, V., et al., "Expression of a Functional Mouse-human Chimeric Anti-cd19 Antibody in the Milk of Transgenic Mice," Transgenic Res, 9(2):155-159, Kluwer Academic Publishers, Netherlands (Apr. 2000).
Lan, R., et al., "Highly selective anti-CCR8 antibody-mediated depletion of regulatory T cells leads to potent antitumor activity alone and in combination with anti-PD-1 in preclinical models," Abstract 6694, Cancer Res 80:6694, American Association for Cancer Research, United States (Aug. 2020).
Langer, R., et al., "Biocompatibility of Polymeric Delivery Systems for Macromolecules," Journal of Biomedical Materials Research 15(2):267-277, John Wiley & Sons, Inc., United States (1981).
Langer, R.,, "Controlled release of macromolecules," Chem. Tech 12:98-105, American Chemical Society, United States (1982).
Laursen, N., et al., "Functional and Structural Characterization of a Potent C1q Inhibitor Targeting the Classical Pathway of the Complement System," Front Immunol 11:1504, Frontiers Media S.A., Switzerland (Jul. 2020).

Lee, D., et al., "ASTCT Consensus Grading for Cytokine Release Syndrome and Neurologic Toxicity Associated with Immune Effector Cells," Biol Blood Marrow Transplant 25(4):625-638, Elsevier, Netherlands (Apr. 2019).
Lee, L.S., et al., "Prolonged Circulating Lives of Single-chain Fv Proteins Conjugated With Polyethylene Glycol: a Comparison of Conjugation Chemistries and Compounds," Bioconjugate Chemistry, 10(6):973-981, American Chemical Society, United States (Nov.-Dec. 1999).
Lin, W., et al., "Fc-dependent expression of CD137 on human NK cells: insights into 'agonistic' effects of anti-CD137 monoclonal antibodies," Blood 112(3):699-707, American Society of Hematology, United States (Aug. 2008).
Liu, S., and Yuan, Y., "Bayesian Optimal Interval Designs for Phase I Clinical Trials," Journal of the Royal Statistical Society 64(3):507-523, Wiley, United States (2014).
Lodmell, D.L., et al., "DNA Vaccination of Mice Against Rabies Virus: Effects of the Rroute of Vaccination and the Adjuvant Monophosphoryl Lipid A (MPL)," Vaccine, 18(11-12):1059-1066, Elsevier Science, Netherlands (Jan. 2000).
Lonberg, N. and Huszar, D., "Human Antibodies from Transgenic Mice," International Reviews of Immunology 13(1):65-93, Informa Healthcare, United Kingdom (1995).
Lonberg, N., "Handbook of Experimental Pharmacology," The Pharmacology of Monoclonal Antibodies 113:49-101, (1994).
Lonberg, N., "Human Antibodies From Transgenic Animals," Nature Biotechnology, 23(9): 1117-1125, Nature America Publishing, United States (Sep. 2005).
Lonberg, N., et al., "Antigen-specific Human Antibodies from Mice Comprising Four Distinct Genetic Modifications," Nature 368(6474):856-859, Nature Publishing Group, United States (Apr. 1994).
Lusky, M. and Botchan, M., "Inhibition of Sv40 Replication in Simian Cells by Specific Pbr322 Dna Sequences," Nature, 293(5827):79-81, Nature Publishing Group, United Kingdom (Sep. 1981).
Magnuson, A., et al., "Identification and validation of a tumor-infiltrating Treg transcriptional signature conserved across species and tumor types," Proc Natl Acad Sci U S A 115(45):E10672-E10681, National Academy of Sciences, United States (Nov. 2018).
McCafferty, J., et al., "Phage Antibodies: Filamentous Phage Displaying Antibody Variable Domains," Nature 348(6301):552-554, Nature Publishing Group, United Kingdom (Dec. 1990).
Mccully, M., et al., "CCR8 Expression Defines Tissue-Resident Memory T Cells in Human Skin," J Immunol 200:1639-1650, American Association of Immunologists, United States (Mar. 2018).
Mccully, M., et al., "Epidermis instructs skin homing receptor expression in human T cells," Blood 120(23):4591-8, American Society of Hematology, United States (Nov. 2012).
Mccully, M., et al., "Skin Metabolites Define a New Paradigm in the Localization of Skin Tropic Memory T Cells," J Immunol 195(1):96-104, American Association of Immunologists, United States (Jul. 2015).
Merle, N., et al., "Complement system part i—molecular mechanisms of activation and regulation," Front Immunol 2;6:262, Frontiers Media S.A., Switzerland (Jun. 2015).
Merz, D.C., et al., "Generating a Phage Display Antibody Library Against an Identified Neuron," Journal of Neuroscience Methods, 62(1-2):213-219, Elsevier/North-Holland Biomedical Press, Netherlands (Nov. 1995).
Michael, S, I., et al., "Addition of a Short Peptide Ligand to the Adenovirus Fiber Protein," Gene Ther, 2(9):660-668, Nature Publishing Group, United Kingdom (Nov. 1995).
Mikhak, Z., et al., "Contribution of CCR4 and CCR8 to antigen-specific Th2 cell trafficking in allergic pulmonary inflammation," J Allergy Clin Immunol 123(1):67-73, Elsevier, Netherlands (Jan. 2009).
Milstein, C. and Cuello, A.C., "Hybrid Hybridomas and their Use in Immunohistochemistry," Nature 305(5934):537-540, Nature Publishing Group, United Kingdom (Oct. 1983).
Misumi, T., et al., "Stimulation of natural killer cells with rhCD137 ligand enhances tumor-targeting antibody efficacy in gastric cancer," PLoS One 13(10):e0204880, PLOS, United States (Oct. 2018).

(56) References Cited

OTHER PUBLICATIONS

Moldenhauer, G., et al., "Identity of HML-1 Antigen on Intestinal Intraepithelial T Cells and of B-ly7 Antigen on Hairy Cell Leukaemia," Scandinavian Journal of Immunology 32(2):77-82, Blackwell Scientific Publications, United Kingdom (1990).
Morel, G.A., et al., "Monoclonal Antibodies to Bovine Serum Albumin: Affinity and Specificity Determinations," Molecular Immunology 25(1):7-15, Pergamon Press, United Kingdom (1988).
Moser, B., "Chemokine Receptor-Targeted Therapies: Special Case for CCR8," Cancers (Basel) 14(3):511, MDPI, Switzerland (Jan. 2022).
Mueller, J.P., et al., "Humanized Porcine VCAM-specific Monoclonal Antibodies With Chimeric IgG2/G4 Constant Regions Block Human Leukocyte Binding to Porcine Endothelial Cells," Molecular Immunology 34(6):441-452, Pergamon Press, United Kingdom (Apr. 1997).
Muenst, S., et al., "The immune system and cancer evasion strategies: therapeutic concepts," J Intern Med 279(6):541-62, Wiley, United States (Jun. 2016).
Mulligan, R.C. and Berg, P., "Selection for Animal Cells that Express the *Escherichia coli* Gene Coding for Xanthine-guanine Phosphoribosyltransferase," Proceedings of the National Academy of Sciences USA 78(4):2072-2076, National Academy of Sciences, United States (Apr. 1981).
Mutalithas, K., et al., "Expression of CCR8 is increased in asthma," Clin Exp Allergy 40(8):1175-85, Wiley, United States (Aug. 2010).
Muyldermans, S., et al., "Recognition of Antigens by Single-Domain Antibody Fragments: the Superfluous Luxury of Paired Domains," Trends in Biochemical Sciences 26(4):230-235, Elsevier Trends Journals, United Kingdom (Apr. 2001).
Myers, E.W. and Miller, W., "Optimal Alignments in Linear Space," Computer Applications in the Biosciences 4(1): 11-17, Oxford University Press, United Kingdom (Mar. 1988).
Needleman, S.B. and Wunsch, C.D., "A General Method Applicable to the Search for Similarities in the Amino Acid Sequence of Two Proteins," Journal of Molecular Biology 48(3):443-453, Academic Press, United Kingdom (Mar. 1970).
Neelapu, S., et al., "Chimeric antigen receptor T-cell therapy—assessment and management of toxicities" Nat Rev Clin Oncol 15(1):47-62, Springer, Germany (Jan. 2018).
Niro R.D., et al., "Characterizing Monoclonal Antibody Epitopes by Filtered Gene Fragment Phage Display," The American Journal of Pathology, 388(Pt 3):889-894, Elsevier, United States (Jun. 2005).
Nuttall, S.D., et al., "Immunoglobulin VH Domains and Beyond: Design and Selection of Single-domain Binding and Targeting Reagents," Current Pharmaceutical Biotechnology 1(3):253-263, Bentham Science Publishers, Netherlands (2000).
Ohtsuka, E., et al., "An Alternative Approach to Deoxyoligonucleotides as Hybridization Probes by Insertion of Deoxyinosine at Ambiguous Codon Positions," The Journal of Biological Chemistry 260(5):2605-2608, Elsevier Inc, United States (Mar. 1985).
Oken, M., et al., "Toxicity and response criteria of the Eastern Cooperative Oncology Group," Am J Clin Oncol 5(6):649-55, American Society of Clinical Oncology, United States (Dec. 1982).
Onda, M., et al., "Depletion of regulatory T cells in tumors with an anti-CD25 immunotoxin induces CD8 T cell-mediated systemic antitumor immunity," Proc Natl Acad Sci U S A 116(10):4575-4582, National Academy of Sciences, United States (Mar. 2019).
Panina-Bordignon, P., et al., "The C-C chemokine receptors CCR4 and CCR8 identify airway T cells of allergen-challenged atopic asthmatics," J Clin Invest 107(11):1357-64, American Society for Clinical Investigation, United States (Jun. 2001).
Pavisic, R., et al., "Recombinant Human Granulocyte Colony Stimulating Factor Pre-screening and Screening of Stabilizing Carbohydrates and Polyols," International Journal of Pharmaceutics, 387(1-2):110-119, Amsterdam, Elsevier/North-Holland Biomedical Press, Netherlands (Mar. 2010).
Pearson, W.R. and Lipman, D.J., "Improved Tools for Biological Sequence Comparison," Proceedings of the National Academy of Sciences of the United States of America 85(8):2444-2448, National Academy of Sciences, United States (Apr. 1988).
Pereboev, A., et al., "Phage Display of Adenovirus Type 5 Fiber Knob as a Tool for Specific Ligand Selection and Validation," Journal of Virology, 75(15):7107-7113, American Society For Microbiology, United States (Aug. 2001).
Persic, L., et al., "An Integrated Vector System for the Eukaryotic Expression of Antibodies or Their Fragments After Selection From Phage Display Libraries," Gene 187(1):9-18, Elsevier/North-Holland, Netherlands (1997).
Petersen, R., et al., "Tumor Infiltrating FOXP31 Regulatory T-cells Are Associated With Recurrence in Pathologic Stage I NSCLC Patients," Cancer 107(12):2866-72, Wiley, United States (Dec. 2006).
Petkova, S.B., et al., "Enhanced Half-Life of Genetically Engineered Human IgG1 Antibodies in a Humanized FcRn Mouse Model: Potential Application in Humorally Mediated Autoimmune Disease," International Immunology 18(12):1759-1769, Oxford University Press, United Kingdom (2006).
Plitas, G., et al., "Regulatory T Cells Exhibit Distinct Features in Human Breast Cancer," Immunity 45(5):1122-1134, Cell Press, United States (Nov. 2016).
Plitas, G., et al., "Regulatory T Cells in Cancer," Annu Rev Cancer Biol 4:459-577, Annual Reviews Inc., United States (Mar. 2020).
Poljak, R.J., "Production and Structure of Diabodies," Structure 2(12):1121-1123, Cell Press, United States (1994).
Pollock, D., et al., "Transgenic milk as a method for the production of recombinant antibodies", Journal of Immunological Methods 231: 147-157, Elsevier, Netherlands (1999).
Ravetch, J.V. and Kinet, J.P., "Fc Receptors," Annual Review of Immunology 9:457-492, Annual Reviews Inc, United States (1991).
Ricard, M., "Survey of CCR8 expression in normal human tissues by immunohistochemistry," Report SRF114-R0014, 34 pages, Surface Oncology, Inc. (Jun. 2022).
Riechmann, L. and Muyldermans, S., "Single Domain Antibodies: Comparison of Camel VH and Camelised Human VH Domains," Journal of Immunological Methods 231(1-2):25-38, Elsevier, Netherlands (Dec. 1999).
Robert, C., et al., "A decade of immune-checkpoint inhibitors in cancer therapy," Nat Commun 11(1):3801, Springer, Germany (Jul. 2020).
Roberts, M.J., et al., "Chemistry for Peptide and Protein Pegylation," Advanced Drug Delivery Reviews, 54(4):459-476, Elsevier Science Publishers, B.V., Netherlands (Jun. 2002).
Rogers, B.E., et al., "Localization of Iodine-125-mip-des-met14-bombesin (7-13)nh2 in Ovarian Carcinoma Induced to Express the Gastrin Releasing Peptide Receptor by Adenoviral Vector-mediated Gene Transfer," The Journal of Nuclear Medicine, 38(8):1221-1229, Society of Nuclear Medicine, United States (Aug. 1997).
Romano, E., et al., "Ipilimumab-dependent cell-mediated cytotoxicity of regulatory T cells ex vivo by nonclassical monocytes in melanoma patients," Proc Natl Acad Sci USA 112(19):6140-5, National Academy of Sciences (May 2015).
Rondon, I.J. and Marasco, W.A., "Intracellular Antibodies (Intrabodies) for Gene Therapy of Infectious Diseases," Annual Review of Microbiology, 51(1):257-283, Annual Reviews, United States (1997).
Roos, R., et al., "Identification of CCR8, the Receptor for the Human CC Chemokine I-309" J Exp Med 186(1):165-70, Rockefeller University Press, United States (Jul. 1997).
Rossolini, G.M., et al., "Use of Deoxyinosine-Containing Primers vs Degenerate Primers for Polymerase Chain Reaction Based on Ambiguous Sequence Information," Molecular and Cellular Probes 8(2):91-98, Academic Press, United Kingdom (Apr. 1994).
Sakaguchi, S., et al., "Regulatory T Cells and Human Disease," Annu Rev Immunol 38:541-566, Annual Reviews Inc., United States (Apr. 2020).
Sarver, N., et al., "Transformation and Replication in Mouse Cells of a Bovine Papillomavirus-pml2 Plasmid Vector That Can Be Rescued in Bacteria," Proceedings of the National Academy of Sciences of the United States of America, 79(23):7147-7151, National Academy of Sciences, United States (Dec. 1982).

(56) References Cited

OTHER PUBLICATIONS

Schaerli, P., et al., "A Skin-selective Homing Mechanism for Human Immune Surveillance T Cells," J Exp Med 199(9):1265-75, Rockefeller University Press, United States (May 2004).

Schaffitzel, C., et al., "Ribosome Display: An in Vitro Method for Selection and Evolution of Antibodies From Libraries," Journal of Immunological Methods 231(1-2):119-135, Elsevier, Netherlands (Dec. 1999).

Schoonbroodt, S., et al., "Oligonucleotide-Assisted Cleavage and Ligation: A Novel Directional DNA Cloning Technology to Capture CDNA s. Application in the Construction of a Human Immune Antibody Phage-Display Library," Nucleic Acids Research, 33(9):e81, Information Retrieval ltd, United Kingdom (May 2005).

Shalaby, M.R., et al., "Development of Humanized Bispecific Antibodies Reactive with Cytotoxic Lymphocytes and Tumor Cells Overexpressing the HER2 Protooncogene," The Journal of Experimental Medicine 175(1):217-225, The Rockefeller University Press, United States (Jan. 1992).

Shen, Z., et al., "Higher intratumoral inWltrated Foxp3+ Treg numbers and Foxp3+/CD8+ ratio are associated with adverse prognosis in resectable gastric cancer," J Cancer Res Clin Oncol 136(10):1585-9, Springer, Germany (Oct. 2010).

Shi, L., et al., "De Novo Selection of High-affinity Antibodies From Synthetic Fab Libraries Displayed on Phage as Pix Fusion Proteins," Journal of Molecular Biology, 397(2):385-396, Academic Press, United Kingdom (Mar. 2010).

Shields, R.L., et al., "High Resolution Mapping of the Binding Site on Human IgG1 for Fc gamma RI, Fc gamma RII, Fc gamma RIII, and FcRn and Design of IgG1 Variants with Improved Binding to the Fc gamma R," The Journal of Biological Chemistry 276(9):6591-6604, American Society for Biochemistry and Molecular Biology, United States (Mar. 2001).

Shiraishi, M., et al., "Short-step Chemical Synthesis of Dna by Use of Mmtrs Group for Protection of 5'-hydroxyl Group," Nucleic Acids Symposium Series, 51:129-130, Oxford University Press, United Kingdom (2007).

Shopes, B., "A Genetically Engineered Human Igg Mutant With Enhanced Cytolytic Activity," Journal of Immunology148(9):2918-2922, American Association of Immunologists, United States (May 1992).

Sidman, et al., "Controlled Release of Macromolecules and Pharmaceuticals from Synthetic Polypeptides Based on Glutamic Acid," Biopolymers 22:547-556, John Wiley & Sons, Inc., United States (Jan. 1983).

Smith, T.F. and Waterman, M.S., "Comparison of Biosequences," Advances in Applied Mathematics 2(4):482-489, Academic Press, Inc., United States (Dec. 1981).

Soler, D., et al., "CCR8 Expression Identifies CD4 Memory T Cells Enriched for FOXP3+ Regulatory and Th2 Effector Lymphocytes," J Immunol 177(10):6940-51, American Association of Immunologists, United States (Nov. 2006).

Songsivilai, S. and Lachmann, P.J., "Bispecific Antibody: A Tool for Diagnosis and Treatment of Disease," Clinical and Experimental Immunology 79(3):315-321, Blackwell Scientific Publications, United Kingdom (1990).

Southern, P.J. and Berg, P., "Transformation of Mammalian Cells to Antibiotic Resistance with a Bacterial Gene Under Control of the SV40 Early Region Promoter," Journal of Molecular and Applied Genetics 1(4):327-341, Raven Press, United States (1982).

Stahli, C., et al., "Distinction of Epitopes by Monoclonal Antibodies," Methods in Enzymology 92:242-253, Academic Press, United States (1983).

Steinberger, P., et al., "Molecular characterization of human 4Ig-B7-H3, a member of the B7 family with four Ig-like domains ," J Immunol 172(4):2352-9, American Association of Immunologists, United States (Feb. 2004).

Subedi, G., et al., "The immunoglobulin G1 N-glycan composition affects binding to each low affinity Fc γ receptor," MAbs 8(8):1512-1524, Taylor & Francis, United Kingdom (May 2016).

Suresh, M.R., et al., "Bispecific Monoclonal Antibodies from Hybrid Hybridomas," Methods in Enzymology 121:210-228, Academic Press Inc., United States (1986).

Tang, Y., et al., "Regulation of Antibody-Dependent Cellular Cytotoxicity by IgG Intrinsic and Apparent Affinity for Target Antigen," J Immunol 179(5):2815-23, American Association of Immunologists, United States (Sep. 2007).

Temming, A., et al., "Functional Attributes of Antibodies, Effector Cells, and Target Cells Affecting NK Cell-Mediated Antibody-Dependent Cellular Cytotoxicity," J Immunol 203(12):3126-3135, American Association of Immunologists, United States (Dec. 2019).

Thyagarajan, H., et al., "CCR8 is expressed by post-positive selection CD4-lineage thymocytes but is dispensable for central tolerance induction," PLoS One 13(7):e0200765, PLOS, United States (Jul. 2018).

Todorovska, A., et al., "Design and Application of Diabodies, Triabodies and Tetrabodies for Cancer Targeting," Journal of Immunological Methods 248(1-2):47-66, Elsevier, Netherlands (Feb. 2001).

Topalian, S., et al., "Safety, activity, and immune correlates of anti-PD-1 antibody in cancer," N Engl J Med 366(26):2443-54, Massachusetts Medical Society, United States (Jun. 2012).

Tutt, A., et al., "Trispecific F(ab')3 Derivatives That Use Cooperative Signaling via the TCR/CD3 Complex and CD2 to Activate and Redirect Resting Cytotoxic T Cells," Journal of Immunology, 147:60-69, American Association of Immunologists, United States (Jul. 1991).

Van Damme, H., et al., "Therapeutic depletion of CCR8+ tumor-infiltrating regulatory T cells elicits antitumor immunity and synergizes with anti-PD-1 therapy," J Immunother Cancer 9(2):e001749, BMJ Publishing Group Ltd and Society for Immunotherapy of Cancer, United Kingdom (Feb. 2021).

Villarreal, D.O., et al., "Targeting CCR8 Induces Protective Antitumor Immunity and Enhances Vaccine-Induced Responses in Colon Cancer," Cancer Research, 78(18):5340-5348, American Association for Cancer Research, United States (Sep. 2018).

Vinay, D., et al., "Immune evasion in cancer: Mechanistic basis and therapeutic strategies," Semin Cancer Biol 35 Suppl:S185-S198, Academic Press Inc., United States (Dec. 2015).

Vogelpoel, L., et al., "Control of cytokine production by human Fc gamma receptors: implications for pathogen defense and autoimmunity," Front Immunol 6:79, Frontiers Media S.A., Switzerland (Feb. 2015).

Wang, L., et al., "Connecting blood and intratumoral Treg cell activity in predicting future relapse in breast cancer," Nat Immunol 20(9):1220-1230, Springer, Germany (Sep. 2019).

Wright, A., et al., "Antibody Variable Region Glycosylation: Position Effects on Antigen Binding and Carbohydrate Structure," The EMBO Journal 10(10):2717-2723, Wiley Blackwell, England (1991).

Wu, C., et al., "Simultaneous Targeting of Multiple Disease Mediators by a Dual-variable-domain Immunoglobulin," Nature Biotechnology 25(11):1290-1297, Nature Publishing Co., United States (2007).

Yang, Y., et al., "Myeloid-Derived Suppressor Cells in Tumors: From Mechanisms to Antigen Specificity and Microenvironmental Regulation," Front Immunol 11:1371, Frontiers Media S.A., Switzerland (Jul. 2020).

Yeung, Y.A., and Wittrup, D.K.,, "Quantitative Screening of Yeast Surface-displayed Polypeptide Libraries by Magnetic Bead Capture", Biotechnology Progress 18(2):212-220, American Institute of Chemical Engineers, United States (Mar.-Apr. 2002).

Yuan, Y., et al., "Bayesian Optimal Interval Design: A Simple and Well-Performing Design for Phase I Oncology Trials," Clin Cancer Res 22(17):4291-301, American Association for Cancer Research, United States (Sep. 2016).

Zapata, G., et al., "Engineering Linear F(ab')2 Fragments for Efficient Production in *Escherichia coli* and Enhanced Antiproliferative Activity," Protein Engineering 8(10):1057-1062, Oxford University Press, United Kingdom (1995).

Zhou, H., et al., "Accuracy, Safety, and Reliability of Novel Phase I Trial Designs" Clin Cancer Res 24(18):4357-4364, American Association for Cancer Research, United States (Sep. 2018).

(56) References Cited

OTHER PUBLICATIONS

Zhou, Y., et al., "BOIN Suite: A Software Platform to Design and Implement Novel Early-Phase Clinical Trials," JCO Clin Cancer Inform 5:91-101, American Society of Clinical Oncology, United States (Jan. 2021).
Zingoni, A., et al., "Cutting Edge: The Chemokine Receptor CCR8 Is Preferentially Expressed in Th2 But Not Th1 Cells," J Immunol 161(2):547-51, American Association of Immunologists, United States (Jul. 1998).
Wigler, M., et al., "Transformation of Mammalian Cells with Genes from Procaryotes and Eucaryotes," Cell 16:777-785, Cell Press, United States (Apr. 1979).
Shipman, L., "Interrogating intratumoral Treg cells," Nature Reviews Immunology, 17:4-5, Springer, Germany (Dec. 2016).
Anonymous, Product technical data sheet for Purified anti-human CD198 (CCR8) Antibody clone L263G8, BioLegend, Inc., United States, revised Oct. 9, 2013, 3 pages.
Anonymous, Product technical data sheet for BV421 Mouse Anti-Human CCR8 (CD198) clone 433H data sheet, Becton, Dickinson and Company, United States, Feb. 2016, 2 pages.
Anonymous, Product technical data sheet for Monoclonal Anti-Human CCR8-Fluorescein clone 191704, R&D Systems, Inc., United States, Oct. 2007, 2 pages.
Zahavi, D., et al., "Enhancing antibody-dependent cell-mediated cytotoxicity: a strategy for improving antibody-based immunotherapy" Antibody Therapeutics 1:7-12, Oxford University Press, United Kingdom (Jun. 2018).
Nelson, A., "Antibody fragments: Hope and hype" mAbs, 2:77-83, Taylor & Francis, United Kingdom (Jan. 2010).
Kipps, T., et al., "Importance of Immunoglobulin Isotype in Human Antibody-Dependent, Cell-Mediated Cytotoxicity Directed by Murine Monoclonal Antibodies" Journal of Experimental Medicine, 161:1-17 (Jan. 1985).
Anonymous, "Immunoglobulin G Review " InvivoGen, United States, 1 page (2011).
Plitas, G., et al., "Preferential expression of the chemokine receptor 8 (CCR8) on regulatory T cells (Treg) infiltrating human breast cancers represents a novel immunotherapeutic target" 76: Abstract P4-04-11, Proceedings of the Thirty-Eighth Annual CTRC-AACR San Antonio Breast Cancer Symposium: Dec. 8-12, 2015; San Antonio, TX. Philadelp,, 2 pages.
Mordant, P., et al., "Bioluminescent Orthotopic Mouse Models of Human Localized Non-Small Cell Lung Cancer: Feasibility and Identification of Circulating Tumour Cells" PLoS ONE, 6:e26073, PLOS, United States (Oct. 2011).
Klages, K., et al., "Selective Depletion of Foxp3+ Regulatory T Cells Improves Effective Therapeutic Vaccination against Established Melanoma" Cancer research 70:7788-99, American Association for Cancer Research, United States (Oct. 2010).
Vargas, F., et al., "Fc-Optimized Anti-CD25 Depletes Tumor-Infiltrating Regulatory T Cells and Synergizes with PD-1 Blockade to Eradicate Established Tumors" Immunity, 46:577-586, Cell Press, United States (Apr. 2017).
Eruslanova, E., et al., "Expansion of CCR8+ Inflammatory Myeloid Cells in Cancer Patients with Urothelial and Renal Carcinomas," Clin Cancer Res 19(7):1670-80, American Association for Cancer Research, United States (Apr. 2013).
Das, S., et al., "Tumor cell entry into the lymph node is controlled by CCL1 chemokine expressed by lymph node lymphatic sinuses," J Exp Med 210(8):1509-28, Rockefeller University Press, United States (Jul. 2013).
Plitas, G., et al., "Regulatory T Cells Exhibit Distinct Features in Human Breast Cancer (Supplemental information)," Immunity 45(5):1122-1134, Cell Press, United States (Nov. 2016).
De Simone, M., et al., "Transcriptional Landscape of Human Tissue Lymphocytes Unveils Uniqueness of Tumor-Infiltrating T Regulatory Cells (Supplemental Information)," Immunity 45(5):1135-1147, Cell Press, United States (Nov. 2016).
Vela, M., et al., "Chemokine receptor-specific antibodies in cancer immunotherapy: achievements and challenges," Front Immunol 6:12, Frontiers Media S.A., Switzerland (Jan. 2015).
Ishii, T., et al., "Defucosylated Humanized Anti-CCR4 Monoclonal Antibody KW-0761 as a Novel Immunotherapeutic Agent for Adult T-cell Leukemia/Lymphoma," Clin Cancer Res 16(5):1520-31, American Association for Cancer Research, United States (Mar. 2010).
Kurose, K., et al., "Phase Ia Study of FoxP3+ CD4 Treg Depletion by Infusion of a Humanized Anti-CCR4 Antibody, KW-0761, in Cancer Patients," Clin Cancer Res 21(19):4327-36, American Association for Cancer Research, United States (Oct. 2015).
Shuptrine, C., et al., "Monoclonal antibodies for the treatment of cancer," Semin Cancer Biol 22(1):3-13, Academic Press Inc., United States (Feb. 2012).
Vashti, I., et al., "Molecular properties of human IgG subclasses and their implications for designing therapeutic monoclonal antibodies against infectious diseases" Mol Immunol 67:171-82, Pergamon Press, United Kingdom (Oct. 2015).
Vashti, I., et al., "Molecular properties of human IgG subclasses and their implications for designing therapeutic monoclonal antibodies against infectious diseases (Annex A)" Mol Immunol 67:171-82, Pergamon Press, United Kingdom (Oct. 2015).
Anonymous, Product technical data sheet for Purified Anti-mMouse CD198 (CCR8) Antibody clone SA214G2, BioLegend, Inc., United States, revised Dec. 16, 2015, 3 pages.

\* cited by examiner

SEQUENCE LISTING

<160> NUMBER OF SEQ ID NOS: 242

<210> SEQ ID NO 1
<211> LENGTH: 121
<212> TYPE: PRT
<213> ORGANISM: Artificial Sequence
<220> FEATURE:
<223> OTHER INFORMATION: Synthetic sequence

<400> SEQUENCE: 1

Val Gln Leu Val Glu Ser Gly Gly Gly Leu Val Gln Pro Gly Arg Ser

```
             1               5                  10                 15
            Leu Arg Leu Ser Cys Ala Ala Ser Gly Phe Thr Phe Asp Asp Tyr Ala
                            20                 25                 30

Met His Trp Val Arg Gln Ala Pro Gly Lys Gly Leu Glu Trp Val Ser
                        35                 40                 45

Gly Ile Ser Trp Asn Ser Gly Ser Ile Gly Tyr Ala Asp Ser Val Lys
                    50                 55                 60

Gly Arg Phe Thr Ile Ser Arg Asp Asn Ser Lys Asn Ser Leu Tyr Leu
             65                 70                 75                 80

Gln Met Asn Ser Leu Arg Ala Glu Asp Thr Ala Leu Tyr Tyr Cys Ala
                            85                 90                 95

Arg Gly Arg Glu Ser Tyr Arg Val Ser Leu Arg Phe Asp Tyr Trp Gly
                            100                105                110

Gln Gly Thr Leu Val Thr Val Ser Ser
                            115                120

<210> SEQ ID NO 2

<400> SEQUENCE: 2

000

<210> SEQ ID NO 3
<211> LENGTH: 108
<212> TYPE: PRT
<213> ORGANISM: Artificial Sequence
<220> FEATURE:
<223> OTHER INFORMATION: Synthetic sequence

<400> SEQUENCE: 3

Gln Ser Val Leu Thr Gln Pro Pro Ser Val Ser Ala Ala Pro Gly Gln
             1               5                  10                 15

Lys Val Thr Ile Ser Cys Ser Gly Ser Ser Ser Asn Ile Gly Asn Asn
                            20                 25                 30

Tyr Val Ser Trp Tyr Gln Gln Leu Pro Gly Thr Ala Pro Lys Leu Leu
                        35                 40                 45

Ile Tyr Asp Asn Asn Lys Arg Pro Ser Gly Ile Pro Asp Arg Phe Ser
                    50                 55                 60

Gly Ser Lys Ser Gly Thr Ser Ala Thr Leu Gly Ile Thr Gly Leu Gln
             65                 70                 75                 80

Thr Gly Asp Glu Ala Asp Tyr Tyr Cys Gly Thr Trp Asp Ser Ser Leu
                            85                 90                 95

Ser Ala Trp Val Phe Gly Gly Gly Thr Lys Leu Thr
                            100                105

<210> SEQ ID NO 4

<400> SEQUENCE: 4

000

<210> SEQ ID NO 5
<211> LENGTH: 5
<212> TYPE: PRT
<213> ORGANISM: Artificial Sequence
<220> FEATURE:
<223> OTHER INFORMATION: Synthetic sequence

<400> SEQUENCE: 5

Asp Tyr Ala Met His
```

<210> SEQ ID NO 6
<211> LENGTH: 17
<212> TYPE: PRT
<213> ORGANISM: Artificial Sequence
<220> FEATURE:
<223> OTHER INFORMATION: Synthetic sequence

<400> SEQUENCE: 6

Gly Ile Ser Trp Asn Ser Gly Ser Ile Gly Tyr Ala Asp Ser Val Lys
1               5                   10                  15
Gly

<210> SEQ ID NO 7
<211> LENGTH: 13
<212> TYPE: PRT
<213> ORGANISM: Artificial Sequence
<220> FEATURE:
<223> OTHER INFORMATION: Synthetic sequence

<400> SEQUENCE: 7

Gly Arg Glu Ser Tyr Arg Val Ser Leu Arg Phe Asp Tyr
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Synthetic sequence

<400> SEQUENCE: 8

Ser Gly Ser Ser Ser Asn Ile Gly Asn Asn Tyr Val Ser
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Synthetic sequence

<400> SEQUENCE: 9

Asp Asn Asn Lys Arg Pro Ser
1               5

<210> SEQ ID NO 10
<211> LENGTH: 11
<212> TYPE: PRT
<213> ORGANISM: Artificial Sequence
<220> FEATURE:
<223> OTHER INFORMATION: Synthetic sequence

<400> SEQUENCE: 10

Gly Thr Trp Asp Ser Ser Leu Ser Ala Trp Val
1               5                   10

<210> SEQ ID NO 11
<211> LENGTH: 118
<212> TYPE: PRT
<213> ORGANISM: Artificial Sequence
<220> FEATURE:
<223> OTHER INFORMATION: Anti-CCR8-2 Heavy Chain

<400> SEQUENCE: 11

```
Glu Val Gln Leu Leu Glu Ser Gly Gly Gly Leu Val Gln Pro Gly
1               5                   10                  15

Ser Leu Arg Leu Ser Cys Ala Ala Gly Gly Phe Thr Phe Ser Ala Tyr
            20                  25                  30

Thr Met Asn Trp Val Arg Gln Ala Pro Gly Lys Gly Leu Glu Trp Val
        35                  40                  45

Ser Ala Ile Ser Ala Ser Gly Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Phe Ala Arg Gly Trp Phe Asp Pro Trp Gly Gln Gly Thr
                100                 105                 110

Leu Val Thr Val Ser Ser
                115
```

<210> SEQ ID NO 12

<400> SEQUENCE: 12

000

<210> SEQ ID NO 13
<211> LENGTH: 108
<212> TYPE: PRT
<213> ORGANISM: Artificial Sequence
<220> FEATURE:
<223> OTHER INFORMATION: Anti-CCR8-2 Light Chain

<400> SEQUENCE: 13

```
Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr
                100                 105
```

<210> SEQ ID NO 14

<400> SEQUENCE: 14

000

<210> SEQ ID NO 15
<211> LENGTH: 5
<212> TYPE: PRT
<213> ORGANISM: Artificial Sequence
<220> FEATURE:
<223> OTHER INFORMATION: Synthetic sequence

<400> SEQUENCE: 15

Ala Tyr Thr Met Asn
1               5

<210> SEQ ID NO 16
<211> LENGTH: 17
<212> TYPE: PRT
<213> ORGANISM: Artificial Sequence
<220> FEATURE:
<223> OTHER INFORMATION: Synthetic sequence

<400> SEQUENCE: 16

Ala Ile Ser Ala Ser Gly Gly Arg Thr Tyr Tyr Ala Asp Ser Val Lys
1               5                   10                  15

Gly

<210> SEQ ID NO 17
<211> LENGTH: 9
<212> TYPE: PRT
<213> ORGANISM: Artificial Sequence
<220> FEATURE:
<223> OTHER INFORMATION: Synthetic sequence

<400> SEQUENCE: 17

Arg Phe Ala Arg Gly Trp Phe Asp Pro
1               5

<210> SEQ ID NO 18
<211> LENGTH: 13
<212> TYPE: PRT
<213> ORGANISM: Artificial Sequence
<220> FEATURE:
<223> OTHER INFORMATION: Synthetic sequence

<400> SEQUENCE: 18

Ser Gly Ser Ser Ser Asn Ile Gly Asn Asn Tyr Val Ser
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Synthetic sequence

<400> SEQUENCE: 19

Asp Asn Asn Lys Arg Pro Ser
1               5

<210> SEQ ID NO 20
<211> LENGTH: 11
<212> TYPE: PRT
<213> ORGANISM: Artificial Sequence
<220> FEATURE:
<223> OTHER INFORMATION: Synthetic sequence

<400> SEQUENCE: 20

Gly Thr Trp Asp Ser Ser Leu Ser Ala Trp Val
1               5                   10

<210> SEQ ID NO 21
<211> LENGTH: 122
<212> TYPE: PRT
<213> ORGANISM: Artificial Sequence
<220> FEATURE:
<223> OTHER INFORMATION: Anti-CCR8-2-4 Heavy Chain, Anti-CCR8-2-5 Heavy
      Chain

<400> SEQUENCE: 21

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Arg Lys Ser Tyr Arg Val Ser Leu Arg Phe Asp Tyr Trp
            100                 105                 110

Gly Gln Gly Thr Leu Val Thr Val Ser Ser
            115                 120
```

<210> SEQ ID NO 22

<400> SEQUENCE: 22

000

<210> SEQ ID NO 23
<211> LENGTH: 108
<212> TYPE: PRT
<213> ORGANISM: Artificial Sequence
<220> FEATURE:
<223> OTHER INFORMATION: Anti-CCR8-2-4 Light Chain, Anti-CCR8-2-5 Light
      Chain

<400> SEQUENCE: 23

```
Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr
            100                 105
```

<210> SEQ ID NO 24

<400> SEQUENCE: 24

000

<210> SEQ ID NO 25
<211> LENGTH: 5
<212> TYPE: PRT
<213> ORGANISM: Artificial Sequence
<220> FEATURE:
<223> OTHER INFORMATION: Synthetic sequence

```
<400> SEQUENCE: 25

Asp Tyr Ala Met His
1               5

<210> SEQ ID NO 26
<211> LENGTH: 17
<212> TYPE: PRT
<213> ORGANISM: Artificial Sequence
<220> FEATURE:
<223> OTHER INFORMATION: Synthetic sequence

<400> SEQUENCE: 26

Gly Ile Ser Trp Asn Ser Gly Ser Ile Gly Tyr Ala Asp Ser Val Lys
1               5                   10                  15

Gly

<210> SEQ ID NO 27
<211> LENGTH: 13
<212> TYPE: PRT
<213> ORGANISM: Artificial Sequence
<220> FEATURE:
<223> OTHER INFORMATION: Synthetic sequence

<400> SEQUENCE: 27

Gly Arg Lys Ser Tyr Arg Val Ser Leu Arg Phe Asp Tyr
1               5                   10

<210> SEQ ID NO 28
<211> LENGTH: 13
<212> TYPE: PRT
<213> ORGANISM: Artificial Sequence
<220> FEATURE:
<223> OTHER INFORMATION: Synthetic sequence

<400> SEQUENCE: 28

Ser Gly Ser Ser Ser Asn Ile Gly Asn Asn Tyr Val Ser
1               5                   10

<210> SEQ ID NO 29
<211> LENGTH: 7
<212> TYPE: PRT
<213> ORGANISM: Artificial Sequence
<220> FEATURE:
<223> OTHER INFORMATION: Synthetic sequence

<400> SEQUENCE: 29

Asp Asn Asn Lys Arg Pro Ser
1               5

<210> SEQ ID NO 30
<211> LENGTH: 11
<212> TYPE: PRT
<213> ORGANISM: Artificial Sequence
<220> FEATURE:
<223> OTHER INFORMATION: Synthetic sequence

<400> SEQUENCE: 30

Gly Thr Trp Asp Ser Ser Leu Ser Ala Trp Val
1               5                   10

<210> SEQ ID NO 31
<211> LENGTH: 122
<212> TYPE: PRT
<213> ORGANISM: Artificial Sequence
<220> FEATURE:
```

<223> OTHER INFORMATION: Anti-CCR8-2-7 Heavy Chain

<400> SEQUENCE: 31

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Arg Asp Ser Tyr Arg Lys Ser Leu Arg Phe Asp Tyr Trp
            100                 105                 110

Gly Gln Gly Thr Leu Val Thr Val Ser Ser
        115                 120

<210> SEQ ID NO 32

<400> SEQUENCE: 32

000

<210> SEQ ID NO 33
<211> LENGTH: 110
<212> TYPE: PRT
<213> ORGANISM: Artificial Sequence
<220> FEATURE:
<223> OTHER INFORMATION: Anti-CCR8-2-7 Light Chain

<400> SEQUENCE: 33

Gln Ser Val Leu Thr Gln Pro Pro Ser Val Ser Gly Ala Pro Gly Gln
1               5                   10                  15

Arg Val Thr Ile Ser Cys Thr Gly Ser Gly Ser Asn Ile Gly Asn Asn
            20                  25                  30

Tyr Val Ser Trp Tyr Gln Gln Leu Pro Gly Thr Ala Pro Lys Met Leu
        35                  40                  45

Ile Tyr Asp Asn Thr Arg Arg Pro Ser Gly Ile Pro Asp Arg Phe Ser
    50                  55                  60

Gly Ser Lys Ser Asp Thr Ser Ala Thr Leu Gly Ile Thr Gly Leu Gln
65                  70                  75                  80

Thr Gly Asp Glu Ala Asp Tyr Tyr Cys Gly Ala Trp Asp Ser Ser Leu
                85                  90                  95

Arg Met Trp Val Phe Gly Gly Gly Thr Lys Leu Thr Val Leu
            100                 105                 110

<210> SEQ ID NO 34

<400> SEQUENCE: 34

000

<210> SEQ ID NO 35
<211> LENGTH: 5
<212> TYPE: PRT
<213> ORGANISM: Artificial Sequence
<220> FEATURE:

<223> OTHER INFORMATION: Synthetic sequence

<400> SEQUENCE: 35

Asp Tyr Ala Met His
1               5

<210> SEQ ID NO 36
<211> LENGTH: 17
<212> TYPE: PRT
<213> ORGANISM: Artificial Sequence
<220> FEATURE:
<223> OTHER INFORMATION: Synthetic sequence

<400> SEQUENCE: 36

Gly Ile Ser Trp Asn Ser Gly Ser Ile Gly Tyr Ala Asp Ser Val Lys
1               5                   10                  15

Gly

<210> SEQ ID NO 37
<211> LENGTH: 13
<212> TYPE: PRT
<213> ORGANISM: Artificial Sequence
<220> FEATURE:
<223> OTHER INFORMATION: Synthetic sequence

<400> SEQUENCE: 37

Gly Arg Asp Ser Tyr Arg Lys Ser Leu Arg Phe Asp Tyr
1               5                   10

<210> SEQ ID NO 38
<211> LENGTH: 13
<212> TYPE: PRT
<213> ORGANISM: Artificial Sequence
<220> FEATURE:
<223> OTHER INFORMATION: Synthetic sequence

<400> SEQUENCE: 38

Thr Gly Ser Gly Ser Asn Ile Gly Asn Asn Tyr Val Ser
1               5                   10

<210> SEQ ID NO 39
<211> LENGTH: 7
<212> TYPE: PRT
<213> ORGANISM: Artificial Sequence
<220> FEATURE:
<223> OTHER INFORMATION: Synthetic sequence

<400> SEQUENCE: 39

Asp Asn Thr Arg Arg Pro Ser
1               5

<210> SEQ ID NO 40
<211> LENGTH: 11
<212> TYPE: PRT
<213> ORGANISM: Artificial Sequence
<220> FEATURE:
<223> OTHER INFORMATION: Synthetic sequence

<400> SEQUENCE: 40

Gly Ala Trp Asp Ser Ser Leu Arg Met Trp Val
1               5                   10

<210> SEQ ID NO 41
<211> LENGTH: 119
<212> TYPE: PRT
<213> ORGANISM: Artificial Sequence
<220> FEATURE:
<223> OTHER INFORMATION: Anti-CCR8-1 Heavy Chain

<400> SEQUENCE: 41

Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ala Val Arg Asn Arg Phe Arg Phe Asp Tyr Trp Gly Gln Gly
            100                 105                 110

Thr Leu Val Thr Val Ser Ser
            115

<210> SEQ ID NO 42

<400> SEQUENCE: 42

000

<210> SEQ ID NO 43
<211> LENGTH: 111
<212> TYPE: PRT
<213> ORGANISM: Artificial Sequence
<220> FEATURE:
<223> OTHER INFORMATION: Anti-CCR8-1 Light Chain

<400> SEQUENCE: 43

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ala Gly Ser
                85                  90                  95

Ser Thr Phe Val Val Phe Gly Gly Gly Thr Lys Leu Thr Val Leu
            100                 105                 110

<210> SEQ ID NO 44

<400> SEQUENCE: 44

000

<210> SEQ ID NO 45
<211> LENGTH: 5
<212> TYPE: PRT
<213> ORGANISM: Artificial Sequence

```
<220> FEATURE:
<223> OTHER INFORMATION: Synthetic sequence

<400> SEQUENCE: 45

Ser Tyr Tyr Met His
1               5

<210> SEQ ID NO 46
<211> LENGTH: 17
<212> TYPE: PRT
<213> ORGANISM: Artificial Sequence
<220> FEATURE:
<223> OTHER INFORMATION: Synthetic sequence

<400> SEQUENCE: 46

Ile Ile Asn Pro Ser Gly Gly Ser Thr Ser Tyr Ala Gln Lys Phe Gln
1               5                   10                  15

Gly

<210> SEQ ID NO 47
<211> LENGTH: 10
<212> TYPE: PRT
<213> ORGANISM: Artificial Sequence
<220> FEATURE:
<223> OTHER INFORMATION: Synthetic sequence

<400> SEQUENCE: 47

Ala Val Arg Asn Arg Phe Arg Phe Asp Tyr
1               5                   10

<210> SEQ ID NO 48
<211> LENGTH: 14
<212> TYPE: PRT
<213> ORGANISM: Artificial Sequence
<220> FEATURE:
<223> OTHER INFORMATION: Synthetic sequence

<400> SEQUENCE: 48

Thr Gly Thr Ser Ser Asp Val Gly Ser Tyr Asn Leu Val Ser
1               5                   10

<210> SEQ ID NO 49
<211> LENGTH: 7
<212> TYPE: PRT
<213> ORGANISM: Artificial Sequence
<220> FEATURE:
<223> OTHER INFORMATION: Synthetic sequence

<400> SEQUENCE: 49

Glu Val Ser Lys Arg Pro Ser
1               5

<210> SEQ ID NO 50
<211> LENGTH: 11
<212> TYPE: PRT
<213> ORGANISM: Artificial Sequence
<220> FEATURE:
<223> OTHER INFORMATION: Synthetic sequence

<400> SEQUENCE: 50

Ser Ser Tyr Ala Gly Ser Ser Thr Phe Val Val
1               5                   10

<210> SEQ ID NO 51
<211> LENGTH: 118
<212> TYPE: PRT
```

<213> ORGANISM: Artificial Sequence
<220> FEATURE:
<223> OTHER INFORMATION: Anti-CCR8-2-1 Heavy Chain

<400> SEQUENCE: 51

```
Glu Val Gln Leu Leu Glu Ser Gly Gly Gly Leu Val Gln Pro Gly Gly
1               5                   10                  15
Ser Leu Arg Leu Ser Cys Ala Ala Arg Gly Phe Ile Phe Ser Gly Tyr
            20                  25                  30
Thr Met Leu Trp Val Arg Gln Ala Pro Gly Lys Gly Leu Glu Trp Val
        35                  40                  45
Ser Ala Ile Thr Ala Ser Gly Gly Arg Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Arg Phe Ala Arg Gly Trp Phe Asp Pro Trp Gly Gln Gly Thr
            100                 105                 110
Leu Val Thr Val Ser Ser
            115
```

<210> SEQ ID NO 52

<400> SEQUENCE: 52

000

<210> SEQ ID NO 53
<211> LENGTH: 108
<212> TYPE: PRT
<213> ORGANISM: Artificial Sequence
<220> FEATURE:
<223> OTHER INFORMATION: Anti-CCR8-2-1 Light Chain

<400> SEQUENCE: 53

```
Gln Ser Val Leu Thr Gln Pro Pro Ser Val Ser Ala Ala Pro Gly Gln
1               5                   10                  15
Lys Val Thr Ile Ser Cys Ser Gly Ser Ser Ser Asn Ile Gly Asn Asn
            20                  25                  30
Tyr Val Ser Trp Tyr Gln Gln Leu Pro Gly Thr Ala Pro Lys Leu Leu
        35                  40                  45
Ile Tyr Asp Asn Asn Lys Arg Pro Ser Gly Ile Pro Asp Arg Phe Ser
    50                  55                  60
Gly Ser Lys Ser Gly Thr Ser Ala Thr Leu Gly Ile Thr Gly Leu Gln
65                  70                  75                  80
Thr Gly Asp Glu Ala Asp Tyr Tyr Cys Gly Thr Trp Asp Ser Ser Leu
                85                  90                  95
Ser Ala Trp Val Phe Gly Gly Gly Thr Lys Leu Thr
            100                 105
```

<210> SEQ ID NO 54

<400> SEQUENCE: 54

000

<210> SEQ ID NO 55
<211> LENGTH: 5
<212> TYPE: PRT

```
<213> ORGANISM: Artificial Sequence
<220> FEATURE:
<223> OTHER INFORMATION: Synthetic sequence

<400> SEQUENCE: 55

Gly Tyr Thr Met Leu
1               5

<210> SEQ ID NO 56
<211> LENGTH: 17
<212> TYPE: PRT
<213> ORGANISM: Artificial Sequence
<220> FEATURE:
<223> OTHER INFORMATION: Synthetic sequence

<400> SEQUENCE: 56

Ala Ile Thr Ala Ser Gly Gly Arg Thr Tyr Tyr Ala Asp Ser Val Lys
1               5                   10                  15

Gly

<210> SEQ ID NO 57
<211> LENGTH: 9
<212> TYPE: PRT
<213> ORGANISM: Artificial Sequence
<220> FEATURE:
<223> OTHER INFORMATION: Synthetic sequence

<400> SEQUENCE: 57

Arg Phe Ala Arg Gly Trp Phe Asp Pro
1               5

<210> SEQ ID NO 58
<211> LENGTH: 13
<212> TYPE: PRT
<213> ORGANISM: Artificial Sequence
<220> FEATURE:
<223> OTHER INFORMATION: Synthetic sequence

<400> SEQUENCE: 58

Ser Gly Ser Ser Ser Asn Ile Gly Asn Asn Tyr Val Ser
1               5                   10

<210> SEQ ID NO 59
<211> LENGTH: 7
<212> TYPE: PRT
<213> ORGANISM: Artificial Sequence
<220> FEATURE:
<223> OTHER INFORMATION: Synthetic sequence

<400> SEQUENCE: 59

Asp Asn Asn Lys Arg Pro Ser
1               5

<210> SEQ ID NO 60
<211> LENGTH: 11
<212> TYPE: PRT
<213> ORGANISM: Artificial Sequence
<220> FEATURE:
<223> OTHER INFORMATION: Synthetic sequence

<400> SEQUENCE: 60

Gly Thr Trp Asp Ser Ser Leu Ser Ala Trp Val
1               5                   10

<210> SEQ ID NO 61
<211> LENGTH: 122
```

```
<212> TYPE: PRT
<213> ORGANISM: Artificial Sequence
<220> FEATURE:
<223> OTHER INFORMATION: Anti-CCR8-2-9 Heavy Chain

<400> SEQUENCE: 61

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Arg Lys Ser Tyr Arg Asp Ser Leu Arg Phe Asp Tyr Trp
            100                 105                 110

Gly Gln Gly Thr Leu Val Thr Val Ser Ser
        115                 120

<210> SEQ ID NO 62

<400> SEQUENCE: 62

000

<210> SEQ ID NO 63
<211> LENGTH: 110
<212> TYPE: PRT
<213> ORGANISM: Artificial Sequence
<220> FEATURE:
<223> OTHER INFORMATION: Anti-CCR8-2-9 Light Chain

<400> SEQUENCE: 63

Gln Ser Val Leu Thr Gln Pro Pro Ser Val Ser Gly Ala Pro Gly Gln
1               5                   10                  15

Arg Val Thr Ile Ser Cys Thr Gly Ser Gly Ser Asn Ile Gly Asn Asn
            20                  25                  30

Tyr Val Ser Trp Tyr Gln Gln Leu Pro Gly Thr Ala Pro Lys Met Leu
        35                  40                  45

Ile Tyr Asp Asn Thr Arg Arg Pro Ser Gly Ile Pro Asp Arg Phe Ser
    50                  55                  60

Gly Ser Lys Ser Asp Thr Ser Ala Thr Leu Gly Ile Thr Gly Leu Gln
65                  70                  75                  80

Thr Gly Asp Glu Ala Asp Tyr Tyr Cys Gly Ala Trp Asp Ser Ser Leu
                85                  90                  95

Arg Met Trp Val Phe Gly Gly Gly Thr Lys Leu Thr Val Leu
            100                 105                 110

<210> SEQ ID NO 64

<400> SEQUENCE: 64

000

<210> SEQ ID NO 65
<211> LENGTH: 5
```

```
<212> TYPE: PRT
<213> ORGANISM: Artificial Sequence
<220> FEATURE:
<223> OTHER INFORMATION: Synthetic sequence

<400> SEQUENCE: 65

Asp Tyr Ala Met His
1               5

<210> SEQ ID NO 66
<211> LENGTH: 17
<212> TYPE: PRT
<213> ORGANISM: Artificial Sequence
<220> FEATURE:
<223> OTHER INFORMATION: Synthetic sequence

<400> SEQUENCE: 66

Gly Ile Ser Trp Asn Ser Gly Ser Ile Gly Tyr Ala Asp Ser Val Lys
1               5                   10                  15

Gly

<210> SEQ ID NO 67
<211> LENGTH: 13
<212> TYPE: PRT
<213> ORGANISM: Artificial Sequence
<220> FEATURE:
<223> OTHER INFORMATION: Synthetic sequence

<400> SEQUENCE: 67

Gly Arg Lys Ser Tyr Arg Asp Ser Leu Arg Phe Asp Tyr
1               5                   10

<210> SEQ ID NO 68
<211> LENGTH: 13
<212> TYPE: PRT
<213> ORGANISM: Artificial Sequence
<220> FEATURE:
<223> OTHER INFORMATION: Synthetic sequence

<400> SEQUENCE: 68

Thr Gly Ser Gly Ser Asn Ile Gly Asn Asn Tyr Val Ser
1               5                   10

<210> SEQ ID NO 69
<211> LENGTH: 7
<212> TYPE: PRT
<213> ORGANISM: Artificial Sequence
<220> FEATURE:
<223> OTHER INFORMATION: Synthetic sequence

<400> SEQUENCE: 69

Asp Asn Thr Arg Arg Pro Ser
1               5

<210> SEQ ID NO 70
<211> LENGTH: 11
<212> TYPE: PRT
<213> ORGANISM: Artificial Sequence
<220> FEATURE:
<223> OTHER INFORMATION: Synthetic sequence

<400> SEQUENCE: 70

Gly Ala Trp Asp Ser Ser Leu Arg Met Trp Val
1               5                   10

<210> SEQ ID NO 71
```

```
<211> LENGTH: 122
<212> TYPE: PRT
<213> ORGANISM: Artificial Sequence
<220> FEATURE:
<223> OTHER INFORMATION: Anti-CCR8-2-8 Heavy Chain

<400> SEQUENCE: 71
```

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Arg Arg Ser Tyr Arg Asp Ser Leu Arg Phe Asp Tyr Trp
            100                 105                 110

Gly Gln Gly Thr Leu Val Thr Val Ser Ser
        115                 120

```
<210> SEQ ID NO 72

<400> SEQUENCE: 72
```

000

```
<210> SEQ ID NO 73
<211> LENGTH: 110
<212> TYPE: PRT
<213> ORGANISM: Artificial Sequence
<220> FEATURE:
<223> OTHER INFORMATION: Anti-CCR8-2-8 Light Chain

<400> SEQUENCE: 73
```

Gln Ser Val Leu Thr Gln Pro Pro Ser Val Ser Gly Ala Pro Gly Gln
1               5                   10                  15

Arg Val Thr Ile Ser Cys Thr Gly Ser Gly Ser Asn Ile Gly Asn Asn
            20                  25                  30

Tyr Val Ser Trp Tyr Gln Gln Leu Pro Gly Thr Ala Pro Lys Met Leu
        35                  40                  45

Ile Tyr Asp Asn Thr Arg Arg Pro Ser Gly Ile Pro Asp Arg Phe Ser
    50                  55                  60

Gly Ser Lys Ser Asp Thr Ser Ala Thr Leu Gly Ile Thr Gly Leu Gln
65                  70                  75                  80

Thr Gly Asp Glu Ala Asp Tyr Tyr Cys Gly Ala Trp Asp Ser Ser Leu
                85                  90                  95

Arg Met Trp Val Phe Gly Gly Gly Thr Lys Leu Thr Val Leu
            100                 105                 110

```
<210> SEQ ID NO 74

<400> SEQUENCE: 74
```

000

```
<210> SEQ ID NO 75
```

```
<211> LENGTH: 5
<212> TYPE: PRT
<213> ORGANISM: Artificial Sequence
<220> FEATURE:
<223> OTHER INFORMATION: Synthetic sequence

<400> SEQUENCE: 75

Asp Tyr Ala Met His
1               5

<210> SEQ ID NO 76
<211> LENGTH: 17
<212> TYPE: PRT
<213> ORGANISM: Artificial Sequence
<220> FEATURE:
<223> OTHER INFORMATION: Synthetic sequence

<400> SEQUENCE: 76

Gly Ile Ser Trp Asn Ser Gly Ser Ile Gly Tyr Ala Asp Ser Val Lys
1               5                   10                  15

Gly

<210> SEQ ID NO 77
<211> LENGTH: 13
<212> TYPE: PRT
<213> ORGANISM: Artificial Sequence
<220> FEATURE:
<223> OTHER INFORMATION: Synthetic sequence

<400> SEQUENCE: 77

Gly Arg Arg Ser Tyr Arg Asp Ser Leu Arg Phe Asp Tyr
1               5                   10

<210> SEQ ID NO 78
<211> LENGTH: 13
<212> TYPE: PRT
<213> ORGANISM: Artificial Sequence
<220> FEATURE:
<223> OTHER INFORMATION: Synthetic sequence

<400> SEQUENCE: 78

Thr Gly Ser Gly Ser Asn Ile Gly Asn Asn Tyr Val Ser
1               5                   10

<210> SEQ ID NO 79
<211> LENGTH: 7
<212> TYPE: PRT
<213> ORGANISM: Artificial Sequence
<220> FEATURE:
<223> OTHER INFORMATION: Synthetic sequence

<400> SEQUENCE: 79

Asp Asn Thr Arg Arg Pro Ser
1               5

<210> SEQ ID NO 80
<211> LENGTH: 11
<212> TYPE: PRT
<213> ORGANISM: Artificial Sequence
<220> FEATURE:
<223> OTHER INFORMATION: Synthetic sequence

<400> SEQUENCE: 80

Gly Ala Trp Asp Ser Ser Leu Arg Met Trp Val
1               5                   10
```

-continued

```
<210> SEQ ID NO 81
<211> LENGTH: 122
<212> TYPE: PRT
<213> ORGANISM: Artificial Sequence
<220> FEATURE:
<223> OTHER INFORMATION: Anti-CCR8-2-10 Heavy Chain

<400> SEQUENCE: 81
```

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Arg Lys Ser Tyr Arg Asp Ser Leu Arg Phe Asp Tyr Trp
            100                 105                 110

Gly Gln Gly Thr Leu Val Thr Val Ser Ser
        115                 120

```
<210> SEQ ID NO 82

<400> SEQUENCE: 82

000

<210> SEQ ID NO 83
<211> LENGTH: 110
<212> TYPE: PRT
<213> ORGANISM: Artificial Sequence
<220> FEATURE:
<223> OTHER INFORMATION: Anti-CCR8-2-10 Light Chain

<400> SEQUENCE: 83
```

Gln Ser Val Leu Thr Gln Pro Pro Ser Val Ser Ala Ala Pro Gly Gln
1               5                   10                  15

Lys Val Thr Ile Ser Cys Ser Gly Thr Ser Ser Asn Ile Gly Lys Asn
            20                  25                  30

Phe Val Ser Trp Tyr Gln Gln Leu Pro Gly Thr Ala Pro Lys Leu Leu
        35                  40                  45

Ile Tyr Asp Asp Asn Lys Arg Pro Ser Gly Ile Pro Asp Arg Phe Ser
    50                  55                  60

Gly Ser Lys Ser Ala Thr Ser Ala Thr Leu Gly Ile Thr Gly Leu Gln
65                  70                  75                  80

Thr Gly Asp Gly Ala Asp Tyr Tyr Cys Gly Thr Trp Asp Ser Ser Leu
                85                  90                  95

Ser Ala Trp Val Phe Gly Gly Gly Thr Lys Leu Thr Val Leu
            100                 105                 110

```
<210> SEQ ID NO 84

<400> SEQUENCE: 84

000
```

```
<210> SEQ ID NO 85
<211> LENGTH: 5
<212> TYPE: PRT
<213> ORGANISM: Artificial Sequence
<220> FEATURE:
<223> OTHER INFORMATION: Synthetic sequence

<400> SEQUENCE: 85

Asp Tyr Ala Met His
1               5

<210> SEQ ID NO 86
<211> LENGTH: 17
<212> TYPE: PRT
<213> ORGANISM: Artificial Sequence
<220> FEATURE:
<223> OTHER INFORMATION: Synthetic sequence

<400> SEQUENCE: 86

Gly Ile Ser Trp Asn Ser Gly Ser Ile Gly Tyr Ala Asp Ser Val Lys
1               5                   10                  15

Gly

<210> SEQ ID NO 87
<211> LENGTH: 13
<212> TYPE: PRT
<213> ORGANISM: Artificial Sequence
<220> FEATURE:
<223> OTHER INFORMATION: Synthetic sequence

<400> SEQUENCE: 87

Gly Arg Lys Ser Tyr Arg Asp Ser Leu Arg Phe Asp Tyr
1               5                   10

<210> SEQ ID NO 88
<211> LENGTH: 13
<212> TYPE: PRT
<213> ORGANISM: Artificial Sequence
<220> FEATURE:
<223> OTHER INFORMATION: Synthetic sequence

<400> SEQUENCE: 88

Ser Gly Thr Ser Ser Asn Ile Gly Lys Asn Phe Val Ser
1               5                   10

<210> SEQ ID NO 89
<211> LENGTH: 7
<212> TYPE: PRT
<213> ORGANISM: Artificial Sequence
<220> FEATURE:
<223> OTHER INFORMATION: Synthetic sequence

<400> SEQUENCE: 89

Asp Asp Asn Lys Arg Pro Ser
1               5

<210> SEQ ID NO 90
<211> LENGTH: 11
<212> TYPE: PRT
<213> ORGANISM: Artificial Sequence
<220> FEATURE:
<223> OTHER INFORMATION: Synthetic sequence

<400> SEQUENCE: 90

Gly Thr Trp Asp Ser Ser Leu Ser Ala Trp Val
1               5                   10
```

<210> SEQ ID NO 91
<211> LENGTH: 122
<212> TYPE: PRT
<213> ORGANISM: Artificial Sequence
<220> FEATURE:
<223> OTHER INFORMATION: Anti-CCR8-2-3 Heavy Chain

<400> SEQUENCE: 91

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Arg Lys Ser Tyr Arg Asp Ser Leu Arg Phe Asp Tyr Trp
            100                 105                 110

Gly Gln Gly Thr Leu Val Thr Val Ser Ser
        115                 120

<210> SEQ ID NO 92

<400> SEQUENCE: 92

000

<210> SEQ ID NO 93
<211> LENGTH: 108
<212> TYPE: PRT
<213> ORGANISM: Artificial Sequence
<220> FEATURE:
<223> OTHER INFORMATION: Anti-CCR8-2-3 Light Chain

<400> SEQUENCE: 93

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr
            100                 105

<210> SEQ ID NO 94

<400> SEQUENCE: 94

000

<210> SEQ ID NO 95
<211> LENGTH: 5
<212> TYPE: PRT
<213> ORGANISM: Artificial Sequence
<220> FEATURE:
<223> OTHER INFORMATION: Synthetic sequence

<400> SEQUENCE: 95

Asp Tyr Ala Met His
1               5

<210> SEQ ID NO 96
<211> LENGTH: 17
<212> TYPE: PRT
<213> ORGANISM: Artificial Sequence
<220> FEATURE:
<223> OTHER INFORMATION: Synthetic sequence

<400> SEQUENCE: 96

Gly Ile Ser Trp Asn Ser Gly Ser Ile Gly Tyr Ala Asp Ser Val Lys
1               5                   10                  15

Gly

<210> SEQ ID NO 97
<211> LENGTH: 13
<212> TYPE: PRT
<213> ORGANISM: Artificial Sequence
<220> FEATURE:
<223> OTHER INFORMATION: Synthetic sequence

<400> SEQUENCE: 97

Gly Arg Lys Ser Tyr Arg Asp Ser Leu Arg Phe Asp Tyr
1               5                   10

<210> SEQ ID NO 98
<211> LENGTH: 13
<212> TYPE: PRT
<213> ORGANISM: Artificial Sequence
<220> FEATURE:
<223> OTHER INFORMATION: Synthetic sequence

<400> SEQUENCE: 98

Ser Gly Ser Ser Ser Asn Ile Gly Asn Asn Tyr Val Ser
1               5                   10

<210> SEQ ID NO 99
<211> LENGTH: 7
<212> TYPE: PRT
<213> ORGANISM: Artificial Sequence
<220> FEATURE:
<223> OTHER INFORMATION: Synthetic sequence

<400> SEQUENCE: 99

Asp Asn Asn Lys Arg Pro Ser
1               5

<210> SEQ ID NO 100
<211> LENGTH: 11
<212> TYPE: PRT
<213> ORGANISM: Artificial Sequence
<220> FEATURE:
<223> OTHER INFORMATION: Synthetic sequence

<400> SEQUENCE: 100

Gly Thr Trp Asp Ser Ser Leu Ser Ala Trp Val
1               5                   10

<210> SEQ ID NO 101
<211> LENGTH: 116
<212> TYPE: PRT
<213> ORGANISM: Artificial Sequence
<220> FEATURE:
<223> OTHER INFORMATION: Anti-CCR8-1-1 Heavy Chain

<400> SEQUENCE: 101

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Val Gly Asn Gly Phe Arg Phe Asp Tyr Trp Gly Gln Gly
            100                 105                 110

Thr Leu Val Thr
            115
```

<210> SEQ ID NO 102

<400> SEQUENCE: 102

000

<210> SEQ ID NO 103
<211> LENGTH: 111
<212> TYPE: PRT
<213> ORGANISM: Artificial Sequence
<220> FEATURE:
<223> OTHER INFORMATION: Anti-CCR8-1-1 Light Chain

<400> SEQUENCE: 103

```
Gln Ser Ala Leu Thr Gln Pro Pro Ser Val Ser Gly Ser Pro Gly Gln
1               5                   10                  15

Ser Ile Thr Ile Ser Cys Thr Gly Thr Ser Ser Asp Val Gly Thr Tyr
            20                  25                  30

Asn Leu Val Ser Trp Tyr Gln Gln His Pro Gly Asn Ala Pro Lys Leu
        35                  40                  45

Met Ile Tyr Glu Val Thr Lys Arg Pro Ser Gly Val Ser Asn Arg Phe
    50                  55                  60

Ser Gly Ser Lys Ser Gly Asn Thr Ala Thr Leu Thr Ile Ser Gly Leu
65                  70                  75                  80

Gln Ala Glu Asp Glu Ala Asp Tyr His Cys Ser Ser Tyr Ala Gly Ser
                85                  90                  95

Ile Thr His Val Val Phe Gly Gly Gly Thr Lys Leu Thr Val Leu
            100                 105                 110
```

<210> SEQ ID NO 104

<400> SEQUENCE: 104

000

<210> SEQ ID NO 105
<211> LENGTH: 5
<212> TYPE: PRT
<213> ORGANISM: Artificial Sequence
<220> FEATURE:
<223> OTHER INFORMATION: Synthetic sequence

<400> SEQUENCE: 105

Ser Tyr Tyr Met His
1               5

<210> SEQ ID NO 106
<211> LENGTH: 17
<212> TYPE: PRT
<213> ORGANISM: Artificial Sequence
<220> FEATURE:
<223> OTHER INFORMATION: Synthetic sequence

<400> SEQUENCE: 106

Ile Ile Asn Pro Ser Gly Gly Ser Thr Ser Tyr Ala Gln Lys Phe Gln
1               5                   10                  15

Gly

<210> SEQ ID NO 107
<211> LENGTH: 10
<212> TYPE: PRT
<213> ORGANISM: Artificial Sequence
<220> FEATURE:
<223> OTHER INFORMATION: Synthetic sequence

<400> SEQUENCE: 107

Gly Val Gly Asn Gly Phe Arg Phe Asp Tyr
1               5                   10

<210> SEQ ID NO 108
<211> LENGTH: 14
<212> TYPE: PRT
<213> ORGANISM: Artificial Sequence
<220> FEATURE:
<223> OTHER INFORMATION: Synthetic sequence

<400> SEQUENCE: 108

Thr Gly Thr Ser Ser Asp Val Gly Thr Tyr Asn Leu Val Ser
1               5                   10

<210> SEQ ID NO 109
<211> LENGTH: 7
<212> TYPE: PRT
<213> ORGANISM: Artificial Sequence
<220> FEATURE:
<223> OTHER INFORMATION: Synthetic sequence

<400> SEQUENCE: 109

Glu Val Thr Lys Arg Pro Ser
1               5

<210> SEQ ID NO 110
<211> LENGTH: 11
<212> TYPE: PRT
<213> ORGANISM: Artificial Sequence
<220> FEATURE:
<223> OTHER INFORMATION: Synthetic sequence

<400> SEQUENCE: 110

Ser Ser Tyr Ala Gly Ser Ile Thr His Val Val

<210> SEQ ID NO 111
<211> LENGTH: 116
<212> TYPE: PRT
<213> ORGANISM: Artificial Sequence
<220> FEATURE:
<223> OTHER INFORMATION: Anti-CCR8-1-2 Heavy Chain

<400> SEQUENCE: 111

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Tyr Met His Trp Val Arg Gln Ala Pro Gly Gln Gly Leu Glu Trp Met
        35                  40                  45
Gly Ile Ile Asn Pro Ser Gly Gly Ser Thr Ser Tyr Ala Gln Lys Phe
    50                  55                  60
Gln Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Gly Val Gly Asn Gly Phe Arg Phe Asp Tyr Trp Gly Gln Gly
            100                 105                 110
Thr Leu Val Thr
        115

<210> SEQ ID NO 112

<400> SEQUENCE: 112

000

<210> SEQ ID NO 113
<211> LENGTH: 112
<212> TYPE: PRT
<213> ORGANISM: Artificial Sequence
<220> FEATURE:
<223> OTHER INFORMATION: Anti-CCR8-1-2 Light Chain

<400> SEQUENCE: 113

Gln Ser Ala Leu Thr Gln Pro Ala Ser Val Ser Gly Ser Pro Gly Gln
1               5                   10                  15
Ser Ile Thr Ile Ser Cys Thr Gly Thr Ser Gly Asp Val Gly Ser Tyr
            20                  25                  30
Ser Leu Val Ser Trp Tyr Gln His His Pro Ser Arg Ala Pro Lys Leu
        35                  40                  45
Ile Ile Tyr Glu Val Asn Lys Arg Pro Ser Gly Val Ser Asp Arg Phe
    50                  55                  60
Ser Gly Ser Lys Ser Gly Asn Thr Ala Ser Leu Thr Ile Thr Gly Leu
65                  70                  75                  80
Gln Ala Glu Asp Glu Ala His Tyr Phe Cys Ser Ser Tyr Thr Gly Asn
                85                  90                  95
Ile Asn Leu Pro Val Val Phe Gly Gly Gly Thr Lys Leu Thr Val Leu
            100                 105                 110

<210> SEQ ID NO 114

<400> SEQUENCE: 114

-continued

```
000

<210> SEQ ID NO 115
<211> LENGTH: 5
<212> TYPE: PRT
<213> ORGANISM: Artificial Sequence
<220> FEATURE:
<223> OTHER INFORMATION: Synthetic sequence

<400> SEQUENCE: 115

Ser Tyr Tyr Met His
1               5

<210> SEQ ID NO 116
<211> LENGTH: 17
<212> TYPE: PRT
<213> ORGANISM: Artificial Sequence
<220> FEATURE:
<223> OTHER INFORMATION: Synthetic sequence

<400> SEQUENCE: 116

Ile Ile Asn Pro Ser Gly Gly Ser Thr Ser Tyr Ala Gln Lys Phe Gln
1               5                   10                  15

Gly

<210> SEQ ID NO 117
<211> LENGTH: 10
<212> TYPE: PRT
<213> ORGANISM: Artificial Sequence
<220> FEATURE:
<223> OTHER INFORMATION: Synthetic sequence

<400> SEQUENCE: 117

Gly Val Gly Asn Gly Phe Arg Phe Asp Tyr
1               5                   10

<210> SEQ ID NO 118
<211> LENGTH: 14
<212> TYPE: PRT
<213> ORGANISM: Artificial Sequence
<220> FEATURE:
<223> OTHER INFORMATION: Synthetic sequence

<400> SEQUENCE: 118

Thr Gly Thr Ser Gly Asp Val Gly Ser Tyr Ser Leu Val Ser
1               5                   10

<210> SEQ ID NO 119
<211> LENGTH: 7
<212> TYPE: PRT
<213> ORGANISM: Artificial Sequence
<220> FEATURE:
<223> OTHER INFORMATION: Synthetic sequence

<400> SEQUENCE: 119

Glu Val Asn Lys Arg Pro Ser
1               5

<210> SEQ ID NO 120
<211> LENGTH: 12
<212> TYPE: PRT
<213> ORGANISM: Artificial Sequence
<220> FEATURE:
<223> OTHER INFORMATION: Synthetic sequence

<400> SEQUENCE: 120
```

Ser Ser Tyr Thr Gly Asn Ile Asn Leu Pro Val Val
1               5                   10

<210> SEQ ID NO 121
<211> LENGTH: 116
<212> TYPE: PRT
<213> ORGANISM: Artificial Sequence
<220> FEATURE:
<223> OTHER INFORMATION: Anti-CCR8-1-3 Heavy Chain

<400> SEQUENCE: 121

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Val Gly Asn Gly Phe Arg Phe Asp Tyr Trp Gly Gln Gly
                100                 105                 110

Thr Leu Val Thr
            115

<210> SEQ ID NO 122

<400> SEQUENCE: 122

000

<210> SEQ ID NO 123
<211> LENGTH: 111
<212> TYPE: PRT
<213> ORGANISM: Artificial Sequence
<220> FEATURE:
<223> OTHER INFORMATION: Anti-CCR8-1-3 Light Chain

<400> SEQUENCE: 123

Gln Ser Ala Leu Thr Gln Pro Pro Ser Val Ser Gly Ser Pro Gly Gln
1               5                   10                  15

Ser Ile Thr Ile Ser Cys Ser Gly Thr Ser Ser Asp Val Gly Ile Tyr
                20                  25                  30

Asn Leu Val Ser Trp Tyr Gln Gln His Pro Gly Lys Ala Pro Lys Leu
            35                  40                  45

Ile Ile Tyr Glu Val Ile Lys Arg Pro Ser Gly Ile Ser Asn Arg Phe
        50                  55                  60

Ser Gly Phe Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ala Gly Pro
                85                  90                  95

Val Thr Tyr Val Val Phe Gly Gly Gly Thr Lys Leu Thr Val Leu
                100                 105                 110

<210> SEQ ID NO 124

<400> SEQUENCE: 124

000

<210> SEQ ID NO 125
<211> LENGTH: 5
<212> TYPE: PRT
<213> ORGANISM: Artificial Sequence
<220> FEATURE:
<223> OTHER INFORMATION: Synthetic sequence

<400> SEQUENCE: 125

Ser Tyr Tyr Met His
1               5

<210> SEQ ID NO 126
<211> LENGTH: 17
<212> TYPE: PRT
<213> ORGANISM: Artificial Sequence
<220> FEATURE:
<223> OTHER INFORMATION: Synthetic sequence

<400> SEQUENCE: 126

Ile Ile Asn Pro Ser Gly Gly Ser Thr Ser Tyr Ala Gln Lys Phe Gln
1               5                   10                  15

Gly

<210> SEQ ID NO 127
<211> LENGTH: 10
<212> TYPE: PRT
<213> ORGANISM: Artificial Sequence
<220> FEATURE:
<223> OTHER INFORMATION: Synthetic sequence

<400> SEQUENCE: 127

Gly Val Gly Asn Gly Phe Arg Phe Asp Tyr
1               5                   10

<210> SEQ ID NO 128
<211> LENGTH: 14
<212> TYPE: PRT
<213> ORGANISM: Artificial Sequence
<220> FEATURE:
<223> OTHER INFORMATION: Synthetic sequence

<400> SEQUENCE: 128

Ser Gly Thr Ser Ser Asp Val Gly Ile Tyr Asn Leu Val Ser
1               5                   10

<210> SEQ ID NO 129
<211> LENGTH: 7
<212> TYPE: PRT
<213> ORGANISM: Artificial Sequence
<220> FEATURE:
<223> OTHER INFORMATION: Synthetic sequence

<400> SEQUENCE: 129

Glu Val Ile Lys Arg Pro Ser
1               5

<210> SEQ ID NO 130
<211> LENGTH: 11
<212> TYPE: PRT
<213> ORGANISM: Artificial Sequence
<220> FEATURE:
<223> OTHER INFORMATION: Synthetic sequence

<400> SEQUENCE: 130

Ser Ser Tyr Ala Gly Pro Val Thr Tyr Val Val
1               5                   10

<210> SEQ ID NO 131
<211> LENGTH: 116
<212> TYPE: PRT
<213> ORGANISM: Artificial Sequence
<220> FEATURE:
<223> OTHER INFORMATION: Anti-CCR8-1-4 Heavy Chain

<400> SEQUENCE: 131

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Val Gly Asn Gly Phe Arg Phe Asp Tyr Trp Gly Gln Gly
            100                 105                 110

Thr Leu Val Thr
            115

<210> SEQ ID NO 132

<400> SEQUENCE: 132

000

<210> SEQ ID NO 133
<211> LENGTH: 111
<212> TYPE: PRT
<213> ORGANISM: Artificial Sequence
<220> FEATURE:
<223> OTHER INFORMATION: Anti-CCR8-1-4 Light Chain

<400> SEQUENCE: 133

Gln Ser Ala Leu Thr Gln Pro Ala Ser Val Ser Gly Ser Pro Gly Gln
1               5                   10                  15

Ser Ile Thr Ile Ser Cys Ser Gly Thr Ser Ser Asn Ile Gly Lys Tyr
                20                  25                  30

Asn Leu Val Ser Trp Tyr Gln Gln His Pro Gly Glu Ala Pro Thr Leu
            35                  40                  45

Leu Ile Tyr Glu Ala Thr Lys Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Ile Cys Ser Ser Tyr Ala Gly Ser
                85                  90                  95

Arg Val Phe Val Val Phe Gly Gly Gly Thr Lys Leu Thr Val Leu
            100                 105                 110

<210> SEQ ID NO 134

```
<400> SEQUENCE: 134

000

<210> SEQ ID NO 135
<211> LENGTH: 5
<212> TYPE: PRT
<213> ORGANISM: Artificial Sequence
<220> FEATURE:
<223> OTHER INFORMATION: Synthetic sequence

<400> SEQUENCE: 135

Ser Tyr Tyr Met His
1               5

<210> SEQ ID NO 136
<211> LENGTH: 17
<212> TYPE: PRT
<213> ORGANISM: Artificial Sequence
<220> FEATURE:
<223> OTHER INFORMATION: Synthetic sequence

<400> SEQUENCE: 136

Ile Ile Asn Pro Ser Gly Gly Ser Thr Ser Tyr Ala Gln Lys Phe Gln
1               5                   10                  15

Gly

<210> SEQ ID NO 137
<211> LENGTH: 10
<212> TYPE: PRT
<213> ORGANISM: Artificial Sequence
<220> FEATURE:
<223> OTHER INFORMATION: Synthetic sequence

<400> SEQUENCE: 137

Gly Val Gly Asn Gly Phe Arg Phe Asp Tyr
1               5                   10

<210> SEQ ID NO 138
<211> LENGTH: 14
<212> TYPE: PRT
<213> ORGANISM: Artificial Sequence
<220> FEATURE:
<223> OTHER INFORMATION: Synthetic sequence

<400> SEQUENCE: 138

Ser Gly Thr Ser Ser Asn Ile Gly Lys Tyr Asn Leu Val Ser
1               5                   10

<210> SEQ ID NO 139
<211> LENGTH: 7
<212> TYPE: PRT
<213> ORGANISM: Artificial Sequence
<220> FEATURE:
<223> OTHER INFORMATION: Synthetic sequence

<400> SEQUENCE: 139

Glu Ala Thr Lys Arg Pro Ser
1               5

<210> SEQ ID NO 140
<211> LENGTH: 11
<212> TYPE: PRT
<213> ORGANISM: Artificial Sequence
<220> FEATURE:
<223> OTHER INFORMATION: Synthetic sequence
```

```
<400> SEQUENCE: 140

Ser Ser Tyr Ala Gly Ser Arg Val Phe Val Val
1               5                   10

<210> SEQ ID NO 141
<211> LENGTH: 116
<212> TYPE: PRT
<213> ORGANISM: Artificial Sequence
<220> FEATURE:
<223> OTHER INFORMATION: Anti-CCR8-1-5 Heavy Chain

<400> SEQUENCE: 141

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Val Gly Asn Gly Phe Arg Phe Asp Tyr Trp Gly Gln Gly
            100                 105                 110

Thr Leu Val Thr
        115

<210> SEQ ID NO 142
<211> LENGTH: 6
<212> TYPE: PRT
<213> ORGANISM: Artificial Sequence
<220> FEATURE:
<223> OTHER INFORMATION: Synthetic sequence

<400> SEQUENCE: 142

His His His His His His
1               5

<210> SEQ ID NO 143
<211> LENGTH: 111
<212> TYPE: PRT
<213> ORGANISM: Artificial Sequence
<220> FEATURE:
<223> OTHER INFORMATION: Anti-CCR8-1-5 Light Chain

<400> SEQUENCE: 143

Gln Ser Ala Leu Thr Gln Pro Pro Ser Val Ser Gly Ser Pro Gly Gln
1               5                   10                  15

Ser Ile Thr Ile Ser Cys Ser Gly Thr Ser Ser Asp Val Gly Ser Tyr
            20                  25                  30

Asn Leu Val Ser Trp Tyr Gln Gln Glu Pro Gly Lys Ala Pro Lys Leu
        35                  40                  45

Ile Ile Tyr Glu Val Asn Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr His Cys Ser Ser Tyr Ala Gly Ser
                85                  90                  95
```

Ser Thr Tyr Val Val Phe Gly Gly Thr Lys Leu Thr Val Leu
            100                 105                 110

<210> SEQ ID NO 144

<400> SEQUENCE: 144

000

<210> SEQ ID NO 145
<211> LENGTH: 5
<212> TYPE: PRT
<213> ORGANISM: Artificial Sequence
<220> FEATURE:
<223> OTHER INFORMATION: Synthetic sequence

<400> SEQUENCE: 145

Ser Tyr Tyr Met His
1               5

<210> SEQ ID NO 146
<211> LENGTH: 17
<212> TYPE: PRT
<213> ORGANISM: Artificial Sequence
<220> FEATURE:
<223> OTHER INFORMATION: Synthetic sequence

<400> SEQUENCE: 146

Ile Ile Asn Pro Ser Gly Gly Ser Thr Ser Tyr Ala Gln Lys Phe Gln
1               5                   10                  15

Gly

<210> SEQ ID NO 147
<211> LENGTH: 10
<212> TYPE: PRT
<213> ORGANISM: Artificial Sequence
<220> FEATURE:
<223> OTHER INFORMATION: Synthetic sequence

<400> SEQUENCE: 147

Gly Val Gly Asn Gly Phe Arg Phe Asp Tyr
1               5                   10

<210> SEQ ID NO 148
<211> LENGTH: 14
<212> TYPE: PRT
<213> ORGANISM: Artificial Sequence
<220> FEATURE:
<223> OTHER INFORMATION: Synthetic sequence

<400> SEQUENCE: 148

Ser Gly Thr Ser Ser Asp Val Gly Ser Tyr Asn Leu Val Ser
1               5                   10

<210> SEQ ID NO 149
<211> LENGTH: 7
<212> TYPE: PRT
<213> ORGANISM: Artificial Sequence
<220> FEATURE:
<223> OTHER INFORMATION: Synthetic sequence

<400> SEQUENCE: 149

Glu Val Asn Lys Arg Pro Ser
1               5

```
<210> SEQ ID NO 150
<211> LENGTH: 11
<212> TYPE: PRT
<213> ORGANISM: Artificial Sequence
<220> FEATURE:
<223> OTHER INFORMATION: Synthetic sequence

<400> SEQUENCE: 150

Ser Ser Tyr Ala Gly Ser Ser Thr Tyr Val Val
1               5                   10

<210> SEQ ID NO 151
<211> LENGTH: 119
<212> TYPE: PRT
<213> ORGANISM: Artificial Sequence
<220> FEATURE:
<223> OTHER INFORMATION: Anti-CCR8-2-6 Heavy Chain

<400> SEQUENCE: 151

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
        50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Arg Val Ser Tyr Arg Glu Ser Leu Arg Phe Asp Tyr Trp
            100                 105                 110

Gly Gln Gly Thr Leu Val Thr
        115

<210> SEQ ID NO 152

<400> SEQUENCE: 152

000

<210> SEQ ID NO 153
<211> LENGTH: 108
<212> TYPE: PRT
<213> ORGANISM: Artificial Sequence
<220> FEATURE:
<223> OTHER INFORMATION: Anti-CCR8-2-6 Light Chain

<400> SEQUENCE: 153

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
```

```
                    85                  90                  95
Ser Ala Trp Val Phe Gly Gly Gly Thr Lys Leu Thr
            100                 105

<210> SEQ ID NO 154

<400> SEQUENCE: 154

000

<210> SEQ ID NO 155
<211> LENGTH: 5
<212> TYPE: PRT
<213> ORGANISM: Artificial Sequence
<220> FEATURE:
<223> OTHER INFORMATION: Synthetic sequence

<400> SEQUENCE: 155

Asp Tyr Ala Met His
1               5

<210> SEQ ID NO 156
<211> LENGTH: 17
<212> TYPE: PRT
<213> ORGANISM: Artificial Sequence
<220> FEATURE:
<223> OTHER INFORMATION: Synthetic sequence

<400> SEQUENCE: 156

Gly Ile Ser Trp Asn Ser Gly Ser Ile Gly Tyr Ala Asp Ser Val Lys
1               5                   10                  15

Gly

<210> SEQ ID NO 157
<211> LENGTH: 13
<212> TYPE: PRT
<213> ORGANISM: Artificial Sequence
<220> FEATURE:
<223> OTHER INFORMATION: Synthetic sequence

<400> SEQUENCE: 157

Gly Arg Val Ser Tyr Arg Glu Ser Leu Arg Phe Asp Tyr
1               5                   10

<210> SEQ ID NO 158
<211> LENGTH: 13
<212> TYPE: PRT
<213> ORGANISM: Artificial Sequence
<220> FEATURE:
<223> OTHER INFORMATION: Synthetic sequence

<400> SEQUENCE: 158

Ser Gly Ser Ser Ser Asn Ile Gly Asn Asn Tyr Val Ser
1               5                   10

<210> SEQ ID NO 159
<211> LENGTH: 7
<212> TYPE: PRT
<213> ORGANISM: Artificial Sequence
<220> FEATURE:
<223> OTHER INFORMATION: Synthetic sequence

<400> SEQUENCE: 159

Asp Asn Asn Lys Arg Pro Ser
1               5
```

<210> SEQ ID NO 160
<211> LENGTH: 11
<212> TYPE: PRT
<213> ORGANISM: Artificial Sequence
<220> FEATURE:
<223> OTHER INFORMATION: Synthetic sequence

<400> SEQUENCE: 160

Gly Thr Trp Asp Ser Ser Leu Ser Ala Trp Val
1               5                   10

<210> SEQ ID NO 161
<211> LENGTH: 115
<212> TYPE: PRT
<213> ORGANISM: Artificial Sequence
<220> FEATURE:
<223> OTHER INFORMATION: Anti-CCR8-2-2 Heavy Chain

<400> SEQUENCE: 161

Glu Val Gln Leu Leu Glu Ser Gly Gly Gly Leu Val Gln Pro Gly Gly
1               5                   10                  15

Ser Leu Arg Leu Ser Cys Ala Ala Gly Gly Phe Thr Phe Ser Ala Tyr
                20                  25                  30

Thr Met Asn Trp Val Arg Gln Ala Pro Gly Lys Gly Leu Glu Trp Val
            35                  40                  45

Ser Ala Ile Ser Ala Ser Gly Gly Arg Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Phe Ala Arg Gly Trp Phe Asp Pro Trp Gly Gln Gly Thr
                100                 105                 110

Leu Val Thr
        115

<210> SEQ ID NO 162

<400> SEQUENCE: 162

000

<210> SEQ ID NO 163
<211> LENGTH: 110
<212> TYPE: PRT
<213> ORGANISM: Artificial Sequence
<220> FEATURE:
<223> OTHER INFORMATION: Anti-CCR8-2-2 Light Chain

<400> SEQUENCE: 163

Gln Ser Val Leu Thr Gln Pro Pro Ser Val Ser Ala Ala Pro Gly Gln
1               5                   10                  15

Arg Val Thr Ile Ser Cys Ser Gly Ser Thr Ser Asn Ile Gly Asn His
                20                  25                  30

Tyr Val Ser Trp Tyr Gln Gln Leu Pro Arg Ala Val Pro Lys Leu Val
            35                  40                  45

Ile Tyr Asp Asn Asp Lys Arg Pro Ser Gly Ile Ser Asp Arg Phe Ser
        50                  55                  60

Gly Ser Arg Ser Gly Thr Ser Ala Thr Leu Asp Ile Ser Gly Leu Gln
65                  70                  75                  80

Ala Gly Asp Glu Ala Asp Tyr Tyr Cys Ala Thr Trp Asp Tyr Ser Leu
            85                  90                  95

Thr Ala Val Val Phe Gly Gly Gly Thr Lys Leu Thr Val Leu
            100                 105                 110

<210> SEQ ID NO 164

<400> SEQUENCE: 164

000

<210> SEQ ID NO 165
<211> LENGTH: 5
<212> TYPE: PRT
<213> ORGANISM: Artificial Sequence
<220> FEATURE:
<223> OTHER INFORMATION: Synthetic sequence

<400> SEQUENCE: 165

Ala Tyr Thr Met Asn
1               5

<210> SEQ ID NO 166
<211> LENGTH: 17
<212> TYPE: PRT
<213> ORGANISM: Artificial Sequence
<220> FEATURE:
<223> OTHER INFORMATION: Synthetic sequence

<400> SEQUENCE: 166

Ala Ile Ser Ala Ser Gly Gly Arg Thr Tyr Tyr Ala Asp Ser Val Lys
1               5                   10                  15

Gly

<210> SEQ ID NO 167
<211> LENGTH: 9
<212> TYPE: PRT
<213> ORGANISM: Artificial Sequence
<220> FEATURE:
<223> OTHER INFORMATION: Synthetic sequence

<400> SEQUENCE: 167

Arg Phe Ala Arg Gly Trp Phe Asp Pro
1               5

<210> SEQ ID NO 168
<211> LENGTH: 13
<212> TYPE: PRT
<213> ORGANISM: Artificial Sequence
<220> FEATURE:
<223> OTHER INFORMATION: Synthetic sequence

<400> SEQUENCE: 168

Ser Gly Ser Thr Ser Asn Ile Gly Asn His Tyr Val Ser
1               5                   10

<210> SEQ ID NO 169
<211> LENGTH: 7
<212> TYPE: PRT
<213> ORGANISM: Artificial Sequence
<220> FEATURE:
<223> OTHER INFORMATION: Synthetic sequence

<400> SEQUENCE: 169

Asp Asn Asp Lys Arg Pro Ser
1               5

<210> SEQ ID NO 170
<211> LENGTH: 11
<212> TYPE: PRT
<213> ORGANISM: Artificial Sequence
<220> FEATURE:
<223> OTHER INFORMATION: Synthetic sequence

<400> SEQUENCE: 170

Ala Thr Trp Asp Tyr Ser Leu Thr Ala Val Val
1               5                   10

<210> SEQ ID NO 171
<211> LENGTH: 355
<212> TYPE: PRT
<213> ORGANISM: Homo sapiens
<220> FEATURE:
<223> OTHER INFORMATION: Human CCR8 Sequence

<400> SEQUENCE: 171

Met Asp Tyr Thr Leu Asp Leu Ser Val Thr Val Thr Asp Tyr Tyr
1               5                   10                  15

Tyr Pro Asp Ile Phe Ser Ser Pro Cys Asp Ala Glu Leu Ile Gln Thr
                20                  25                  30

Asn Gly Lys Leu Leu Leu Ala Val Phe Tyr Cys Leu Leu Phe Val Phe
            35                  40                  45

Ser Leu Leu Gly Asn Ser Leu Val Ile Leu Val Leu Val Val Cys Lys
        50                  55                  60

Lys Leu Arg Ser Ile Thr Asp Val Tyr Leu Leu Asn Leu Ala Leu Ser
65                  70                  75                  80

Asp Leu Leu Phe Val Phe Ser Phe Pro Phe Gln Thr Tyr Tyr Leu Leu
                85                  90                  95

Asp Gln Trp Val Phe Gly Thr Val Met Cys Lys Val Val Ser Gly Phe
            100                 105                 110

Tyr Tyr Ile Gly Phe Tyr Ser Ser Met Phe Phe Ile Thr Leu Met Ser
        115                 120                 125

Val Asp Arg Tyr Leu Ala Val Val His Ala Val Tyr Ala Leu Lys Val
130                 135                 140

Arg Thr Ile Arg Met Gly Thr Thr Leu Cys Leu Ala Val Trp Leu Thr
145                 150                 155                 160

Ala Ile Met Ala Thr Ile Pro Leu Leu Val Phe Tyr Gln Val Ala Ser
                165                 170                 175

Glu Asp Gly Val Leu Gln Cys Tyr Ser Phe Tyr Asn Gln Gln Thr Leu
            180                 185                 190

Lys Trp Lys Ile Phe Thr Asn Phe Lys Met Asn Ile Leu Gly Leu Leu
        195                 200                 205

Ile Pro Phe Thr Ile Phe Met Phe Cys Tyr Ile Lys Ile Leu His Gln
    210                 215                 220

Leu Lys Arg Cys Gln Asn His Asn Lys Thr Lys Ala Ile Arg Leu Val
225                 230                 235                 240

Leu Ile Val Val Ile Ala Ser Leu Leu Phe Trp Val Pro Phe Asn Val
                245                 250                 255

Val Leu Phe Leu Thr Ser Leu His Ser Met His Ile Leu Asp Gly Cys
            260                 265                 270

Ser Ile Ser Gln Gln Leu Thr Tyr Ala Thr His Val Thr Glu Ile Ile
        275                 280                 285

Ser Phe Thr His Cys Cys Val Asn Pro Val Ile Tyr Ala Phe Val Gly

```
                    290                 295                 300

Glu Lys Phe Lys Lys His Leu Ser Glu Ile Phe Gln Lys Ser Cys Ser
305                 310                 315                 320

Gln Ile Phe Asn Tyr Leu Gly Arg Gln Met Pro Arg Glu Ser Cys Glu
                325                 330                 335

Lys Ser Ser Cys Gln Gln His Ser Arg Ser Ser Val Asp
            340                 345                 350

Tyr Ile Leu
        355

<210> SEQ ID NO 172
<211> LENGTH: 35
<212> TYPE: PRT
<213> ORGANISM: Homo sapiens
<220> FEATURE:
<223> OTHER INFORMATION: N-terminal extracellular domain of human CCR8

<400> SEQUENCE: 172

Met Asp Tyr Thr Leu Asp Leu Ser Val Thr Thr Val Asp Tyr Tyr
1               5                   10                  15

Tyr Pro Asp Ile Phe Ser Ser Pro Cys Asp Ala Glu Leu Ile Gln Thr
                20                  25                  30

Asn Gly Lys
        35

<210> SEQ ID NO 173
<211> LENGTH: 299
<212> TYPE: PRT
<213> ORGANISM: Homo sapiens
<220> FEATURE:
<223> OTHER INFORMATION: Human CCR8-Fc

<400> SEQUENCE: 173

Met Gly Trp Ser Cys Ile Ile Leu Phe Leu Val Ala Thr Ala Thr Gly
1               5                   10                  15

Ala His Ser Met Asp Tyr Thr Leu Asp Leu Ser Val Thr Thr Val Thr
                20                  25                  30

Asp Tyr Tyr Tyr Pro Asp Ile Phe Ser Ser Pro Ser Asp Ala Glu Leu
            35                  40                  45

Ile Gln Thr Asn Gly Lys His His His His His Ser Gly Gly Gly
        50                  55                  60

Gly Ser Glu Pro Arg Gly Pro Thr Ile Lys Pro Cys Pro Pro Cys Lys
65                  70                  75                  80

Cys Pro Ala Pro Asn Leu Leu Gly Gly Pro Ser Val Phe Ile Phe Pro
                85                  90                  95

Pro Lys Ile Lys Asp Val Leu Met Ile Ser Leu Ser Pro Ile Val Thr
            100                 105                 110

Cys Val Val Val Asp Val Ser Glu Asp Asp Pro Asp Val Gln Ile Ser
        115                 120                 125

Trp Phe Val Asn Asn Val Glu Val His Thr Ala Gln Thr Gln Thr His
130                 135                 140

Arg Glu Asp Tyr Asn Ser Thr Leu Arg Val Val Ser Ala Leu Pro Ile
145                 150                 155                 160

Gln His Gln Asp Trp Met Ser Gly Lys Glu Phe Lys Cys Lys Val Asn
                165                 170                 175

Asn Lys Asp Leu Pro Ala Pro Ile Glu Arg Thr Ile Ser Lys Pro Lys
            180                 185                 190
```

Gly Ser Val Arg Ala Pro Gln Val Tyr Val Leu Pro Pro Glu Glu
            195                 200                 205

Glu Met Thr Lys Lys Gln Val Thr Leu Thr Cys Met Val Thr Asp Phe
    210                 215                 220

Met Pro Glu Asp Ile Tyr Val Glu Trp Thr Asn Asn Gly Lys Thr Glu
225                 230                 235                 240

Leu Asn Tyr Lys Asn Thr Glu Pro Val Leu Asp Ser Asp Gly Ser Tyr
                245                 250                 255

Phe Met Tyr Ser Lys Leu Arg Val Glu Lys Lys Asn Trp Val Glu Arg
            260                 265                 270

Asn Ser Tyr Ser Cys Ser Val Val His Glu Gly Leu His Asn His His
        275                 280                 285

Thr Thr Lys Ser Phe Ser Arg Thr Pro Gly Lys
    290                 295

<210> SEQ ID NO 174
<211> LENGTH: 299
<212> TYPE: PRT
<213> ORGANISM: Artificial Sequence
<220> FEATURE:
<223> OTHER INFORMATION: Cynomolgus CCR8-Fc

<400> SEQUENCE: 174

Met Gly Trp Ser Cys Ile Ile Leu Phe Leu Val Ala Thr Ala Thr Gly
1               5                   10                  15

Ala His Ser Met Asp Tyr Thr Leu Asp Pro Ser Met Thr Thr Met Thr
            20                  25                  30

Asp Tyr Tyr Tyr Pro Asp Ser Leu Ser Ser Pro Ser Asp Gly Glu Leu
        35                  40                  45

Ile Gln Arg Asn Asp Lys His His His His His Ser Gly Gly Gly
    50                  55                  60

Gly Ser Glu Pro Arg Gly Pro Thr Ile Lys Pro Cys Pro Pro Cys Lys
65                  70                  75                  80

Cys Pro Ala Pro Asn Leu Leu Gly Gly Pro Ser Val Phe Ile Phe Pro
                85                  90                  95

Pro Lys Ile Lys Asp Val Leu Met Ile Ser Leu Ser Pro Ile Val Thr
            100                 105                 110

Cys Val Val Asp Val Ser Glu Asp Asp Pro Asp Val Gln Ile Ser
        115                 120                 125

Trp Phe Val Asn Asn Val Glu Val His Thr Ala Gln Thr Gln Thr His
    130                 135                 140

Arg Glu Asp Tyr Asn Ser Thr Leu Arg Val Val Ser Ala Leu Pro Ile
145                 150                 155                 160

Gln His Gln Asp Trp Met Ser Gly Lys Glu Phe Lys Cys Lys Val Asn
                165                 170                 175

Asn Lys Asp Leu Pro Ala Pro Ile Glu Arg Thr Ile Ser Lys Pro Lys
            180                 185                 190

Gly Ser Val Arg Ala Pro Gln Val Tyr Val Leu Pro Pro Glu Glu
        195                 200                 205

Glu Met Thr Lys Lys Gln Val Thr Leu Thr Cys Met Val Thr Asp Phe
    210                 215                 220

Met Pro Glu Asp Ile Tyr Val Glu Trp Thr Asn Asn Gly Lys Thr Glu
225                 230                 235                 240

Leu Asn Tyr Lys Asn Thr Glu Pro Val Leu Asp Ser Asp Gly Ser Tyr
                245                 250                 255

Phe Met Tyr Ser Lys Leu Arg Val Glu Lys Lys Asn Trp Val Glu Arg
            260                 265                 270

Asn Ser Tyr Ser Cys Ser Val Val His Glu Gly Leu His Asn His His
        275                 280                 285

Thr Thr Lys Ser Phe Ser Arg Thr Pro Gly Lys
    290                 295

<210> SEQ ID NO 175
<211> LENGTH: 19
<212> TYPE: PRT
<213> ORGANISM: Artificial Sequence
<220> FEATURE:
<223> OTHER INFORMATION: Synthetic sequence

<400> SEQUENCE: 175

Met Gly Trp Ser Cys Ile Ile Leu Phe Leu Val Ala Thr Ala Thr Gly
1               5                   10                  15

Ala His Ser

<210> SEQ ID NO 176

<400> SEQUENCE: 176

000

<210> SEQ ID NO 177

<400> SEQUENCE: 177

000

<210> SEQ ID NO 178

<400> SEQUENCE: 178

000

<210> SEQ ID NO 179

<400> SEQUENCE: 179

000

<210> SEQ ID NO 180

<400> SEQUENCE: 180

000

<210> SEQ ID NO 181

<400> SEQUENCE: 181

000

<210> SEQ ID NO 182

<400> SEQUENCE: 182

000

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189

<400> SEQUENCE: 189

000

<210> SEQ ID NO 190

<400> SEQUENCE: 190

000

<210> SEQ ID NO 191

<400> SEQUENCE: 191

000

<210> SEQ ID NO 192

<400> SEQUENCE: 192

000

<210> SEQ ID NO 193

<400> SEQUENCE: 193

000

<210> SEQ ID NO 194

<400> SEQUENCE: 194

000

<210> SEQ ID NO 195

<400> SEQUENCE: 195

000

<210> SEQ ID NO 196

<400> SEQUENCE: 196

000

<210> SEQ ID NO 197

<400> SEQUENCE: 197

000

<210> SEQ ID NO 198

<400> SEQUENCE: 198

000

<210> SEQ ID NO 199

<400> SEQUENCE: 199

000

<210> SEQ ID NO 200

<400> SEQUENCE: 200

000

<210> SEQ ID NO 201
<211> LENGTH: 5
<212> TYPE: PRT
<213> ORGANISM: Artificial Sequence
<220> FEATURE:
<223> OTHER INFORMATION: VH CDR1 Consensus Sequence
<220> FEATURE:
<221> NAME/KEY: MISC_FEATURE
<222> LOCATION: (1)..(1)
<223> OTHER INFORMATION: Wherein Xaa is Ser, Asp, Gly, or Ala
<220> FEATURE:
<221> NAME/KEY: MISC_FEATURE
<222> LOCATION: (3)..(3)
<223> OTHER INFORMATION: Wherein Xaa is Tyr, Ala, or Thr
<220> FEATURE:
<221> NAME/KEY: MISC_FEATURE
<222> LOCATION: (5)..(5)
<223> OTHER INFORMATION: Wherein Xaa is His, Leu, or Asn

<400> SEQUENCE: 201

Xaa Tyr Xaa Met Xaa
1               5

<210> SEQ ID NO 202
<211> LENGTH: 5
<212> TYPE: PRT
<213> ORGANISM: Artificial Sequence
<220> FEATURE:
<223> OTHER INFORMATION: VH CDR1 Consensus Sequence
<220> FEATURE:
<221> NAME/KEY: MISC_FEATURE
<222> LOCATION: (1)..(1)
<223> OTHER INFORMATION: Wherein Xaa is Asp, Gly, or Ala
<220> FEATURE:
<221> NAME/KEY: MISC_FEATURE -continued

```
<222> LOCATION: (3)..(3)
<223> OTHER INFORMATION: Wherein Xaa is either Ala or Thr
<220> FEATURE:
<221> NAME/KEY: MISC_FEATURE
<222> LOCATION: (5)..(5)
<223> OTHER INFORMATION: Wherein Xaa is His, Leu, or Asn

<400> SEQUENCE: 202

Xaa Tyr Xaa Met Xaa
1               5

<210> SEQ ID NO 203
<211> LENGTH: 5
<212> TYPE: PRT
<213> ORGANISM: Artificial Sequence
<220> FEATURE:
<223> OTHER INFORMATION: VH CDR1 Consensus Sequence
<220> FEATURE:
<221> NAME/KEY: MISC_FEATURE
<222> LOCATION: (1)..(1)
<223> OTHER INFORMATION: Wherein Xaa is either Gly or Ala
<220> FEATURE:
<221> NAME/KEY: MISC_FEATURE
<222> LOCATION: (5)..(5)
<223> OTHER INFORMATION: Wherein Xaa is either Leu or Asn

<400> SEQUENCE: 203

Xaa Tyr Thr Met Xaa
1               5

<210> SEQ ID NO 204
<211> LENGTH: 5
<212> TYPE: PRT
<213> ORGANISM: Artificial Sequence
<220> FEATURE:
<223> OTHER INFORMATION: VH CDR1 Consensus Sequence
<220> FEATURE:
<221> NAME/KEY: MISC_FEATURE
<222> LOCATION: (1)..(1)
<223> OTHER INFORMATION: Wherein Xaa is either Ser or Asp
<220> FEATURE:
<221> NAME/KEY: MISC_FEATURE
<222> LOCATION: (3)..(3)
<223> OTHER INFORMATION: Wherein Xaa is either Tyr or Ala

<400> SEQUENCE: 204

Xaa Tyr Xaa Met His
1               5

<210> SEQ ID NO 205
<211> LENGTH: 17
<212> TYPE: PRT
<213> ORGANISM: Artificial Sequence
<220> FEATURE:
<223> OTHER INFORMATION: VH CDR2 Consensus Sequence
<220> FEATURE:
<221> NAME/KEY: MISC_FEATURE
<222> LOCATION: (1)..(1)
<223> OTHER INFORMATION: Wherein Xaa is Ile, Gly, or Ala
<220> FEATURE:
<221> NAME/KEY: MISC_FEATURE
<222> LOCATION: (3)..(3)
<223> OTHER INFORMATION: Wherein Xaa is Asn, Ser, or Thr
<220> FEATURE:
<221> NAME/KEY: MISC_FEATURE
<222> LOCATION: (4)..(4)
<223> OTHER INFORMATION: Wherein Xaa is Pro, Trp, or Ala
<220> FEATURE:
<221> NAME/KEY: MISC_FEATURE
<222> LOCATION: (5)..(5)
<223> OTHER INFORMATION: Wherein Xaa is either Ser or Asn
<220> FEATURE:
<221> NAME/KEY: MISC_FEATURE
```

```
<222> LOCATION: (6)..(6)
<223> OTHER INFORMATION: Wherein Xaa is either Gly or Ser
<220> FEATURE:
<221> NAME/KEY: MISC_FEATURE
<222> LOCATION: (8)..(8)
<223> OTHER INFORMATION: Wherein Xaa is either Ser or Arg
<220> FEATURE:
<221> NAME/KEY: MISC_FEATURE
<222> LOCATION: (9)..(9)
<223> OTHER INFORMATION: Wherein Xaa is either Thr or Ile
<220> FEATURE:
<221> NAME/KEY: MISC_FEATURE
<222> LOCATION: (10)..(10)
<223> OTHER INFORMATION: Wherein Xaa is Ser, Gly, or Tyr
<220> FEATURE:
<221> NAME/KEY: MISC_FEATURE
<222> LOCATION: (13)..(13)
<223> OTHER INFORMATION: Wherein Xaa is either Gln or Asp
<220> FEATURE:
<221> NAME/KEY: MISC_FEATURE
<222> LOCATION: (14)..(14)
<223> OTHER INFORMATION: Wherein Xaa is either Lys or Ser
<220> FEATURE:
<221> NAME/KEY: MISC_FEATURE
<222> LOCATION: (15)..(15)
<223> OTHER INFORMATION: Wherein Xaa is either Phe or Val
<220> FEATURE:
<221> NAME/KEY: MISC_FEATURE
<222> LOCATION: (16)..(16)
<223> OTHER INFORMATION: Wherein Xaa is either Gln or Lys

<400> SEQUENCE: 205

Xaa Ile Xaa Xaa Xaa Xaa Gly Xaa Xaa Xaa Tyr Ala Xaa Xaa Xaa Xaa
1               5                   10                  15

Gly

<210> SEQ ID NO 206
<211> LENGTH: 17
<212> TYPE: PRT
<213> ORGANISM: Artificial Sequence
<220> FEATURE:
<223> OTHER INFORMATION: VH CDR2 Consensus Sequence
<220> FEATURE:
<221> NAME/KEY: MISC_FEATURE
<222> LOCATION: (3)..(3)
<223> OTHER INFORMATION: Wherein Xaa is either Thr or Ser

<400> SEQUENCE: 206

Ala Ile Xaa Ala Ser Gly Gly Arg Thr Tyr Tyr Ala Asp Ser Val Lys
1               5                   10                  15

Gly

<210> SEQ ID NO 207
<211> LENGTH: 17
<212> TYPE: PRT
<213> ORGANISM: Artificial Sequence
<220> FEATURE:
<223> OTHER INFORMATION: VH CDR2 Consensus Sequence
<220> FEATURE:
<221> NAME/KEY: MISC_FEATURE
<222> LOCATION: (1)..(1)
<223> OTHER INFORMATION: Wherein Xaa is either Gly or Ala
<220> FEATURE:
<221> NAME/KEY: MISC_FEATURE
<222> LOCATION: (3)..(3)
<223> OTHER INFORMATION: Wherein Xaa is either Thr or Ser
<220> FEATURE:
<221> NAME/KEY: MISC_FEATURE
<222> LOCATION: (4)..(4)
<223> OTHER INFORMATION: Wherein Xaa is either Trp or Ala
<220> FEATURE:
<221> NAME/KEY: MISC_FEATURE
<222> LOCATION: (5)..(5)
```

```
<223> OTHER INFORMATION: Wherein Xaa is either Asn or Ser
<220> FEATURE:
<221> NAME/KEY: MISC_FEATURE
<222> LOCATION: (6)..(6)
<223> OTHER INFORMATION: Wherein Xaa is either Ser or Gly
<220> FEATURE:
<221> NAME/KEY: MISC_FEATURE
<222> LOCATION: (8)..(8)
<223> OTHER INFORMATION: Wherein Xaa is either Ser or Arg
<220> FEATURE:
<221> NAME/KEY: MISC_FEATURE
<222> LOCATION: (9)..(9)
<223> OTHER INFORMATION: Wherein Xaa is either Ile or Thr
<220> FEATURE:
<221> NAME/KEY: MISC_FEATURE
<222> LOCATION: (10)..(10)
<223> OTHER INFORMATION: Wherein Xaa is either Gly or Tyr

<400> SEQUENCE: 207

Xaa Ile Xaa Xaa Xaa Xaa Gly Xaa Xaa Xaa Tyr Ala Asp Ser Val Lys
1               5                   10                  15

Gly

<210> SEQ ID NO 208
<211> LENGTH: 17
<212> TYPE: PRT
<213> ORGANISM: Artificial Sequence
<220> FEATURE:
<223> OTHER INFORMATION: VH CDR2 Consensus Sequence
<220> FEATURE:
<221> NAME/KEY: MISC_FEATURE
<222> LOCATION: (1)..(1)
<223> OTHER INFORMATION: Wherein Xaa is either Ile or Gly
<220> FEATURE:
<221> NAME/KEY: MISC_FEATURE
<222> LOCATION: (3)..(3)
<223> OTHER INFORMATION: Wherein Xaa is either Asn or Ser
<220> FEATURE:
<221> NAME/KEY: MISC_FEATURE
<222> LOCATION: (4)..(4)
<223> OTHER INFORMATION: Wherein Xaa is either Pro or Trp
<220> FEATURE:
<221> NAME/KEY: MISC_FEATURE
<222> LOCATION: (5)..(5)
<223> OTHER INFORMATION: Wherein Xaa is either Ser or Asn
<220> FEATURE:
<221> NAME/KEY: MISC_FEATURE
<222> LOCATION: (6)..(6)
<223> OTHER INFORMATION: Wherein Xaa is either Gly or Ser
<220> FEATURE:
<221> NAME/KEY: MISC_FEATURE
<222> LOCATION: (9)..(9)
<223> OTHER INFORMATION: Wherein Xaa is either Thr or Ile
<220> FEATURE:
<221> NAME/KEY: MISC_FEATURE
<222> LOCATION: (10)..(10)
<223> OTHER INFORMATION: Wherein Xaa is either Ser or Gly
<220> FEATURE:
<221> NAME/KEY: MISC_FEATURE
<222> LOCATION: (13)..(13)
<223> OTHER INFORMATION: Wherein Xaa is either Gln or Asp
<220> FEATURE:
<221> NAME/KEY: MISC_FEATURE
<222> LOCATION: (14)..(14)
<223> OTHER INFORMATION: Wherein Xaa is either Lys or Ser
<220> FEATURE:
<221> NAME/KEY: MISC_FEATURE
<222> LOCATION: (15)..(15)
<223> OTHER INFORMATION: Wherein Xaa is either Phe or Val
<220> FEATURE:
<221> NAME/KEY: MISC_FEATURE
<222> LOCATION: (16)..(16)
<223> OTHER INFORMATION: Wherein Xaa is either Gln or Lys

<400> SEQUENCE: 208
```

```
Xaa Ile Xaa Xaa Xaa Xaa Gly Ser Xaa Xaa Tyr Ala Xaa Xaa Xaa Xaa
1               5                   10                  15

Gly

<210> SEQ ID NO 209
<211> LENGTH: 10
<212> TYPE: PRT
<213> ORGANISM: Artificial Sequence
<220> FEATURE:
<223> OTHER INFORMATION: VH CDR3 Consensus Sequence
<220> FEATURE:
<221> NAME/KEY: MISC_FEATURE
<222> LOCATION: (1)..(1)
<223> OTHER INFORMATION: Wherein Xaa is either Ala or Gly
<220> FEATURE:
<221> NAME/KEY: MISC_FEATURE
<222> LOCATION: (3)..(3)
<223> OTHER INFORMATION: Wherein Xaa is either Arg or Gly
<220> FEATURE:
<221> NAME/KEY: MISC_FEATURE
<222> LOCATION: (5)..(5)
<223> OTHER INFORMATION: Wherein Xaa is either Arg or Gly

<400> SEQUENCE: 209

Xaa Val Xaa Asn Xaa Phe Arg Phe Asp Tyr
1               5                   10

<210> SEQ ID NO 210
<211> LENGTH: 13
<212> TYPE: PRT
<213> ORGANISM: Artificial Sequence
<220> FEATURE:
<223> OTHER INFORMATION: VH CDR3 Consensus Sequence
<220> FEATURE:
<221> NAME/KEY: MISC_FEATURE
<222> LOCATION: (3)..(3)
<223> OTHER INFORMATION: Wherein Xaa is Lys, Val, Asp, Glu, or Arg
<220> FEATURE:
<221> NAME/KEY: MISC_FEATURE
<222> LOCATION: (7)..(7)
<223> OTHER INFORMATION: Wherein Xaa is Asp, Glu, Lys, or Val

<400> SEQUENCE: 210

Gly Arg Xaa Ser Tyr Arg Xaa Ser Leu Arg Phe Asp Tyr
1               5                   10

<210> SEQ ID NO 211
<211> LENGTH: 12
<212> TYPE: PRT
<213> ORGANISM: Artificial Sequence
<220> FEATURE:
<223> OTHER INFORMATION: VL CDR1 Consensus Sequence
<220> FEATURE:
<221> NAME/KEY: MISC_FEATURE
<222> LOCATION: (4)..(4)
<223> OTHER INFORMATION: Wherein Xaa is Thr or Ala
<220> FEATURE:
<221> NAME/KEY: MISC_FEATURE
<222> LOCATION: (6)..(6)
<223> OTHER INFORMATION: Wherein Xaa is Asn, Ser, or Pro
<220> FEATURE:
<221> NAME/KEY: MISC_FEATURE
<222> LOCATION: (7)..(7)
<223> OTHER INFORMATION: Wherein Xaa is Ile, Arg, Val, or Ser
<220> FEATURE:
<221> NAME/KEY: MISC_FEATURE
<222> LOCATION: (8)..(8)
<223> OTHER INFORMATION: Wherein Xaa is Asn, Val, or Thr
<220> FEATURE:
<221> NAME/KEY: MISC_FEATURE
<222> LOCATION: (9)..(9)
<223> OTHER INFORMATION: Wherein Xaa is Leu or the absence of an amino
      acid
```

```
<220> FEATURE:
<221> NAME/KEY: MISC_FEATURE
<222> LOCATION: (10)..(10)
<223> OTHER INFORMATION: Wherein Xaa is Pro, Phe, Tyr, or His

<400> SEQUENCE: 211

Ser Ser Tyr Xaa Gly Xaa Xaa Xaa Xaa Xaa Val Val
1               5                   10

<210> SEQ ID NO 212
<211> LENGTH: 12
<212> TYPE: PRT
<213> ORGANISM: Artificial Sequence
<220> FEATURE:
<223> OTHER INFORMATION: VL CDR1 Consensus Sequence
<220> FEATURE:
<221> NAME/KEY: MISC_FEATURE
<222> LOCATION: (4)..(4)
<223> OTHER INFORMATION: Wherein Xaa is either Thr or Ala
<220> FEATURE:
<221> NAME/KEY: MISC_FEATURE
<222> LOCATION: (6)..(6)
<223> OTHER INFORMATION: Wherein Xaa is either Asn or Ser
<220> FEATURE:
<221> NAME/KEY: MISC_FEATURE
<222> LOCATION: (7)..(7)
<223> OTHER INFORMATION: Wherein Xaa is Ile, Arg, or Ser
<220> FEATURE:
<221> NAME/KEY: MISC_FEATURE
<222> LOCATION: (8)..(8)
<223> OTHER INFORMATION: Wherein Xaa is Asn, Val, or Thr
<220> FEATURE:
<221> NAME/KEY: MISC_FEATURE
<222> LOCATION: (9)..(9)
<223> OTHER INFORMATION: Wherein Xaa is Leu or the absence of an amino
      acid
<220> FEATURE:
<221> NAME/KEY: MISC_FEATURE
<222> LOCATION: (10)..(10)
<223> OTHER INFORMATION: Wherein Xaa is Pro, Phe, Tyr, or His

<400> SEQUENCE: 212

Ser Ser Tyr Xaa Gly Xaa Xaa Xaa Xaa Xaa Val Val
1               5                   10

<210> SEQ ID NO 213
<211> LENGTH: 11
<212> TYPE: PRT
<213> ORGANISM: Artificial Sequence
<220> FEATURE:
<223> OTHER INFORMATION: VL CDR1 Consensus Sequence
<220> FEATURE:
<221> NAME/KEY: MISC_FEATURE
<222> LOCATION: (9)..(9)
<223> OTHER INFORMATION: Wherein Xaa is either Phe or Tyr

<400> SEQUENCE: 213

Ser Ser Tyr Ala Gly Ser Ser Thr Xaa Val Val
1               5                   10

<210> SEQ ID NO 214
<211> LENGTH: 11
<212> TYPE: PRT
<213> ORGANISM: Artificial Sequence
<220> FEATURE:
<223> OTHER INFORMATION: VL CDR1 Consensus Sequence
<220> FEATURE:
<221> NAME/KEY: MISC_FEATURE
<222> LOCATION: (7)..(7)
<223> OTHER INFORMATION: Wherein Xaa is either Arg or Ile
<220> FEATURE:
<221> NAME/KEY: MISC_FEATURE
<222> LOCATION: (8)..(8)
```

```
<223> OTHER INFORMATION: Wherein Xaa is either Val or Thr
<220> FEATURE:
<221> NAME/KEY: MISC_FEATURE
<222> LOCATION: (9)..(9)
<223> OTHER INFORMATION: Wherein Xaa is either Phe or His

<400> SEQUENCE: 214

Ser Ser Tyr Ala Gly Ser Xaa Xaa Xaa Val Val
1               5                   10

<210> SEQ ID NO 215
<211> LENGTH: 11
<212> TYPE: PRT
<213> ORGANISM: Artificial Sequence
<220> FEATURE:
<223> OTHER INFORMATION: VL CDR1 Consensus Sequence
<220> FEATURE:
<221> NAME/KEY: MISC_FEATURE
<222> LOCATION: (1)..(1)
<223> OTHER INFORMATION: Wherein Xaa is either Ala or Gly
<220> FEATURE:
<221> NAME/KEY: MISC_FEATURE
<222> LOCATION: (2)..(2)
<223> OTHER INFORMATION: Wherein Xaa is either Thr or Ala
<220> FEATURE:
<221> NAME/KEY: MISC_FEATURE
<222> LOCATION: (5)..(5)
<223> OTHER INFORMATION: Wherein Xaa is either Tyr or Ser
<220> FEATURE:
<221> NAME/KEY: MISC_FEATURE
<222> LOCATION: (8)..(8)
<223> OTHER INFORMATION: Wherein Xaa is either Thr or Arg
<220> FEATURE:
<221> NAME/KEY: MISC_FEATURE
<222> LOCATION: (9)..(9)
<223> OTHER INFORMATION: Wherein Xaa is either Ala or Met
<220> FEATURE:
<221> NAME/KEY: MISC_FEATURE
<222> LOCATION: (10)..(10)
<223> OTHER INFORMATION: Wherein Xaa is either Val or Trp

<400> SEQUENCE: 215

Xaa Xaa Trp Asp Xaa Ser Leu Xaa Xaa Xaa Val
1               5                   10

<210> SEQ ID NO 216
<211> LENGTH: 11
<212> TYPE: PRT
<213> ORGANISM: Artificial Sequence
<220> FEATURE:
<223> OTHER INFORMATION: VL CDR1 Consensus Sequence
<220> FEATURE:
<221> NAME/KEY: MISC_FEATURE
<222> LOCATION: (1)..(1)
<223> OTHER INFORMATION: Wherein Xaa is either Ala or Gly
<220> FEATURE:
<221> NAME/KEY: MISC_FEATURE
<222> LOCATION: (2)..(2)
<223> OTHER INFORMATION: Wherein Xaa is either Thr or Ala
<220> FEATURE:
<221> NAME/KEY: MISC_FEATURE
<222> LOCATION: (5)..(5)
<223> OTHER INFORMATION: Wherein Xaa is either Tyr or Ser
<220> FEATURE:
<221> NAME/KEY: MISC_FEATURE
<222> LOCATION: (8)..(8)
<223> OTHER INFORMATION: Wherein Xaa is Thr, Arg, or Ser
<220> FEATURE:
<221> NAME/KEY: MISC_FEATURE
<222> LOCATION: (9)..(9)
<223> OTHER INFORMATION: Wherein Xaa is either Ala or Met
<220> FEATURE:
<221> NAME/KEY: MISC_FEATURE
<222> LOCATION: (10)..(10)
<223> OTHER INFORMATION: Wherein Xaa is either Val or Trp
```

<400> SEQUENCE: 216

Xaa Xaa Trp Asp Xaa Ser Leu Xaa Xaa Xaa Val
1               5                   10

<210> SEQ ID NO 217
<211> LENGTH: 11
<212> TYPE: PRT
<213> ORGANISM: Artificial Sequence
<220> FEATURE:
<223> OTHER INFORMATION: VL CDR1 Consensus Sequence
<220> FEATURE:
<221> NAME/KEY: MISC_FEATURE
<222> LOCATION: (1)..(1)
<223> OTHER INFORMATION: Wherein Xaa is either Ala or Gly
<220> FEATURE:
<221> NAME/KEY: MISC_FEATURE
<222> LOCATION: (5)..(5)
<223> OTHER INFORMATION: Wherein Xaa is either Tyr or Ser
<220> FEATURE:
<221> NAME/KEY: MISC_FEATURE
<222> LOCATION: (8)..(8)
<223> OTHER INFORMATION: Wherein Xaa is either Thr or Ser
<220> FEATURE:
<221> NAME/KEY: MISC_FEATURE
<222> LOCATION: (10)..(10)
<223> OTHER INFORMATION: Wherein Xaa is either Val or Trp

<400> SEQUENCE: 217

Xaa Thr Trp Asp Xaa Ser Leu Xaa Ala Xaa Val
1               5                   10

<210> SEQ ID NO 218
<211> LENGTH: 11
<212> TYPE: PRT
<213> ORGANISM: Artificial Sequence
<220> FEATURE:
<223> OTHER INFORMATION: VL CDR1 Consensus Sequence
<220> FEATURE:
<221> NAME/KEY: MISC_FEATURE
<222> LOCATION: (2)..(2)
<223> OTHER INFORMATION: Wherein Xaa is either Ala or Thr
<220> FEATURE:
<221> NAME/KEY: MISC_FEATURE
<222> LOCATION: (8)..(8)
<223> OTHER INFORMATION: Wherein Xaa is either Arg or Ser
<220> FEATURE:
<221> NAME/KEY: MISC_FEATURE
<222> LOCATION: (9)..(9)
<223> OTHER INFORMATION: Wherein Xaa is either Met or Ala

<400> SEQUENCE: 218

Gly Xaa Trp Asp Ser Ser Leu Xaa Xaa Trp Val
1               5                   10

<210> SEQ ID NO 219
<211> LENGTH: 13
<212> TYPE: PRT
<213> ORGANISM: Artificial Sequence
<220> FEATURE:
<223> OTHER INFORMATION: VL CDR1 Consensus Sequence
<220> FEATURE:
<221> NAME/KEY: MISC_FEATURE
<222> LOCATION: (1)..(1)
<223> OTHER INFORMATION: Wherein Xaa is either Ser or Thr
<220> FEATURE:
<221> NAME/KEY: MISC_FEATURE
<222> LOCATION: (3)..(3)
<223> OTHER INFORMATION: Wherein Xaa is either Ser or Thr
<220> FEATURE:
<221> NAME/KEY: MISC_FEATURE
<222> LOCATION: (4)..(4)
<223> OTHER INFORMATION: Wherein Xaa is either Gly or Ser -continued

```
<220> FEATURE:
<221> NAME/KEY: MISC_FEATURE
<222> LOCATION: (9)..(9)
<223> OTHER INFORMATION: Wherein Xaa is either Asn or Lys
<220> FEATURE:
<221> NAME/KEY: MISC_FEATURE
<222> LOCATION: (11)..(11)
<223> OTHER INFORMATION: Wherein Xaa is either Tyr or Phe

<400> SEQUENCE: 219

Xaa Gly Xaa Xaa Ser Asn Ile Gly Xaa Asn Xaa Val Ser
1               5                   10

<210> SEQ ID NO 220
<211> LENGTH: 7
<212> TYPE: PRT
<213> ORGANISM: Artificial Sequence
<220> FEATURE:
<223> OTHER INFORMATION: VL CDR2 Consensus Sequence
<220> FEATURE:
<221> NAME/KEY: MISC_FEATURE
<222> LOCATION: (2)..(2)
<223> OTHER INFORMATION: Wherein Xaa is either Val or Ala
<220> FEATURE:
<221> NAME/KEY: MISC_FEATURE
<222> LOCATION: (3)..(3)
<223> OTHER INFORMATION: Wherein Xaa is Asn, Thr, Ile, or Ser

<400> SEQUENCE: 220

Glu Xaa Xaa Lys Arg Pro Ser
1               5

<210> SEQ ID NO 221
<211> LENGTH: 7
<212> TYPE: PRT
<213> ORGANISM: Artificial Sequence
<220> FEATURE:
<223> OTHER INFORMATION: VL CDR2 Consensus Sequence
<220> FEATURE:
<221> NAME/KEY: MISC_FEATURE
<222> LOCATION: (2)..(2)
<223> OTHER INFORMATION: Wherein Xaa is either Val or Ala
<220> FEATURE:
<221> NAME/KEY: MISC_FEATURE
<222> LOCATION: (3)..(3)
<223> OTHER INFORMATION: Wherein Xaa is Asn, Thr, or Ser

<400> SEQUENCE: 221

Glu Xaa Xaa Lys Arg Pro Ser
1               5

<210> SEQ ID NO 222
<211> LENGTH: 7
<212> TYPE: PRT
<213> ORGANISM: Artificial Sequence
<220> FEATURE:
<223> OTHER INFORMATION: VL CDR2 Consensus Sequence
<220> FEATURE:
<221> NAME/KEY: MISC_FEATURE
<222> LOCATION: (3)..(3)
<223> OTHER INFORMATION: Wherein Xaa is either Thr or Ser

<400> SEQUENCE: 222

Glu Val Xaa Lys Arg Pro Ser
1               5

<210> SEQ ID NO 223
<211> LENGTH: 7
<212> TYPE: PRT
<213> ORGANISM: Artificial Sequence
<220> FEATURE:
```

```
<223> OTHER INFORMATION: VL CDR2 Consensus Sequence
<220> FEATURE:
<221> NAME/KEY: MISC_FEATURE
<222> LOCATION: (2)..(2)
<223> OTHER INFORMATION: Wherein Xaa is either Ala or Val

<400> SEQUENCE: 223

Glu Xaa Thr Lys Arg Pro Ser
1               5

<210> SEQ ID NO 224
<211> LENGTH: 7
<212> TYPE: PRT
<213> ORGANISM: Artificial Sequence
<220> FEATURE:
<223> OTHER INFORMATION: VL CDR2 Consensus Sequence
<220> FEATURE:
<221> NAME/KEY: MISC_FEATURE
<222> LOCATION: (3)..(3)
<223> OTHER INFORMATION: Wherein Xaa is either Asn or Ser

<400> SEQUENCE: 224

Glu Val Xaa Lys Arg Pro Ser
1               5

<210> SEQ ID NO 225
<211> LENGTH: 7
<212> TYPE: PRT
<213> ORGANISM: Artificial Sequence
<220> FEATURE:
<223> OTHER INFORMATION: VL CDR2 Consensus Sequence
<220> FEATURE:
<221> NAME/KEY: MISC_FEATURE
<222> LOCATION: (3)..(3)
<223> OTHER INFORMATION: Wherein Xaa is either Asn or Thr

<400> SEQUENCE: 225

Glu Val Xaa Lys Arg Pro Ser
1               5

<210> SEQ ID NO 226
<211> LENGTH: 6
<212> TYPE: PRT
<213> ORGANISM: Artificial Sequence
<220> FEATURE:
<223> OTHER INFORMATION: VL CDR2 Consensus Sequence
<220> FEATURE:
<221> NAME/KEY: MISC_FEATURE
<222> LOCATION: (3)..(3)
<223> OTHER INFORMATION: Wherein Xaa is either Asp or Thr
<220> FEATURE:
<221> NAME/KEY: MISC_FEATURE
<222> LOCATION: (4)..(4)
<223> OTHER INFORMATION: Wherein Xaa is either Lys or Arg

<400> SEQUENCE: 226

Asp Asn Xaa Xaa Pro Ser
1               5

<210> SEQ ID NO 227
<211> LENGTH: 7
<212> TYPE: PRT
<213> ORGANISM: Artificial Sequence
<220> FEATURE:
<223> OTHER INFORMATION: VL CDR2 Consensus Sequence
<220> FEATURE:
<221> NAME/KEY: MISC_FEATURE
<222> LOCATION: (3)..(3)
<223> OTHER INFORMATION: Wherein Xaa is Asp, Thr, or Asn
<220> FEATURE:
<221> NAME/KEY: MISC_FEATURE
```

```
<222> LOCATION: (4)..(4)
<223> OTHER INFORMATION: Wherein Xaa is either Lys or Arg

<400> SEQUENCE: 227

Asp Asn Xaa Xaa Arg Pro Ser
1               5

<210> SEQ ID NO 228
<211> LENGTH: 7
<212> TYPE: PRT
<213> ORGANISM: Artificial Sequence
<220> FEATURE:
<223> OTHER INFORMATION: VL CDR2 Consensus Sequence
<220> FEATURE:
<221> NAME/KEY: MISC_FEATURE
<222> LOCATION: (3)..(3)
<223> OTHER INFORMATION: Wherein Xaa is either Asp or Asn

<400> SEQUENCE: 228

Asp Asn Xaa Lys Arg Pro Ser
1               5

<210> SEQ ID NO 229
<211> LENGTH: 7
<212> TYPE: PRT
<213> ORGANISM: Artificial Sequence
<220> FEATURE:
<223> OTHER INFORMATION: VL CDR2 Consensus Sequence
<220> FEATURE:
<221> NAME/KEY: MISC_FEATURE
<222> LOCATION: (3)..(3)
<223> OTHER INFORMATION: Wherein Xaa is either Thr or Asn
<220> FEATURE:
<221> NAME/KEY: MISC_FEATURE
<222> LOCATION: (4)..(4)
<223> OTHER INFORMATION: Wherein Xaa is either Lys or Arg

<400> SEQUENCE: 229

Asp Asn Xaa Xaa Arg Pro Ser
1               5

<210> SEQ ID NO 230
<211> LENGTH: 7
<212> TYPE: PRT
<213> ORGANISM: Artificial Sequence
<220> FEATURE:
<223> OTHER INFORMATION: VL CDR2 Consensus Sequence
<220> FEATURE:
<221> NAME/KEY: MISC_FEATURE
<222> LOCATION: (2)..(2)
<223> OTHER INFORMATION: Wherein Xaa is either Asn or Asp
<220> FEATURE:
<221> NAME/KEY: MISC_FEATURE
<222> LOCATION: (3)..(3)
<223> OTHER INFORMATION: Wherein Xaa is Asp, Thr, or Asn
<220> FEATURE:
<221> NAME/KEY: MISC_FEATURE
<222> LOCATION: (4)..(4)
<223> OTHER INFORMATION: Wherein Xaa is either Lys or Arg

<400> SEQUENCE: 230

Asp Xaa Xaa Xaa Arg Pro Ser
1               5

<210> SEQ ID NO 231
<211> LENGTH: 7
<212> TYPE: PRT
<213> ORGANISM: Artificial Sequence
<220> FEATURE:
<223> OTHER INFORMATION: VL CDR2 Consensus Sequence
<220> FEATURE:
```

```
<221> NAME/KEY: MISC_FEATURE
<222> LOCATION: (2)..(2)
<223> OTHER INFORMATION: Wherein Xaa is either Asn or Asp
<220> FEATURE:
<221> NAME/KEY: MISC_FEATURE
<222> LOCATION: (3)..(3)
<223> OTHER INFORMATION: Wherein Xaa is either Asn or Asp

<400> SEQUENCE: 231

Asp Xaa Xaa Lys Arg Pro Ser
1               5

<210> SEQ ID NO 232
<211> LENGTH: 7
<212> TYPE: PRT
<213> ORGANISM: Artificial Sequence
<220> FEATURE:
<223> OTHER INFORMATION: VL CDR2 Consensus Sequence
<220> FEATURE:
<221> NAME/KEY: MISC_FEATURE
<222> LOCATION: (2)..(2)
<223> OTHER INFORMATION: Wherein Xaa is either Asn or Asp
<220> FEATURE:
<221> NAME/KEY: MISC_FEATURE
<222> LOCATION: (3)..(3)
<223> OTHER INFORMATION: Wherein Xaa is either Thr or Asn
<220> FEATURE:
<221> NAME/KEY: MISC_FEATURE
<222> LOCATION: (4)..(4)
<223> OTHER INFORMATION: Wherein Xaa is either Lys or Arg

<400> SEQUENCE: 232

Asp Xaa Xaa Xaa Arg Pro Ser
1               5

<210> SEQ ID NO 233
<211> LENGTH: 12
<212> TYPE: PRT
<213> ORGANISM: Artificial Sequence
<220> FEATURE:
<223> OTHER INFORMATION: VL CDR3 Consensus Sequence
<220> FEATURE:
<221> NAME/KEY: MISC_FEATURE
<222> LOCATION: (4)..(4)
<223> OTHER INFORMATION: Wherein Xaa is either Thr or Ala
<220> FEATURE:
<221> NAME/KEY: MISC_FEATURE
<222> LOCATION: (6)..(6)
<223> OTHER INFORMATION: Wherein Xaa is Asn, Ser, or Pro
<220> FEATURE:
<221> NAME/KEY: MISC_FEATURE
<222> LOCATION: (7)..(7)
<223> OTHER INFORMATION: Wherein Xaa is Ile, Arg, Val, or Ser
<220> FEATURE:
<221> NAME/KEY: MISC_FEATURE
<222> LOCATION: (8)..(8)
<223> OTHER INFORMATION: Wherein Xaa is Asn, Val, or Thr
<220> FEATURE:
<221> NAME/KEY: MISC_FEATURE
<222> LOCATION: (9)..(9)
<223> OTHER INFORMATION: Wherein Xaa is Leu or the absence of an amino
      acid
<220> FEATURE:
<221> NAME/KEY: MISC_FEATURE
<222> LOCATION: (10)..(10)
<223> OTHER INFORMATION: Wherein Xaa is Pro, Phe, Tyr, or His

<400> SEQUENCE: 233

Ser Ser Tyr Xaa Gly Xaa Xaa Xaa Xaa Xaa Val Val
1               5                   10

<210> SEQ ID NO 234
<211> LENGTH: 12
```

```
<212> TYPE: PRT
<213> ORGANISM: Artificial Sequence
<220> FEATURE:
<223> OTHER INFORMATION: VL CDR3 Consensus Sequence
<220> FEATURE:
<221> NAME/KEY: MISC_FEATURE
<222> LOCATION: (4)..(4)
<223> OTHER INFORMATION: Wherein Xaa is either Thr or Ala
<220> FEATURE:
<221> NAME/KEY: MISC_FEATURE
<222> LOCATION: (6)..(6)
<223> OTHER INFORMATION: Wherein Xaa is either Asn or Ser
<220> FEATURE:
<221> NAME/KEY: MISC_FEATURE
<222> LOCATION: (7)..(7)
<223> OTHER INFORMATION: Wherein Xaa is Ile, Arg, or Ser
<220> FEATURE:
<221> NAME/KEY: MISC_FEATURE
<222> LOCATION: (8)..(8)
<223> OTHER INFORMATION: Wherein Xaa is Asn, Val, or Thr
<220> FEATURE:
<221> NAME/KEY: MISC_FEATURE
<222> LOCATION: (9)..(9)
<223> OTHER INFORMATION: Wherein Xaa is Leu or the absence of an amino
     acid
<220> FEATURE:
<221> NAME/KEY: MISC_FEATURE
<222> LOCATION: (10)..(10)
<223> OTHER INFORMATION: Wherein Xaa is Pro, Phe, Tyr, or His

<400> SEQUENCE: 234

Ser Ser Tyr Xaa Gly Xaa Xaa Xaa Xaa Xaa Val Val
1               5                   10

<210> SEQ ID NO 235
<211> LENGTH: 11
<212> TYPE: PRT
<213> ORGANISM: Artificial Sequence
<220> FEATURE:
<223> OTHER INFORMATION: VL CDR3 Consensus Sequence
<220> FEATURE:
<221> NAME/KEY: MISC_FEATURE
<222> LOCATION: (9)..(9)
<223> OTHER INFORMATION: Wherein Xaa is Phe or Tyr

<400> SEQUENCE: 235

Ser Ser Tyr Ala Gly Ser Ser Thr Xaa Val Val
1               5                   10

<210> SEQ ID NO 236
<211> LENGTH: 11
<212> TYPE: PRT
<213> ORGANISM: Artificial Sequence
<220> FEATURE:
<223> OTHER INFORMATION: VL CDR3 Consensus Sequence
<220> FEATURE:
<221> NAME/KEY: MISC_FEATURE
<222> LOCATION: (7)..(7)
<223> OTHER INFORMATION: Wherein Xaa is either Arg or Ile
<220> FEATURE:
<221> NAME/KEY: MISC_FEATURE
<222> LOCATION: (8)..(8)
<223> OTHER INFORMATION: Wherein Xaa is either Val or Thr
<220> FEATURE:
<221> NAME/KEY: MISC_FEATURE
<222> LOCATION: (9)..(9)
<223> OTHER INFORMATION: Wherein Xaa is either Phe or His

<400> SEQUENCE: 236

Ser Ser Tyr Ala Gly Ser Xaa Xaa Xaa Val Val
1               5                   10

<210> SEQ ID NO 237
```

```
<211> LENGTH: 11
<212> TYPE: PRT
<213> ORGANISM: Artificial Sequence
<220> FEATURE:
<223> OTHER INFORMATION: VL CDR3 Consensus Sequence
<220> FEATURE:
<221> NAME/KEY: MISC_FEATURE
<222> LOCATION: (1)..(1)
<223> OTHER INFORMATION: Wherein Xaa is either Ala or Gly
<220> FEATURE:
<221> NAME/KEY: MISC_FEATURE
<222> LOCATION: (2)..(2)
<223> OTHER INFORMATION: Wherein Xaa is either Thr or Ala
<220> FEATURE:
<221> NAME/KEY: MISC_FEATURE
<222> LOCATION: (5)..(5)
<223> OTHER INFORMATION: Wherein Xaa is either Tyr or Ser
<220> FEATURE:
<221> NAME/KEY: MISC_FEATURE
<222> LOCATION: (8)..(8)
<223> OTHER INFORMATION: Wherein Xaa is either Thr or Arg
<220> FEATURE:
<221> NAME/KEY: MISC_FEATURE
<222> LOCATION: (9)..(9)
<223> OTHER INFORMATION: Wherein Xaa is either Ala or Met
<220> FEATURE:
<221> NAME/KEY: MISC_FEATURE
<222> LOCATION: (10)..(10)
<223> OTHER INFORMATION: Wherein Xaa is either Val or Trp

<400> SEQUENCE: 237

Xaa Xaa Trp Asp Xaa Ser Leu Xaa Xaa Xaa Val
1               5                   10

<210> SEQ ID NO 238
<211> LENGTH: 11
<212> TYPE: PRT
<213> ORGANISM: Artificial Sequence
<220> FEATURE:
<223> OTHER INFORMATION: VL CDR3 Consensus Sequence
<220> FEATURE:
<221> NAME/KEY: MISC_FEATURE
<222> LOCATION: (1)..(1)
<223> OTHER INFORMATION: Wherein Xaa is either Ala or Gly
<220> FEATURE:
<221> NAME/KEY: MISC_FEATURE
<222> LOCATION: (2)..(2)
<223> OTHER INFORMATION: Wherein Xaa is either Thr or Ala
<220> FEATURE:
<221> NAME/KEY: MISC_FEATURE
<222> LOCATION: (5)..(5)
<223> OTHER INFORMATION: Wherein Xaa is either Tyr or Ser
<220> FEATURE:
<221> NAME/KEY: MISC_FEATURE
<222> LOCATION: (8)..(8)
<223> OTHER INFORMATION: Wherein Xaa is Thr, Arg, or Ser
<220> FEATURE:
<221> NAME/KEY: MISC_FEATURE
<222> LOCATION: (9)..(9)
<223> OTHER INFORMATION: Wherein Xaa is either Ala or Met
<220> FEATURE:
<221> NAME/KEY: MISC_FEATURE
<222> LOCATION: (10)..(10)
<223> OTHER INFORMATION: Wherein Xaa is either Val or Trp

<400> SEQUENCE: 238

Xaa Xaa Trp Asp Xaa Ser Leu Xaa Xaa Xaa Val
1               5                   10

<210> SEQ ID NO 239
<211> LENGTH: 11
<212> TYPE: PRT
<213> ORGANISM: Artificial Sequence
<220> FEATURE:
<223> OTHER INFORMATION: VL CDR3 Consensus Sequence
```

```
<220> FEATURE:
<221> NAME/KEY: MISC_FEATURE
<222> LOCATION: (1)..(1)
<223> OTHER INFORMATION: Wherein Xaa is either Ala or Gly
<220> FEATURE:
<221> NAME/KEY: MISC_FEATURE
<222> LOCATION: (5)..(5)
<223> OTHER INFORMATION: Wherein Xaa is either Tyr or Ser
<220> FEATURE:
<221> NAME/KEY: MISC_FEATURE
<222> LOCATION: (8)..(8)
<223> OTHER INFORMATION: Wherein Xaa is either Thr or Ser
<220> FEATURE:
<221> NAME/KEY: MISC_FEATURE
<222> LOCATION: (10)..(10)
<223> OTHER INFORMATION: Wherein Xaa is either Val or Trp

<400> SEQUENCE: 239

Xaa Thr Trp Asp Xaa Ser Leu Xaa Ala Xaa Val
1               5                   10

<210> SEQ ID NO 240
<211> LENGTH: 11
<212> TYPE: PRT
<213> ORGANISM: Artificial Sequence
<220> FEATURE:
<223> OTHER INFORMATION: VL CDR3 Consensus Sequence
<220> FEATURE:
<221> NAME/KEY: MISC_FEATURE
<222> LOCATION: (2)..(2)
<223> OTHER INFORMATION: Wherein Xaa is either Ala or Thr
<220> FEATURE:
<221> NAME/KEY: MISC_FEATURE
<222> LOCATION: (8)..(8)
<223> OTHER INFORMATION: Wherein Xaa is either Arg or Ser
<220> FEATURE:
<221> NAME/KEY: MISC_FEATURE
<222> LOCATION: (9)..(9)
<223> OTHER INFORMATION: Wherein Xaa is either Met or Ala

<400> SEQUENCE: 240

Gly Xaa Trp Asp Ser Ser Leu Xaa Xaa Trp Val
1               5                   10

<210> SEQ ID NO 241
<211> LENGTH: 8
<212> TYPE: PRT
<213> ORGANISM: Artificial Sequence
<220> FEATURE:
<223> OTHER INFORMATION: Synthetic sequence - antigenic tag

<400> SEQUENCE: 241

Asp Tyr Lys Asp Asp Asp Asp Lys
1               5

<210> SEQ ID NO 242
<211> LENGTH: 9
<212> TYPE: PRT
<213> ORGANISM: Artificial Sequence
<220> FEATURE:
<223> OTHER INFORMATION: Synthetic sequence - hemagglutinin

<400> SEQUENCE: 242

Tyr Pro Tyr Asp Val Pro Asp Tyr Ala
1               5
```

ANTI-CCR8 ANTIBODIES AND USES THEREOF

CROSS REFERENCE TO RELATED APPLICATIONS

This PCT application claims the priority benefit of U.S. Provisional Application Nos. 62/957,758, filed Jan. 6, 2020; 62/985,152, filed Mar. 4, 2020; and 63/198,803, filed Nov. 13, 2020, each of which is incorporated herein by reference in its entirety.

REFERENCE TO SEQUENCE LISTING

The content of the electronically submitted sequence listing (Name: 4416_0100004_Seglisting_ST25; Size: 91,925 bytes; Date of Creation: Jan. 6, 2021) filed with this application is incorporated herein by reference in its entirety.

FIELD OF THE DISCLOSURE

The present disclosure provides antibodies and antigen-binding portions thereof that specifically bind human CCR8.

BACKGROUND OF THE DISCLOSURE

Immunotherapy is a rapidly advancing and very promising treatment for various forms of cancer, with many recent successes. However, some patients have limited to no response to current immunotherapies, and others exhibit relapse following initial responsiveness.

The human immune system includes checks and balances that serve to stop an overactive immune system from harming the body. Regulatory T cells ("Tregs") have a vital role in maintaining a functional immune system by suppressing the immune response. However, the ability of Tregs, and especially tumor infiltrating Tregs, to dampen an immune response can block a natural immune response to a tumor.

In part because of the essential role of immune cells, it has been very difficult to generate therapies that specifically target Tregs, and more particularly, tumor infiltrating Tregs. Thus, there remains a need for therapies that are specifically able to target and inhibit the activity of Tregs in the tumor microenvironment.

SUMMARY OF THE DISCLOSURE

Certain aspects of the present disclosure are directed to an antibody or an antigen-binding portion thereof that specifically binds to one or more amino acids within the N-terminal extracellular domain of human CCR8. In some aspects, the antibody is capable of: (a) enhancing an immune response to a tumor; (b) reducing, depleting, or killing tumor infiltrating regulatory T ("Treg") cells; (c) inducing internalization of CCR8 in tumor infiltrating regulatory T ("Treg") cells; (d) activating NK cells; (e) inducing NK cell mediated killing of tumor infiltrating regulatory T ("Treg") cells; (f) binding to cynomolgus monkey ("cyno") CCR8; (g) binding to human CCR8 with $K_D$ of 10 nM or less as measured by BIACORE™; or (h) any combination thereof.

In some aspects, the N-terminal extracellular domain of human CCR8 comprises the amino acid sequence set forth in SEQ ID NO: 172. In some aspects, the antibody binds to at least two, at least three, at least four, at least five, at least six, at least seven, at least eight, at least nine, or at least ten amino acids set forth in SEQ ID NO: 172. In some aspects, the antibody binds to at least two, at least three, at least four, at least five, at least six, at least seven, at least eight, at least nine, or at least ten contiguous amino acids set forth in SEQ ID NO: 172. In some aspects, the antibody binds to an amino acid sequence selected from SEQ ID NOs: 180-200.

In some aspects, the antibody further binds cyno CCR8. In some aspects, the antibody binds human CCR8 with a $K_D$ of 10 nM or less as measured by BIACORE™. In some aspects, the antibody binds human CCR8 with a $K_D$ of 1 nM or less as measured by BIACORE™.

In some aspects, the antibody induces antibody-dependent cellular cytotoxicity (ADCC) in a subject following administration of the anti-CCR8 antibody. In some aspects, the ADCC comprises an EC50 of 1 µg/mL or less following the administration of the antibody or antigen-binding portion thereof. In some aspects, the ADCC comprises an EC50 of 0.1 µg/mL or less following the administration of the antibody or antigen-binding portion thereof.

In some aspects, the antibody is capable of inducing activation of NK cells. In some aspects, the antibody is capable of inducing upregulation of 4-1BB, ICAM-1, or both 4-1BB and ICAM-1 on the surface of NK cells. In some aspects, the antibody is capable of inducing down-regulation of CD16 on the surface of NK cells in the subject.

In some aspects, the antibody is capable of inducing NK cell mediated killing of tumor infiltrating $T_{reg}$ cells in the subject. In some aspects, the antibody induces depletion in the number of tumor infiltrating $T_{reg}$ cells in a subject following administration of the antibody or antigen-binding portion thereof, relative to the number of tumor infiltrating $T_{reg}$ cells prior to the administration. In some aspects, the number of tumor infiltrating $T_{reg}$ cells is depleted by at least about 10%, at least about 15%, at least about 20%, at least about 25%, at least about 30%, at least about 35%, at least about 40%, at least about 45%, or at least about 50% relative to the number of tumor infiltrating $T_{reg}$ cells prior to the administration. In some aspects, the antibody induces internalization of CCR8 by tumor infiltrating $T_{reg}$ cells.

In some aspects, the antibody comprises a variable heavy (VH) chain, comprising a VH complementarity-determining region (CDR) 1, a VH CDR2, and a VH CDR3; wherein the VH CDR3 comprises an amino acid sequence selected from the amino acid sequence set forth in SEQ ID NOs: 7, 17, 27, 37, 47, 57, 67, 77, 87, 97, 107, 117, 127, 137, 147, 157, and 167.

In some aspects, the VH CDR2 comprises an amino acid sequence selected from the amino acid sequence set forth in SEQ ID NOs: 6, 16, 26, 36, 46, 56, 66, 76, 86, 96, 106, 116, 126, 136, 146, 156, and 166.

In some aspects, the VH CDR1 comprises an amino acid sequence selected from the amino acid sequence set forth in SEQ ID NOs: 5, 15, 25, 35, 45, 55, 65, 75, 85, 95, 105, 115, 125, 135, 145, 155, and 165.

In some aspects, the VL CDR3 comprises an amino acid sequence selected from the amino acid sequence set forth in SEQ ID NOs: 10, 20, 30, 40, 50, 60, 70, 80, 90, 100, 110, 120, 130, 140, 150, 160, and 170.

In some aspects, the VL CDR2 comprises an amino acid sequence selected from the amino acid sequence set forth in SEQ ID NOs: 9, 19, 29, 39, 49, 59, 69, 79, 89, 99, 109, 119, 129, 139, 149, 159, and 169.

In some aspects, the VL CDR1 comprises an amino acid sequence selected from the amino acid sequence set forth in SEQ ID NOs: 8, 18, 28, 38, 48, 58, 68, 78, 88, 98, 108, 118, 128, 138, 148, 158, and 168.

In some aspects, the antibody does not bind cyno CCR8.
In some aspects, the antibody comprises a variable heavy (VH) chain, comprising a VH complementarity-determining region (CDR) 1, a VH CDR2, and a VH CDR3; wherein the VH CDR3 comprises an amino acid sequence selected from the amino acid sequence set forth in SEQ ID NOs: 47, 107, 117, 137, and 147.

In some aspects, the VH CDR2 comprises an amino acid sequence selected from the amino acid sequence set forth in SEQ ID NOs: 46, 106, 116, 136, and 146.

In some aspects, the VH CDR1 comprises an amino acid sequence selected from the amino acid sequence set forth in SEQ ID NOs: 45, 105, 115, 135, and 145.

In some aspects, the VL CDR3 comprises an amino acid sequence selected from the amino acid sequence set forth in SEQ ID NOs: 50, 110, 120, 140, and 150.

In some aspects, the VL CDR2 comprises an amino acid sequence selected from the amino acid sequence set forth in SEQ ID NOs: 49, 109, 119, 139, and 149.

In some aspects, the VL CDR1 comprises an amino acid sequence selected from the amino acid sequence set forth in SEQ ID NOs: 48, 108, 118, 138, and 148.

In some aspects, the antibody comprises: (a) a VH CDR1 comprising the amino acid sequence set forth in SEQ ID NO: 45, a VH CDR2 comprising the amino acid sequence set forth in SEQ ID NO: 46, a VH CDR3 comprising the amino acid sequence set forth in SEQ ID NO: 47, a VL CDR1 comprising the amino acid sequence set forth in SEQ ID NO: 48, a VL CDR2 comprising the amino acid sequence set forth in SEQ ID NO: 49, and a VL CDR3 comprising the amino acid sequence set forth in SEQ ID NO: 50; (b) a VH CDR1 comprising the amino acid sequence set forth in SEQ ID NO: 105, a VH CDR2 comprising the amino acid sequence set forth in SEQ ID NO: 106, a VH CDR3 comprising the amino acid sequence set forth in SEQ ID NO: 107, a VL CDR1 comprising the amino acid sequence set forth in SEQ ID NO: 108, a VL CDR2 comprising the amino acid sequence set forth in SEQ ID NO: 109, and a VL CDR3 comprising the amino acid sequence set forth in SEQ ID NO: 110; (c) a VH CDR1 comprising the amino acid sequence set forth in SEQ ID NO: 115, a VH CDR2 comprising the amino acid sequence set forth in SEQ ID NO: 116, a VH CDR3 comprising the amino acid sequence set forth in SEQ ID NO: 117, a VL CDR1 comprising the amino acid sequence set forth in SEQ ID NO: 118, a VL CDR2 comprising the amino acid sequence set forth in SEQ ID NO: 119, and a VL CDR3 comprising the amino acid sequence set forth in SEQ ID NO: 120; (d) a VH CDR1 comprising the amino acid sequence set forth in SEQ ID NO: 135, a VH CDR2 comprising the amino acid sequence set forth in SEQ ID NO: 136, a VH CDR3 comprising the amino acid sequence set forth in SEQ ID NO: 137, a VL CDR1 comprising the amino acid sequence set forth in SEQ ID NO: 138, a VL CDR2 comprising the amino acid sequence set forth in SEQ ID NO: 139, and a VL CDR3 comprising the amino acid sequence set forth in SEQ ID NO: 140; or (e) a VH CDR1 comprising the amino acid sequence set forth in SEQ ID NO: 145, a VH CDR2 comprising the amino acid sequence set forth in SEQ ID NO: 146, a VH CDR3 comprising the amino acid sequence set forth in SEQ ID NO: 147, a VL CDR1 comprising the amino acid sequence set forth in SEQ ID NO: 148, a VL CDR2 comprising the amino acid sequence set forth in SEQ ID NO: 149, and a VL CDR3 comprising the amino acid sequence set forth in SEQ ID NO: 150.

In some aspects, the VH chain comprises an amino acid sequence selected from the amino acid sequence set forth in SEQ ID NOs: 41, 101, 111, 131, and 141. In some aspects, the VL chain comprises an amino acid sequence selected from the amino acid sequence set forth in SEQ ID NOs: 42, 102, 112, 132, and 142.

In some aspects, the antibody comprises: (a) a VH chain comprising the amino acid sequence set forth in SEQ ID NO: 41 and a VL chain comprising the amino acid sequence set forth in SEQ ID NO: 42; (b) a VH chain comprising the amino acid sequence set forth in SEQ ID NO: 101 and a VL chain comprising the amino acid sequence set forth in SEQ ID NO: 102; (c) a VH chain comprising the amino acid sequence set forth in SEQ ID NO: 111 and a VL chain comprising the amino acid sequence set forth in SEQ ID NO: 112; (d) a VH chain comprising the amino acid sequence set forth in SEQ ID NO: 131 and a VL chain comprising the amino acid sequence set forth in SEQ ID NO: 132; or (e) a VH chain comprising the amino acid sequence set forth in SEQ ID NO: 141 and a VL chain comprising the amino acid sequence set forth in SEQ ID NO: 142.

In some aspects, the antibody binds human CCR8 and cyno CCR8.

In some aspects, the antibody comprises a variable heavy (VH) chain, comprising a VH complementarity-determining region (CDR) 1, a VH CDR2, and a VH CDR3; wherein the VH CDR3 comprises an amino acid sequence selected from the amino acid sequence set forth in SEQ ID NOs: 7, 17, 27, 37, 57, 67, 77, 87, 97, 127, 157, and 167.

In some aspects, the VH CDR2 comprises an amino acid sequence selected from the amino acid sequence set forth in SEQ ID NOs: 6, 16, 26, 36, 56, 66, 76, 86, 96, 126, 156, and 166.

In some aspects, the VH CDR1 comprises an amino acid sequence selected from the amino acid sequence set forth in SEQ ID NOs: 5, 15, 25, 35, 55, 65, 75, 85, 95, 125, 155, and 165.

In some aspects, the VL CDR3 comprises an amino acid sequence selected from the amino acid sequence set forth in SEQ ID NOs: 10, 20, 30, 40, 60, 70, 80, 90, 100, 130, 160, and 170.

In some aspects, the VL CDR2 comprises an amino acid sequence selected from the amino acid sequence set forth in SEQ ID NOs: 9, 19, 29, 39, 59, 69, 79, 89, 99, 129, 159, and 169.

In some aspects, the VL CDR1 comprises an amino acid sequence selected from the amino acid sequence set forth in SEQ ID NOs: 8, 18, 28, 38, 58, 68, 78, 88, 98, 128, 158, and 168.

In some aspects, the antibody comprises: (a) a VH CDR1 comprising the amino acid sequence set forth in SEQ ID NO: 5, a VH CDR2 comprising the amino acid sequence set forth in SEQ ID NO: 6, a VH CDR3 comprising the amino acid sequence set forth in SEQ ID NO: 7, a VL CDR1 comprising the amino acid sequence set forth in SEQ ID NO: 8, a VL CDR2 comprising the amino acid sequence set forth in SEQ ID NO: 9, and a VL CDR3 comprising the amino acid sequence set forth in SEQ ID NO: 10; (b) a VH CDR1 comprising the amino acid sequence set forth in SEQ ID NO: 15, a VH CDR2 comprising the amino acid sequence set forth in SEQ ID NO: 16, a VH CDR3 comprising the amino acid sequence set forth in SEQ ID NO: 17, a VL CDR1 comprising the amino acid sequence set forth in SEQ ID NO: 18, a VL CDR2 comprising the amino acid sequence set forth in SEQ ID NO: 19, and a VL CDR3 comprising the amino acid sequence set forth in SEQ ID NO: 20; (c) a VH CDR1 comprising the amino acid sequence set forth in SEQ ID NO: 25, a VH CDR2 comprising the amino acid sequence set forth in SEQ ID NO: 26, a VH CDR3 comprising the amino acid sequence set forth in SEQ ID NO: 27, a VL CDR1 comprising the amino acid sequence set forth in SEQ ID NO: 28, a VL CDR2 comprising the amino acid sequence set forth in SEQ ID NO: 29, and a VL CDR3 comprising the amino acid sequence set forth in SEQ ID NO: 30; (d) a VH CDR1 comprising the amino acid sequence set forth in SEQ ID NO: 35, a VH CDR2 comprising the amino acid sequence set forth in SEQ ID NO: 36, a VH CDR3 comprising the amino acid sequence set forth in SEQ ID NO: 37, a VL CDR1 comprising the amino acid sequence set forth in SEQ ID NO: 38, a VL CDR2 comprising the amino acid sequence set forth in SEQ ID NO: 39, and a VL CDR3 comprising the amino acid sequence set forth in SEQ ID NO: 40; (e) a VH CDR1 comprising the amino acid sequence set forth in SEQ ID NO: 55, a VH CDR2 comprising the amino acid sequence set forth in SEQ ID NO: 56, a VH CDR3 comprising the amino acid sequence set forth in SEQ ID NO: 57, a VL CDR1 comprising the amino acid sequence set forth in SEQ ID NO: 58, a VL CDR2 comprising the amino acid sequence set forth in SEQ ID NO: 59, and a VL CDR3 comprising the amino acid sequence set forth in SEQ ID NO: 60; (f) a VH CDR1 comprising the amino acid sequence set forth in SEQ ID NO: 65, a VH CDR2 comprising the amino acid sequence set forth in SEQ ID NO: 66, a VH CDR3 comprising the amino acid sequence set forth in SEQ ID NO: 67, a VL CDR1 comprising the amino acid sequence set forth in SEQ ID NO: 68, a VL CDR2 comprising the amino acid sequence set forth in SEQ ID NO: 69, and a VL CDR3 comprising the amino acid sequence set forth in SEQ ID NO: 70; (g) a VH CDR1 comprising the amino acid sequence set forth in SEQ ID NO: 75, a VH CDR2 comprising the amino acid sequence set forth in SEQ ID NO: 76, a VH CDR3 comprising the amino acid sequence set forth in SEQ ID NO: 77, a VL CDR1 comprising the amino acid sequence set forth in SEQ ID NO: 78, a VL CDR2 comprising the amino acid sequence set forth in SEQ ID NO: 79, and a VL CDR3 comprising the amino acid sequence set forth in SEQ ID NO: 80; (h) a VH CDR1 comprising the amino acid sequence set forth in SEQ ID NO: 85, a VH CDR2 comprising the amino acid sequence set forth in SEQ ID NO: 86, a VH CDR3 comprising the amino acid sequence set forth in SEQ ID NO: 87, a VL CDR1 comprising the amino acid sequence set forth in SEQ ID NO: 88, a VL CDR2 comprising the amino acid sequence set forth in SEQ ID NO: 89, and a VL CDR3 comprising the amino acid sequence set forth in SEQ ID NO: 90; (i) a VH CDR1 comprising the amino acid sequence set forth in SEQ ID NO: 95, a VH CDR2 comprising the amino acid sequence set forth in SEQ ID NO: 96, a VH CDR3 comprising the amino acid sequence set forth in SEQ ID NO: 97, a VL CDR1 comprising the amino acid sequence set forth in SEQ ID NO: 98, a VL CDR2 comprising the amino acid sequence set forth in SEQ ID NO: 99, and a VL CDR3 comprising the amino acid sequence set forth in SEQ ID NO: 100; (j) a VH CDR1 comprising the amino acid sequence set forth in SEQ ID NO: 125, a VH CDR2 comprising the amino acid sequence set forth in SEQ ID NO: 126, a VH CDR3 comprising the amino acid sequence set forth in SEQ ID NO: 127, a VL CDR1 comprising the amino acid sequence set forth in SEQ ID NO: 128, a VL CDR2 comprising the amino acid sequence set forth in SEQ ID NO: 129, and a VL CDR3 comprising the amino acid sequence set forth in SEQ ID NO: 130; (k) a VH CDR1 comprising the amino acid sequence set forth in SEQ ID NO: 155, a VH CDR2 comprising the amino acid sequence set forth in SEQ ID NO: 156, a VH CDR3 comprising the amino acid sequence set forth in SEQ ID NO: 157, a VL CDR1 comprising the amino acid sequence set forth in SEQ ID NO: 158, a VL CDR2 comprising the amino acid sequence set forth in SEQ ID NO: 159, and a VL CDR3 comprising the amino acid sequence set forth in SEQ ID NO: 160; or (1) a VH CDR1 comprising the amino acid sequence set forth in SEQ ID NO: 165, a VH CDR2 comprising the amino acid sequence set forth in SEQ ID NO: 166, a VH CDR3 comprising the amino acid sequence set forth in SEQ ID NO: 167, a VL CDR1 comprising the amino acid sequence set forth in SEQ ID NO: 168, a VL CDR2 comprising the amino acid sequence set forth in SEQ ID NO: 169, and a VL CDR3 comprising the amino acid sequence set forth in SEQ ID NO: 170.

In some aspects, the VH chain comprises an amino acid sequence selected from the amino acid sequence set forth in SEQ ID NOs: 1, 11, 21, 31, 51, 61, 71, 81, 91, 121, 151, and 161. In some aspects, the VL chain comprises an amino acid sequence selected from the amino acid sequence set forth in SEQ ID NOs: 2, 12, 22, 32, 52, 62, 72, 82, 92, 122, 152, and 162.

In some aspects, the antibody comprises: (a) a VH chain comprising the amino acid sequence set forth in SEQ ID NO: 1 and a VL chain comprising the amino acid sequence set forth in SEQ ID NO: 2; (b) a VH chain comprising the amino acid sequence set forth in SEQ ID NO: 11 and a VL chain comprising the amino acid sequence set forth in SEQ ID NO: 12; (c) a VH chain comprising the amino acid sequence set forth in SEQ ID NO: 21 and a VL chain comprising the amino acid sequence set forth in SEQ ID NO: 22; (d) a VH chain comprising the amino acid sequence set forth in SEQ ID NO: 31 and a VL chain comprising the amino acid sequence set forth in SEQ ID NO: 32; (e) a VH chain comprising the amino acid sequence set forth in SEQ ID NO: 51 and a VL chain comprising the amino acid sequence set forth in SEQ ID NO: 52; (f) a VH chain comprising the amino acid sequence set forth in SEQ ID NO: 61 and a VL chain comprising the amino acid sequence set forth in SEQ ID NO: 62; (g) a VH chain comprising the amino acid sequence set forth in SEQ ID NO: 71 and a VL chain comprising the amino acid sequence set forth in SEQ ID NO: 72; (h) a VH chain comprising the amino acid sequence set forth in SEQ ID NO: 81 and a VL chain comprising the amino acid sequence set forth in SEQ ID NO: 82; (i) a VH chain comprising the amino acid sequence set forth in SEQ ID NO: 91 and a VL chain comprising the amino acid sequence set forth in SEQ ID NO: 92; (j) a VH chain comprising the amino acid sequence set forth in SEQ ID NO: 121 and a VL chain comprising the amino acid sequence set forth in SEQ ID NO: 122; (k) a VH chain comprising the amino acid sequence set forth in SEQ ID NO: 151 and a VL chain comprising the amino acid sequence set forth in SEQ ID NO: 152; or (1) a VH chain comprising the amino acid sequence set forth in SEQ ID NO: 161 and a VL chain comprising the amino acid sequence set forth in SEQ ID NO: 162.

In some aspects, the antibody is a human antibody, a humanized antibody, or a chimeric antibody. In some aspects, the antibody comprises a single-chain variable fragment (scFv) of an antibody.

In some aspects, the antibody or the antigen-binding portion thereof is afucosylated.

In some aspects, the antibody is a bispecific antibody, a bispecific T cell engager (BiTE), a multispecific antibody, a biparatopic antibody, an immunoconjugate, an antibody drug conjugate, or any combination thereof.

Certain aspects of the present disclosure are directed to a bispecific antibody comprising an antibody or an antigen-binding portion thereof disclosed herein.

Certain aspects of the present disclosure are directed to a BiTe comprising an antibody or an antigen-binding portion thereof disclosed herein.

Certain aspects of the present disclosure are directed to a multispecific antibody comprising an antibody or an antigen-binding portion thereof disclosed herein.

Certain aspects of the present disclosure are directed to a biparatopic antibody comprising an antibody or an antigen-binding portion thereof disclosed herein.

In some aspects, the bispecific antibody, BiTe, multispecific antibody, or biparatopic antibody comprises a first VH domain, comprising a first VH CDR1, a first VH CDR2, and a first VH CDR3; a first VL domain, comprising a first VL CDR1, a first VL CDR2, and a first VL CDR3; a second VH domain, comprising a second VH CDR1, a second VH CDR2, and a second VH CDR3; and a second VL domain, comprising a second VL CDR1, a second VL CDR2, and a second VL CDR3; wherein (a) the first VH CDR1 comprises an amino acid sequence selected from the amino acid sequence set forth in SEQ ID NOs: 45, 105, 115, 135, and 145; (b) the first VH CDR2 comprises an amino acid sequence selected from the amino acid sequence set forth in SEQ ID NOs: 46, 106, 116, 136, and 146; and (c) the first VH CDR3 comprises an amino acid sequence selected from the amino acid sequence set forth in SEQ ID NOs: 47, 107, 117, 137, and 147.

In some aspects, (a) the first VL CDR1 comprises an amino acid sequence selected from the amino acid sequence set forth in SEQ ID NOs: 48, 108, 118, 138, and 148; (b) the first VL CDR2 comprises an amino acid sequence selected from the amino acid sequence set forth in SEQ ID NOs: 49, 109, 119, 139, and 149; and (c) the first VL CDR3 comprises an amino acid sequence selected from the amino acid sequence set forth in SEQ ID NOs: 50, 110, 120, 140, and 150. In some aspects, (a) the second VH CDR1 comprises an amino acid sequence selected from the amino acid sequence set forth in SEQ ID NOs: 5, 15, 25, 35, 55, 65, 75, 85, 95, 125, 155, and 165; (b) the second VH CDR2 comprises an amino acid sequence selected from the amino acid sequence set forth in SEQ ID NOs: 6, 16, 26, 36, 56, 66, 76, 86, 96, 126, 156, and 166; and (c) the second VH CDR3 comprises an amino acid sequence selected from the amino acid sequence set forth in SEQ ID NOs: 7, 17, 27, 37, 57, 67, 77, 87, 97, 127, 157, and 167. In some aspects, (a) the second VL CDR1 comprises an amino acid sequence selected from the amino acid sequence set forth in SEQ ID NOs: 8, 18, 28, 38, 58, 68, 78, 88, 98, 128, 158, and 168; (b) the second VL CDR2 comprises an amino acid sequence selected from the amino acid sequence set forth in SEQ ID NOs: 9, 19, 29, 39, 59, 69, 79, 89, 99, 129, 159, and 169; and (c) the second VL CDR3 comprises an amino acid sequence selected from the amino acid sequence set forth in SEQ ID NOs: 10, 20, 30, 40, 60, 70, 80, 90, 100, 130, 160, and 170.

Certain aspects of the present disclosure are directed to an immunoconjugate comprising an antibody or antigen-binding portion thereof disclosed herein. In some aspects, the immunoconjugate is an antibody-drug conjugate.

Certain aspects of the present disclosure are directed to a chimeric antigen receptor (CAR) comprising an antibody or antigen-binding portion thereof disclosed herein.

Certain aspects of the present disclosure are directed to a T cell receptor (TCR) comprising an antibody or antigen-binding portion thereof disclosed herein.

Certain aspects of the present disclosure are directed to a nucleic acid molecule or a set of nucleic acid molecules encoding the antibody or antigen-binding portion thereof disclosed herein, a bispecific antibody disclosed herein, a BiTE disclosed herein, a multispecific antibody disclosed herein, a biparatopic antibody disclosed herein, an immunoconjugate disclosed herein, a CAR disclosed herein, or a TCR disclosed herein.

Certain aspects of the present disclosure are directed to a vector or a set of vectors comprising a nucleic acid molecule or a set of nucleic acid molecules disclosed herein.

Certain aspects of the present disclosure are directed to a cell comprising a CAR disclosed herein, a TCR disclosed herein, a nucleic acid molecule or a set of nucleic acid molecules disclosed herein, or a vector or a set of vectors disclosed herein. In some aspects, the cell is a host cell. In some aspects, the cell is an immune cell. In some aspects, the cell is a T cell.

Certain aspects of the present disclosure are directed to a pharmaceutical composition comprising an antibody or an antigen-binding portion thereof disclosed herein, a bispecific antibody disclosed herein, a bispecific antibody disclosed herein, a BiTE disclosed herein, a multispecific antibody disclosed herein, a biparatopic antibody disclosed herein, an immunoconjugate disclosed herein, a CAR disclosed herein, a TCR disclosed herein, a nucleic acid molecule or a set of nucleic acid molecules disclosed herein, a vector or a set of vectors disclosed herein, or a cell disclosed herein, and a pharmaceutically acceptable carrier.

Certain aspects of the present disclosure are directed to a method of treating a tumor in a subject in need thereof, comprising administering to the subject an antibody or an antigen-binding portion thereof disclosed herein, a bispecific antibody disclosed herein, a bispecific antibody disclosed herein, a BiTE disclosed herein, a multispecific antibody disclosed herein, a biparatopic antibody disclosed herein, an immunoconjugate disclosed herein, a CAR disclosed herein, a TCR disclosed herein, a nucleic acid molecule or a set of nucleic acid molecules disclosed herein, a vector or a set of vectors disclosed herein, a cell disclosed herein, or a pharmaceutical composition disclosed herein.

Certain aspects of the present disclosure are directed to a method of reducing, depleting, or killing tumor infiltrating regulatory T ("$T_{reg}$") cells, comprising contacting Treg cells with an antibody or an antigen-binding portion thereof disclosed herein, a bispecific antibody disclosed herein, a bispecific antibody disclosed herein, a BiTE disclosed herein, a multispecific antibody disclosed herein, a biparatopic antibody disclosed herein, an immunoconjugate disclosed herein, a CAR disclosed herein, a TCR disclosed herein, a nucleic acid molecule or a set of nucleic acid molecules disclosed herein, a vector or a set of vectors disclosed herein, a cell disclosed herein, or a pharmaceutical composition disclosed herein.

Certain aspects of the present disclosure are directed to a method of activating NK cells or inducing NK cell mediated killing of tumor infiltrating regulatory T ("$T_{reg}$") cells, comprising contacting Treg cells with an antibody or an antigen-binding portion thereof disclosed herein, a bispecific antibody disclosed herein, a bispecific antibody disclosed herein, a BiTE disclosed herein, a multispecific antibody disclosed herein, a biparatopic antibody disclosed herein, an immunoconjugate disclosed herein, a CAR disclosed herein, a TCR disclosed herein, a nucleic acid molecule or a set of nucleic acid molecules disclosed herein, a vector or a set of vectors disclosed herein, a cell disclosed herein, or a pharmaceutical composition disclosed herein.

In some aspects, the contacting is in vitro or ex vivo. In some aspects, the contacting is in vivo.

In some aspects, the antibody or antigen-binding portion thereof induces activation of NK cells. In some aspects, the antibody or antigen-binding portion thereof induces upregulation of 4-1BB, ICAM-1, or both 4-1BB and ICAM-1 on the surface of NK cells.

In some aspects, the antibody or antigen-binding portion thereof induces down-regulation of CD16 on the surface of NK cells. In some aspects, the antibody or antigen-binding portion thereof induces NK cell mediated killing of tumor infiltrating $T_{reg}$ cells. In some aspects, the antibody or antigen-binding portion thereof depletes the number of tumor infiltrating $T_{reg}$ cells relative to the number of tumor infiltrating $T_{reg}$ cells in the absence of the antibody or antigen binding portion thereof. In some aspects, the antibody or antigen-binding portion thereof depletes the number of tumor infiltrating $T_{reg}$ cells by at least about 10%, at least about 15%, at least about 20%, at least about 25%, at least about 30%, at least about 35%, at least about 40%, at least about 45%, or at least about 50% relative to the number of tumor infiltrating $T_{reg}$ cells in the absence of the antibody or antigen binding portion thereof. In some aspects, the antibody or antigen-binding portion thereof induces internalization of CCR8 by tumor infiltrating $T_{reg}$ cells.

In some aspects, the tumor is selected from the group consisting of Kaposi's sarcoma, leukemia, acute lymphocytic leukemia, acute myelocytic leukemia, myeloblasts promyelocyte myelomonocytic monocytic erythroleukemia, chronic leukemia, chronic myelocytic (granulocytic) leukemia, chronic lymphocytic leukemia, mantle cell lymphoma, primary central nervous system lymphoma, Burkitt's lymphoma and marginal zone B cell lymphoma, Polycythemia vera Lymphoma, Hodgkin's disease, non-Hodgkin's disease, multiple myeloma, Waldenstrom's macroglobulinemia, heavy chain disease, solid tumors, sarcomas, and carcinomas, fibrosarcoma, myxosarcoma, liposarcoma, chrondrosarcoma, osteogenic sarcoma, osteosarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon sarcoma, colorectal carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatocellular carcinoma (HCC), hepatoma, bile duct carcinoma, choriocarcinoma, seminoma, embryonal carcinoma, Wilm's tumor, cervical cancer, uterine cancer, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, retinoblastoma, nasopharyngeal carcinoma, esophageal carcinoma, basal cell carcinoma, biliary tract cancer, bladder cancer, bone cancer, brain and central nervous system (CNS) cancer, cervical cancer, choriocarcinoma, colorectal cancers, connective tissue cancer, cancer of the digestive system, endometrial cancer, esophageal cancer, eye cancer, head and neck cancer, gastric cancer, intraepithelial neoplasm, kidney cancer, larynx cancer, liver cancer, lung cancer (small cell, large cell), melanoma, neuroblastoma; oral cavity cancer (for example lip, tongue, mouth and pharynx), ovarian cancer, pancreatic cancer, retinoblastoma, rhabdomyosarcoma, rectal cancer; cancer of the respiratory system, sarcoma, skin cancer, stomach cancer, testicular cancer, thyroid cancer, uterine cancer, and cancer of the urinary system, or any combination thereof. In some aspects, the tumor is refractory or relapsed. In some aspects, the tumor is advanced, locally advanced, or metastatic.

In some aspects, the method further comprises administering an additional anticancer agent. In some aspects, the additional anticancer agent is selected from a small molecule, a polypeptide, a radiation therapy, a surgery, and a combination thereof. In some aspects, the additional anticancer agent comprises a chemotherapy. In some aspects, the chemotherapy comprises a platinum-based chemotherapy. In some aspects, the additional anticancer agent comprises a PD-1 antagonist, a PD-L1 inhibitor, a TIM-3 inhibitor, a LAG-3 inhibitor, a TIGIT inhibitor, a CD112R inhibitor, a TAM inhibitor, a STING agonist, a 4-1BB agonist, a CCL22 inhibitor, an agent that induces NK cell activation or a combination thereof. In some aspects, the additional anticancer agent comprises a PD-1 antagonist. In some aspects, the PD-1 antagonist is selected from the group consisting of PDR001, nivolumab, pembrolizumab, pidilizumab, MEDI680, REGN2810, TSR-042, PF-06801591, and AMP-224. In some aspects, the additional anticancer agent comprises a PD-L1 inhibitor. In some aspects, the PD-L1 inhibitor is selected from the group consisting of FAZ053, Atezolizumab, Avelumab, Durvalumab, and BMS-936559. In some aspects, the additional anticancer agent comprises an anticancer agent selected from the group consisting of Sunitinib (SUTENT®), Cabozantinib (CABOMETYX®), Axitinib (INLYTA®), Lenvatinib (LENVIMA®), Everolimus (AFINITOR®), Bevacizumab (AVASTIN®), epacadostat, NKTR-214 (CD-122-biased agonist), Tivozanib (FOTIVDA®), abexinostat, Ipilimumab (YERVOY®), tremelimumab, Pazopanib (VOTRIENT®), Sorafenib (NEXAVAR®), Temsirolimus (TORISEL®), Ramucirumab (CYRAMZA®), niraparib, savolitinib, vorolanib (X-82), Regorafenib (STIVARGO®), Donafenib (multikinase inhibitor), Camrelizumab (SHR-1210), pexastimogene devacirepvec (JX-594), Ramucirumab (CYRAMZA®), apatinib (YN968D1), encapsulated doxorubicin (THERMODOX®), Tivantinib (ARQ197), ADI-PEG 20, binimetinib, apatinib mesylate, nintedanib, lirilumab, Nivolumab (OPDIVO®), Pembrolizumab (KEYTRUDA®), Atezolizumab (TECENTRIQ®), Avelumab (BAVENCIO®), Durvalumab (IMFIMZI®), Cemiplimab-rwlc (LIBTAYO®), tislelizumab, spartalizumab, and any combination thereof. In some aspects, the additional anticancer agent comprises a TIM-3 inhibitor. In some aspects, the TIM-3 inhibitor is MGB453 or TSR-022. In some aspects, the additional anticancer agent comprises a LAG-3 inhibitor. In some aspects, the LAG-3 inhibitor is selected from the group consisting of LAG525, BMS-986016, and TSR-033. In some aspects, the additional anticancer agent comprises a TIGIT inhibitor. In some aspects, the additional anticancer agent comprises a CD112R inhibitor. In some aspects, the additional anticancer agent comprises a TAM (Axl, Mer, Tyro) inhibitor. In some aspects, the additional anticancer agent comprises a 4-1BB agonist. In some aspects, the additional anticancer agent comprises a Tyrosine Kinase Inhibitor (TKI). In some aspects, the additional anticancer agent comprises an agent that induces NK cell activation, and therefore enhances ADCC activity. In some aspects, the additional anticancer agent comprises a CCL2 inhibitor. In some aspects, the additional anticancer agent comprises an agent that induces NK cell activation.

In some aspects, the antibody or antigen-binding portion thereof is administered prior to the additional anticancer agent. In some aspects, the antibody or antigen-binding portion thereof is administered after the additional anticancer agent. In some aspects, the antibody or antigen-binding portion thereof and the additional anticancer agent are co-administered.

Certain aspects of the present disclosure are directed to a method of making an antibody or an antigen-binding portion thereof, comprising culturing a cell disclosed herein under suitable conditions. In some aspects, the method further comprises isolating the antibody or antigen-binding portion thereof.

In some aspects, the antibody or the antigen-binding portion thereof is afucosylated.

Certain aspects of the present disclosure are directed to a use of an antibody or antigen-binding portion thereof disclosed herein, a bispecific antibody disclosed herein, a bispecific antibody disclosed herein, a BiTE disclosed herein, a multispecific antibody disclosed herein, a biparatopic antibody disclosed herein, an immunoconjugate disclosed herein, a CAR of disclosed herein, a TCR disclosed herein, a nucleic acid molecule or a set of nucleic acid molecules disclosed herein, a vector or a set of vectors disclosed herein, a cell disclosed herein, or a pharmaceutical composition disclosed herein for the manufacture of a medicament in treating a tumor in a subject in need thereof.

Certain aspects of the present disclosure are directed to a use of an antibody or antigen-binding portion thereof disclosed herein, a bispecific antibody disclosed herein, a bispecific antibody disclosed herein, a BiTE disclosed herein, a multispecific antibody disclosed herein, a biparatopic antibody disclosed herein, an immunoconjugate disclosed herein, a CAR of disclosed herein, a TCR disclosed herein, a nucleic acid molecule or a set of nucleic acid molecules disclosed herein, a vector or a set of vectors disclosed herein, a cell disclosed herein, or a pharmaceutical composition disclosed herein for the manufacture of a medicament in reducing, depleting, or killing tumor infiltrating $T_{reg}$ cells in a subject in need thereof.

Certain aspects of the present disclosure are directed to a use of an antibody or antigen-binding portion thereof disclosed herein, a bispecific antibody disclosed herein, a bispecific antibody disclosed herein, a BiTE disclosed herein, a multispecific antibody disclosed herein, a biparatopic antibody disclosed herein, an immunoconjugate disclosed herein, a CAR of disclosed herein, a TCR disclosed herein, a nucleic acid molecule or a set of nucleic acid molecules disclosed herein, a vector or a set of vectors disclosed herein, a cell disclosed herein, or a pharmaceutical composition disclosed herein for the manufacture of a medicament in activating NK cells or inducing NK cell mediated killing of tumor infiltrating $T_{reg}$ cells in a subject in need thereof.

Certain aspects of the present disclosure are directed to an antibody or antigen-binding portion thereof disclosed herein, a bispecific antibody disclosed herein, a bispecific antibody disclosed herein, a BiTE disclosed herein, a multispecific antibody disclosed herein, a biparatopic antibody disclosed herein, an immunoconjugate disclosed herein, a CAR of disclosed herein, a TCR disclosed herein, a nucleic acid molecule or a set of nucleic acid molecules disclosed herein, a vector or a set of vectors disclosed herein, a cell disclosed herein, or a pharmaceutical composition disclosed herein for use in a method of treating a tumor in a subject in need thereof.

Certain aspects of the present disclosure are directed to an antibody or antigen-binding portion thereof disclosed herein, a bispecific antibody disclosed herein, a bispecific antibody disclosed herein, a BiTE disclosed herein, a multispecific antibody disclosed herein, a biparatopic antibody disclosed herein, an immunoconjugate disclosed herein, a CAR of disclosed herein, a TCR disclosed herein, a nucleic acid molecule or a set of nucleic acid molecules disclosed herein, a vector or a set of vectors disclosed herein, a cell disclosed herein, or a pharmaceutical composition disclosed herein for use in a method of reducing, depleting, or killing tumor infiltrating $T_{reg}$ cells in a subject in need thereof.

Certain aspects of the present disclosure are directed to an antibody or antigen-binding portion thereof disclosed herein, a bispecific antibody disclosed herein, a bispecific antibody disclosed herein, a BiTE disclosed herein, a multispecific antibody disclosed herein, a biparatopic antibody disclosed herein, an immunoconjugate disclosed herein, a CAR of disclosed herein, a TCR disclosed herein, a nucleic acid molecule or a set of nucleic acid molecules disclosed herein, a vector or a set of vectors disclosed herein, a cell disclosed herein, or a pharmaceutical composition disclosed herein for use in a method of activating NK cells or inducing NK cell mediated killing of tumor infiltrating $T_{reg}$ cells in a subject in need thereof.

BRIEF DESCRIPTION OF THE DRAWINGS

FIGS. 1B, 1D, 1F, 1H, 1J, and 1L) illustrating the binding of the anti-CCR8-1 (FIGS. 1A-1B), anti-CCR8-1-1 (FIGS. 1C-1D), anti-CCR8-1-2 (FIGS. 1E-1F), anti-CCR8-1-3 (FIGS. 1G-1H), anti-CCR8-1-4 (FIGS. 1I-1J), and anti-CCR8-1-5 (FIGS. 1K-1L) antibodies.

FIGS. 2B, 2D, 2F, 2H, 2J, 2L, 2N, 2P, 2R, 2T, and 2V) illustrating the binding of the anti-CCR8-2 (FIGS. 2A-2B), anti-CCR8-2-1 (FIGS. 2C-2D), anti-CCR8-2-2 (FIGS. 2E-2F), anti-CCR8-2-3 (FIGS. 2G-2H), anti-CCR8-2-4 (FIGS. 2I-2J), anti-CCR8-2-5 (FIGS. 2K-2L), anti-CCR8-2-6 (FIGS. 2M-2N), anti-CCR8-2-7 (FIGS. 2O-2P), anti-CCR8-2-8 (FIGS. 2Q-2R), anti-CCR8-2-9 (FIGS. 2S-2T), and anti-CCR8-2-10 (FIGS. 2U-2V) antibodies.

FIG. 7B), following contacting with either an anti-CCR8-1 or an anti-CCR8-2 antibody, as indicated.

FIG. 13A is a scatter plot showing the antibody to positive control binding ratio on T$_{reg}$ contacted with the anti-CCR8-1 antibody, a positive control, and secondary only (negative control). FIG. 13B shows two histogram tracings depicting APC-A staining on gated Tregs from human kidney tumors with frequency normalized to the mode for an IgG isotype control (gray tracing) or anti-CCR8-1 (black tracing).

DETAILED DESCRIPTION OF THE DISCLOSURE

Figure 1A:
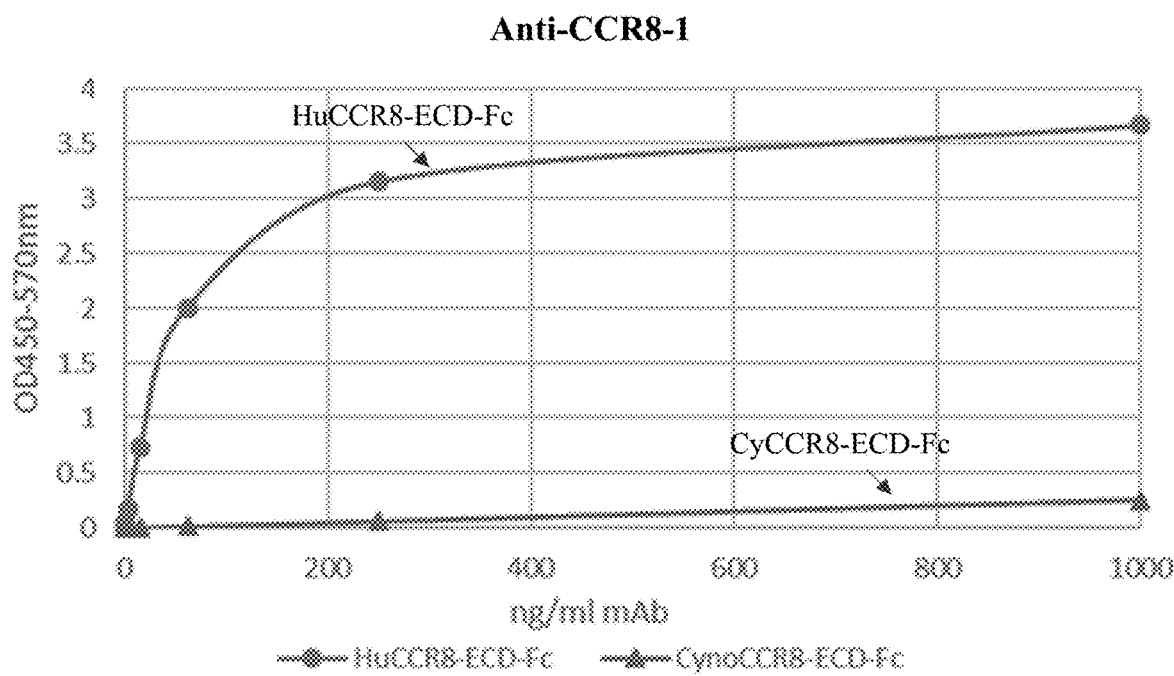
FIGS. 1A-1L are graphical representations of binding to human CCR8 (HuCCR8-ECD-Fc) or cyno CCR8 (CyCCR8-ECD-Fc) as measured by fluorescent absorbance (FIGS. 1A, 1C, 1E, 1G, 1, and 1K) and the relative binding over a secondary antibody to 293T cells expressing human CCR8, Cyno CCR8, human CCR2, mouse CCR8, and negative control 293T cells (as indicated.
Figure 1B:
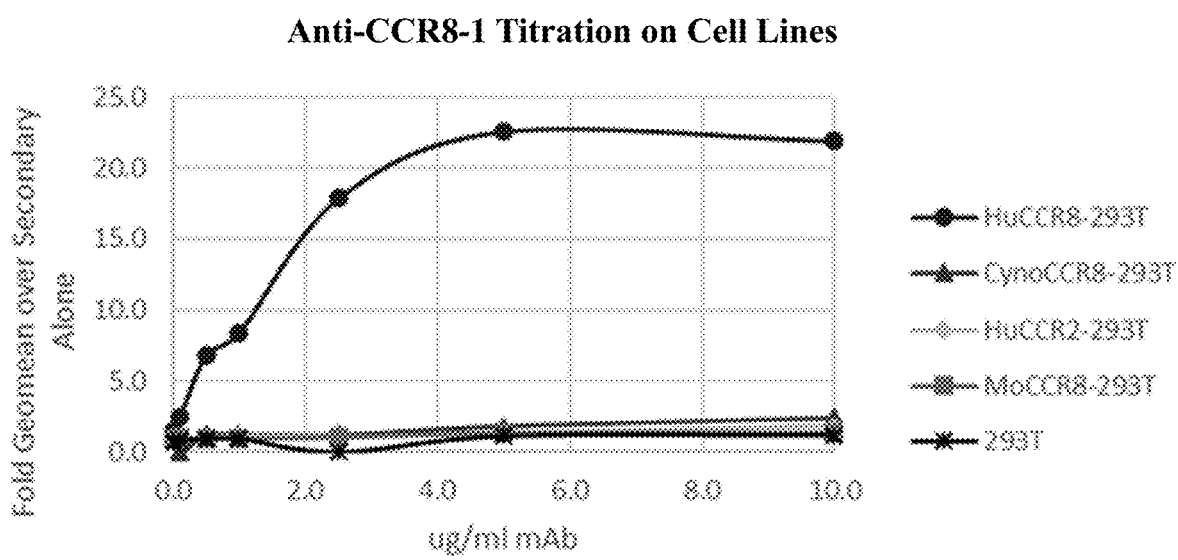
Figure 1C:
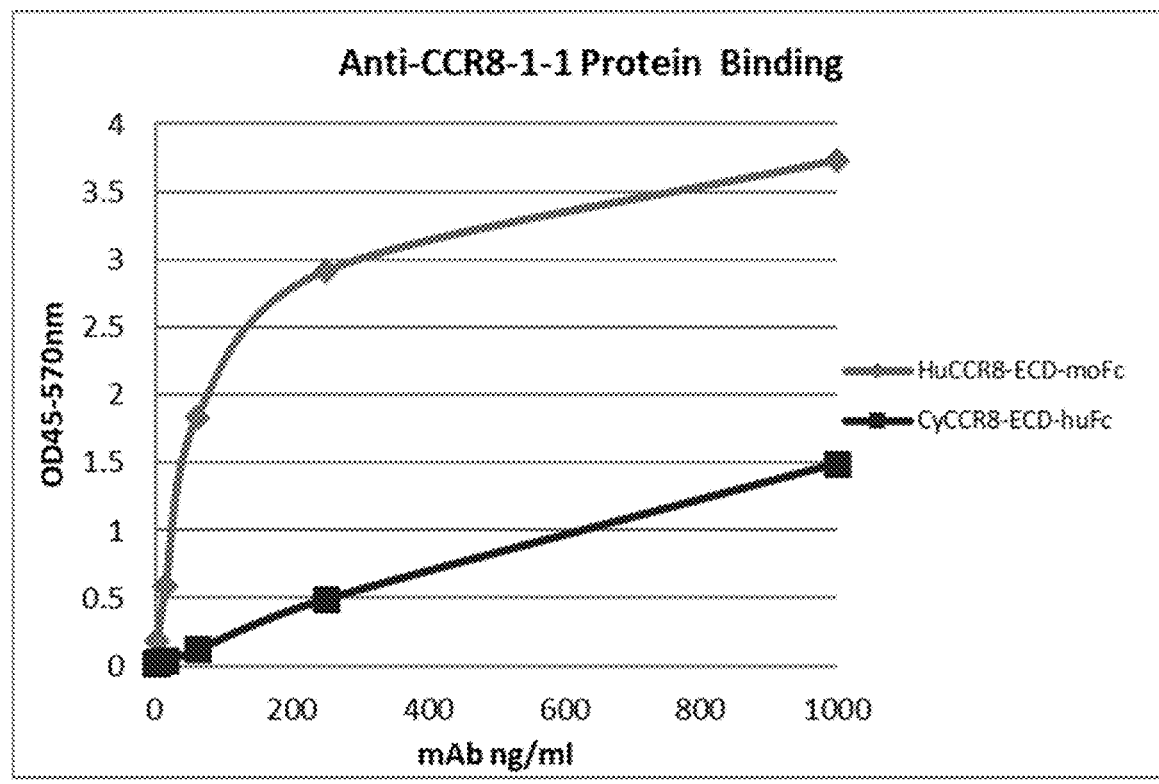
Figure 1D:
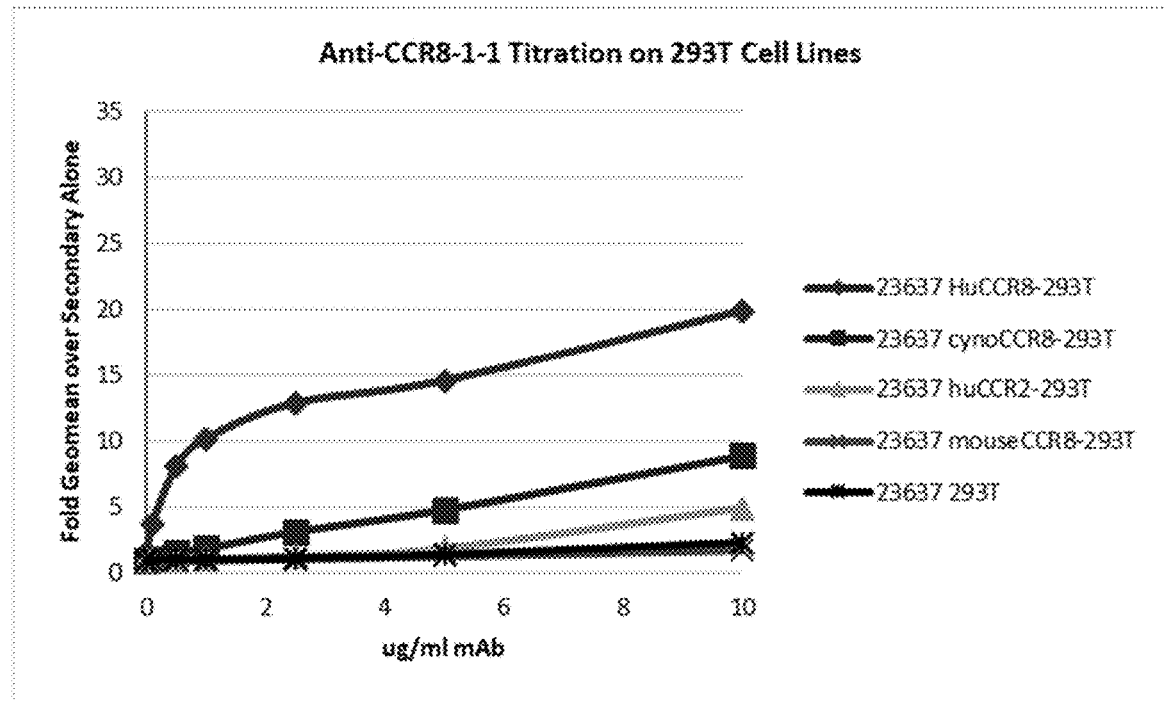
Figure 1E:
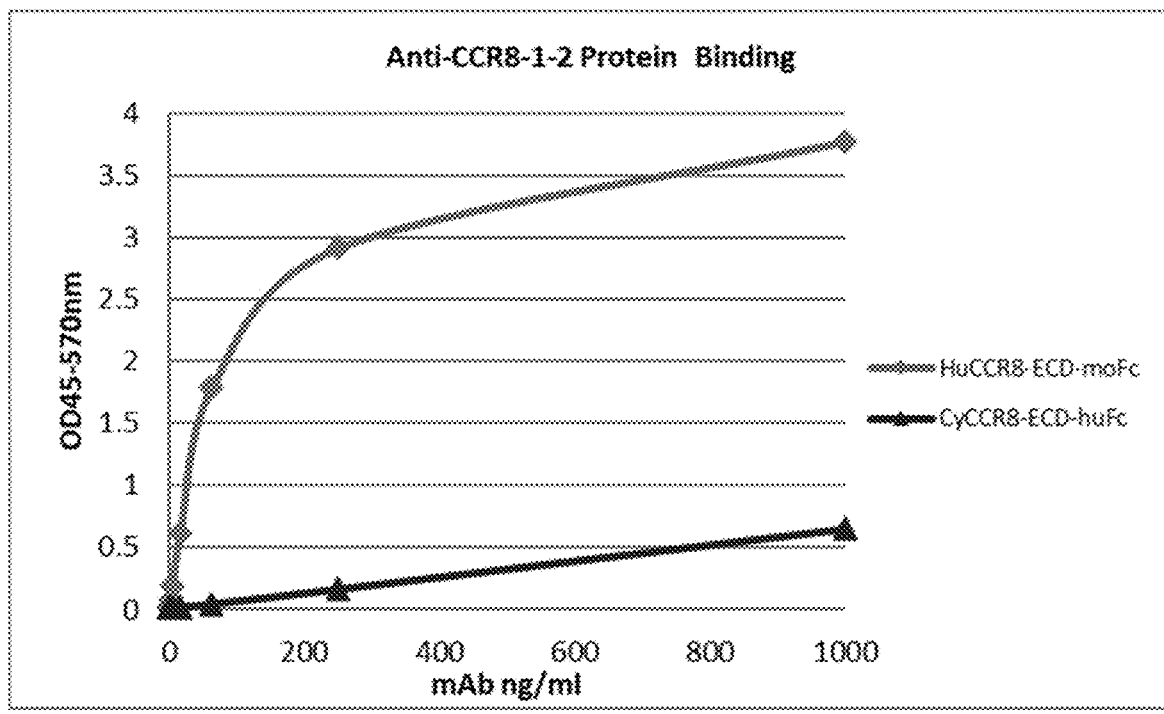
Figure 1F:
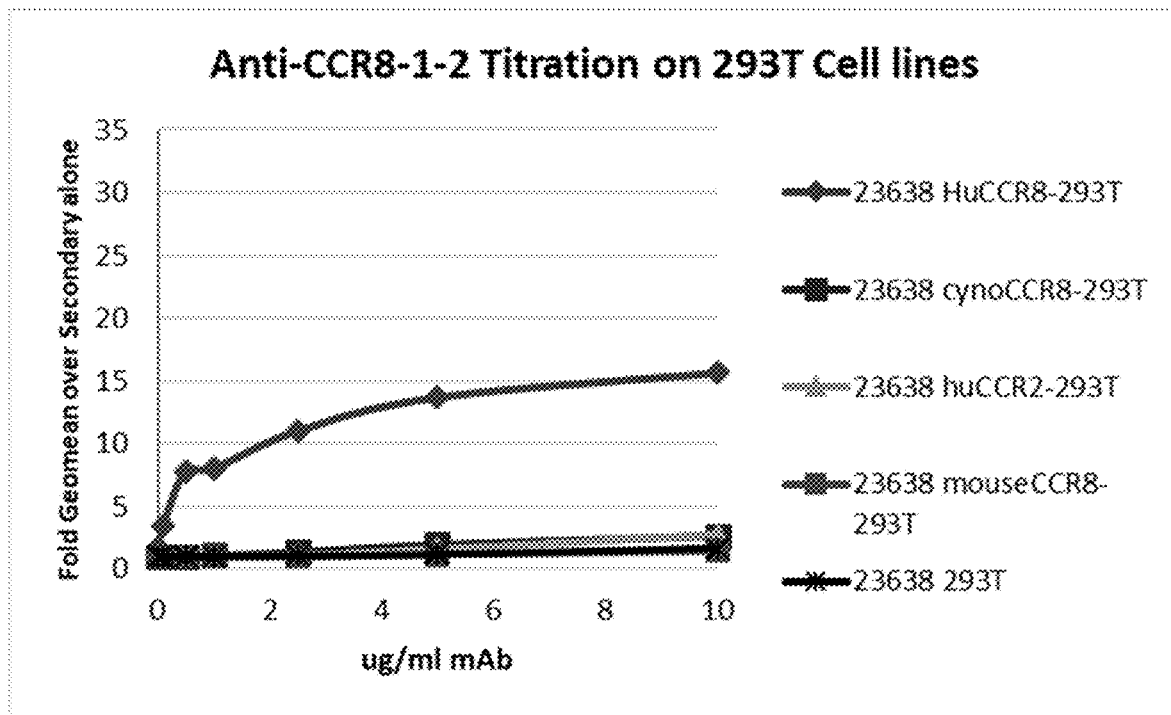
Figure 1G:
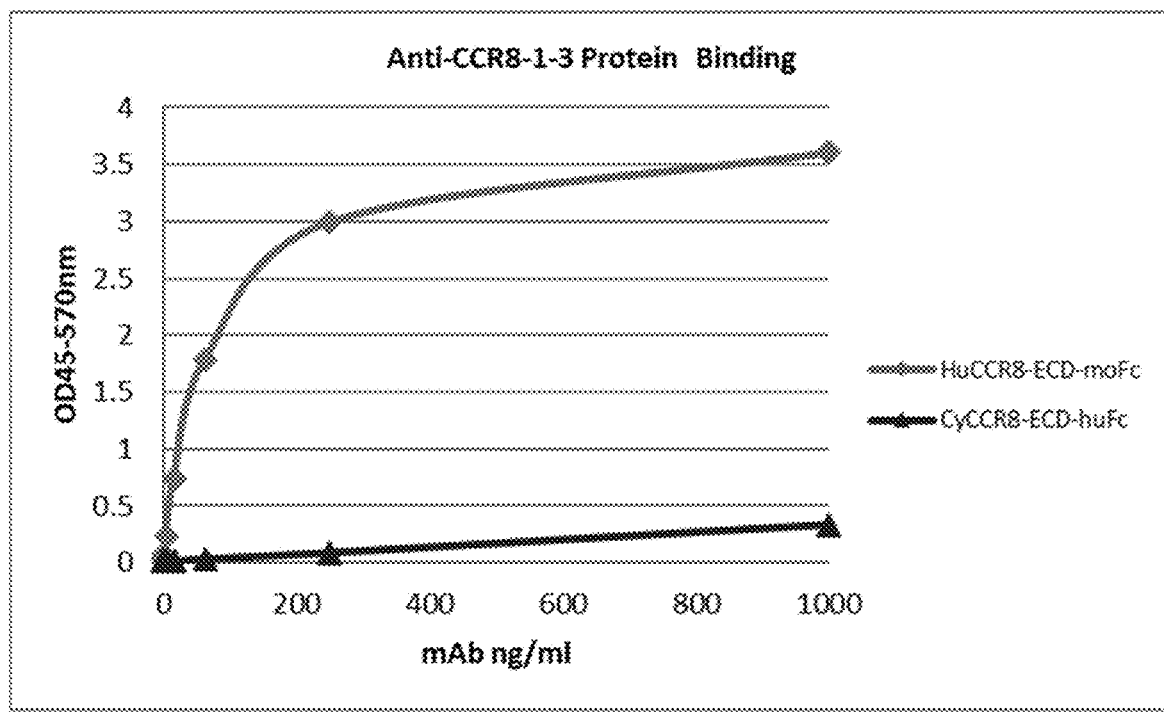
Figure 1H:
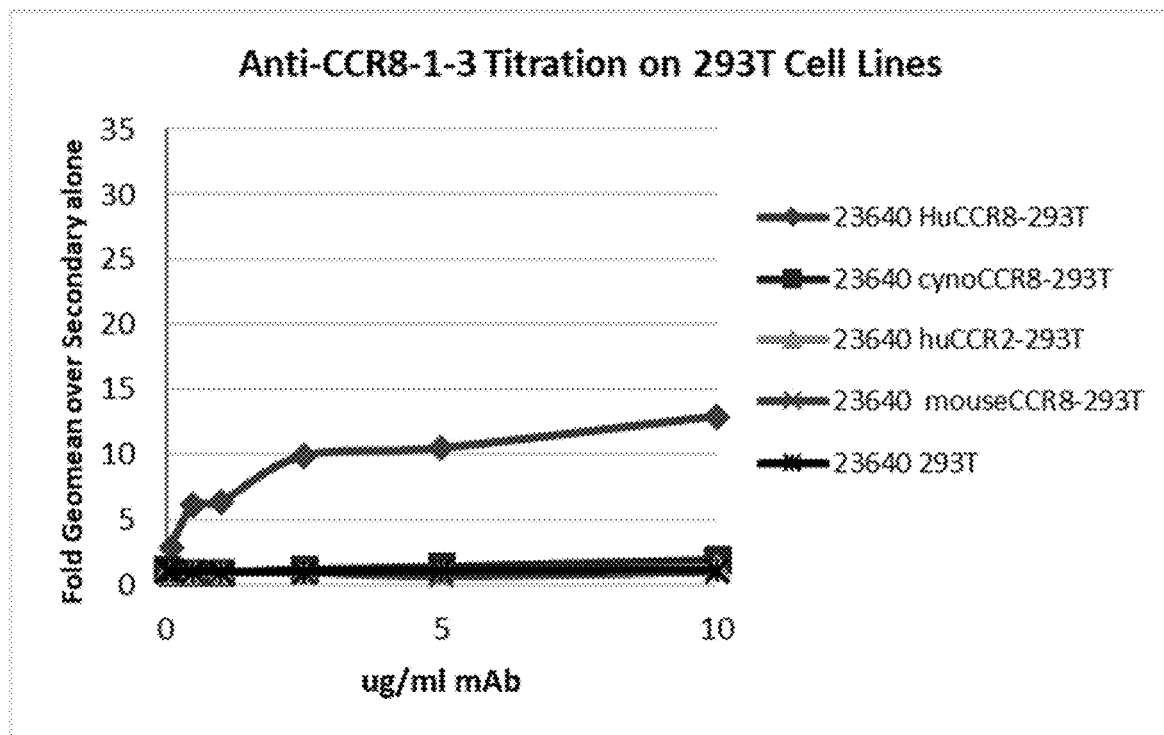
Figure 1I:
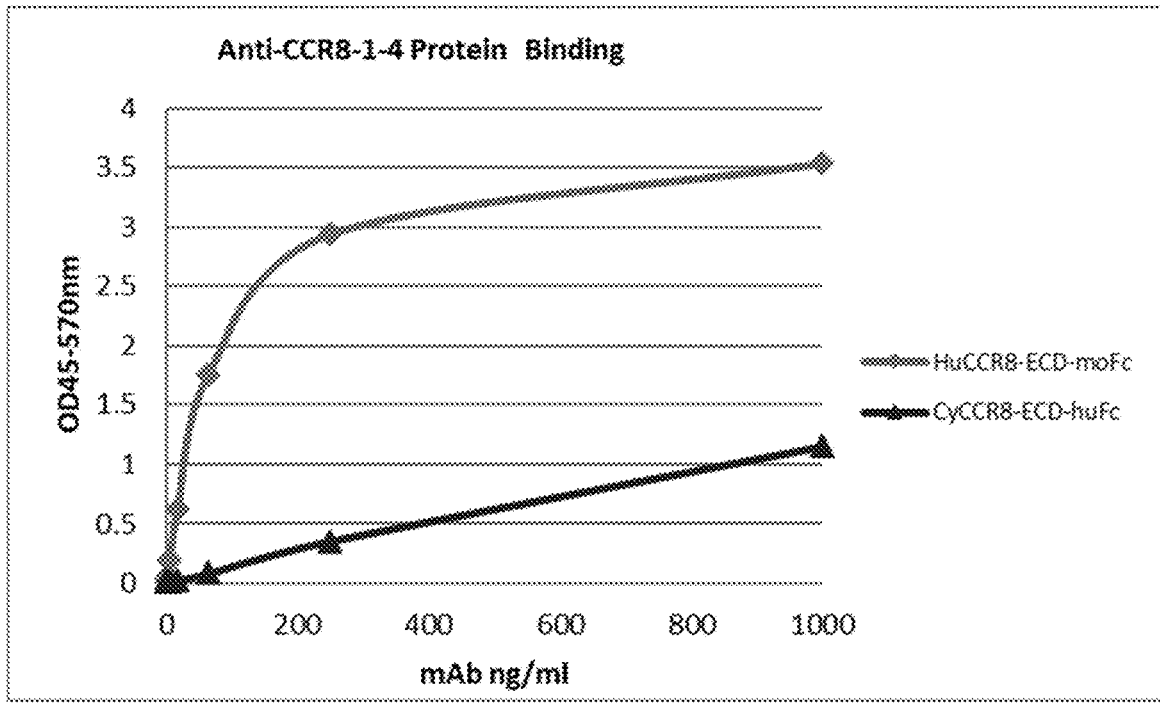
Figure 1J:
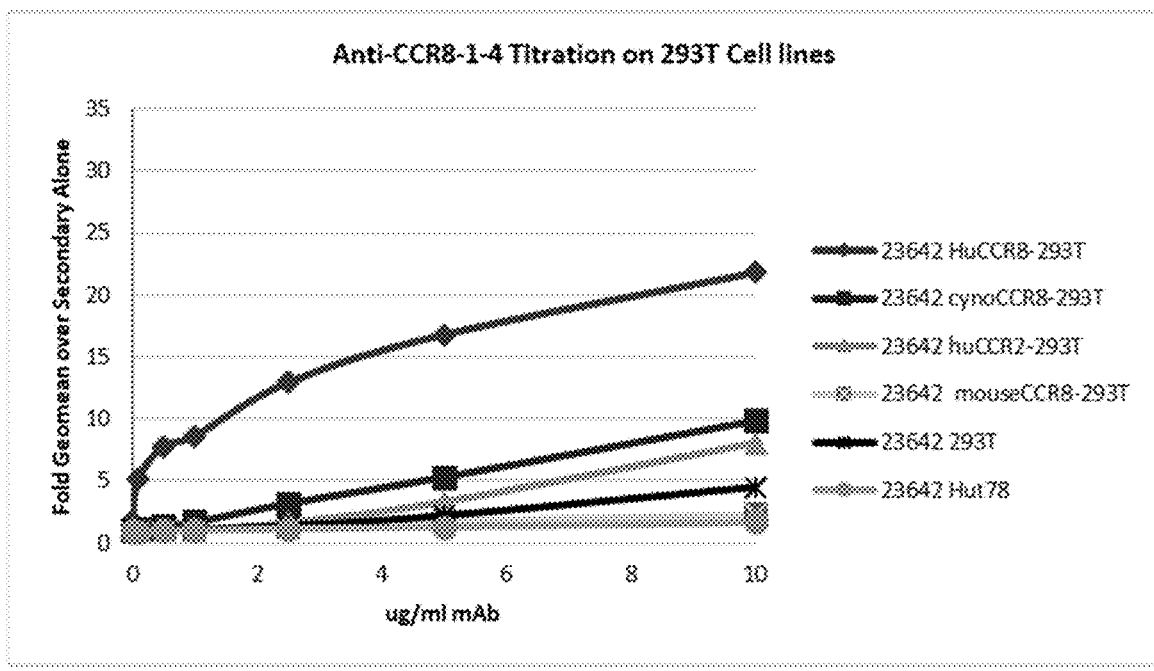
Figure 1K:
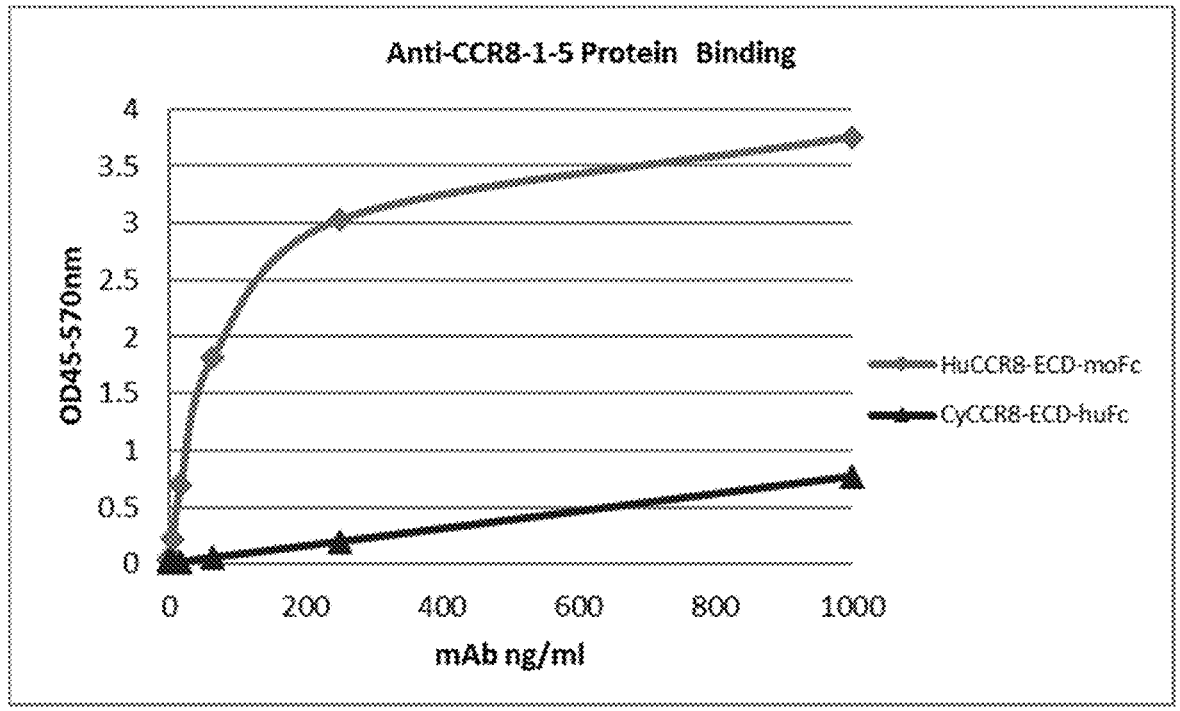
Figure 1L:
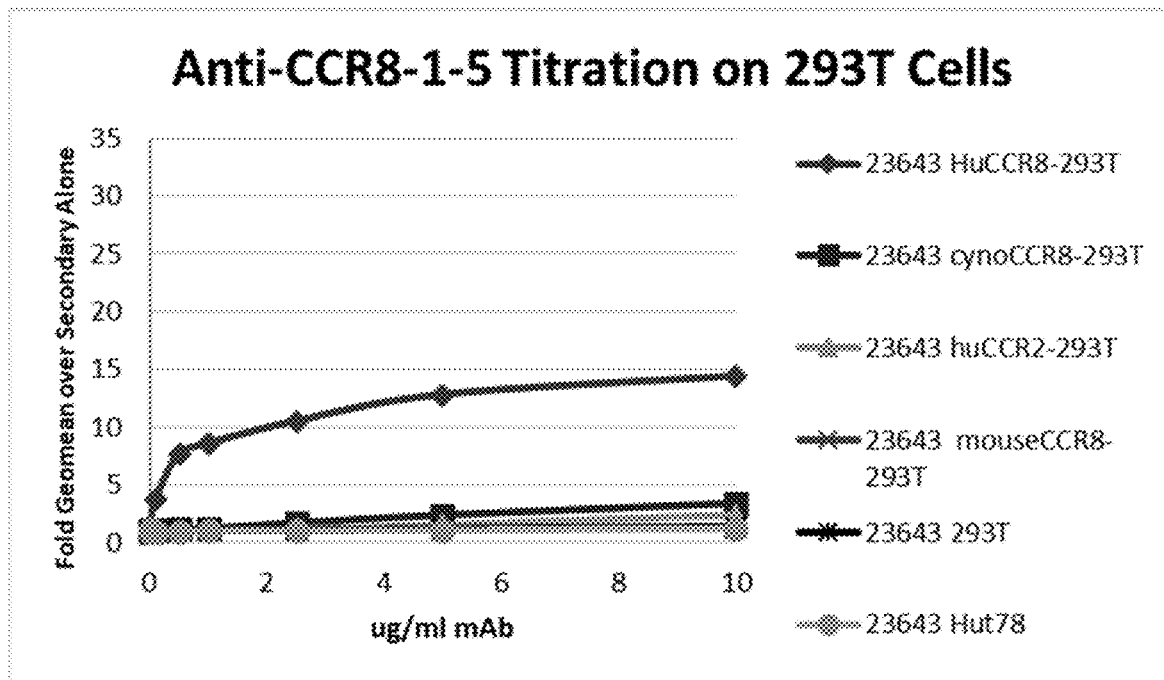

Certain aspects of the present disclosure are directed to antibodies or antigen-binding portions thereof the specifically bind CCR8 ("anti-CCR8 antibody"). In certain aspects, the anti-CCR8 antibody specifically binds the N-terminal extracellular domain of human CCR8. Other aspects of the present disclosure are directed to methods of treating a subject in need thereof comprising administering the anti-CCR8 antibodies disclosed herein.

I. Terms

In order that the present disclosure can be more readily understood, certain terms are first defined. As used in this application, except as otherwise expressly provided herein, each of the following terms shall have the meaning set forth below. Additional definitions are set forth throughout the application.

It is to be noted that the term "a" or "an" entity refers to one or more of that entity; for example, "a nucleotide sequence," is understood to represent one or more nucleotide sequences. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The term "about" is used herein to mean approximately, roughly, around, or in the regions of. When the term "about" is used in conjunction with a numerical range, it modifies that range by extending the boundaries above and below the numerical values set forth. In general, the term "about" is used herein to modify a numerical value above and below the stated value by a variance of 10 percent, up or down (higher or lower).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, nucleotide sequences are written left to right in 5' to 3' orientation. Amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

As used herein, the term "amount" or "level" is used in the broadest sense and refers to a quantity, concentration or abundance of a substance (e.g., a metabolite, a small molecule, a protein, an mRNA, a marker). When referring to a metabolite or small molecule (e.g. a drug), the terms "amount", "level" and "concentration" are generally used interchangeably and generally refer to a detectable amount in a biological sample. "Elevated levels" or "increased levels" refers to an increase in the quantity, concentration or abundance of a substance within a sample relative to a control sample, such as from an individual or individuals who are not suffering from the disease or disorder (e.g., cancer) or an internal control. In some aspects, the elevated level of a substance (e.g., a drug) in a sample refers to an increase in the amount of the substance of about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100% relative to the amount of the substance in a control sample, as determined by techniques known in the art (e.g., HPLC). "Reduced levels" refers to a decrease in the quantity, concentration or abundance of a substance (e.g., a drug) in an individual relative to a control, such as from an individual or individuals who are not suffering from the disease or disorder (e.g., cancer) or an internal control. In some aspects, a reduced level is little or no detectable quantity, concentration or abundance. In some aspects, the reduced level of a substance (e.g., a drug) in a sample refers to a decrease in the amount of the substance of about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100% relative to the amount of the substance in a control sample, as determined by techniques known in the art (e.g, HPLC).

When referring to a protein, mRNA or a marker, such as those described herein, the terms "level of expression" or "expression level" in general are used interchangeably and generally refer to a detectable amount of a protein, mRNA, or marker in a biological sample. In some aspects, a detectable amount or detectable level of a protein, mRNA or a marker is associated with a likelihood of a response to an agent, such as those described herein. "Expression" generally refers to the process by which information contained within a gene is converted into the structures (e.g., a protein marker, such as PD-L1) present and operating in the cell. Therefore, as used herein, "expression" may refer to transcription into a polynucleotide, translation into a polypeptide, or even polynucleotide and/or polypeptide modifications (e.g., posttranslational modification of a polypeptide). Fragments of the transcribed polynucleotide, the translated polypeptide, or polynucleotide and/or polypeptide modifications (e.g., posttranslational modification of a polypeptide) shall also be regarded as expressed whether they originate from a transcript generated by alternative splicing or a degraded transcript, or from a post-translational processing of the polypeptide, e.g., by proteolysis. "Expressed genes" include those that are transcribed into a polynucleotide as mRNA and then translated into a polypeptide, and also those that are transcribed into RNA but not translated into a polypeptide (for example, transfer and ribosomal RNAs). "Elevated expression," "elevated expression levels," or "elevated levels" refers to an increased expression or increased levels of a substance within a sample relative to a control sample, such as an individual or individuals who are not suffering from the disease or disorder (e.g., cancer) or an internal control. In some aspects, the elevated expression of a substance (e.g., a protein marker, such as PD-L1) in a sample refers to an increase in the amount of the substance of about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100% relative to the amount of the substance in a control sample, as determined by techniques known in the art (e.g., FACS). "Reduced expression," "reduced expression levels," or "reduced levels" refers to a decrease expression or decreased levels of a substance (e.g., a protein marker) in an individual relative to a control, such as an individual or individuals who are not suffering from the disease or disorder (e.g., cancer) or an internal control. In some aspects, reduced expression is little or no expression. In some aspects, the reduced expression of a substance (e.g., a protein marker) in a sample refers to a decrease in the amount of the substance of about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100% relative to the amount of the substance in a control sample, as determined by techniques known in the art (e.g, FACS).

As used herein, the term "antagonist" refers to any molecule that partially or fully blocks, inhibits, or neutralizes a biological activity of a native polypeptide disclosed herein. Suitable antagonist molecules specifically include antagonist antibodies or antibody fragments, fragments or amino acid sequence variants of native polypeptides, peptides or proteins. In some aspects, inhibition in the presence of the antagonist is observed in a dose-dependent manner. In some aspects, the measured signal (e.g., biological activity) is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% lower than the signal measured with a negative control under comparable conditions. Also disclosed herein, are methods of identifying antagonists suitable for use in the methods of the disclosure. For example, these methods include, but are not limited to, binding assays such as enzyme-linked immuno-absorbent assay (ELISA), ForteBio® systems, radioimmunoassay (RIA), Meso Scale Discovery assay (e.g., Meso Scale Discovery Electrochemiluminescence (MSD-ECL), and bead-based Luminex® assay. These assays determine the ability of an antagonist to bind the polypeptide of interest (e.g., a receptor or ligand) and therefore indicate the ability of the antagonist to inhibit, neutralize or block the activity of the polypeptide. Efficacy of an antagonist can also be determined using functional assays, such as the ability of an antagonist to inhibit the function of the polypeptide or an agonist. For example, a functional assay may comprise contacting a polypeptide with a candidate antagonist molecule and measuring a detectable change in one or more biological activities normally associated with the polypeptide. The potency of an antagonist is usually defined by its $IC_{50}$ value (concentration required to inhibit 50% of the agonist response). The lower the $IC_{50}$ value the greater the potency of the antagonist and the lower the concentration that is required to inhibit the maximum biological response.

As used herein, the term "anti-CCR8 antibody" refers to an antibody that specifically binds to CCR8. In some aspects, the anti-CCR8 antibody inhibits a CCR8 biological activity and/or a downstream pathway(s) mediated by CCR8 signaling or other CCR8-mediated function. An anti-CCR8 antibody includes, but is not limited to, antibodies that block, antagonize, suppress, inhibit or reduce a CCR8 biological activity (e.g., ligand binding, activation of G-protein signaling), including downstream pathways mediated by CCR8 signaling or function, such as receptor binding and/or elicitation of a cellular response to CCR8 or its metabolites (e.g., immune suppression). In some aspects, an anti-CCR8 antibody provided by the disclosure binds to human CCR8 and prevents, blocks, or inhibits binding of human CCR8 to a ligand (e.g., CCL1) or interaction between CCR8 and G-protein. In some aspects, the anti-CCR8 antibody prevents, blocks, or inhibits the binding of human CCR8 to CCL1. In some aspects, the anti-CCR8 antibody prevents, blocks, or inhibits the binding of human CCR8 to the CCL8. In some aspects, the anti-CCR8 antibody prevents, blocks, or inhibits the binding of human CCR8 to the CCL16. In some aspects, the anti-CCR8 antibody prevents, blocks, or inhibits the binding of human CCR8 to the CCL18.

As used herein, the term "antibody" refers to a whole antibody comprising two light chain polypeptides and two heavy chain polypeptides. Whole antibodies include different antibody isotypes including IgM, IgG, IgA, IgD, and IgE antibodies. The term "antibody" includes a polyclonal antibody, a monoclonal antibody, a chimerized or chimeric antibody, a humanized antibody, a primatized antibody, a deimmunized antibody, and a fully human antibody. The antibody can be made in or derived from any of a variety of species, e.g., mammals such as humans, non-human primates (e.g., orangutan, baboons, or chimpanzees), horses, cattle, pigs, sheep, goats, dogs, cats, rabbits, guinea pigs, gerbils, hamsters, rats, and mice. The antibody can be a purified or a recombinant antibody. As used herein, the term "antibody fragment," "antigen-binding fragment," or similar terms refer to a fragment of an antibody that retains the ability to bind to a target antigen (e.g., CCR8) and inhibit the activity of the target antigen. Such fragments include, e.g., a single chain antibody, a single chain Fv fragment (scFv), an Fd fragment, an Fab fragment, an Fab' fragment, or an F(ab')2 fragment. An scFv fragment is a single polypeptide chain that includes both the heavy and light chain variable regions of the antibody from which the scFv is derived. In addition, intrabodies, minibodies, triabodies, and diabodies are also included in the definition of antibody and are compatible for use in the methods described herein. See, e.g., Todorovska et al., (2001) J. Immunol. Methods 248(1): 47-66; Hudson and Kortt, (1999) J. Immunol. Methods 231(1):177-189; Poljak, (1994) Structure 2(12):1121-1123; Rondon and Marasco, (1997) Annu. Rev. Microbiol. 51:257-283, the disclosures of each of which are incorporated herein by reference in their entirety.

As used herein, the term "antibody fragment" also includes, e.g., single domain antibodies such as camelized single domain antibodies. See, e.g., Muyldermans et al., (2001) Trends Biochem. Sci. 26:230-235; Nuttall et al., (2000) Curr. Pharm. Biotech. 1:253-263; Reichmann et al., (1999) J. Immunol. Meth. 231:25-38; PCT application publication nos. WO 94/04678 and WO 94/25591; and U.S. Pat. No. 6,005,079, all of which are incorporated herein by reference in their entireties. In some aspects, the disclosure provides single domain antibodies comprising two VH domains with modifications such that single domain antibodies are formed.

In some aspects, an antigen-binding fragment includes the variable region of a heavy chain polypeptide and the variable region of a light chain polypeptide. In some aspects, an antigen-binding fragment described herein comprises the CDRs of the light chain and heavy chain polypeptide of an antibody.

As used herein, the term "bispecific" or "bifunctional antibody" refers to an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, (1990) Clin. Exp. Immunol. 79:315-321; Kostelny et al., (1992) J. Immunol. 148:1547-1553.

Traditionally, the recombinant production of bispecific antibodies is based on the co-expression of two immunoglobulin heavy-chain/light-chain pairs, where the two heavy chain/light chain pairs have different specificities (Milstein and Cuello, (1983) Nature 305:537-539). Antibody variable domains with the desired binding specificities (antibody-antigen combining sites) can be fused to immunoglobulin constant domain sequences. The fusion of the heavy chain variable region is preferably with an immunoglobulin heavy-chain constant domain, including at least part of the hinge, CH2, and CH3 regions. For further details of illustrative currently known methods for generating bispecific antibodies see, e.g., Suresh et al., (1986) Methods Enzymol. 121:210; PCT Publication No. WO 96/27011; Brennan et al., (1985) Science 229:81; Shalaby et al., J. Exp. Med. (1992) 175:217-225; Kostelny et al., (1992) J. Immunol. 148(5): 1547-1553; Hollinger et al., (1993) Proc. Nat. Acad. Sci. USA 90:6444-6448; Gruber et al., (1994) J. Immunol. 152: 5368; and Tutt et al., (1991) J. Immunol. 147:60. Bispecific antibodies also include cross-linked or heteroconjugate antibodies. Heteroconjugate antibodies may be made using any convenient cross-linking methods. Suitable cross-linking agents are well known in the art, and are disclosed in U.S. Pat. No. 4,676,980, along with a number of cross-linking techniques.

Various techniques for making and isolating bispecific antibody fragments directly from recombinant cell culture have also been described. For example, bispecific antibodies have been produced using leucine zippers. See, e.g., Kostelny et al. (1992) J Immunol 148(5):1547-1553. The leucine zipper peptides from the Fos and Jun proteins may be linked to the Fab' portions of two different antibodies by gene fusion. The antibody homodimers may be reduced at the hinge region to form monomers and then re-oxidized to form the antibody heterodimers. This method can also be utilized for the production of antibody homodimers. The "diabody" technology described by Hollinger et al. (1993) Proc Natl Acad Sci USA 90:6444-6448 has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (scFv) dimers has also been reported. See, e.g., Gruber et al. (1994) J Immunol 152:5368. Alternatively, the antibodies can be "linear antibodies" as described in, e.g., Zapata et al. (1995) Protein Eng. 8(10):1057-1062. Briefly, these antibodies comprise a pair of tandem Fd segments (VH—CH1-VH—CH1) which form a pair of antigen binding regions. Linear antibodies can be bispecific or monospecific.

Antibodies with more than two valencies (e.g., trispecific antibodies) are contemplated and described in, e.g., Tutt et al. (1991) J Immunol 147:60.

As used herein, the term "biparatopic" refers to an antibody that is capable of binding two epitopes on a single antigen, e.g., polypeptide, target. In some aspects, the biparatopic antibody comprises a first antigen-binding region and a second antigen-binding region, wherein the first antigen-binding region binds a first epitope and the second antigen-binding region binds a second epitope on the same antigen.

The disclosure also embraces variant forms of multi-specific antibodies such as the dual variable domain immunoglobulin (DVD-Ig) molecules described in Wu et al. (2007) Nat Biotechnol 25(11): 1290-1297. The DVD-Ig molecules are designed such that two different light chain variable domains (VL) from two different parent antibodies are linked in tandem directly or via a short linker by recombinant DNA techniques, followed by the light chain constant domain. Similarly, the heavy chain comprises two different heavy chain variable domains (VH) linked in tandem, followed by the constant domain CH1 and Fc region. Methods for making DVD-Ig molecules from two parent antibodies are further described in, e.g., PCT Publication Nos. WO 08/024188 and WO 07/024715. In some aspects, the bispecific antibody is a Fabs-in-Tandem immunoglobulin, in which the light chain variable region with a second specificity is fused to the heavy chain variable region of a whole antibody. Such antibodies are described in, e.g., International Patent Application Publication No. WO 2015/103072.

As used herein, "cancer antigen" or "tumor antigen" refers to (i) tumor-specific antigens, (ii) tumor-associated antigens, (iii) cells that express tumor-specific antigens, (iv) cells that express tumor-associated antigens, (v) embryonic antigens on tumors, (vi) autologous tumor cells, (vii) tumor-specific membrane antigens, (viii) tumor-associated membrane antigens, (ix) growth factor receptors, (x) growth factor ligands, and (xi) any other type of antigen or antigen-presenting cell or material that is associated with a cancer.

As used herein, the term "cancer-specific immune response" refers to the immune response induced by the presence of tumors, cancer cells, or cancer antigens. In certain aspects, the response includes the proliferation of cancer antigen specific lymphocytes. In certain aspects, the response includes expression and upregulation of antibodies and T-cell receptors and the formation and release of lymphokines, chemokines, and cytokines. Both innate and acquired immune systems interact to initiate antigenic responses against the tumors, cancer cells, or cancer antigens. In certain aspects, the cancer-specific immune response is a T cell response.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. The anti-CCR8 antibodies described herein can be used to treat patients who have, who are suspected of having, or who may be at high risk for developing any type of cancer, including renal carcinoma or melanoma, or any viral disease. Exemplary carcinomas include those forming from tissue of the cervix, lung, prostate, breast, head and neck, colon and ovary. The term also includes carcinosarcomas, which include malignant tumors composed of carcinomatous and sarcomatous tissues. An "adenocarcinoma" refers to a carcinoma derived from glandular tissue or in which the tumor cells form recognizable glandular structures.

As used herein, the term "CCR8" or "C—C chemokine receptor type 8" refers to a G-protein coupled receptor. CCR8 is known to have at least four ligands: CCL1, CCL8, CCL16, and CCL18. CCL1 is thought to potentiate human $T_{reg}$ cells by inducing CCR8, FOXp3, CD39, Granzyme B, and IL-10 Expression, in a STAT3-dependent manner. See, e.g., Barsheshet et al., PNAS 114(23):6086-91 (Jun. 6, 2017). CCR8 is expressed primarily on $T_{reg}$ cells and to a lesser extent on small fractions of TH2 cells, monocytic cells, NK cells, and CD8+ cells. CCR8 is a transmembrane receptor having seven transmembrane domains, an extracellular N-terminal domain (SEQ ID NO: 172), and an intracellular C-terminal domain, which interacts with G-protein. The amino acid sequence for human CCR8 (UniProt P51685; SEQ ID NO: 171) is shown in Table 1, below.

```
                                         (SEQ ID NO: 171)
MDYTLDLSVTTVTDYYYPDIFSSPCDAELIQTNGKLLLAVFYCLLFVFSL

LGNSLVILVLVVCKKLRSITDVYLLNLALSDLLFVFSFPFQTYYLLDQWV

FGTVMCKVVSGFYYIGFYSSMFFITLMSVDRYLAVVHAVYALKVRTIRMG

TTLCLAVWLTAIMATIPLLVFYQVASEDGVLQCYSFYNQQTLKWKIFTNF

KMNILGLLIPFTIFMFCYIKILHQLKRCQNHNKTKAIRLVLIVVIASLLF

WVPFNVVLFLTSLHSMHILDGCSISQQLTYATHVTEIISFTHCCVNPVIY

AFVGEKFKKHLSEIFQKSCSQIFNYLGRQMPRESCEKSSSCQQHSSRSSS

VDYIL
```

As used herein the term "compete," when used in the context of antigen-binding proteins (e.g., immunoglobulins, antibodies, or antigen-binding fragments thereof) that compete for binding to the same epitope, refers to a interaction between antigen-binding proteins as determined by an assay (e.g., a competitive binding assay; a cross-blocking assay), wherein a test antigen-binding protein (e.g., a test antibody) inhibits (e.g., reduces or blocks) specific binding of a reference antigen-binding protein (e.g., a reference antibody) to a common antigen (e.g., CCR8 or a fragment thereof).

A polypeptide or amino acid sequence "derived from" a designated polypeptide or protein refers to the origin of the polypeptide. Preferably, the polypeptide or amino acid sequence which is derived from a particular sequence has an amino acid sequence that is essentially identical to that sequence or a portion thereof, wherein the portion consists of at least 10-20 amino acids, preferably at least 20-30 amino acids, more preferably at least 30-50 amino acids, or which is otherwise identifiable to one of ordinary skill in the art as having its origin in the sequence. Polypeptides derived from another peptide may have one or more mutations relative to the starting polypeptide, e.g., one or more amino acid residues which have been substituted with another amino acid residue or which has one or more amino acid residue insertions or deletions.

A polypeptide can comprise an amino acid sequence that is not naturally occurring. Such variants necessarily have less than 100% sequence identity or similarity with the starting molecule. In certain aspects, the variant will have an amino acid sequence from about 75% to less than 100% amino acid sequence identity or similarity with the amino acid sequence of the starting polypeptide, more preferably from about 80% to less than 100%, more preferably from about 85% to less than 100%, more preferably from about 90% to less than 100% (e.g., 91%, 92%, 93%, 94%, 95%, 96%, 97%, 98%, 99%) and most preferably from about 95% to less than 100%, e.g., over the length of the variant molecule.

In certain aspects, the antibodies of the disclosure are encoded by a nucleotide sequence. Nucleotide sequences of the invention can be useful for a number of applications, including cloning, gene therapy, protein expression and purification, mutation introduction, DNA vaccination of a host in need thereof, antibody generation for, e.g., passive immunization, PCR, primer and probe generation, and the like.

It will also be understood by one of ordinary skill in the art that the antibodies suitable for use in the methods disclosed herein may be altered such that they vary in sequence from the naturally occurring or native sequences from which they were derived, while retaining the desirable activity of the native sequences. For example, nucleotide or amino acid substitutions leading to conservative substitutions or changes at "non-essential" amino acid residues may be made. Mutations may be introduced by standard techniques, such as site-directed mutagenesis and PCR-mediated mutagenesis.

The antibodies suitable for use in the methods disclosed herein may comprise conservative amino acid substitutions at one or more amino acid residues, e.g., at essential or non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in a binding polypeptide is preferably replaced with another amino acid residue from the same side chain family. In certain aspects, a string of amino acids can be replaced with a structurally similar string that differs in order and/or composition of side-chain family members. Alternatively, in certain aspects, mutations may be introduced randomly along all or part of a coding sequence, such as by saturation mutagenesis, and the resultant mutants can be incorporated into binding polypeptides of the invention and screened for their ability to bind to the desired target.

As used herein, the term "cross-reacts" refers to the ability of an antibody of the disclosure to bind to CCR8 from a different species. For example, an antibody of the present disclosure that binds human CCR8 can also bind another species of CCR8. As used herein, cross-reactivity is measured by detecting a specific reactivity with purified antigen in binding assays (e.g., SPR, ELISA) or binding to, or otherwise functionally interacting with, cells physiologically expressing CCR8. Methods for determining cross-reactivity include standard binding assays as described herein, for example, by BIACORE™ surface plasmon resonance (SPR) analysis using a BIACORE™ 2000 SPR instrument (BIACORE AB, Uppsala, Sweden), or flow cytometric techniques.

As used herein, the term "cytotoxic T lymphocyte (CTL) response" refers to an immune response induced by cytotoxic T cells. CTL responses are mediated primarily by $CD8^+$ T cells.

As used herein, the term "$EC_{50}$" refers to the concentration of an antibody or an antigen-binding portion thereof, which induces a response, either in an in vitro or an in vivo assay, which is 50% of the maximal response, i.e., halfway between the maximal response and the baseline.

As used herein, the term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity of the disorder being treated and the general state of the patient's own immune system.

As used herein, the term "epitope" or "antigenic determinant" refers to a site on an antigen to which an immunoglobulin or antibody specifically binds. The term "epitope mapping" refers to a process or method of identifying the binding site, or epitope, of an antibody, or antigen-binding fragment thereof, on its target protein antigen. Epitope mapping methods and techniques are provided herein. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods for determining what epitopes are bound by a given antibody (i.e., epitope mapping) are well known in the art and include, for example, immunoblotting and immunoprecipitation assays, wherein overlapping or contiguous peptides from CCR8 are tested for reactivity with the given anti-CCR8 antibody. Methods of determining spatial conformation of epitopes include techniques in the art and those described herein, for example, x-ray crystallography and 2-dimensional nuclear magnetic resonance (see, e.g., *Epitope Mapping Protocols in Methods in Molecular Biology*, Vol. 66, G. E. Morris, Ed. (1996)).

Also encompassed by the present disclosure are antibodies that bind to an epitope on CCR8 which comprises all or a portion of an epitope recognized by the particular antibodies described herein (e.g., the same or an overlapping region or a region between or spanning the region).

Also encompassed by the present disclosure are antibodies that bind the same epitope and/or antibodies that compete for binding to human CCR8 with the antibodies described herein. Antibodies that recognize the same epitope or compete for binding can be identified using routine techniques. Such techniques include, for example, an immunoassay, which shows the ability of one antibody to block the binding of another antibody to a target antigen, i.e., a competitive binding assay. Competitive binding is determined in an assay in which the immunoglobulin under test inhibits specific binding of a reference antibody to a common antigen, such as CCR8. Numerous types of competitive binding assays are known, for example: solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, *Antibodies: A Laboratory Manual*, Cold Spring Harbor Press (1988)); solid phase direct label RIA using I-125 label (see Morel et al., *Mol. Immunol.* 25(1):7

(1988)); solid phase direct biotin-avidin EIA (Cheung et al., *Virology* 176:546 (1990)); and direct labeled RIA. (Moldenhauer et al., Scand. *J. Immunol.* 32:77 (1990)). Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more.

Other techniques include, for example, epitope mapping methods, such as, x-ray analyses of crystals of antigen: antibody complexes which provides atomic resolution of the epitope and mass spectrometry combined with hydrogen/deuterium (H/D) exchange which studies the conformation and dynamics of antigen:antibody interactions. Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. The peptides are then regarded as leads for the definition of the epitope corresponding to the antibody used to screen the peptide library. For epitope mapping, computational algorithms have also been developed which have been shown to map conformational discontinuous epitopes.

As used herein, the term "Fc-mediated effector functions" or "Fc effector functions" refer to the biological activities of an antibody other than the antibody's primary function and purpose. For example, the effector functions of a therapeutic agnostic antibody are the biological activities other than the activation of the target protein or pathway. Examples of antibody effect functions include C1q binding and complement dependent cytotoxicity; Fc receptor binding; antibody-dependent cell-mediated cytotoxicity (ADCC); phagocytosis; down regulation of cell surface receptors (e.g., B cell receptor); lack of activation of platelets that express Fc receptor; and B cell activation. Many effector functions begin with Fc binding to an Fcγ receptor. In some aspects, the tumor antigen-targeting antibody has effector function, e.g., ADCC activity. In some aspects, a tumor antigen-targeting antibody described herein comprises a variant constant region having increased effector function (e.g. increased ability to mediate ADCC) relative to the unmodified form of the constant region.

As used herein, the term "Fc receptor" refers to a polypeptide found on the surface of immune effector cells, which is bound by the Fc region of an antibody. In some aspects, the Fc receptor is an Fcγ receptor. There are three subclasses of Fcγ receptors, FcγRI (CD64), FcγRII (CD32) and FγcRIII (CD16). All four IgG isotypes (IgG1, IgG2, IgG3 and IgG4) bind and activate Fc receptors FcγRI, FcγRIIA and FcγRIIIA. FcγRIIB is an inhibitory receptor, and therefore antibody binding to this receptor does not activate complement and cellular responses. FcγRI is a high affinity receptor that binds to IgG in monomeric form, whereas FcγRIIA and FcγRIIA are low affinity receptors that bind IgG only in multimeric form and have slightly lower affinity. The binding of an antibody to an Fc receptor and/or C1q is governed by specific residues or domains within the Fc regions. Binding also depends on residues located within the hinge region and within the CH2 portion of the antibody. In some aspects, the agonistic and/or therapeutic activity of the antibodies described herein is dependent on binding of the Fc region to the Fc receptor (e.g., FcγR). In some aspects, the agonistic and/or therapeutic activity of the antibodies described herein is enhanced by binding of the Fc region to the Fc receptor (e.g., FcγR).

As used herein, the term "human antibody" includes antibodies having variable and constant regions (if present) of human germline immunoglobulin sequences. Human antibodies of the disclosure can include amino acid residues not encoded by human germline immunoglobulin sequences (e.g., mutations introduced by random or site-specific mutagenesis in vitro or by somatic mutation in vivo) (See, e.g., Lonberg et al., (1994) *Nature* 368(6474): 856-859); Lonberg, (1994) *Handbook of Experimental Pharmacology* 113: 49-101; Lonberg & Huszar, (1995) *Intern. Rev. Immunol.* 13:65-93, and Harding & Lonberg, (1995) Ann. N.Y. Acad. Sci. 764:536-546). However, the term "human antibody" does not include antibodies in which CDR sequences derived from the germline of another mammalian species, such as a mouse, have been grafted onto human framework sequences (i.e. humanized antibodies).

As used herein, the term "humanized" refers to an antibody in which some, most or all of the amino acids outside the CDR domains of a non-human antibody are replaced with corresponding amino acids derived from human immunoglobulins. In some embodiments of a humanized form of an antibody, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody.

As used herein, the term a "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

The terms "inducing an immune response" and "enhancing an immune response" are used interchangeably and refer to the stimulation of an immune response (i.e., either passive or adaptive) to a particular antigen. The terms "induce" as used with respect to inducing CDC or ADCC refer to the stimulation of particular direct cell killing mechanisms.

As used herein, the term "immunogenic cell death" (alternatively known as "immunogenic apoptosis" refers to a cell death modality associated with the activation of one or more signaling pathways that induces the pre-mortem expression and emission of damaged-associated molecular pattern (DAMPs) molecules (e.g., adenosine triphosphate, ATP) from the tumor cell, resulting in the increase of immunogenicity of the tumor cell and the death of the tumor cell in an immunogenic manner (e.g., by phagocytosis). As used herein, the term "immunogenic cell death-inducing agent" refers to a chemical, biological, or pharmacological agent that induces an immunogenic cell death process, pathway, or modality.

As used herein, the terms "inhibits", "reduces" or "blocks" (e.g., referring to inhibition or reduction of human CCR8-mediated phosphorylation of STAT1 and/or STAT3 in a cell) are used interchangeably and encompass both partial and complete inhibition/blocking. The inhibition/blocking of CCR8 reduces or alters the normal level or type of activity that occurs without inhibition or blocking. Inhibition and blocking are also intended to include any measurable decrease in the binding affinity of CCR8 when in contact with an anti-CCR8 antibody as compared to CCR8 not in contact with an anti-CCR8 antibody, e.g., inhibits binding of CCR8 by at least about 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100%.

As used herein, the term "inhibits growth" (e.g., referring to a tumor or cells, e.g., tumor cells) is intended to include any measurable decrease in the growth of a tumor or a cell, e.g., the inhibition of growth of a tumor by at least about 10%, 20%, 30%, 40%, 50%, 60%, 70%, 80%, 90%, 99%, or 100%.

As used herein, a subject "in need of prevention," "in need of treatment," or "in need thereof," refers to one, who by the judgment of an appropriate medical practitioner (e.g., a doctor, a nurse, or a nurse practitioner in the case of humans; a veterinarian in the case of non-human mammals), would reasonably benefit from a given treatment (such as treatment with a composition comprising an anti-CCR8 antibody).

The term "in vivo" refers to processes that occur in a living organism.

As used herein, the term "isolated antibody" is intended to refer to an antibody that is substantially free of other antibodies having different antigenic specificities (e.g., an isolated antibody that specifically binds to human CCR8 is substantially free of antibodies that specifically bind antigens other than CCR8). An isolated antibody that specifically binds to an epitope may, however, have cross-reactivity to other CCR8 proteins from different species. However, the antibody continues to display specific binding to human CCR8 in a specific binding assay as described herein. In addition, an isolated antibody is typically substantially free of other cellular material and/or chemicals. In some aspects, a combination of "isolated" antibodies having different CCR8 specificities is combined in a well-defined composition.

As used herein, the term "isolated nucleic acid molecule" refers to nucleic acids encoding antibodies or antibody portions (e.g., VH, VL, CDR3) that bind to CCR8, and is intended to refer to a nucleic acid molecule in which the nucleotide sequences encoding the antibody or antibody portion are free of other nucleotide sequences encoding antibodies or antibody portions that bind antigens other than CCR8, which other sequences may naturally flank the nucleic acid in human genomic DNA. For example, a sequence selected from a sequence set forth in Table 8 corresponds to the nucleotide sequences comprising the heavy chain (VH) and light chain (VL) variable regions of anti-CCR8 antibody monoclonal antibodies described herein.

As used herein, "isotype" refers to the antibody class (e.g., IgM or IgG1) that is encoded by heavy chain constant region genes. In some aspects, a human monoclonal antibody of the disclosure is of the IgG1 isotype. In some aspects, a human monoclonal antibody of the disclosure is of the IgG2 isotype. In some aspects, a human monoclonal antibody of the disclosure is of the IgG3 isotype. In some aspects, a human monoclonal antibody of the disclosure is of the IgG4 isotype. As is apparent to a skilled artisan, identification of antibody isotypes (e.g., IgG1, IgG2, IgG3, IgG4, IgM, IgA1 IgA2, IgD, and IgE) is routine in the art and commonly involves a combination of sequence alignments with known antibodies, published Fc variant sequences and conserved sequences.

As used herein the term "KD" or "$K_D$" refers to the equilibrium dissociation constant of a binding reaction between an antibody and an antigen. The value of $K_D$ is a numeric representation of the ratio of the antibody off-rate constant (kd) to the antibody on-rate constant (ka). The value of $K_D$ is inversely related to the binding affinity of an antibody to an antigen. The smaller the $K_D$ value the greater the affinity of the antibody for its antigen. Affinity is the strength of binding of a single molecule to its ligand and is typically measured and reported by the equilibrium dissociation constant ($K_D$), which is used to evaluate and rank order strengths of bimolecular interactions.

As used herein, the term "kd" or "$k_d$" (alternatively "koff" or "$k_{off}$") is intended to refer to the off-rate constant for the dissociation of an antibody from an antibody/antigen complex. The value of $k_d$ is a numeric representation of the fraction of complexes that decay or dissociate per second, and is expressed in units $sec^{-1}$.

As used herein, the term "ka" or "$k_a$" (alternatively "kon" or "$k_{on}$") is intended to refer to the on-rate constant for the association of an antibody with an antigen. The value of ka is a numeric representation of the number of antibody/antigen complexes formed per second in a 1 molar (1M) solution of antibody and antigen, and is expressed in units $M^{-1} sec^{-1}$.

As used herein, the term "lymphocytes" refers to a type of leukocyte or white blood cell that is involved in the immune defenses of the body. There are two main types of lymphocytes: B-cells and T-cells. The term "tumor-infiltrating lymphocyte" (abbreviated "TIL") or "tumor-infiltrating $T_{reg}$," as used herein, refers to a lymphocyte or a $T_{reg}$, respectively, that is associated with tumor cells, e.g., that is localized within a tumor mass.

As used herein, the terms "linked," "fused," or "fusion," are used interchangeably. These terms refer to the joining of two more elements, components, or domains by whatever means including chemical conjugation or recombinant means. Methods of chemical conjugation (e.g., using heterobifunctional crosslinking agents) are known in the art.

As used herein, the term "monoclonal antibody" refers to an antibody that displays a single binding specificity and affinity for a particular epitope. Accordingly, the term "human monoclonal antibody" refers to an antibody which displays a single binding specificity and which has variable and optional constant regions derived from human germline immunoglobulin sequences. In some aspects, human monoclonal antibodies are produced by a hybridoma that includes a B cell obtained from a transgenic non-human animal, e.g., a transgenic mouse, having a genome comprising a human heavy chain transgene and a light chain transgene fused to an immortalized cell.

As used herein, the term "natural killer (NK) cell" refers to a type of cytotoxic lymphocyte. These are large, usually granular, non-T, non-B lymphocytes, which kill certain tumor cells and play an important role in innate immunity to viruses and other intracellular pathogens, as well as in antibody-dependent cell-mediated cytotoxicity (ADCC).

As used herein, the term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

As used herein, the term "nucleic acid" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues (Batzer et al., Nucleic Acid Res. 19:5081, 1991; Ohtsuka et al., Biol. Chem. 260:2605-2608, 1985; and Cassol et al, 1992; Rossolini et al, Mol. Cell. Probes 8:91-98, 1994). For arginine and leucine, modifications at the second base can also be conservative. The term nucleic acid is used interchangeably with gene, cDNA, and mRNA encoded by a gene.

Polynucleotides used herein can be composed of any polyribonucleotide or polydeoxribonucleotide, which can be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, the polynucleotide can be composed of triple-stranded regions comprising RNA or DNA or both RNA and DNA. A polynucleotide can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

As used herein, "parenteral administration," "administered parenterally," and other grammatically equivalent phrases, refer to modes of administration other than enteral and topical administration, usually by injection, and include, without limitation, intravenous, intranasal, intraocular, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural, intracerebral, intracranial, intracarotid and intrasternal injection and infusion.

As used herein, the term "patient" includes human and other mammalian subjects that receive either prophylactic or therapeutic treatment.

The term "percent identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the "percent identity" can exist over a region of the sequence being compared, e.g., over a functional domain, or, alternatively, exist over the full length of the two sequences to be compared. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information website.

As generally used herein, "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

As used herein, a "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt (see, e.g., Berge et al. (1977) J Pharm Sci 66:1-19).

As used herein, the terms "polypeptide," "peptide," and "protein" are used interchangeably to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

As used herein, the term "preventing" when used in relation to a condition, refers to administration of a composition that reduces the frequency of, or delays the onset of, symptoms of a medical condition in a subject relative to a subject that does not receive the composition.

As used herein, the term "purified" or "isolated" as applied to any of the proteins (antibodies or fragments) described herein refers to a polypeptide that has been separated or purified from components (e.g., proteins or other naturally-occurring biological or organic molecules) which naturally accompany it, e.g., other proteins, lipids, and nucleic acid in a prokaryote expressing the proteins. Typically, a polypeptide is purified when it constitutes at least 60% (e.g., at least 65%, 70%, 75%, 80%, 85%, 90%, 92%, 95%, 97%, or 99%), by weight, of the total protein in a sample.

As used herein, the term "rearranged" refers to a configuration of a heavy chain or light chain immunoglobulin locus wherein a V segment is positioned immediately adjacent to a D-J or J segment in a conformation encoding essentially a complete VH or VL domain, respectively. A rearranged immunoglobulin gene locus can be identified by comparison to germline DNA; a rearranged locus will have at least one recombined heptamer/nonamer homology element.

As used herein, the term "recombinant host cell" (or simply "host cell") is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the term "recombinant antibody" includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies comprise variable and constant regions that utilize particular human germline immunoglobulin sequences are encoded by the germline genes, but include subsequent rearrangements and mutations which occur, for example, during antibody maturation. As known in the art (see, e.g., Lonberg (2005) Nature Biotech. 23(9):1117-1125), the variable region contains the antigen binding domain, which is encoded by various genes that rearrange to form an antibody specific for a foreign antigen. In addition to rearrangement, the variable region can be further modified by multiple single amino acid changes (referred to as somatic mutation or hypermutation) to increase the affinity of the antibody to the foreign antigen. The constant region will change in further response to an antigen (i.e., isotype switch). Therefore, the rearranged and somatically mutated nucleic acid molecules that encode the light chain and heavy chain immunoglobulin polypeptides in response to an antigen may not have sequence identity with the original nucleic acid molecules, but instead will be substantially identical or similar (i.e., have at least 80% identity).

As used herein, the term "reference antibody" (used interchangeably with "reference mAb") or "reference antigen-binding protein" refers to an antibody, or an antigen-binding fragment thereof, that binds to a specific epitope on CCR8 and is used to establish a relationship between itself and one or more distinct antibodies, wherein the relationship is the binding of the reference antibody and the one or more distinct antibodies to the same epitope on CCR8. As used herein, the term connotes an anti-CCR8 antibody that is useful in a test or assay, such as those described herein, (e.g., a competitive binding assay), as a competitor, wherein the assay is useful for the discovery, identification or development, of one or more distinct antibodies that bind to the same epitope.

As used herein, the terms "specific binding," "selective binding," "selectively binds," and "specifically binds," refer to antibody binding to an epitope on a predetermined antigen. Typically, the antibody binds with an equilibrium dissociation constant ($K_D$) of approximately less than $10^{-6}$ M, such as approximately less than $10^{-7}$, $10^{-1}$ M, $10^{-9}$ M or $10^{-10}$ M or even lower when determined by surface plasmon resonance (SPR) technology in a BIACORE™ 2000 instrument using recombinant human CCR8 as the analyte and the antibody as the ligand and binds to the predetermined antigen with an affinity that is at least two-fold greater than its affinity for binding to a non-specific antigen (e.g., BSA, casein) other than the predetermined antigen or a closely-related antigen. In certain aspects, an antibody that specifically binds to CCR8 binds with an equilibrium dissociation constant ($K_D$) of approximately less than 100 nM ($10^{-7}$ M), optionally approximately less than 50 nM ($5 \times 10^{-8}$ M), optionally approximately less than 15 nM ($1.5 \times 10^{-8}$ M), optionally approximately less than 10 nM ($10^{-8}$ M), optionally approximately less than 5 nM ($5 \times 10^{-9}$ M), optionally approximately less than 1 nM ($10^{-9}$ M), optionally approximately less than 0.1 nM ($10^{-10}$ M), optionally approximately less than 0.01 nM ($10^{-11}$ M), or even lower, when determined by surface plasmon resonance (SPR) technology in a BIACORE™ 2000 instrument using recombinant human CCR8 as the analyte and the antibody as the ligand, where binding to the predetermined antigen occurs with an affinity that is at least two-fold greater than the antibody's affinity for binding to a non-specific antigen (e.g., BSA, casein) other than the predetermined antigen or a closely-related antigen The phrases "an antibody recognizing an antigen" and "an antibody specific for an antigen" are used interchangeably herein with the term "an antibody which binds specifically to an antigen."

As used herein, the term "subject" includes any human or non-human animal. For example, the methods and compositions of the present invention can be used to treat a subject with an immune disorder. The term "non-human animal" includes all vertebrates, e.g., mammals and non-mammals, such as non-human primates, sheep, dog, cow, chickens, amphibians, reptiles, etc.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package, using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present disclosure can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

The nucleic acid compositions of the present disclosure, while often in a native sequence (except for modified restriction sites and the like), from either cDNA, genomic or mixtures thereof may be mutated, in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

The term "T cell" refers to a type of white blood cell that can be distinguised from other white blood cells by the presence of a T cell receptor on the cell surface. There are several subsets of T cells, including, but not limited to, T helper cells (a.k.a. $T_H$ cells or CD4$^+$ T cells) and subtypes, including $T_H1$, $T_H2$, $T_H3$, $T_H17$, $T_H9$, and $T_{FH}$ cells, cytotoxic T cells (a.k.a $T_C$ cells, CD8$^+$ T cells, cytotoxic T lymphocytes, T-killer cells, killer T cells), memory T cells and subtypes, including central memory T cells ($T_{CM}$ cells), effector memory T cells ($T_{EM}$ and $T_{EMRA}$ cells), and resident memory T cells ($T_{RM}$ cells), regulatory T cells (a.k.a. $T_{reg}$ cells or suppressor T cells) and subtypes, including CD4$^+$FOXP3$^+$ $T_{reg}$ cells, CD4$^+$FOXP3$^-$ $T_{reg}$ cells, Tr1 cells, Th3 cells, and $T_{reg}17$ cells, natural killer T cells (a.k.a. NKT cells), mucosal associated invariant T cells (MAITs), and gamma delta T cells (γδ T cells), including Vγ9/Vδ2 T cells. Any one or more of the aforementioned or unmentioned T cells may be the target cell type for a method of use of the invention.

As used herein, the term "T cell-mediated response" refers to any response mediated by T cells, including, but not limited to, effector T cells (e.g., CD8$^+$ cells) and helper T cells (e.g., CD4$^+$ cells). T cell mediated responses include, for example, T cell cytotoxicity and proliferation.

As used herein, the term "regulatory T cell," "T regulatory cell," $T_{reg}$," or "$T_{reg}$", used interchangeably herein, refers to a subpopulation of T cells that modulate the immune system, maintain tolerance to self-antigens, and prevent autoimmune disease. Tregs are immunosuppressive and generally suppress or downregulate induction and proliferation of effector T cells. Tregs are known to direct effector T cell lysis, support tolerogenic dendritic cell formation, support M2 macrophage formation, produce immunosuppressive metabolites and cytokines, serve as an IL-2 sink, and to promote neovasculature formation. Though there are many types of Tregs, many Tregs express CD4 and FOXP3, with FOXP3 serving as a marker for Tregs in many cases.

As used herein, the terms "therapeutically effective amount" or "therapeutically effective dose," or similar terms used herein are intended to mean an amount of an agent (e.g., an anti-CCR8 antibody or an antigen-binding fragment thereof) that will elicit the desired biological or medical response (e.g., an improvement in one or more symptoms of a cancer).

The terms "treat," "treating," and "treatment," as used herein, refer to therapeutic or preventative measures described herein. The methods of "treatment" employ administration to a subject, in need of such treatment, a human antibody of the present disclosure, for example, a subject in need of an enhanced immune response against a particular antigen or a subject who ultimately may acquire such a disorder, in order to prevent, cure, delay, reduce the severity of, or ameliorate one or more symptoms of the disorder or recurring disorder, or in order to prolong the survival of a subject beyond that expected in the absence of such treatment.

As used herein, the term "tumor microenvironment" (alternatively "cancer microenvironment;" abbreviated TME) refers to the cellular environment or milieu in which the tumor or neoplasm exists, including surrounding blood vessels as well as non-cancerous cells including, but not limited to, immune cells, fibroblasts, bone marrow-derived inflammatory cells, and lymphocytes. Signaling molecules and the extracellular matrix also comprise the TME. The tumor and the surrounding microenvironment are closely related and interact constantly. Tumors can influence the microenvironment by releasing extracellular signals, promoting tumor angiogenesis and inducing peripheral immune tolerance, while the immune cells in the microenvironment can affect the growth and evolution of tumor cells.

As used herein, the term "vector" is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

Unless otherwise defined, all technical and scientific terms used herein have the same meaning as commonly understood by one of ordinary skill in the art to which this disclosure pertains. Preferred methods and materials are described below, although methods and materials similar or equivalent to those described herein can also be used in the practice or testing of the presently disclosed methods and compositions. All publications, patent applications, patents, and other references mentioned herein are incorporated by reference in their entirety.

Various aspects of the disclosure are described in further detail in the following subsections.

II. Compositions of the Disclosure

Certain aspects of the present disclosure are directed to antibodies or antigen-binding portions thereof the specifically bind CCR8 ("anti-CCR8 antibody"). In certain aspects, the anti-CCR8 antibody specifically binds the N-terminal extracellular domain of human CCR8. Historically, it has been very difficult to generate therapeutic antibodies to CCR8. CCR8, like other GPCRs, is challenging to raise antibodies against due to their strong membrane association, lack of exposure of sequence on the cell surface, and difficulty expressing the CCR8 full-length protein itself. Numerous previous attempts leveraging multiple antibody generation platforms have failed. (See also Jo and Jung, *Experimental & Molecular Medicine* 48:e207 (2016).) The present disclosure solves this problem by specifically targeting the N-terminal extracellular domain of human CCR8. By raising antibodies specifically targeting to the N-terminal domain, the present disclosure focused on generating antibodies that target the longest extracelluar portion of CCR8. This enabled the achievement of previously unattainable anti-CCR8 antibodies. In doing so, the antibodies described herein are capable of inhibiting CCR8 activity in a way not previously described. In particular, the antibodies disclosed herein are capabale of (a) enhancing an immune response to a tumor; (b) reducing, depleting, or killing tumor infiltrating regulatory T ("Treg") cells; (c) inducing internalization of CCR8 in tumor infiltrating regulatory T ("Treg") cells; (d) activating NK cells, (e) inducing NK cell mediated killing of tumor infiltrating regulatory T ("Treg") cells; (f) binding to cynomolgus monkey ("cyno") CCR8; (g) binding to human CCR8 with KD of 10 nM or less as measured by BIA-CORE™; or (h) any combination thereof.

In some aspects, the antibody or the antigen-binding portion thereof is further engineered by removing one or more post-translation modification. In some aspects, the antibody or the antigen-binding portion thereof is engineered to remove one or more fucose sugar units. In some aspects, the antibody or the antigen-binding portion thereof is modified to remove one or more fucose sugar units from the (IgG1) Fc region of the antibody. In some aspects, the antibody or the antigen-binding portion thereof is afucosylated. In some aspects, removal of one or more fucose sugar units increases the ADCC of the antibody or antigen-binding fragment thereof. In some aspects, the ADCC of the anti-CCR8 antibody modified to remove one or more fucose sugar units (e.g., afucosylated antibody) is at least about 1.5-fold, at least about 2.0-fold, at least about 2.5-fold, at least about 3.0-fold, at least about 3.5-fold, at least about 4.0-fold, at least about 4.5-fold, or at least about 5.0-fold higher than the anti-CCR8 antibody that is not modified to remove one or more fucose sugar units (e.g., fucosylated antibody). In some aspects, the ADCC of the anti-CCR8 antibody modified to remove one or more fucose sugar units is at least about 3.0-fold higher than the anti-CCR8 antibody that is not modified to remove one or more fucose sugar units. In some aspects, the ADCC of the anti-CCR8 antibody modified to remove one or more fucose sugar units is at least about 3.5-fold higher than the anti-CCR8 antibody that is not modified to remove one or more fucose sugar units. In some aspects, the ADCC of the anti-CCR8 antibody modified to remove one or more fucose sugar units is at least about 4.0-fold higher than the anti-CCR8 antibody that is not modified to remove one or more fucose sugar units.

In certain aspects, the anti-CCR8 antibody is capable of inducing an immune response to a tumor. Treg cells serve to regulate the immune response by down regulating the activity of T cells as a means of keeping the immune system in check. Tumor infiltrating Tregs can act to prevent an immune response targeting the tumor, thereby allowing the tumor to evade destruction by a subject's immune system. The antibodies described herein are capable of inhibiting tumor infiltrating Tregs, thereby reducing this barrier to an anti-tumor immune response. In some aspects, the anti-CCR8 antibody increases an immune response to a tumor in a subject in need thereof by at least about 50%, at least about 100%, at least about 150%, at least about 200%, at least about 250%, at least about 300%, at least about 350%, at least about 400%, at least about 450%, or at least about 500% relative to an immune response in the absence of the anti-CCR8 antibody.

An anti-tumor immune response can be measured using any indicators known in the art. In some aspects, the anti-tumor immune response is determined by comparing the number of tumor infiltrating T cells (TILs) in a tumor sample obtained by a subject before and after contacting the tumor with the anti-CCR8 antibody. In some aspects, the number of TILs is measured by immunohistochemistry or quantitative polymerase chain reaction (qPCR). In some aspects, the number of TILs in the tumor sample is increase by at least about 1.5 fold, at least about 2 fold, at least about 2.5 fold, at least about 3 fold, at least about 3.5 fold, at least about 4 fold, at least about 4.5 fold, at least about 5 fold, at least about 6 fold, at least about 7 fold, at least about 8 fold, at least about 9 fold, at least about 10 fold, at least about 15 fold, or at least about 20 fold, relative to the number of TILs in a tumor sample obtained from the subject prior to contacting the tumor with the anti-CCR8 antibody.

In certain aspects, the anti-CCR8 antibody is capable of reducing, depleting, or killing tumor infiltrating Treg cells. In some aspects, the anti-CCR8 antibody induces depletion in the number of tumor infiltrating Treg cells in a subject following administration of the antibody or antigen-binding portion thereof, relative to the number of tumor infiltrating Treg cells prior to the administration. In some aspects, the number of tumor infiltrating Treg cells is depleted by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or about 100% relative to the number of tumor infiltrating Treg cells prior to the administration. In some aspects, the anti-CCR8 preferentially reduces, depletes, or kills tumor infiltrating Treg cells relative to peripheral Treg cells.

In some aspects, the anti-CCR8 antibody induces antibody-dependent cellular cytotoxicity (ADCC) in a subject following administration of the anti-CCR8 antibody. In some aspects, the ADCC comprises an EC50 of about 100 μg/mL or less following the administration of the antibody or antigen-binding portion thereof. In some aspects, the ADCC comprises an EC50 of about 100 μg/mL or less, about 90 μg/mL or less, about 80 μg/mL or less, about 70 μg/mL or less, about 60 μg/mL or less, about 50 μg/mL or less, about 45 μg/mL or less, about 40 μg/mL or less, about 35 μg/mL or less, about 30 μg/mL or less, about 30 μg/mL or less, about 25 μg/mL or less, about 20 μg/mL or less, about 15 μg/mL or less, about 10 μg/mL or less, about 5 μg/mL or less, about 1 μg/mL or less, about 0.5 μg/mL or less, about μg/mL or less, about 0.1 μg/mL or less, or about 0.01 μg/mL or less following the administration of the ant-CCR8 antibody. In some aspects, the ADCC comprises an EC50 of about 1 μg/mL or less following the administration of the antibody or antigen-binding portion thereof. In some aspects, the ADCC comprises an EC50 of about 0.1 μg/mL or less following the administration of the antibody or antigen-binding portion thereof.

Without being bound by any theory or particular mechanism, it is hypothesized that inhibition of CCR8 signaling in tumor infiltrating Tregs leads to activation of NK cells in the tumor microenvironment. Activated NK cells are then able to target and kill tumor infiltrating Tregs, reducing their number and enhancing the immune response to the tumor. Accordingly, in some aspects, the anti-CCR8 antibody is capable of activating NK cells. In some aspects, the NK cells are activated in the tumor microenvironment. In some aspects, the NK cells are tumor infiltrating NK cells. NK cell activation can be measured using any techniques known in the art. In some aspects, NK cell activation is determined by measuring the percent of cells that express one or more marker of activated NK cells. In certain aspects, NK cell activation is determined by measuring the percent of cells in the tumor microenvironment that express NKp46, but do not express CD3 (e.g., NKp46+/CD3− cells).

In some aspects, NK cell activation is characterized by increased expression of one or more target genes by NK cells. In some aspects, the anti-CCR8 antibody is capable of inducing upregulation of 4-1BB on the surface of NK cells. In some aspects, the anti-CCR8 antibody is capable of inducing upregulation of ICAM-1 on the surface of NK cells. In some aspects, the anti-CCR8 antibody is capable of inducing upregulation of 4-1BB and ICAM-1 on the surface of NK cells. In some aspects, the level of 4-1BB and/or ICAM-1 on the surface of NK cells following the contacting of the anti-CCR8 antibody to a tumor is upregulated by at least about 1.5 fold, 2 fold, 2.5 fold, 3.0 fold, 3.5 fold, 4.0 fold, 4.5 fold, 5 fold, 6 fold, 7 fold, 8 fold, 9 fold, or 10 fold, relative to the level of 4-1BB and/or ICAM-1 on the surface of NK cells in a tumor sample taken prior to the contacting.

In some aspects, NK cell activation is characterized by decreased expression of one or more target genes by NK cells. In some aspects, the anti-CCR8 antibody is capable of inducing downregulation of CD16 on the surface of NK cells. In some aspects, the level of CD16 on the surface of NK cells following the contacting of the anti-CCR8 antibody to a tumor is downregulated by at least about 1.5 fold, 2 fold, 2.5 fold, 3.0 fold, 3.5 fold, 4.0 fold, 4.5 fold, 5 fold, 6 fold, 7 fold, 8 fold, 9 fold, or 10 fold, relative to the level of CD16 on the surface of NK cells in a tumor sample taken prior to the contacting.

In some aspects, the number of activated NK cells in the tumor microenvironment is increased by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or about 100% relative to the percent of activated NK cells in a tumor sample obtained from the subject prior to contacting the tumor with the anti-CCR8 antibody. In some aspects, the percent of activated NK cells in the tumor microenvironment is increased by at least about 1.5 fold, at least about 2 fold, at least about 2.5 fold, at least about 3 fold, at least about 3.5 fold, at least about 4 fold, at least about 4.5 fold, at least about 5 fold, at least about 6 fold, at least about 7 fold, at least about 8 fold, at least about 9 fold, at least about 10 fold, at least about 15 fold, or at least about 20 fold, relative to the number of activated NK cells in a tumor sample obtained from the subject prior to contacting the tumor with the anti-CCR8 antibody. In some aspects, the anti-CCR8 antibody is capable of inducing NK cell mediated killing of tumor infiltrating Tregs.

The anti-CCR8 antibodies described herein are capable of specific binding to human CCR8. However, in some aspects, the anti-CCR8 antibodies are capable of binding CCR8 from non-human animals. In some aspects, the anti-CCR8 antibody are capable of specifically binding human CCR8 and non-human primate CCR8. In some aspects, the anti-CCR8 antibody is capable of binding human CCR8 and cynomolgus (cyno) CCR8. In some aspects, the anti-CCR8 antibody binds human CCR8 with a higher affinity that non-human CC8 (e.g., cyno CCR8). In some aspects, the anti-CCR8 antibody binds human CCR8 but does not bind cyno CCR8.

In some aspects, the anti-CCR8 antibody binds human CCR8 with an equilibrium dissociation constant ($K_D$) of about 100 nM or less. In some aspects, the anti-CCR8 antibody binds human CCR8 with a $K_D$ of about 50 nM or less. In some aspects, the anti-CCR8 antibody binds human CCR8 with a $K_D$ of about 25 nM or less. In some aspects, the anti-CCR8 antibody binds human CCR8 with a $K_D$ of about 20 nM or less. In some aspects, the anti-CCR8 antibody binds human CCR8 with a $K_D$ of about 15 nM or less. In some aspects, the anti-CCR8 antibody binds human CCR8 with a $K_D$ of about 10 nM or less. In some aspects, the anti-CCR8 antibody binds human CCR8 with a $K_D$ of about 5 nM or less. In some aspects, the anti-CCR8 antibody binds human CCR8 with a $K_D$ of about 1 nM or less. In some aspects, $K_D$ is measured by BIACORE™ In certain aspects, the anti-CCR8 antibody binds human CCR8 with a $K_D$ of about 10 nM or less as measured by BIACORE™. In certain aspects, the anti-CCR8 antibody binds human CCR8 with a $K_D$ of about 1 nM or less as measured by BIACORE™.

Inhibition of CCR8 by the antibodies and antigen-binding portions thereof disclosed herein can occur through any mechanism. Without being bound by any particular mechanism, in some aspects, the anti-CCR8 antibody induces internalization of CCR8 by tumor infiltrating Treg cells. Internalization of the CCR8 receptor from the surface eliminates the ability of the receptor to bind its ligand and potentiate intracellular signaling, effectively inhibiting CCR8 activity in tumor infiltrating Treg cells. In certain aspects, the anti-CCR8 antibody binds CCR8 expressed by tumor infiltrating Treg cells.

In some aspects, the anti-CCR8 antibody block the interaction between CCR8 and its ligand, e.g., through steric hindrance, a confirmation change, internalization of the CCR8 receptor, or any combination thereof. In some aspects, binding of the anti-CCR8 antibody to the N-terminal extracellular domain of CCR8 inhibits the ability of the CCR8 receptor to interact with G-protein, e.g., through a conformational change and/or through internalization of the CCR8 receptor.

II.A. Epitopes

The antibodies described herein specifically bind the N-terminal extracellular domain of CCR8 or a fragment thereof. The N-terminal extracellular domain of human CCR8 is generally defined as consisting of amino acids 1-35 of the full-length CCR8 sequence (e.g., amino acids 1-35 of SEQ ID NO: 171) (see uniprot.org/uniprot/P51685). The amino acid sequence of the N-terminal extracellular domain of human CCR8 comprises the amino acid sequence (SEQ ID NO: 172)
MDYTLDLSVTTVTDYYYPDIFSSPCDAELIQTNGK In some aspects, the anti-CCR8 antibody binds at least one, at least two, at least three, at least four, at least five, at least six, at least seven, at least eight, at least nine, or at least ten amino acids within the N-terminal extracellular domain of human CCR8, e.g., as set forth in SEQ ID NO: 172. In some aspects, the at least two, at least three, at least four, at least five, at least six, at least seven, at least eight, at least nine, or at least ten amino acids within the N-terminal extracellular domain of human CCR8, e.g., as set forth in SEQ ID NO: 172 are contiguous. In some aspects, the anti-CCR8 antibody binds at least one, at least two, at least three, at least four, at least five, at least six, at least seven, at least eight, at least nine, or at least ten contiguous amino acids within the N-terminal extracellular domain of human CCR8, e.g., as set forth in SEQ ID NO: 172. In some aspects, the at least two, at least three, at least four, at least five, at least six, at least seven, at least eight, at least nine, or at least ten amino acids within the N-terminal extracellular domain of human CCR8, e.g., as set forth in SEQ ID NO: 172 are not contiguous. In some aspects, the anti-CCR8 antibody binds at least one amino acid in the N-terminal extracellular domain of human CCR8 and at least one amino acid of human CCR8 that is not within the N-terminal extracellular domain of human CCR8.

In some aspects, the anti-CCR8 antibody binds an epitope on human CCR8, comprising one or more amino acids selected from amino acid residues 1-10 of SEQ ID NO: 172. In some aspects, the anti-CCR8 antibody binds an epitope on human CCR8, comprising one or more amino acids selected from amino acid residues 1-15 of SEQ ID NO: 172. In some aspects, the anti-CCR8 antibody binds an epitope on human CCR8, comprising one or more amino acids selected from amino acid residues 1-20 of SEQ ID NO: 172. In some aspects, the anti-CCR8 antibody binds an epitope on human CCR8, comprising one or more amino acids selected from amino acid residues 1-25 of SEQ ID NO: 172. In some aspects, the anti-CCR8 antibody binds an epitope on human CCR8, comprising one or more amino acids selected from amino acid residues 1-30 of SEQ ID NO: 172. In some aspects, the anti-CCR8 antibody binds an epitope on human CCR8, comprising one or more amino acids selected from amino acid residues 5-10 of SEQ ID NO: 172. In some aspects, the anti-CCR8 antibody binds an epitope on human CCR8, comprising one or more amino acids selected from amino acid residues 5-15 of SEQ ID NO: 172. In some aspects, the anti-CCR8 antibody binds an epitope on human CCR8, comprising one or more amino acids selected from amino acid residues 5-20 of SEQ ID NO: 172. In some aspects, the anti-CCR8 antibody binds an epitope on human CCR8, comprising one or more amino acids selected from amino acid residues 5-25 of SEQ ID NO: 172. In some aspects, the anti-CCR8 antibody binds an epitope on human CCR8, comprising one or more amino acids selected from amino acid residues 5-30 of SEQ ID NO: 172. In some aspects, the anti-CCR8 antibody binds an epitope on human CCR8, comprising one or more amino acids selected from amino acid residues 5-35 of SEQ ID NO: 172. In some aspects, the anti-CCR8 antibody binds an epitope on human CCR8, comprising one or more amino acids selected from amino acid residues 10-15 of SEQ ID NO: 172. In some aspects, the anti-CCR8 antibody binds an epitope on human CCR8, comprising one or more amino acids selected from amino acid residues 10-20 of SEQ ID NO: 172. In some aspects, the anti-CCR8 antibody binds an epitope on human CCR8, comprising one or more amino acids selected from amino acid residues 10-25 of SEQ ID NO: 172. In some aspects, the anti-CCR8 antibody binds an epitope on human CCR8, comprising one or more amino acids selected from amino acid residues 10-30 of SEQ ID NO: 172. In some aspects, the anti-CCR8 antibody binds an epitope on human CCR8, comprising one or more amino acids selected from amino acid residues 10-35 of SEQ ID NO: 172. In some aspects, the anti-CCR8 antibody binds an epitope on human CCR8, comprising one or more amino acids selected from amino acid residues 15-20 of SEQ ID NO: 172. In some aspects, the anti-CCR8 antibody binds an epitope on human CCR8, comprising one or more amino acids selected from amino acid residues 15-25 of SEQ ID NO: 172. In some aspects, the anti-CCR8 antibody binds an epitope on human CCR8, comprising one or more amino acids selected from amino acid residues 15-30 of SEQ ID NO: 172. In some aspects, the anti-CCR8 antibody binds an epitope on human CCR8, comprising one or more amino acids selected from amino acid residues 15-35 of SEQ ID NO: 172. In some aspects, the anti-CCR8 antibody binds an epitope on human CCR8, comprising one or more amino acids selected from amino acid residues 20-25 of SEQ ID NO: 172. In some aspects, the anti-CCR8 antibody binds an epitope on human CCR8, comprising one or more amino acids selected from amino acid residues 20-30 of SEQ ID NO: 172. In some aspects, the anti-CCR8 antibody binds an epitope on human CCR8, comprising one or more amino acids selected from amino acid residues 20-35 of SEQ ID NO: 172. In some aspects, the anti-CCR8 antibody binds an epitope on human CCR8, comprising one or more amino acids selected from amino acid residues 25-30 of SEQ ID NO: 172. In some aspects, the anti-CCR8 antibody binds an epitope on human CCR8, comprising one or more amino acids selected from amino acid residues 25-35 of SEQ ID NO: 172. In some aspects, the anti-CCR8 antibody binds an epitope on human CCR8, comprising one or more amino acids selected from amino acid residues 30-35 of SEQ ID NO: 172.

In some aspects, the anti-CCR8 antibody binds an epitope on human CCR8 comprising an amino acid sequence selected from SEQ ID NOs: 180-200.

II.B. Antibody Sequences

In some aspects, the anti-CCR8 antibody comprises a whole antibody, e.g., an antibody comprising two light chain polypeptides and two heavy chain polypeptides. In some aspects, the anti-CCR8 antibody comprises a fragment of a whole antibody that retains the ability to bind CCR8. In some aspects, the anti-CCR8 antibody is a single chain antibody. In some aspects, the anti-CCR8 antibody is a single chain Fv fragment (scFv). In some aspects, the anti-CCR8 antibody is an Fd fragment. In some aspects, the anti-CCR8 antibody is an Fab fragment. In some aspects, the anti-CCR8 antibody is an Fab' fragment. In some aspects, the anti-CCR8 antibody is an F(ab')2 fragment. In some aspects, In some aspects, the anti-CCR8 antibody is selected from an intrabody, a minibody, a triabody, or a diabody.

In some aspects, the anti-CCR8 antibody comprises a variable heavy (VH) chain and a variable light (VL) chain. In some aspects, the VH comprises a VH complementarity-determining region (CDR) 1, a VH CDR2, and a VH CDR3; and the VL comprises a VL CDR1, a VL CDR2, and a VL CDR3. In some aspects, the VH CDR1 comprises the amino acid sequence set forth in Table 2A. In some aspects, the VH CDR1 comprises the amino acid sequence set forth in SEQ ID NO: 201. In some aspects, the VH CDR1 comprises the amino acid sequence set forth in SEQ ID NO: 202. In some aspects, the VH CDR1 comprises the amino acid sequence set forth in SEQ ID NO: 203. In some aspects, the VH CDR1 comprises the amino acid sequence set forth in SEQ ID NO: 204.

TABLE 2A

VH CDR1 Consensus Sequences

| SEQ ID NO: | VH CDR1 Consensus Sequence |
|---|---|
| 201 | S/D/G/A)Y(Y/A/T)M(H/L/N) |
| 202 | D/G/A)Y(A/T)M(H/L/N) |

TABLE 2A-continued

VH CDR1 Consensus Sequences

| SEQ ID NO: | VH CDR1 Consensus Sequence |
|---|---|
| 203 | (G/A)YTM(L/N) |
| 204 | S/D)Y(Y/A)MH |

Note: amino acid residue listed in parenthesis above (and elsewhere in the present disclosure) designate the amino acid at that particular position in the alternative. For example, Y(Y/A)MH means that the sequence can be either YYMH or YAMH.

In some aspects, the VH CDR2 comprises the amino acid sequence set forth in Table 2B. In some aspects, the VH CDR2 comprises the amino acid sequence set forth in SEQ ID NO: 205. In some aspects, the VH CDR2 comprises the amino acid sequence set forth in SEQ ID NO: 206. In some aspects, the VH CDR2 comprises the amino acid sequence set forth in SEQ ID NO: 207. In some aspects, the VH CDR2 comprises the amino acid sequence set forth in SEQ ID NO: 208.

TABLE 2B

VH CDR2 Consensus Sequences

| SEQ ID NO: | VH CDR2 Consensus Sequence |
|---|---|
| 205 | (I/G/A)I(N/S/T)(P/W/A)(S/N)(G/S)G(S/R)(T/I)(S/G/Y)YA(Q/D)(K/S)(F/V)(Q/K)G |
| 206 | AI(T/S)ASGGRTYYADSVKG |
| 207 | (G/A)I(T/S)(W/A)(N/S)(S/G)G(S/R)(I/T)(G/Y)YADSVKG |
| 208 | (I/G)I(N/S)(P/W)(S/N)(G/S)GS(T/I)(S/G)YA(Q/D)(K/S)(F/V)(Q/K)G |

In some aspects, the VH CDR3 comprises the amino acid sequence set forth in Table 2C. In some aspects, the VH CDR3 comprises the amino acid sequence set forth in SEQ ID NO: 209. In some aspects, the VH CDR3 comprises the amino acid sequence set forth in SEQ ID NO: 210.

TABLE 2C

VH CDR3 Consensus Sequences

| SEQ ID NO: | VH CDR3 Consensus Sequence |
|---|---|
| 209 | (A/G)V(R/G)N(R/G)FRFDY |
| 210 | GR(K/V/D/E/R)SYR(D/E/K/V)SLRFDY |

In some aspects, the anti-CCR8 antibody comprises a VH CDR1 having the amino acid sequence set forth in SEQ ID NO: 201, a VH CDR2 having the amino acid sequence set forth in SEQ ID NO: 205, and a VH CDR3 having the amino acid sequence set forth in SEQ ID NO: 209. In some aspects, the anti-CCR8 antibody comprises a VH CDR1 having the amino acid sequence set forth in SEQ ID NO: 204, a VH CDR2 having the amino acid sequence set forth in SEQ ID NO: 205, and a VH CDR3 having the amino acid sequence set forth in SEQ ID NO: 209. In some aspects, the anti-CCR8 antibody comprises a VH CDR1 having the amino acid sequence set forth in SEQ ID NO: 201, a VH CDR2 having the amino acid sequence set forth in SEQ ID NO:

208, and a VH CDR3 having the amino acid sequence set forth in SEQ ID NO: 209. In some aspects, the anti-CCR8 antibody comprises a VH CDR1 having the amino acid sequence set forth in SEQ ID NO: 204, a VH CDR2 having the amino acid sequence set forth in SEQ ID NO: 208, and a VH CDR3 having the amino acid sequence set forth in SEQ ID NO: 209. In some aspects, the anti-CCR8 antibody comprises a VH CDR1 having the amino acid sequence set forth in SEQ ID NO: 201, a VH CDR2 having the amino acid sequence set forth in SEQ ID NO: 208, and a VH CDR3 having the amino acid sequence set forth in SEQ ID NO: 209. In some aspects, the anti-CCR8 antibody comprises a VH CDR1 having the amino acid sequence set forth in SEQ ID NO: 201, a VH CDR2 having the amino acid sequence set forth in SEQ ID NO: 208, and a VH CDR3 having the amino acid sequence set forth in SEQ ID NO: 209. In some aspects, the anti-CCR8 antibody comprises a VH CDR1 having the amino acid sequence set forth in SEQ ID NO: 202, a VH CDR2 having the amino acid sequence set forth in SEQ ID NO: 206, and a VH CDR3 having the amino acid sequence set forth in SEQ ID NO: 210. In some aspects, the anti-CCR8 antibody comprises a VH CDR1 having the amino acid sequence set forth in SEQ ID NO: 202, a VH CDR2 having the amino acid sequence set forth in SEQ ID NO: 207, and a VH CDR3 having the amino acid sequence set forth in SEQ ID NO: 210. In some aspects, the anti-CCR8 antibody comprises a VH CDR1 having the amino acid sequence set forth in SEQ ID NO: 203, a VH CDR2 having the amino acid sequence set forth in SEQ ID NO: 206, and a VH CDR3 having the amino acid sequence set forth in SEQ ID NO: 210. In some aspects, the anti-CCR8 antibody comprises a VH CDR1 having the amino acid sequence set forth in SEQ ID NO: 203, a VH CDR2 having the amino acid sequence set forth in SEQ ID NO: 207, and a VH CDR3 having the amino acid sequence set forth in SEQ ID NO: 210.

In some aspects, the VL CDR1 comprises the amino acid sequence set forth in Table 3A. In some aspects, the VL CDR1 comprises the amino acid sequence set forth in SEQ ID NO: 211. In some aspects, the VL CDR1 comprises the amino acid sequence set forth in SEQ ID NO: 212. In some aspects, the VL CDR1 comprises the amino acid sequence set forth in SEQ ID NO: 213. In some aspects, the VL CDR1 comprises the amino acid sequence set forth in SEQ ID NO: 214. In some aspects, the VL CDR1 comprises the amino acid sequence set forth in SEQ ID NO: 215. In some aspects, the VL CDR1 comprises the amino acid sequence set forth in SEQ ID NO: 216. In some aspects, the VL CDR1 comprises the amino acid sequence set forth in SEQ ID NO: 217. In some aspects, the VL CDR1 comprises the amino acid sequence set forth in SEQ ID NO: 218. In some aspects, the VL CDR1 comprises the amino acid sequence set forth in SEQ ID NO: 219.

TABLE 3A

VL CDR1 Consensus Sequences

| SEQ ID NO: | VL CDR1 Consensus Sequence |
|---|---|
| 211 | SSY(T/A)G(N/S/P)(I/R/V/S)(N/V/T)(L/-)(P/F/Y/H)VV |
| 212 | SSY(T/A)G(N/S)(I/R/S)(N/V/T)(L/-)(P/F/Y/H)VV |
| 213 | SSYAGSST(F/Y)VV |
| 214 | SSYAGS(R/I)(V/T)(F/H)VV |
| 215 | (A/G)(T/A)WD(Y/S)SL(T/R)(A/M)(V/W)V |
| 216 | (A/G)(T/A)WD(Y/S)SL(T/R/S)(A/M)(V/W)V |
| 217 | (A/G)TWD(Y/S)SL(T/S)A(V/W)V |
| 218 | G(A/T)WDSSL(R/S)(M/A)WV |
| 219 | (S/T)G(S/T)(G/S)SNIG(N/K)N(Y/F)VS |

In some aspects, the VL CDR2 comprises the amino acid sequence set forth in Table 3B. In some aspects, the VL CDR2 comprises the amino acid sequence set forth in SEQ ID NO: 220. In some aspects, the VL CDR2 comprises the amino acid sequence set forth in SEQ ID NO: 221. In some aspects, the VL CDR2 comprises the amino acid sequence set forth in SEQ ID NO: 222. In some aspects, the VL CDR2 comprises the amino acid sequence set forth in SEQ ID NO: 223. In some aspects, the VL CDR2 comprises the amino acid sequence set forth in SEQ ID NO: 224. In some aspects, the VL CDR2 comprises the amino acid sequence set forth in SEQ ID NO: 225. In some aspects, the VL CDR2 comprises the amino acid sequence set forth in SEQ ID NO: 226. In some aspects, the VL CDR2 comprises the amino acid sequence set forth in SEQ ID NO: 227. In some aspects, the VL CDR2 comprises the amino acid sequence set forth in SEQ ID NO: 228. In some aspects, the VL CDR2 comprises the amino acid sequence set forth in SEQ ID NO: 229. In some aspects, the VL CDR2 comprises the amino acid sequence set forth in SEQ ID NO: 230. In some aspects, the VL CDR2 comprises the amino acid sequence set forth in SEQ ID NO: 231. In some aspects, the VL CDR2 comprises the amino acid sequence set forth in SEQ ID NO: 232.

TABLE 3B

VL CDR2 Consensus Sequences

| SEQ ID NO: | VL CDR2 Consensus Sequence |
|---|---|
| 220 | E(V/A)(N/T/I/S)KRPS |
| 221 | E(V/A)(N/T/S)KRPS |
| 222 | EV(T/S)KRPS |

TABLE 3B-continued

VL CDR2 Consensus Sequences

| SEQ ID NO: | VL CDR2 Consensus Sequence |
|---|---|
| 223 | E(A/V)TKRPS |
| 224 | EV(N/S)KRPS |
| 225 | EV(N/T)KRPS |
| 226 | DN(D/T)(K/R)PS |
| 227 | DN(D/T/N)(K/R)RPS |
| 228 | DN(D/N)KRPS |
| 229 | DN(T/N)(K/R)RPS |
| 230 | D(N/D)(D/T/N)(K/R)RPS |
| 231 | D(N/D)(D/N)KRPS |
| 232 | D(N/D)(T/N)(K/R)RPS |

In some aspects, the VL CDR3 comprises the amino acid sequence set forth in Table 3C. In some aspects, the VL CDR3 comprises the amino acid sequence set forth in SEQ ID NO: 233. In some aspects, the VL CDR3 comprises the amino acid sequence set forth in SEQ ID NO: 234. In some aspects, the VL CDR3 comprises the amino acid sequence set forth in SEQ ID NO: 235. In some aspects, the VL CDR3 comprises the amino acid sequence set forth in SEQ ID NO: 236. In some aspects, the VL CDR3 comprises the amino acid sequence set forth in SEQ ID NO: 237. In some aspects, the VL CDR3 comprises the amino acid sequence set forth in SEQ ID NO: 238. In some aspects, the VL CDR3 comprises the amino acid sequence set forth in SEQ ID NO: 239. In some aspects, the VL CDR3 comprises the amino acid sequence set forth in SEQ ID NO: 240.

TABLE 3C

VL CDR3 Consensus Sequences

| SEQ ID NO: | VL CDR3 Consensus Sequence |
|---|---|
| 233 | SSY(T/A)G(N/S/P)(I/R/V/S)(N/V/T)(L/-)(P/F/Y/H)VV |
| 234 | SSY(T/A)G(N/S)(I/R/S)(N/V/T)(L/-)(P/F/Y/H)VV |
| 235 | SSYAGSST(F/Y)VV |
| 236 | SSYAGS(R/I)(V/T)(F/H)VV |
| 237 | (A/G)(T/A)WD(Y/S)SL(T/R)(A/M)(V/W)V |
| 238 | (A/G)(T/A)WD(Y/S)SL(T/R/S)(A/M)(V/W)V |
| 239 | (A/G)TWD(Y/S)SL(T/S)A(V/W)V |
| 240 | G(A/T)WDSSL(R/S)(M/A)WV |

In some aspects, the anti-CCR8 antibody comprises a VL CDR1 having the amino acid sequence set forth in SEQ ID NO: 211, a VL CDR2 having the amino acid sequence set forth in SEQ ID NO: 220, and a VL CDR3 having the amino acid sequence set forth in SEQ ID NO: 233. In some aspects, the anti-CCR8 antibody comprises a VL CDR1 having the amino acid sequence set forth in SEQ ID NO: 212, a VL CDR2 having the amino acid sequence set forth in SEQ ID NO: 221, and a VL CDR3 having the amino acid sequence set forth in SEQ ID NO: 234. In some aspects, the anti-CCR8 antibody comprises a VL CDR1 having the amino acid sequence set forth in SEQ ID NO: 213, a VL CDR2 having the amino acid sequence set forth in SEQ ID NO: 222, and a VL CDR3 having the amino acid sequence set forth in SEQ ID NO: 235. In some aspects, the anti-CCR8 antibody comprises a VL CDR1 having the amino acid sequence set forth in SEQ ID NO: 213, a VL CDR2 having the amino acid sequence set forth in SEQ ID NO: 222, and a VL CDR3 having the amino acid sequence set forth in SEQ ID NO: 236. In some aspects, the anti-CCR8 antibody comprises a VL CDR1 having the amino acid sequence set forth in SEQ ID NO: 213, a VL CDR2 having the amino acid sequence set forth in SEQ ID NO: 223, and a VL CDR3 having the amino acid sequence set forth in SEQ ID NO: 235. In some aspects, the anti-CCR8 antibody comprises a VL CDR1 having the amino acid sequence set forth in SEQ ID NO: 213, a VL CDR2 having the amino acid sequence set forth in SEQ ID NO: 223, and a VL CDR3 having the amino acid sequence set forth in SEQ ID NO: 236. In some aspects, the anti-CCR8 antibody comprises a VL CDR1 having the amino acid sequence set forth in SEQ ID NO: 217, a VL CDR2 having the amino acid sequence set forth in SEQ ID NO: 227, and a VL CDR3 having the amino acid sequence set forth in SEQ ID NO: 238. In some aspects, the anti-CCR8 antibody comprises a VL CDR1 having the amino acid sequence set forth in SEQ ID NO: 218, a VL CDR2 having the amino acid sequence set forth in SEQ ID NO: 231, and a VL CDR3 having the amino acid sequence set forth in SEQ ID NO: 239. In some aspects, the anti-CCR8 antibody comprises a VL CDR1 having the amino acid sequence set forth in SEQ ID NO: 219, a VL CDR2 having the amino acid sequence set forth in SEQ ID NO: 232, and a VL CDR3 having the amino acid sequence set forth in SEQ ID NO: 240.

In some aspects, the VH CDR3 of the anti-CCR8 antibody comprises an amino acid sequence selected from the amino acid sequence set forth in SEQ ID NOs: 7, 17, 27, 37, 47, 57, 67, 77, 87, 97, 107, 117, 127, 137, 147, 157, and 167. In some aspects, the VH CDR2 of the anti-CCR8 antibody comprises an amino acid sequence selected from the amino acid sequence set forth in SEQ ID NOs: 6, 16, 26, 36, 46, 56, 66, 76, 86, 96, 106, 116, 126, 136, 146, 156, and 166. In some aspects, the VH CDR1 of the anti-CCR8 antibody comprises an amino acid sequence selected from the amino acid sequence set forth in SEQ ID NOs: 5, 15, 25, 35, 45, 55, 65, 75, 85, 95, 105, 115, 125, 135, 145, 155, and 165.

In some aspects, the VH CDR3 of the anti-CCR8 antibody comprises an amino acid sequence selected from the amino acid sequence set forth in SEQ ID NOs: 47, 107, 117, 137, and 147. In some aspects, the VH CDR2 of the anti-CCR8 antibody comprises an amino acid sequence selected from the amino acid sequence set forth in SEQ ID NOs: 46, 106, 116, 136, and 146. In some aspects, the VH CDR1 of the anti-CCR8 antibody comprises an amino acid sequence selected from the amino acid sequence set forth in SEQ ID NOs: 45, 105, 115, 135, and 145.

In some aspects, the VH CDR3 of the anti-CCR8 antibody comprises an amino acid sequence selected from the amino acid sequence set forth in SEQ ID NOs: 7, 17, 27, 37, 57, 67, 77, 87, 97, 127, 157, and 167. In some aspects, the VH CDR2 of the anti-CCR8 antibody comprises an amino acid sequence selected from the amino acid sequence set forth in SEQ ID NOs: 6, 16, 26, 36, 56, 66, 76, 86, 96, 126, 156, and 166. In some aspects, the VH CDR2 of the anti-CCR8 antibody comprises an amino acid sequence selected from the amino acid sequence set forth in SEQ ID NOs: 5, 15, 25, 35, 55, 65, 75, 85, 95, 125, 155, and 165.

In some aspects, the VL CDR3 of the anti-CCR8 antibody comprises an amino acid sequence selected from the amino acid sequence set forth in SEQ ID NOs: 10, 20, 30, 40, 50, 60, 70, 80, 90, 100, 110, 120, 130, 140, 150, 160, and 170. In some aspects, the VL CDR2 of the anti-CCR8 antibody comprises an amino acid sequence selected from the amino acid sequence set forth in SEQ ID NOs: 9, 19, 29, 39, 49, 59, 69, 79, 89, 99, 109, 119, 129, 139, 149, 159, and 169. In some aspects, the VL CDR1 of the anti-CCR8 antibody comprises an amino acid sequence selected from the amino acid sequence set forth in SEQ ID NOs: 8, 18, 28, 38, 48, 58, 68, 78, 88, 98, 108, 118, 128, 138, 148, 158, and 168.

In some aspects, the VL CDR3 of the anti-CCR8 antibody comprises an amino acid sequence selected from the amino acid sequence set forth in SEQ ID NOs: 50, 110, 120, 140, and 150. In some aspects, the VL CDR2 of the anti-CCR8 antibody comprises an amino acid sequence selected from the amino acid sequence set forth in SEQ ID NOs: 49, 109, 119, 139, and 149. In some aspects, the VL CDR1 of the anti-CCR8 antibody comprises an amino acid sequence selected from the amino acid sequence set forth in SEQ ID NOs: 48, 108, 118, 138, and 148.

In some aspects, the VL CDR3 of the anti-CCR8 antibody comprises an amino acid sequence selected from the amino acid sequence set forth in SEQ ID NOs: 10, 20, 30, 40, 60, 70, 80, 90, 100, 130, 160, and 170. In some aspects, the VL CDR2 of the anti-CCR8 antibody comprises an amino acid sequence selected from the amino acid sequence set forth in SEQ ID NOs: 9, 19, 29, 39, 59, 69, 79, 89, 99, 129, 159, and 169. In some aspects, the VL CDR2 of the anti-CCR8 antibody comprises an amino acid sequence selected from the amino acid sequence set forth in SEQ ID NOs: 8, 18, 28, 38, 58, 68, 78, 88, 98, 128, 158, and 168.

In some aspects the anti-CCR8 antibody comprises a VH CDR1 comprising the amino acid sequence set forth in SEQ ID NO: 45, a VH CDR2 comprising the amino acid sequence set forth in SEQ ID NO: 46, a VH CDR3 comprising the amino acid sequence set forth in SEQ ID NO: 47, a VL CDR1 comprising the amino acid sequence set forth in SEQ ID NO: 48, a VL CDR2 comprising the amino acid sequence set forth in SEQ ID NO: 49, and a VL CDR3 comprising the amino acid sequence set forth in SEQ ID NO: 50.

In some aspects the anti-CCR8 antibody comprises a VH CDR1 comprising the amino acid sequence set forth in SEQ ID NO: 105, a VH CDR2 comprising the amino acid sequence set forth in SEQ ID NO: 106, a VH CDR3 comprising the amino acid sequence set forth in SEQ ID NO: 107, a VL CDR1 comprising the amino acid sequence set forth in SEQ ID NO: 108, a VL CDR2 comprising the amino acid sequence set forth in SEQ ID NO: 109, and a VL CDR3 comprising the amino acid sequence set forth in SEQ ID NO: 110.

In some aspects the anti-CCR8 antibody comprises a VH CDR1 comprising the amino acid sequence set forth in SEQ ID NO: 115, a VH CDR2 comprising the amino acid sequence set forth in SEQ ID NO: 116, a VH CDR3 comprising the amino acid sequence set forth in SEQ ID NO: 117, a VL CDR1 comprising the amino acid sequence set forth in SEQ ID NO: 118, a VL CDR2 comprising the amino acid sequence set forth in SEQ ID NO: 119, and a VL CDR3 comprising the amino acid sequence set forth in SEQ ID NO: 120.

In some aspects the anti-CCR8 antibody comprises a VH CDR1 comprising the amino acid sequence set forth in SEQ ID NO: 135, a VH CDR2 comprising the amino acid sequence set forth in SEQ ID NO: 136, a VH CDR3 comprising the amino acid sequence set forth in SEQ ID NO: 137, a VL CDR1 comprising the amino acid sequence set forth in SEQ ID NO: 138, a VL CDR2 comprising the amino acid sequence set forth in SEQ ID NO: 139, and a VL CDR3 comprising the amino acid sequence set forth in SEQ ID NO: 140.

In some aspects the anti-CCR8 antibody comprises a VH CDR1 comprising the amino acid sequence set forth in SEQ ID NO: 145, a VH CDR2 comprising the amino acid sequence set forth in SEQ ID NO: 146, a VH CDR3 comprising the amino acid sequence set forth in SEQ ID NO: 147, a VL CDR1 comprising the amino acid sequence set forth in SEQ ID NO: 148, a VL CDR2 comprising the amino acid sequence set forth in SEQ ID NO: 149, and a VL CDR3 comprising the amino acid sequence set forth in SEQ ID NO: 150.

In some aspects the anti-CCR8 antibody comprises a VH CDR1 comprising the amino acid sequence set forth in SEQ ID NO: 5, a VH CDR2 comprising the amino acid sequence set forth in SEQ ID NO: 6, a VH CDR3 comprising the amino acid sequence set forth in SEQ ID NO: 7, a VL CDR1 comprising the amino acid sequence set forth in SEQ ID NO: 8, a VL CDR2 comprising the amino acid sequence set forth in SEQ ID NO: 9, and a VL CDR3 comprising the amino acid sequence set forth in SEQ ID NO: 10.

In some aspects the anti-CCR8 antibody comprises a VH CDR1 comprising the amino acid sequence set forth in SEQ ID NO: 15, a VH CDR2 comprising the amino acid sequence set forth in SEQ ID NO: 16, a VH CDR3 comprising the amino acid sequence set forth in SEQ ID NO: 17, a VL CDR1 comprising the amino acid sequence set forth in SEQ ID NO: 18, a VL CDR2 comprising the amino acid sequence set forth in SEQ ID NO: 19, and a VL CDR3 comprising the amino acid sequence set forth in SEQ ID NO: 20.

In some aspects the anti-CCR8 antibody comprises a VH CDR1 comprising the amino acid sequence set forth in SEQ ID NO: 25, a VH CDR2 comprising the amino acid sequence set forth in SEQ ID NO: 26, a VH CDR3 comprising the amino acid sequence set forth in SEQ ID NO: 27, a VL CDR1 comprising the amino acid sequence set forth in SEQ ID NO: 28, a VL CDR2 comprising the amino acid sequence set forth in SEQ ID NO: 29, and a VL CDR3 comprising the amino acid sequence set forth in SEQ ID NO: 30.

In some aspects the anti-CCR8 antibody comprises a VH CDR1 comprising the amino acid sequence set forth in SEQ ID NO: 35, a VH CDR2 comprising the amino acid sequence set forth in SEQ ID NO: 36, a VH CDR3 comprising the amino acid sequence set forth in SEQ ID NO: 37, a VL CDR1 comprising the amino acid sequence set forth in SEQ ID NO: 38, a VL CDR2 comprising the amino acid sequence set forth in SEQ ID NO: 39, and a VL CDR3 comprising the amino acid sequence set forth in SEQ ID NO: 40.

In some aspects the anti-CCR8 antibody comprises a VH CDR1 comprising the amino acid sequence set forth in SEQ ID NO: 55, a VH CDR2 comprising the amino acid sequence set forth in SEQ ID NO: 56, a VH CDR3 comprising the amino acid sequence set forth in SEQ ID NO: 57, a VL CDR1 comprising the amino acid sequence set forth in SEQ ID NO: 58, a VL CDR2 comprising the amino acid sequence set forth in SEQ ID NO: 59, and a VL CDR3 comprising the amino acid sequence set forth in SEQ ID NO: 60.

In some aspects the anti-CCR8 antibody comprises a VH CDR1 comprising the amino acid sequence set forth in SEQ ID NO: 65, a VH CDR2 comprising the amino acid sequence set forth in SEQ ID NO: 66, a VH CDR3 comprising the amino acid sequence set forth in SEQ ID NO: 67, a VL CDR1 comprising the amino acid sequence set forth in SEQ ID NO: 68, a VL CDR2 comprising the amino acid sequence set forth in SEQ ID NO: 69, and a VL CDR3 comprising the amino acid sequence set forth in SEQ ID NO: 70.

In some aspects the anti-CCR8 antibody comprises a VH CDR1 comprising the amino acid sequence set forth in SEQ ID NO: 75, a VH CDR2 comprising the amino acid sequence set forth in SEQ ID NO: 76, a VH CDR3 comprising the amino acid sequence set forth in SEQ ID NO: 77, a VL CDR1 comprising the amino acid sequence set forth in SEQ ID NO: 78, a VL CDR2 comprising the amino acid sequence set forth in SEQ ID NO: 79, and a VL CDR3 comprising the amino acid sequence set forth in SEQ ID NO: 80.

In some aspects the anti-CCR8 antibody comprises a VH CDR1 comprising the amino acid sequence set forth in SEQ ID NO: 85, a VH CDR2 comprising the amino acid sequence set forth in SEQ ID NO: 86, a VH CDR3 comprising the amino acid sequence set forth in SEQ ID NO: 87, a VL CDR1 comprising the amino acid sequence set forth in SEQ ID NO: 88, a VL CDR2 comprising the amino acid sequence set forth in SEQ ID NO: 89, and a VL CDR3 comprising the amino acid sequence set forth in SEQ ID NO: 90.

In some aspects the anti-CCR8 antibody comprises a VH CDR1 comprising the amino acid sequence set forth in SEQ ID NO: 95, a VH CDR2 comprising the amino acid sequence set forth in SEQ ID NO: 96, a VH CDR3 comprising the amino acid sequence set forth in SEQ ID NO: 97, a VL CDR1 comprising the amino acid sequence set forth in SEQ ID NO: 98, a VL CDR2 comprising the amino acid sequence set forth in SEQ ID NO: 99, and a VL CDR3 comprising the amino acid sequence set forth in SEQ ID NO: 100.

In some aspects the anti-CCR8 antibody comprises a VH CDR1 comprising the amino acid sequence set forth in SEQ ID NO: 125, a VH CDR2 comprising the amino acid sequence set forth in SEQ ID NO: 126, a VH CDR3 comprising the amino acid sequence set forth in SEQ ID NO: 127, a VL CDR1 comprising the amino acid sequence set forth in SEQ ID NO: 128, a VL CDR2 comprising the amino acid sequence set forth in SEQ ID NO: 129, and a VL CDR3 comprising the amino acid sequence set forth in SEQ ID NO: 130.

In some aspects the anti-CCR8 antibody comprises a VH CDR1 comprising the amino acid sequence set forth in SEQ ID NO: 155, a VH CDR2 comprising the amino acid sequence set forth in SEQ ID NO: 156, a VH CDR3 comprising the amino acid sequence set forth in SEQ ID NO: 157, a VL CDR1 comprising the amino acid sequence set forth in SEQ ID NO: 158, a VL CDR2 comprising the amino acid sequence set forth in SEQ ID NO: 159, and a VL CDR3 comprising the amino acid sequence set forth in SEQ ID NO: 160.

In some aspects the anti-CCR8 antibody comprises a VH CDR1 comprising the amino acid sequence set forth in SEQ ID NO: 165, a VH CDR2 comprising the amino acid sequence set forth in SEQ ID NO: 166, a VH CDR3 comprising the amino acid sequence set forth in SEQ ID NO: 167, a VL CDR1 comprising the amino acid sequence set forth in SEQ ID NO: 168, a VL CDR2 comprising the amino acid sequence set forth in SEQ ID NO: 169, and a VL CDR3 comprising the amino acid sequence set forth in SEQ ID NO: 170.

In some aspects, the VH chain comprises an amino acid sequence having at least about 80%, at least about 85%, at least about 90%, at least about 95%, at least about 96%, at least about 97%, at least about 98%, or at least about 99% sequence identity to an amino acid selected from SEQ ID NOs: 41, 101, 111, 131, and 141. In some aspects, the VH chain comprises an amino acid sequence selected from the amino acid sequence set forth in SEQ ID NOs: 41, 101, 111, 131, and 141. In some aspects, the VL chain comprises an amino acid sequence having at least about 80%, at least about 85%, at least about 90%, at least about 95%, at least about 96%, at least about 97%, at least about 98%, or at least about 99% sequence identity to an amino acid selected from SEQ ID NOs: 42, 102, 112, 132, and 142. In some aspects, the VL chain comprises an amino acid sequence selected from the amino acid sequence set forth in SEQ ID NOs: 42, 102, 112, 132, and 142. In some aspects, the VH chain comprises an amino acid sequence having at least about 80%, at least about 85%, at least about 90%, at least about 95%, at least about 96%, at least about 97%, at least about 98%, or at least about 99% sequence identity to an amino acid selected from SEQ ID NOs: 41, 101, 111, 131, and 141; and the VL chain comprises an amino acid sequence having at least about 80%, at least about 85%, at least about 90%, at least about 95%, at least about 96%, at least about 97%, at least about 98%, or at least about 99% sequence identity to an amino acid selected from SEQ ID NOs: 42, 102, 112, 132, and 142; wherein the anti-CCR8 antibody does not bind cyno CCR8. In some aspects, the VH chain comprises an amino acid sequence selected from the amino acid sequence set forth in SEQ ID NOs: 41, 101, 111, 131, and 141; and the VL chain comprises an amino acid sequence selected from the amino acid sequence set forth in SEQ ID NOs: 42, 102, 112, 132, and 142; wherein the anti-CCR8 antibody does not bind cyno CCR8.

In some aspects, the anti-CCR8 antibody comprises a VH chain comprising an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 41 and a VL chain comprising an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 42; wherein the anti-CCR8 antibody does not bind cyno CCR8. In some aspects, the anti-CCR8 antibody comprises a VH chain comprising the amino acid sequence set forth in SEQ ID NO: 41 and a VL chain comprising the amino acid sequence set forth in SEQ ID NO: 42; wherein the anti-CCR8 antibody does not bind cyno CCR8.

In some aspects, the anti-CCR8 antibody comprises a VH chain comprising an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 101 and a VL chain comprising an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 102; wherein the anti-CCR8 antibody does not bind cyno CCR8. In some aspects, the anti-CCR8 antibody comprises a VH chain comprising the amino acid sequence set forth in SEQ ID NO: 101 and a VL chain comprising the amino acid sequence set forth in SEQ ID NO: 102; wherein the anti-CCR8 antibody does not bind cyno CCR8.

In some aspects, the anti-CCR8 antibody comprises a VH chain comprising an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 111 and a VL chain comprising an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 112; wherein the anti-CCR8 antibody does not bind cyno CCR8. In some aspects, the anti-CCR8 antibody comprises a VH chain comprising the amino acid sequence set forth in SEQ ID NO: 111 and a VL chain comprising the amino acid sequence set forth in SEQ ID NO: 112; wherein the anti-CCR8 antibody does not bind cyno CCR8.

In some aspects, the anti-CCR8 antibody comprises a VH chain comprising an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 131 and a VL chain comprising an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 132; wherein the anti-CCR8 antibody does not bind cyno CCR8. In some aspects, the anti-CCR8 antibody comprises a VH chain comprising the amino acid sequence set forth in SEQ ID NO: 131 and a VL chain comprising the amino acid sequence set forth in SEQ ID NO: 132; wherein the anti-CCR8 antibody does not bind cyno CCR8.

In some aspects, the anti-CCR8 antibody comprises a VH chain comprising an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 141 and a VL chain comprising an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 142; wherein the anti-CCR8 antibody does not bind cyno CCR8. In some aspects, the anti-CCR8 antibody comprises a VH chain comprising the amino acid sequence set forth in SEQ ID NO: 141 and a VL chain comprising the amino acid sequence set forth in SEQ ID NO: 142; wherein the anti-CCR8 antibody does not bind cyno CCR8.

In some aspects, the VH chain comprises an amino acid sequence having at least about 80%, at least about 85%, at least about 90%, at least about 95%, at least about 96%, at least about 97%, at least about 98%, or at least about 99% sequence identity to an amino acid sequence selected from the amino acid sequence set forth in SEQ ID NOs: 1, 11, 21, 31, 51, 61, 71, 81, 91, 121, 151, and 161. In some aspects, the VH chain comprises an amino acid sequence selected from the amino acid sequence set forth in SEQ ID NOs: 1, 11, 21, 31, 51, 61, 71, 81, 91, 121, 151, and 161. In some aspects, the VL chain comprises an amino acid sequence having at least about 80%, at least about 85%, at least about 90%, at least about 95%, at least about 96%, at least about 97%, at least about 98%, or at least about 99% sequence identity to an amino acid sequence selected from the amino acid sequence set forth in SEQ ID NOs: 2, 12, 22, 32, 52, 62, 72, 82, 92, 122, 152, and 162. In some aspects, the VL chain comprises an amino acid sequence selected from the amino acid sequence set forth in SEQ ID NOs: 2, 12, 22, 32, 52, 62, 72, 82, 92, 122, 152, and 162. In some aspects, the VH chain comprises an amino acid sequence having at least about 80%, at least about 85%, at least about 90%, at least about 95%, at least about 96%, at least about 97%, at least about 98%, or at least about 99% sequence identity to an amino acid sequence selected from the amino acid sequence set forth in SEQ ID NOs: 1, 11, 21, 31, 51, 61, 71, 81, 91, 121, 151, and 161; and the VL chain comprises an amino acid sequence having at least about 80%, at least about 85%, at least about 90%, at least about 95%, at least about 96%, at least about 97%, at least about 98%, or at least about 99% sequence identity to an amino acid sequence selected from the amino acid sequence set forth in SEQ ID NOs: 2, 12, 22, 32, 52, 62, 72, 82, 92, 122, 152, and 162; wherein the anti-CCR8 antibody binds human CCR8 and cyno CCR8. In some aspects, the VH chain comprises an amino acid sequence selected from the amino acid sequence set forth in SEQ ID NOs: 1, 11, 21, 31, 51, 61, 71, 81, 91, 121, 151, and 161; and the VL chain comprises an amino acid sequence selected from the amino acid sequence set forth in SEQ ID NOs: 2, 12, 22, 32, 52, 62, 72, 82, 92, 122, 152, and 162; wherein the anti-CCR8 antibody binds human CCR8 and cyno CCR8.

In some aspects, the anti-CCR8 antibody comprises a VH chain comprising an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 1 and a VL chain comprising an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 2; wherein the anti-CCR8 antibody binds human CCR8 and cyno CCR8. In some aspects, the anti-CCR8 antibody comprises a VH chain comprising the amino acid sequence set forth in SEQ ID NO: 1 and a VL chain comprising the amino acid sequence set forth in SEQ ID NO: 2; wherein the anti-CCR8 antibody binds human CCR8 and cyno CCR8.

In some aspects, the anti-CCR8 antibody comprises a VH chain comprising an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 11 and a VL chain comprising an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 12; wherein the anti-CCR8 antibody binds human CCR8 and cyno CCR8. In some aspects, the anti-CCR8 antibody comprises a VH chain comprising the amino acid sequence set forth in SEQ ID NO: 11 and a VL chain comprising the amino acid sequence set forth in SEQ ID NO: 12; wherein the anti-CCR8 antibody binds human CCR8 and cyno CCR8.

In some aspects, the anti-CCR8 antibody comprises a VH chain comprising an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 21 and a VL chain comprising an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 22; wherein the anti-CCR8 antibody binds human CCR8 and cyno CCR8. In some aspects, the anti-CCR8 antibody comprises a VH chain comprising the amino acid sequence set forth in SEQ ID NO: 21 and a VL chain comprising the amino acid sequence set forth in SEQ ID NO: 22; wherein the anti-CCR8 antibody binds human CCR8 and cyno CCR8.

In some aspects, the anti-CCR8 antibody comprises a VH chain comprising an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 31 and a VL chain comprising an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 32; wherein the anti-CCR8 antibody binds human CCR8 and cyno CCR8. In some aspects, the anti-CCR8 antibody comprises a VH chain comprising the amino acid sequence set forth in SEQ ID NO: 31 and a VL chain comprising the amino acid sequence set forth in SEQ ID NO: 32; wherein the anti-CCR8 antibody binds human CCR8 and cyno CCR8.

In some aspects, the anti-CCR8 antibody comprises a VH chain comprising an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 51 and a VL chain comprising an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 52; wherein the anti-CCR8 antibody binds human CCR8 and cyno CCR8. In some aspects, the anti-CCR8 antibody comprises a VH chain comprising the amino acid sequence set forth in SEQ ID NO: 51 and a VL chain comprising the amino acid sequence set forth in SEQ ID NO: 52; wherein the anti-CCR8 antibody binds human CCR8 and cyno CCR8.

In some aspects, the anti-CCR8 antibody comprises a VH chain comprising an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 61 and a VL chain comprising an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 62; wherein the anti-CCR8 antibody binds human CCR8 and cyno CCR8. In some aspects, the anti-CCR8 antibody comprises a VH chain comprising the amino acid sequence set forth in SEQ ID NO: 61 and a VL chain comprising the amino acid sequence set forth in SEQ ID NO: 62; wherein the anti-CCR8 antibody binds human CCR8 and cyno CCR8.

In some aspects, the anti-CCR8 antibody comprises a VH chain comprising an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 71 and a VL chain comprising an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 72; wherein the anti-CCR8 antibody binds human CCR8 and cyno CCR8. In some aspects, the anti-CCR8 antibody comprises a VH chain comprising the amino acid sequence set forth in SEQ ID NO: 71 and a VL chain comprising the amino acid sequence set forth in SEQ ID NO: 72; wherein the anti-CCR8 antibody binds human CCR8 and cyno CCR8.

In some aspects, the anti-CCR8 antibody comprises a VH chain comprising an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 81 and a VL chain comprising an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 82; wherein the anti-CCR8 antibody binds human CCR8 and cyno CCR8. In some aspects, the anti-CCR8 antibody comprises a VH chain comprising the amino acid sequence set forth in SEQ ID NO: 81 and a VL chain comprising the amino acid sequence set forth in SEQ ID NO: 82; wherein the anti-CCR8 antibody binds human CCR8 and cyno CCR8.

In some aspects, the anti-CCR8 antibody comprises a VH chain comprising an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 91 and a VL chain comprising an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 92; wherein the anti-CCR8 antibody binds human CCR8 and cyno CCR8. In some aspects, the anti-CCR8 antibody comprises a VH chain comprising the amino acid sequence set forth in SEQ ID NO: 91 and a VL chain comprising the amino acid sequence set forth in SEQ ID NO: 92; wherein the anti-CCR8 antibody binds human CCR8 and cyno CCR8.

In some aspects, the anti-CCR8 antibody comprises a VH chain comprising an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 121 and a VL chain comprising an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 122; wherein the anti-CCR8 antibody binds human CCR8 and cyno CCR8. In some aspects, the anti-CCR8 antibody comprises a VH chain comprising the amino acid sequence set forth in SEQ ID NO: 121 and a VL chain comprising the amino acid sequence set forth in SEQ ID NO: 122; wherein the anti-CCR8 antibody binds human CCR8 and cyno CCR8.

In some aspects, the anti-CCR8 antibody comprises a VH chain comprising an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 151 and a VL chain comprising an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 152; wherein the anti-CCR8 antibody binds human CCR8 and cyno CCR8. In some aspects, the anti-CCR8 antibody comprises a VH chain comprising the amino acid sequence set forth in SEQ ID NO: 151 and a VL chain comprising the amino acid sequence set forth in SEQ ID NO: 152; wherein the anti-CCR8 antibody binds human CCR8 and cyno CCR8.

In some aspects, the anti-CCR8 antibody comprises a VH chain comprising an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 161 and a VL chain comprising an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 162; wherein the anti-CCR8 antibody binds human CCR8 and cyno CCR8. In some aspects, the anti-CCR8 antibody comprises a VH chain comprising the amino acid sequence set forth in SEQ ID NO: 161 and a VL chain comprising the amino acid sequence set forth in SEQ ID NO: 162; wherein the anti-CCR8 antibody binds human CCR8 and cyno CCR8.

In some aspects, the anti-CCR8 antibody is a human antibody. In some aspects, the anti-CCR8 antibody is a humanized antibody. In some aspects, the anti-CCR8 is a chimeric antibody.

In some aspects, the anti-CCR8 antibody is selected from the group consisting of an IgG1, an IgG2, an IgG3, an IgG4, an IgM, an IgA1 an IgA2, an IgD, and an IgE antibody. In some aspects, the anti-CCR8 antibody is an IgG1 antibody. In some aspects, the anti-CCR8 antibody is an IgG4 antibody. In some aspects, the anti-CCR8 antibody comprises a wild type IgG1 heavy chain constant region. In some aspects, the anti-CCR8 antibody comprises a wild type IgG4 heavy chain constant region. In some aspects, the anti-CCR8 antibody comprises an Fc domain comprising at least one mutation. In some aspects, the anti-CCR8 antibody comprises a mutant IgG1 heavy chain constant region. In some aspects, the anti-CCR8 antibody comprises a mutant IgG4 heavy chain constant region. In some aspects, the mutant IgG4 heavy chain constant region comprises any one of the substitutions S228P, L235E, L235A, or a combination thereof, according to EU numbering.

In some aspects, the disclosure provides an antibody or antigen-binding portion thereof that binds to substantially the same epitope on human CCR8 as the anti-CCR8 antibody according to any one of the aforementioned aspects. In some aspects, the disclosure provides an antibody or antigen-binding portion thereof that cross-competes for binding to human CCR8 as the anti-CCR8 antibody according to any one of the aforementioned aspects.

In some aspects, the anti-CCR8 antibody comprises an altered heavy chain constant region that has modified effector function relative to its corresponding unaltered constant region. Effector functions involving the constant region of the anti-CCR8 antibody may be modulated by altering properties of the constant or Fc region. Altered effector functions include, for example, a modulation in one or more of the following activities: antibody-dependent cellular cytotoxicity (ADCC), complement-dependent cytotoxicity (CDC), apoptosis, binding to one or more Fc-receptors, and pro-inflammatory responses. Modulation refers to an increase, decrease, or elimination of an effector function activity exhibited by a subject antibody containing an altered constant region as compared to the activity of the unaltered form of the constant region. In particular aspects, modulation includes situations in which an activity is abolished or completely absent.

In one aspect, the anti-CCR8 antibody comprises an IgG4 heavy chain constant region. In one aspect, the IgG4 heavy chain constant region is a wild type IgG4 heavy chain constant region. In another aspect, the IgG4 constant region comprises a mutation, e.g., one or both of S228P and L235E or L235A, e.g., according to EU numbering (Kabat, E. A., et al., supra). In one aspect, the anti-CCR8 antibody described herein comprises an IgG1 constant region. In one aspect, the IgG1 heavy chain constant region is a wild type IgG1 heavy chain constant region. In another aspect, the IgG1 heavy chain constant region comprises a mutation.

An altered constant region with altered FcR binding affinity and/or ADCC activity and/or altered CDC activity is a polypeptide that has either an enhanced or diminished FcR binding activity and/or ADCC activity and/or CDC activity compared to the unaltered form of the constant region. An altered constant region that displays increased binding to an FcR binds at least one FcR with greater affinity than the unaltered polypeptide. An altered constant region that displays decreased binding to an FcR binds at least one FcR with lower affinity than the unaltered form of the constant region. Such variants which display decreased binding to an FcR may possess little or no appreciable binding to an FcR, e.g., 0 to 50% (e.g., less than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1%) of the binding to the FcR as compared to the level of binding of a native sequence immunoglobulin constant or Fc region to the FcR. Similarly, an altered constant region that displays modulated ADCC and/or CDC activity may exhibit either increased or reduced ADCC and/or CDC activity compared to the unaltered constant region.

In some aspects, the anti-CCR8 antibody exhibits increased effector function. In some aspects, an anti-CCR8 antibody comprises a hybrid constant region, or a portion thereof, such as a G2/G4 hybrid constant region (see e.g., Burton et al. (1992) *Adv Immun* 51:1-18; Canfield et al. (1991) *J Exp Med* 173:1483-1491; and Mueller et al. (1997) *Mol Immunol* 34(6):441-452).

In some aspects, the anti-CCR8 antibody comprises an altered constant region exhibiting enhanced complement dependent cytotoxicity (CDC). Modulated CDC activity may be achieved by introducing one or more amino acid substitutions, insertions, or deletions in an Fc region of the antibody. See, e.g., U.S. Pat. No. 6,194,551. Alternatively, or additionally, cysteine residue(s) may be introduced in the Fc region, thereby allowing interchain disulfide bond formation in this region. The homodimeric antibody thus generated may have improved internalization capability and/or increased complement-mediated cell killing. See, e.g., Caron et al. (1992) *J Exp Med* 176:1191-1195 and Shopes (1992) *Immunol* 148:2918-2922; PCT publication nos. WO 99/51642 and WO 94/29351; Duncan and Winter (1988) *Nature* 322:738-40; and U.S. Pat. Nos. 5,648,260 and 5,624,821.

In some aspects, the anti-CCR8 antibody is a bispecific antibody, a bispecific T cell engager (BiTE), a multispecific antibody, a biparatopic antibody, an immunoconjugate, an antibody drug conjugate, or any combination thereof.

II.C. Antibody Variants and Immunoconjugates

Certain aspects of the present disclosure are directed to antibodies comprising a first antigen-binding region that binds to human CCR8 and a second antigen-binding region that binds a second antigen, wherein the first antigen-binding region comprises an anti-CCR8 antibody described herein. In some aspects, the antibody is a bispecific antibody, e.g., capable of binding only two antigens. In some aspects, the antibody is a multispecific antibody, e.g., capable of binding more than two antigens. In some aspects, the multispecific antibody is capable of binding at least about 3 antigens, at least about 4 antigens, at least about 5 antigens, or at least about 6 antigens.

In some aspects, the antibody is a biparatopic antibody. Biparatopic antibodies are capable of binding two epitopes on a single polypeptide target. In some aspects, the biparatopic antibody comprises a first antigen-binding region and a second antigen-binding region, wherein the first antigen-binding region and/or the second antigen-binding region comprises an anti-CCR8 antibody disclosed herein.

In some aspects, the multispecific antibody is a bispecific T cell engager (BiTE). BiTE constructs comprises a first antigen-binding region that binds CD3 receptor on T cell and a second antigen-specific binding region. In some aspects, the BiTE comprises a first antigen-binding region that binds CD3 and a second antigen-binding region that binds human CCR8, wherein the second antigen-binding region comprises an anti-CCR8 antibody disclosed herein.

In some aspects, the bispecific antibody, the multispecific antibody, the BiTE, or the biparatopic antibody comprises a first VH CDR1, a first VH CDR2, and a first VH CDR3; a first VL domain, comprising a first VL CDR1, a first VL CDR2, and a first VL CDR3; a second VH domain, comprising a second VH CDR1, a second VH CDR2, and a second VH CDR3; and a second VL domain, comprising a second VL CDR1, a second VL CDR2, and a second VL CDR3; wherein (a) the first VH CDR1 comprises an amino acid sequence selected from the amino acid sequence set forth in SEQ ID NOs: 45, 105, 115, 135, and 145; (b) the first VH CDR2 comprises an amino acid sequence selected from the amino acid sequence set forth in SEQ ID NOs: 46, 106, 116, 136, and 146; and (c) the first VH CDR3 comprises an amino acid sequence selected from the amino acid sequence set forth in SEQ ID NOs: 47, 107, 117, 137, and 147. In some aspects, the first VL CDR1 comprises an amino acid sequence selected from the amino acid sequence set forth in SEQ ID NOs: 48, 108, 118, 138, and 148; (b) the first VL CDR2 comprises an amino acid sequence selected from the amino acid sequence set forth in SEQ ID NOs: 49, 109, 119, 139, and 149; and (c) the first VL CDR3 comprises an amino acid sequence selected from the amino acid sequence set forth in SEQ ID NOs: 50, 110, 120, 140, and 150.

In some aspects, (a) the VH CDR1 comprises an amino acid sequence selected from the amino acid sequence set forth in SEQ ID NOs: 5, 15, 25, 35, 55, 65, 75, 85, 95, 125, 155, and 165; (b) the VH CDR2 comprises an amino acid sequence selected from the amino acid sequence set forth in SEQ ID NOs: 6, 16, 26, 36, 56, 66, 76, 86, 96, 126, 156, and 166; and (c) the VH CDR3 comprises an amino acid sequence selected from the amino acid sequence set forth in SEQ ID NOs: 7, 17, 27, 37, 57, 67, 77, 87, 97, 127, 157, and 167. In some aspects, (a) the VL CDR1 comprises an amino acid sequence selected from the amino acid sequence set forth in SEQ ID NOs: 8, 18, 28, 38, 58, 68, 78, 88, 98, 128, 158, and 168; (b) the VL CDR2 comprises an amino acid sequence selected from the amino acid sequence set forth in SEQ ID NOs: 9, 19, 29, 39, 59, 69, 79, 89, 99, 129, 159, and 169; and (c) the VL CDR3 comprises an amino acid sequence selected from the amino acid sequence set forth in SEQ ID NOs: 10, 20, 30, 40, 60, 70, 80, 90, 100, 130, 160, and 170.

In some aspects, the antibody is a biparatopic antibody, and (a) the second VH CDR1 comprises an amino acid sequence selected from the amino acid sequence set forth in SEQ ID NOs: 5, 15, 25, 35, 55, 65, 75, 85, 95, 125, 155, and 165; (b) the second VH CDR2 comprises an amino acid sequence selected from the amino acid sequence set forth in SEQ ID NOs: 6, 16, 26, 36, 56, 66, 76, 86, 96, 126, 156, and 166; and (c) the second VH CDR3 comprises an amino acid sequence selected from the amino acid sequence set forth in SEQ ID NOs: 7, 17, 27, 37, 57, 67, 77, 87, 97, 127, 157, and 167. In some aspects, the antibody is a biparatopic antibody, and (a) the second VL CDR1 comprises an amino acid sequence selected from the amino acid sequence set forth in SEQ ID NOs: 8, 18, 28, 38, 58, 68, 78, 88, 98, 128, 158, and 168; (b) the second VL CDR2 comprises an amino acid sequence selected from the amino acid sequence set forth in SEQ ID NOs: 9, 19, 29, 39, 59, 69, 79, 89, 99, 129, 159, and 169; and (c) the second VL CDR3 comprises an amino acid sequence selected from the amino acid sequence set forth in SEQ ID NOs: 10, 20, 30, 40, 60, 70, 80, 90, 100, 130, 160, and 170.

Certain aspects of the present disclosure are directed to an immunoconjugate comprising an anti-CCR8 antibody disclosed herein. In some aspects, the immunoconjugate is an antibody-drug conjugate. The immunoconjugate can include any cytotoxic agent known in the art linked to an anti-CCR8 antibody disclosed herein. In some aspects, the antibody-drug conjugate comprises a cytotoxic agent selected from the group consisting of a maytansinoid (e.g., maytansine), a dolastatin, an auristatin drug analogue, cryptophycin, a duocarmycin deriative (e.g., a CC-1065 analog and duocarmycin), an enediyne antibiotic (e.g., esperamicin and calicheamicin), pyrolobenodiazepine (PBD), and any combination thereof. An antibody-drug conjugate comprising an anti-CCR8 antibody and a cytotoxic agent may allow efficacy in tumor indications with low numbers of effector cells, including NK cells and macrophages.

II.D. Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcTR binding (hence likely lacking ADCC activity), but retains FcRn binding ability. The primary cells for mediating ADCC, NK cells, express FcTRIII only, whereas monocytes express FcTRI, FcTRII and FcTRIII. FcR expression on hematopoietic cells is summarized in Table 3 on page 464 of Ravetch and Kinet, Annu. Rev. Immunol. 9:457-492 (1991). Non-limiting examples of in vitro assays to assess ADCC activity of a molecule of interest is described in U.S. Pat. No. 5,500,362 (see, e.g. Hellstrom, I. et al. Proc. Nat'l Acad. Sci. USA 83:7059-7063 (1986)) and Hellstrom, I et al., Proc. Nat'l Acad. Sci. USA 82:1499-1502 (1985); U.S. Pat. No. 5,821,337 (see Bruggemann, M. et al., J. Exp. Med. 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96 non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. Proc. Nat'l Acad. Sci. USA 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., J. Immunol. Methods 202:163 (1996); Cragg, M. S. et al., Blood 101:1045-1052 (2003); and Cragg, M. S. and M. J. Glennie, Blood 103:2738-2743 (2004)). FcRn binding and in vivo clearance/half-life determinations can also be performed using methods known in the art (see, e.g., Petkova, S. B. et al., Int'l. Immunol. 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., J. Biol. Chem. 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. J. Immunol. 164: 4178-4184 (2000).

Antibodies with increased half-lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 252, 254, 256, 265, 272, 286, 303, 305, 307, 311, 312, 317, 340, 356, 360, 362, 376, 378, 380, 382, 413, 424 or 434, e.g., substitution of Fc region residue 434 (e.g., U.S. Pat. No. 7,371,826).

See also Duncan & Winter, Nature 322:738-40 (1988); U.S. Pat. Nos. 5,648,260; 5,624,821; and WO 94/29351 concerning other examples of Fc region variants.

In some embodiments, an antibody is provided, wherein the isotype is human IgG1. In some embodiments, an antibody is provided, wherein the isotype is human IgG4. In some embodiments, an antibody is provided, wherein the isotype is human IgG4, wherein there is a single mutation at serine 228 to proline (S228P). In some embodiments, an antibody is provided, wherein the isotype is human IgG4, wherein there are two mutations at serine 228 to proline (S228P) and leucine 235 to glutamate (L235E). The S228P mutation occurs at position 228 in the literature, however the exact location of a mutation in an antibody may vary depending on how such antibody is produced.

I.E. Chimeric Antigen Receptors (CAR) and T Cell Receptors (TCR)

Certain aspects of the present disclosure are directed to a chimeric antigen receptor (CAR) comprising an antigen-binding region that specifically binds the N-terminal extracellular domain of human CCR8. In some aspects, the antigen-binding region comprises an anti-CCR8 antibody disclosed herein or an antibody or antigen-binding fragment thereof that binds the same epitope as an anti-CCR8 antibody disclosed herein. In some aspects, the CAR further comprises a transmembrane domain. In some aspects, the CAR further comprises an intracellular signaling domain. In some aspects, the CAR further comprises a hinge region and/or a spacer region.

Certain aspects of the present disclosure are directed to a T cell receptor (TCT) comprising an antigen-binding region that specifically binds the N-terminal extracellular domain of human CCR8. In some aspects, the antigen-binding region comprises an anti-CCR8 antibody disclosed herein or an antibody or antigen-binding fragment thereof that binds the same epitope as an anti-CCR8 antibody disclosed herein. In some aspects, the TCR further comprises a transmembrane domain. In some aspects, the TCR further comprises an intracellular signaling domain.

I.F. Nucleic Acid Molecules, Vectors, and Cells

Certain aspects of the present disclosure are directed to nucleic acid molecules that encode the anti-CCR8 antibodies disclose herein. The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids (e.g., other chromosomal DNA, e.g., the chromosomal DNA that is linked to the isolated DNA in nature) or proteins, by standard techniques, including alkaline/SDS treatment, CsCl banding, column chromatography, restriction enzymes, agarose gel electrophoresis and others well known in the art. See, F. Ausubel, et al., ed. (1987) Current Protocols in Molecular Biology, Greene Publishing and Wiley Interscience, New York. A nucleic acid described herein can be, for example, DNA or RNA and can or cannot contain intronic sequences. In some embodiments, the nucleic acid is a cDNA molecule.

Nucleic acids described herein can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

In some aspects, the nucleic acids can further encode a signal peptide.

The nucleic acid molecules described herein may be modified to delete specific sequences, e.g., restriction enzyme recognition sequences, or to optimize codons.

A method for making the anti-CCR8 antibody disclosed herein can comprise expressing the heavy chain and the light chains in a cell line comprising the nucleotide sequences encoding the heavy and light chains with a signal peptide. Host cells comprising these nucleotide sequences are encompassed herein.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked," as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (hinge, CH1, CH2, and/or CH3). The sequences of human heavy chain constant region genes are known in the art (see, e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, for example, an IgG1 region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see, e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region.

To create a scFv gene, the VH- and VL-encoding DNA fragments are operatively linked to another fragment encoding a flexible linker, e.g., encoding the amino acid sequence (Gly4-Ser)3, such that the VH and VL sequences can be expressed as a contiguous single-chain protein, with the VL and VH regions joined by the flexible linker (see, e.g., Bird et al., (1988) Science 242:423-426; Huston et al., (1988) Proc. Natl. Acad. Sci. USA 85:5879-5883; McCafferty et al., (1990) Nature 348:552-554).

Also provided herein are nucleic acid molecules encoding VH and VL sequences that are homologous to those of the anti-CCR8 antibodies disclosed herein. Exemplary nucleic acid molecules encode VH and VL sequences that are at least 70% identical, for example, at least 75%, at least 80%, at least 85%, at least 90%, at least 95%, or at least 99% identical, to nucleic acid molecules encoding the VH and VL sequences disclosed herein. Also provided herein are nucleic acid molecules with conservative substitutions (i.e., substitutions that do not alter the resulting amino acid sequence upon translation of nucleic acid molecule), e.g., for codon optimization.

Also provided are nucleic acids encoding the VH and/or VL regions of anti-CCR8 antibodies, such as the anti-CCR8 antibodies described herein, which nucleic acids comprise a nucleotide sequence that is at least about 75%, 80%, 85%, 90%, 95%, 96%, 97%, 98% or 99% identical to any of the nucleotide sequences encoding the VH and/or VL regions of anti-CCR8 antibodies described herein.

Also provided are nucleic acids encoding the heavy chain and/or the light chain of anti-CCR8 antibodies, such as the anti-CCR8 antibodies described herein, which nucleic acids comprise a nucleotide sequence that is at least about 75%, 80%, 85%, 90%, 95%, 96%, 97%, 98% or 99% identical to any of the nucleotide sequences encoding the heavy and/or light chains of anti-CCR8 antibodies described herein.

Certain aspects of the present disclosure are directed to vectors comprising a nucleic acid molecule disclosed herein. In some aspects, the vector is selected from a viral vector, a mammalian vector, and a bacterial vector. In some aspects, the vector is a viral particle or a virus. In some aspects, the vector is a mammalian vector. In some aspects, the vector is a bacterial vector.

In certain aspects, the viral vector is a retroviral vector. In some aspects, the viral vector is selected from the group consisting of an adenoviral vector, a lentivirus, a Sendai virus, a baculoviral vector, an Epstein Barr viral vector, a papovaviral vector, a vaccinia viral vector, a herpes simplex viral vector, and an adeno associated virus (AAV) vector. In particular aspects, the vector is an AAV vector. In some aspects, the vector is a lentivirus. In particular aspects, the vector is an AAV vector. In some aspects, the vector is a Sendai virus. In some aspects, the vector is a hybrid vector. Examples of hybrid vectors that can be used in the present disclosure can be found in Huang and Kamihira, *Biotechnol. Adv.* 31(2):208-23 (2103), which is incorporated by reference herein in its entirety.

In some aspects, the vector further comprises one or more regulatory elements, including but not limited to one or more enhancers, promoters, miRNA binding sequences, polyA sequences, intronic sequences, splice acceptor sites, and any combination thereof. In some aspects, the vector comprises a tissue specific enhancer. In some aspects, the vector comprises a tissue specific promoter.

Certain aspects of the present disclosure are directed to cells, e.g., host cells, comprising an anti-CCR8 antibody disclosed herein, a bispecific antibody disclosed herein, a BiTE disclosed herein, a multispecific antibody disclosed herein, a biparatopic antibody disclosed herein, a CAR disclosed herein, a TCR disclosed herein, a nucleic acid molecule disclosed herein, or a vector disclosed herein. The cell can be any type of cell. In some aspects, the cell is selected from a mammalian cell, a bacterial cell, an insect cell, a plant cell, and a yeast cell. In some aspects, the cell is selected from the group consisting of an *E. coli* cell, a fungi such as *Saccharomyces cerevisiae* and *Pichia pastoris*, an insect cell such as SF9, a mammalian cell lines (e.g., human cell lines), and a primary cell line.

In some aspects, the cell is an immune cell. In some aspects, the cell is a T cell. As such, certain aspects of the present disclosure are directed to an immune cell, e.g., a T cell, comprising a CAR or a TCR disclosed herein.

II.G. Pharmaceutical Compositions

In certain aspects, the disclosure provides for a pharmaceutical composition comprising an anti-CCR8 antibody with a pharmaceutically acceptable diluent, carrier, solubilizer, emulsifier, preservative and/or adjuvant.

In certain aspects, acceptable formulation materials preferably are nontoxic to recipients at the dosages and concentrations employed. In certain aspects, the formulation material(s) are for s.c. and/or I.V. administration. In certain aspects, the pharmaceutical composition can contain formulation materials for modifying, maintaining or preserving, for example, the pH, osmolality, viscosity, clarity, color, isotonicity, odor, sterility, stability, rate of dissolution or release, adsorption or penetration of the composition. In certain aspects, suitable formulation materials include, but are not limited to, amino acids (such as glycine, glutamine, asparagine, arginine or lysine); antimicrobials; antioxidants (such as ascorbic acid, sodium sulfite or sodium hydrogensulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (Remington's Pharmaceutical Sciences, 18th Edition, A. R. Gennaro, ed., Mack Publishing Company (1995). In certain aspects, the formulation comprises PBS; 20 mM NaOAC, pH 5.2, 50 mM NaCl; and/or 10 mM NAOAC, pH 5.2, 9% Sucrose. In certain aspects, the optimal pharmaceutical composition will be determined by one skilled in the art depending upon, for example, the intended route of administration, delivery format and desired dosage. See, for example, Remington's Pharmaceutical Sciences, supra. In certain aspects, such compositions may influence the physical state, stability, rate of in vivo release and/or rate of in vivo clearance of the anti-CCR8 antibody.

In certain aspects, the primary vehicle or carrier in a pharmaceutical composition can be either aqueous or non-aqueous in nature. For example, in certain aspects, a suitable vehicle or carrier can be water for injection, physiological saline solution or artificial cerebrospinal fluid, possibly supplemented with other materials common in compositions for parenteral administration. In certain aspects, the saline comprises isotonic phosphate-buffered saline. In certain aspects, neutral buffered saline or saline mixed with serum albumin are further exemplary vehicles. In certain aspects, pharmaceutical compositions comprise Tris buffer of about pH 7.0-8.5, or acetate buffer of about pH 4.0-5.5, which can further include sorbitol or a suitable substitute therefore. In certain aspects, a composition comprising an anti-CCR8 antibody can be prepared for storage by mixing the selected composition having the desired degree of purity with optional formulation agents (Remington's Pharmaceutical Sciences, supra) in the form of a lyophilized cake or an aqueous solution. Further, in certain aspects, a composition comprising an anti-CCR8 antibody can be formulated as a lyophilizate using appropriate excipients such as sucrose.

In certain aspects, the pharmaceutical composition can be selected for parenteral delivery. In certain aspects, the compositions can be selected for inhalation or for delivery through the digestive tract, such as orally. The preparation of such pharmaceutically acceptable compositions is within the ability of one skilled in the art.

In certain aspects, the formulation components are present in concentrations that are acceptable to the site of administration. In certain aspects, buffers are used to maintain the composition at physiological pH or at a slightly lower pH, typically within a pH range of from about 5 to about 8.

In certain aspects, when parenteral administration is contemplated, a therapeutic composition can be in the form of a pyrogen-free, parenterally acceptable aqueous solution comprising an anti-CCR8 antibody, in a pharmaceutically acceptable vehicle. In certain aspects, a vehicle for parenteral injection is sterile distilled water in which an anti-CCR8 antibody is formulated as a sterile, isotonic solution, and properly preserved. In certain aspects, the preparation can involve the formulation of the desired molecule with an agent, such as injectable microspheres, bio-erodible particles, polymeric compounds (such as polylactic acid or polyglycolic acid), beads or liposomes, that can provide for the controlled or sustained release of the product which can then be delivered via a depot injection. In certain aspects, hyaluronic acid can also be used, and can have the effect of promoting sustained duration in the circulation. In certain aspects, implantable drug delivery devices can be used to introduce the desired molecule.

In certain aspects, a pharmaceutical composition can be formulated for inhalation. In certain aspects, an anti-CCR8 antibody can be formulated as a dry powder for inhalation. In certain aspects, an inhalation solution comprising an anti-CCR8 antibody can be formulated with a propellant for aerosol delivery. In certain aspects, solutions can be nebulized. Pulmonary administration is further described in PCT application No. PCT/US94/001875, which describes pulmonary delivery of chemically modified proteins.

In certain aspects, it is contemplated that formulations can be administered orally. In certain aspects, an anti-CCR8 antibody that is administered in this fashion can be formulated with or without those carriers customarily used in the compounding of solid dosage forms such as tablets and capsules. In certain aspects, a capsule can be designed to release the active portion of the formulation at the point in the gastrointestinal tract when bioavailability is maximized and pre-systemic degradation is minimized. In certain aspects, at least one additional agent can be included to facilitate absorption of an anti-CCR8 antibody. In certain aspects, diluents, flavorings, low melting point waxes, vegetable oils, lubricants, suspending agents, tablet disintegrating agents, and binders can also be employed.

In certain aspects, a pharmaceutical composition can involve an effective quantity of an anti-CCR8 antibody in a mixture with non-toxic excipients that are suitable for the manufacture of tablets. In certain aspects, by dissolving the tablets in sterile water, or another appropriate vehicle, solutions can be prepared in unit-dose form. In certain aspects, suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving an anti-CCR8 antibody in sustained- or controlled-delivery formulations. In certain aspects, techniques for formulating a variety of other sustained- or controlled-delivery means, such as liposome carriers, bio-erodible microparticles or porous beads and depot injections, are also known to those skilled in the art. See for example, PCT Application No. PCT/US93/00829, which describes the controlled release of porous polymeric microparticles for the delivery of pharmaceutical compositions. In certain aspects, sustained-release preparations can include semipermeable polymer matrices in the form of shaped articles, e.g. films, or microcapsules. Sustained release matrices can include polyesters, hydrogels, polylactides (U.S. Pat. No. 3,773,919 and EP 058,481), copolymers of L-glutamic acid and gamma ethyl-L-glutamate (Sidman et al., Biopolymers, 22:547-556 (1983)), poly (2-hydroxyethyl-methacrylate) (Langer et al., J. Biomed. Mater. Res., 15: 167-277 (1981) and Langer, Chem. Tech., 12:98-105 (1982)), ethylene vinyl acetate (Langer et al., supra) or poly-D(−)-3-hydroxybutyric acid (EP 133,988). In certain aspects, sustained release compositions can also include liposomes, which can be prepared by any of several methods known in the art. See, e.g., Eppstein et al, Proc. Natl. Acad. Sci. USA, 82:3688-3692 (1985); EP 036,676; EP 088,046 and EP 143,949.

The pharmaceutical composition to be used for in vivo administration typically is sterile. In certain aspects, this can be accomplished by filtration through sterile filtration membranes. In certain aspects, where the composition is lyophilized, sterilization using this method can be conducted either prior to or following lyophilization and reconstitution. In certain aspects, the composition for parenteral administration can be stored in lyophilized form or in a solution. In certain aspects, parenteral compositions generally are placed into a container having a sterile access port, for example, an intravenous solution bag or vial having a stopper pierceable by a hypodermic injection needle.

In certain aspects, once the pharmaceutical composition has been formulated, it can be stored in sterile vials as a solution, suspension, gel, emulsion, solid, or as a dehydrated or lyophilized powder. In certain aspects, such formulations can be stored either in a ready-to-use form or in a form (e.g., lyophilized) that is reconstituted prior to administration.

In certain aspects, kits are provided for producing a single-dose administration unit. In certain aspects, the kit can contain both a first container having a dried protein and a second container having an aqueous formulation. In certain aspects, kits containing single and multi-chambered pre-filled syringes (e.g., liquid syringes and lyosyringes) are included.

In certain aspects, the effective amount of a pharmaceutical composition comprising an anti-CCR8 antibody to be employed therapeutically will depend, for example, upon the therapeutic context and objectives. One skilled in the art will appreciate that the appropriate dosage levels for treatment, according to certain aspects, will thus vary depending, in part, upon the molecule delivered, the indication for which an anti-CCR8 antibody is being used, the route of administration, and the size (body weight, body surface or organ size) and/or condition (the age and general health) of the patient. In certain aspects, the clinician can titer the dosage and modify the route of administration to obtain the optimal therapeutic effect.

In certain aspects, the frequency of dosing will take into account the pharmacokinetic parameters of an anti-CCR8 antibody in the formulation used. In certain aspects, a clinician will administer the composition until a dosage is reached that achieves the desired effect. In certain aspects, the composition can therefore be administered as a single dose or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. In certain aspects, appropriate dosages can be ascertained through use of appropriate dose-response data.

In certain aspects, the route of administration of the pharmaceutical composition is in accord with known methods, e.g. orally, through injection by intravenous, intraperitoneal, intracerebral (intra-parenchymal), intracerebroventricular, intramuscular, subcutaneously, intra-ocular, intraarterial, intraportal, or intralesional routes; by sustained release systems or by implantation devices. In certain aspects, the compositions can be administered by bolus injection or continuously by infusion, or by implantation device. In certain aspects, individual elements of the combination therapy may be administered by different routes.

In certain aspects, the composition can be administered locally via implantation of a membrane, sponge or another appropriate material onto which the desired molecule has been absorbed or encapsulated. In certain aspects, where an implantation device is used, the device can be implanted into any suitable tissue or organ, and delivery of the desired molecule can be via diffusion, timed-release bolus, or continuous administration. In certain aspects, it can be desirable to use a pharmaceutical composition comprising an anti-CCR8 antibody in an ex vivo manner. In such instances, cells, tissues and/or organs that have been removed from the patient are exposed to a pharmaceutical composition comprising an anti-CCR8 antibody after which the cells, tissues and/or organs are subsequently implanted back into the patient.

In certain aspects, an anti-CCR8 antibody can be delivered by implanting certain cells that have been genetically engineered, using methods such as those described herein, to express and secrete the polypeptides. In certain aspects, such cells can be animal or human cells, and can be autologous, heterologous, or xenogeneic. In certain aspects, the cells can be immortalized. In certain aspects, in order to decrease the chance of an immunological response, the cells can be encapsulated to avoid infiltration of surrounding tissues. In certain aspects, the encapsulation materials are typically biocompatible, semi-permeable polymeric enclosures or membranes that allow the release of the protein product(s) but prevent the destruction of the cells by the patient's immune system or by other detrimental factors from the surrounding tissues.

III. Methods of the Disclosure

Certain aspects of the present disclosure are directed to methods of making and/or using the anti-CCR8 antibodies disclosed herein.

III.A. Methods of Use

Certain aspects of the present disclosure are directed to methods of reducing, depleting, or killing tumor infiltrating Tregs, comprising administering to the subject an anti-CCR8 antibody disclosed herein. Some aspects of the present disclosure are directed to methods of reducing, depleting, or killing tumor infiltrating Tregs, comprising administering a bispecific antibody, a BiTE, a multispecific antibody, a biparatopic antibody, an immunoconjugate, a CAR, a TCR, a nucleic acid molecule or a set of nucleic acid molecules, a vector or a set of vectors, a cell, or a pharmaceutical composition disclosed herein.

Certain aspects of the present disclosure are directed to methods of activating NK cells or inducing NK cell mediated killing of tumor infiltrating regulatory Tregs, comprising administering to the subject an anti-CCR8 antibody disclosed herein. Some aspects of the present disclosure are directed to methods of activating NK cells or inducing NK cell mediated killing of tumor infiltrating regulatory Tregs, comprising administering a bispecific antibody, a BiTE, a multispecific antibody, a biparatopic antibody, an immunoconjugate, a CAR, a TCR, a nucleic acid molecule or a set of nucleic acid molecules, a vector or a set of vectors, a cell, or a pharmaceutical composition disclosed herein.

In some aspects, the contacting is in vitro. In some aspects the contacting is in vivo. In some aspects, the contacting treats a disease or condition in a subject in need thereof. In some aspects, the contacting promotes an immune response in a subject. In some aspects, the subject has a tumor, and the contacting enhances an immune response to the tumor.

Certain aspects of the present disclosure are directed to methods of treating a tumor in a subject in need thereof, comprising administering to the subject an anti-CCR8 antibody disclosed herein. Some aspects of the present disclosure are directed to methods of treating a tumor in a subject in need thereof comprising administering a bispecific antibody, a BiTE, a multispecific antibody, a biparatopic antibody, an immunoconjugate, a CAR, a TCR, a nucleic acid molecule or a set of nucleic acid molecules, a vector or a set of vectors, a cell, or a pharmaceutical composition disclosed herein.

In some aspects, the subject has a tumor. In some aspects, the tumor is selected form the group consisting of Kaposi's sarcoma, leukemia, acute lymphocytic leukemia, acute myelocytic leukemia, myeloblasts promyelocyte myelomonocytic monocytic erythroleukemia, chronic leukemia, chronic myelocytic (granulocytic) leukemia, chronic lymphocytic leukemia, mantle cell lymphoma, primary central nervous system lymphoma, Burkitt's lymphoma and marginal zone B cell lymphoma, Polycythemia vera Lymphoma, Hodgkin's disease, non-Hodgkin's disease, multiple myeloma, Waldenstrom's macroglobulinemia, heavy chain disease, solid tumors, sarcomas, and carcinomas, fibrosarcoma, myxosarcoma, liposarcoma, chrondrosarcoma, osteogenic sarcoma, osteosarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon sarcoma, colorectal carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatocellular carcinoma (HCC), hepatoma, bile duct carcinoma, choriocarcinoma, seminoma, embryonal carcinoma, Wilm's tumor, cervical cancer, uterine cancer, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, retinoblastoma, nasopharyngeal carcinoma, esophageal carcinoma, basal cell carcinoma, biliary tract cancer, bladder cancer, bone cancer, brain and central nervous system (CNS) cancer, cervical cancer, choriocarcinoma, colorectal cancers, connective tissue cancer, cancer of the digestive system, endometrial cancer, esophageal cancer, eye cancer, head and neck cancer, gastric cancer, intraepithelial neoplasm, kidney cancer, larynx cancer, liver cancer, lung cancer (small cell, large cell), melanoma, neuroblastoma; oral cavity cancer (for example lip, tongue, mouth and pharynx), ovarian cancer, pancreatic cancer, retinoblastoma, rhabdomyosarcoma, rectal cancer; cancer of the respiratory system, sarcoma, skin cancer, stomach cancer, testicular cancer, thyroid cancer, uterine cancer, and cancer of the urinary system, or any combination thereof.

In some aspects, the tumor is refractory to a prior therapy. In some aspects, the tumor is refractory to a prior standard of care therapy. In some aspects, the prior therapy comprises an immunotherapy, a chemotherapy, a surgery, a radiotherapy, or any combination thereof. In some aspects, the tumor is refractory to a prior chemotherapy. In some aspects, the tumor is refractory to a prior immunotherapy. In some aspects, the tumor is relapsed.

In some aspects, the tumor is advanced. In some aspects, the tumor is locally advanced. In some aspects, the tumor is metastatic.

In some aspects, the anti-CCR8 antibody is administered in combination with an additional anticancer agent. In some aspects, the additional anticancer agent is selected from a small molecule, a polypeptide, a radiation therapy, a surgery, and a combination thereof.

In some aspects, the anti-CCR8 antibody is administered prior to the additional anticancer agent. In some aspects, the anti-CCR8 antibody is administered after the additional anticancer agent. In some aspects, the anti-CCR8 antibody is administered at the same time as the additional anticancer agent. In some aspects, the anti-CCR8 antibody and the additional anticancer agent are formulated in a single composition.

In some aspects, the additional anticancer agent comprises a chemotherapy. The chemotherapy can be any chemotherapy known in the art. In some aspects, the chemotherapy is a standard of care treatment for the particular cancer type. In some aspects, the chemotherapy is a platinum-based chemotherapy. In some aspects, the chemotherapy is selected from the group consisting of doxorubicin (ADRIAMYCIN®), cisplatin, carboplatin, bleomycin sulfate, carmustine, chlorambucil (LEUKERAN®), cyclophosphamide (CYTOXAN®; NEOSAR®), lenalidomide (REVLIMID®), bortezomib (VELCADE®), dexamethasone, mitoxantrone, etoposide, cytarabine, bendamustine (TREANDA®), rituximab (RITUXAN®), ifosfamide, vincristine (ONCOVIN®), fludarabine (FLUDARA®), thalidomide (THALOMID®), alemtuzumab (CAMPATH®), ofatumumab (ARZERRA®), everolimus (AFINITOR®, ZORTRESS®), carfilzomib (KYPROLIS™), and any combination thereof.

In some aspects, the additional anticancer agent comprises an immunotherapy. In some aspects, the immunotherapy is selected from a PD-1 antagonist, a PD-L1 inhibitor, a TIM-3 inhibitor, a LAG-3 inhibitor, a TIGIT inhibitor, a CD112R inhibitor, a TAM inhibitor, a STING agonist, a 4-1BB agonist, a CCL22 inhibitor, an agent that induces NK cell activation, and any combination thereof.

In some aspects, the additional anticancer therapy comprises a PD-1 antagonist. Any PD-1 antagonist known in the art can be used in combination with the anti-CCR8 antibodies disclosed herein. In some aspects, the PD-1 antagonist is is an antibody or antigen-binding portion thereof that specifically binds PD-1. Nonlimiting examples of PD-1 antagonists that can be used in combination with the anti-CCR8 antibodies disclosed herein include PDR001, nivolumab, pembrolizumab, pidilizumab, MEDI0680, REGN2810, TSR-042, PF-06801591, and AMP-224.

In some aspects, the additional anticancer therapy comprises a PD-L1 inhibitor. Any PD-L1 inhibitor known in the art can be used in combination with the anti-CCR8 antibodies disclosed herein. In some aspects, the PD-L1 inhibitor is is an antibody or antigen-binding portion thereof that specifically binds PD-L1. Nonlimiting examples of PD-L1 inhibitors that can be used in combination with the anti-CCR8 antibodies disclosed herein include FAZ053, Atezolizumab, Avelumab, Durvalumab, and BMS-936559.

In some aspects, the additional anticancer therapy comprises a TIM-3 inhibitor. Any TIM-3 inhibitor known in the art can be used in combination with the anti-CCR8 antibodies disclosed herein. In some aspects, the TIM-3 inhibitor is is an antibody or antigen-binding portion thereof that specifically binds TIM-3. Nonlimiting examples of TIM-3 inhibitors that can be used in combination with the anti-CCR8 antibodies disclosed herein include MGB453 and TSR-022.

In some aspects, the additional anticancer therapy comprises a LAG-3 inhibitor. Any LAG-3 inhibitor known in the art can be used in combination with the anti-CCR8 antibodies disclosed herein. In some aspects, the LAG-3 inhibitor is is an antibody or antigen-binding portion thereof that specifically binds LAG-3. Nonlimiting examples of LAG-3 inhibitors that can be used in combination with the anti-CCR8 antibodies disclosed herein include LAG525, BMS-986016, and TSR-033.

In some aspects, the additional anticancer therapy comprises a TIGIT inhibitor. Any TIGIT inhibitor known in the art can be used in combination with the anti-CCR8 antibodies disclosed herein. In some aspects, the TIGIT inhibitor is is an antibody or antigen-binding portion thereof that specifically binds TIGIT.

In some aspects, the additional anticancer therapy comprises a CD112R inhibitor. Any CD112R inhibitor known in the art can be used in combination with the anti-CCR8 antibodies disclosed herein. In some aspects, the CD112R inhibitor is is an antibody or antigen-binding portion thereof that specifically binds CD112R.

In some aspects, the additional anticancer therapy comprises a CCL22 inhibitor. Any CCL22 inhibitor known in the art can be used in combination with the anti-CCR8 antibodies disclosed herein. In some aspects, the CCL22 inhibitor is is an antibody or antigen-binding portion thereof that specifically binds CCL22.

In some aspects, the additional anticancer therapy an agent that induces NK cell activation, and therefore enhances ADCC activity of the CCR8 antibody. In some aspects, the agent that induces NK cell activation is an antibody or antigen-binding portion thereof, a small molecule, a cytokine, or a cytokine fusion.

In certain aspects, the additional anticancer agent comprises an anticancer agent selected from the group consisting of Sunitinib (SUTENT®), Cabozantinib (CABOMETYX®), Axitinib (INLYTA®), Lenvatinib (LENVIMA®), Everolimus (AFINITOR®), Bevacizumab (AVASTIN®), epacadostat, NKTR-214 (CD-122-biased agonist), Tivozanib (FOTIVDA®), abexinostat, Ipilimumab (YERVOY®), tremelimumab, Pazopanib (VOTRIENT®), Sorafenib (NEXAVAR®), Temsirolimus (TORISEL®), Ramucirumab (CYRAMZA®), niraparib, savolitinib, vorolanib (X-82), Regorafenib (STIVARGO®), Donafenib (multikinase inhibitor), Camrelizumab (SHR-1210), pexastimogene devacirepvec (JX-594), Ramucirumab (CYRAMZA®), apatinib (YN968D1), encapsulated doxorubicin (THERMODOX®), Tivantinib (ARQ197), ADI-PEG 20, binimetinib, apatinib mesylate, nintedanib, lirilumab, Nivolumab (OPDIVO®), Pembrolizumab (KEYTRUDA®), Atezolizumab (TECENTRIQ®), Avelumab (BAVENCIO®), Durvalumab (IMFIMZI®), Cemiplimab-rwlc (LIBTAYO®), tislelizumab, spartalizumab, and any combination thereof.

In some aspects, the additional anticancer agent comprises a TAM (Axl, Mer, Tyro) inhibitor. In some aspects, the additional anticancer agent comprises a 4-1BB agonist. In some aspects, the additional anticancer agent comprises a Tyrosine Kinase Inhibitor (TKI). Nonlimiting examples of TKIs that can be used in combination with the anti-CCR8 antibodies disclosed herein include imatinib mesylate, dasatinib, nilotinib, and bosutinib.

The anti-CCR8 antibodies of the present disclosure can be administered by any suitable route. In some aspects, the anti-CCR8 antibody is administered intravenously. In some aspects, the anti-CCR8 antibody is subcutaneously. In some aspects, the anti-CCR8 antibody is administered intramuscularly. In some aspects, the anti-CCR8 antibody is administered intraperitoneally. In some aspects, the anti-CCR8 antibody is administered orally.

III.B. Methods for Producing Anti-CCR8 Antibodies

The disclosure also features methods for producing any of the anti-CCR8 antibodies described herein. In some aspects, methods for preparing an antibody described herein can include immunizing a subject (e.g., a non-human mammal) with an appropriate immunogen. Suitable immunogens for generating any of the antibodies described herein are set forth herein. For example, to generate an antibody that binds to the N-terminal extracellular domain of human CCR8, a skilled artisan can immunize a suitable subject (e.g., a non-human mammal such as a rat, a mouse, a gerbil, a hamster, a dog, a cat, a pig, a goat, a horse, or a non-human primate) with a fragment of human CCR8 comprising the N-terminal extracellular domain. In some aspects, a fragment polypeptide comprising the amino acid sequence set forth in SEQ ID NO: 172 is used as the immunogen.

A suitable subject (e.g., a non-human mammal) can be immunized with the appropriate antigen along with subsequent booster immunizations a number of times sufficient to elicit the production of an antibody by the mammal. The immunogen can be administered to a subject (e.g., a non-human mammal) with an adjuvant. Adjuvants useful in producing an antibody in a subject include, but are not limited to, protein adjuvants; bacterial adjuvants, e.g., whole bacteria (BCG, *Corynebacterium parvum* or *Salmonella minnesota*) and bacterial components including cell wall skeleton, trehalose dimycolate, monophosphoryl lipid A, methanol extractable residue (MER) of tubercle *bacillus*, complete or incomplete Freund's adjuvant; viral adjuvants; chemical adjuvants, e.g., aluminum hydroxide, and iodoacetate and cholesteryl hemisuccinate. Other adjuvants that can be used in the methods for inducing an immune response include, e.g., cholera toxin and parapoxvirus proteins. See also Bieg et al. (1999) *Autoimmunity* 31(1):15-24. See also, e.g., Lodmell et al. (2000) *Vaccine* 18:1059-1066; Johnson et al. (1999) *J Med Chem* 42:4640-4649; Baldridge et al. (1999) *Methods* 19:103-107; and Gupta et al. (1995) *Vaccine* 13(14): 1263-1276.

In some aspects, the methods include preparing a hybridoma cell line that secretes a monoclonal antibody that binds to the immunogen. For example, a suitable mammal such as a laboratory mouse is immunized with a CCR8 polypeptide as described above. Antibody-producing cells (e.g., B cells of the spleen) of the immunized mammal can be isolated two to four days after at least one booster immunization of the immunogen and then grown briefly in culture before fusion with cells of a suitable myeloma cell line. The cells can be fused in the presence of a fusion promoter such as, e.g., vaccinia virus or polyethylene glycol. The hybrid cells obtained in the fusion are cloned, and cell clones secreting the desired antibodies are selected. For example, spleen cells of Balb/c mice immunized with a suitable immunogen can be fused with cells of the myeloma cell line PAI or the myeloma cell line Sp2/0-Ag 14. After the fusion, the cells are expanded in suitable culture medium, which is supplemented with a selection medium, for example HAT medium, at regular intervals in order to prevent normal myeloma cells from overgrowing the desired hybridoma cells. The obtained hybrid cells are then screened for secretion of the desired antibodies, e.g., an antibody that binds to human CCR8 and In some aspects, a skilled artisan can identify an anti-CCR8 antibody from a non-immune biased library as described in, e.g., U.S. Pat. No. 6,300,064 (to Knappik et al.; Morphosys AG) and Schoonbroodt et al. (2005) *Nucleic Acids Res* 33(9):e81.

In some aspects, the methods described herein can involve, or be used in conjunction with, e.g., phage display technologies, bacterial display, yeast surface display, eukaryotic viral display, mammalian cell display, and cell-free (e.g., ribosomal display) antibody screening techniques (see, e.g., Etz et al. (2001) *J Bacteriol* 183:6924-6935; Cornelis (2000) *Curr Opin Biotechnol* 11:450-454; Klemm et al. (2000) *Microbiology* 146:3025-3032; Kieke et al. (1997) *Protein Eng* 10:1303-1310; Yeung et al. (2002) *Biotechnol Prog* 18:212-220; Boder et al. (2000) *Methods Enzymology* 328:430-444; Grabherr et al. (2001) *Comb Chem High Throughput Screen* 4:185-192; Michael et al. (1995) *Gene Ther* 2:660-668; Pereboev et al. (2001) *J Virol* 75:7107-7113; Schaffitzel et al. (1999) *J Immunol Methods* 231:119-135; and Hanes et al. (2000) *Nat Biotechnol* 18:1287-1292).

Methods for identifying antibodies using various phage display methods are known in the art. In phage display methods, functional antibody domains are displayed on the surface of phage particles which carry the polynucleotide sequences encoding them. Such phage can be utilized to display antigen-binding domains of antibodies, such as Fab, Fv, or disulfide-bond stabilized Fv antibody fragments, expressed from a repertoire or combinatorial antibody library (e.g., human or murine). Phage used in these methods are typically filamentous phage such as fd and M13. The antigen binding domains are expressed as a recombinantly fused protein to any of the phage coat proteins pIII, pVIII, or pIX. See, e.g., Shi et al. (2010) *JMB* 397:385-396. Examples of phage display methods that can be used to make the immunoglobulins, or fragments thereof, described herein include those disclosed in Brinkman et al. (1995) *J Immunol Methods* 182:41-50; Ames et al. (1995) *J Immunol Methods* 184:177-186; Kettleborough et al. (1994) *Eur J Immunol* 24:952-958; Persic et al. (1997) *Gene* 187:9-18; Burton et al. (1994) *Advances in Immunology* 57:191-280; and PCT publication nos. WO 90/02809, WO 91/10737, WO 92/01047, WO 92/18619, WO 93/11236, WO 95/15982, and WO 95/20401. Suitable methods are also described in, e.g., U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

In some aspects, the phage display antibody libraries can be generated using mRNA collected from B cells from the immunized mammals. For example, a splenic cell sample comprising B cells can be isolated from mice immunized with a CCR8 polypeptide as described above. mRNA can be isolated from the cells and converted to cDNA using standard molecular biology techniques. See, e.g., Sambrook et al. (1989) "Molecular Cloning: A Laboratory Manual, $2^{nd}$ Edition," Cold Spring Harbor Laboratory Press, Cold Spring Harbor, N.Y.; Harlow and Lane (1988), supra; Benny K. C. Lo (2004), supra; and Borrebaek (1995), supra. The cDNA coding for the variable regions of the heavy chain and light chain polypeptides of immunoglobulins are used to construct the phage display library. Methods for generating such a library are described in, e.g., Merz et al. (1995) *J Neurosci Methods* 62(1-2):213-9; Di Niro et al. (2005) *Biochem J* 388(Pt 3):889-894; and Engberg et al. (1995) *Methods Mol Biol* 51:355-376.

In some aspects, a combination of selection and screening can be employed to identify an antibody of interest from, e.g., a population of hybridoma-derived antibodies or a phage display antibody library. Suitable methods are known in the art and are described in, e.g., Hoogenboom (1997) *Trends in Biotechnology* 15:62-70; Brinkman et al. (1995), supra; Ames et al. (1995), supra; Kettleborough et al. (1994), supra; Persic et al. (1997), supra; and Burton et al. (1994), supra. For example, a plurality of phagemid vectors, each encoding a fusion protein of a bacteriophage coat protein (e.g., pIII, pVIII, or pIX of M13 phage) and a different antigen-combining region are produced using standard molecular biology techniques and then introduced into a population of bacteria (e.g., *E. coli*). Expression of the bacteriophage in bacteria can, in some aspects, require use of a helper phage. In some aspects, no helper phage is required (see, e.g., Chasteen et al., (2006) *Nucleic Acids Res* 34(21):e145). Phage produced from the bacteria are recovered and then contacted to, e.g., a target antigen bound to a solid support (immobilized). Phage may also be contacted to antigen in solution, and the complex is subsequently bound to a solid support.

A subpopulation of antibodies screened using the above methods can be characterized for their specificity and binding affinity for a particular antigen (e.g., human CCR8) using any immunological or biochemical based method known in the art. For example, specific binding of an antibody to CCR8, may be determined for example using immunological or biochemical based methods such as, but not limited to, an ELISA assay, SPR assays, immunoprecipitation assay, affinity chromatography, and equilibrium dialysis as described above. Immunoassays which can be used to analyze immunospecific binding and cross-reactivity of the antibodies include, but are not limited to, competitive and non-competitive assay systems using techniques such as Western blots, RIA, ELISA (enzyme linked immunosorbent assay), "sandwich" immunoassays, immunoprecipitation assays, immunodiffusion assays, agglutination assays, complement-fixation assays, immunoradiometric assays, fluorescent immunoassays, and protein A immunoassays. Such assays are routine and well known in the art.

In aspects where the selected CDR amino acid sequences are short sequences (e.g., fewer than 10-15 amino acids in length), nucleic acids encoding the CDRs can be chemically synthesized as described in, e.g., Shiraishi et al. (2007) *Nucleic Acids Symposium Series* 51(1):129-130 and U.S. Pat. No. 6,995,259. For a given nucleic acid sequence encoding an acceptor antibody, the region of the nucleic acid sequence encoding the CDRs can be replaced with the chemically synthesized nucleic acids using standard molecular biology techniques. The 5' and 3' ends of the chemically synthesized nucleic acids can be synthesized to comprise sticky end restriction enzyme sites for use in cloning the nucleic acids into the nucleic acid encoding the variable region of the donor antibody.

III.C. Recombinant Antibody Expression and Purification

The antibodies or antigen-binding fragments thereof described herein can be produced using a variety of techniques known in the art of molecular biology and protein chemistry. For example, a nucleic acid encoding one or both of the heavy and light chain polypeptides of an antibody can be inserted into an expression vector that contains transcriptional and translational regulatory sequences, which include, e.g., promoter sequences, ribosomal binding sites, transcriptional start and stop sequences, translational start and stop sequences, transcription terminator signals, polyadenylation signals, and enhancer or activator sequences. The regulatory sequences include a promoter and transcriptional start and stop sequences. In addition, the expression vector can include more than one replication system such that it can be maintained in two different organisms, for example in mammalian or insect cells for expression and in a prokaryotic host for cloning and amplification.

Several possible vector systems are available for the expression of cloned heavy chain and light chain polypeptides from nucleic acids in mammalian cells. One class of vectors relies upon the integration of the desired gene sequences into the host cell genome. Cells which have stably integrated DNA can be selected by simultaneously introducing drug resistance genes such as *E. coli* gpt (Mulligan and Berg (1981) *Proc Natl Acad Sci USA* 78:2072) or Tn5 neo (Southern and Berg (1982) *Mol Appl Genet* 1:327). The selectable marker gene can be either linked to the DNA gene sequences to be expressed, or introduced into the same cell by co-transfection (Wigler et al. (1979) *Cell* 16:77). A second class of vectors utilizes DNA elements which confer autonomously replicating capabilities to an extrachromosomal plasmid. These vectors can be derived from animal viruses, such as bovine papillomavirus (Sarver et al. (1982) *Proc Natl Acad Sci USA,* 79:7147), cytomegalovirus, polyoma virus (Deans et al. (1984) *Proc Natl Acad Sci USA* 81:1292), or SV40 virus (Lusky and Botchan (1981) *Nature* 293:79).

The expression vectors can be introduced into cells in a manner suitable for subsequent expression of the nucleic acid. The method of introduction is largely dictated by the targeted cell type, discussed below. Exemplary methods include $CaPO_4$ precipitation, liposome fusion, cationic liposomes, electroporation, viral infection, dextran-mediated transfection, polybrene-mediated transfection, protoplast fusion, and direct microinjection.

Appropriate host cells for the expression of antibodies or antigen-binding fragments thereof include yeast, bacteria, insect, plant, and mammalian cells. Of particular interest are bacteria such as *E. coli*, fungi such as *Saccharomyces cerevisiae* and *Pichia pastoris*, insect cells such as SF9, mammalian cell lines (e.g., human cell lines), as well as primary cell lines.

In some aspects, an antibody or fragment thereof can be expressed in, and purified from, transgenic animals (e.g., transgenic mammals). For example, an antibody can be produced in transgenic non-human mammals (e.g., rodents) and isolated from milk as described in, e.g., Houdebine (2002) *Curr Opin Biotechnol* 13(6):625-629; van Kuik-Romeijn et al. (2000) Transgenic Res 9(2):155-159; and Pollock et al. (1999) *J Immunol Methods* 231(1-2):147-157.

The antibodies and fragments thereof can be produced from the cells by culturing a host cell transformed with the expression vector containing nucleic acid encoding the antibodies or fragments, under conditions, and for an amount of time, sufficient to allow expression of the proteins. Such conditions for protein expression will vary with the choice of the expression vector and the host cell, and will be easily ascertained by one skilled in the art through routine experimentation. For example, antibodies expressed in *E. coli* can be refolded from inclusion bodies (see, e.g., Hou et al. (1998) *Cytokine* 10:319-30). Bacterial expression systems and methods for their use are well known in the art (see Current Protocols in Molecular Biology, Wiley & Sons, and Molecular Cloning—A Laboratory Manual—3rd Ed., Cold Spring Harbor Laboratory Press, New York (2001)). The choice of codons, suitable expression vectors and suitable host cells will vary depending on a number of factors, and may be easily optimized as needed. An antibody (or fragment thereof) described herein can be expressed in mammalian cells or in other expression systems including but not limited to yeast, baculovirus, and in vitro expression systems (see, e.g., Kaszubska et al. (2000) *Protein Expression and Purification* 18:213-220).

Following expression, the antibodies and fragments thereof can be isolated. An antibody or fragment thereof can be isolated or purified in a variety of ways known to those skilled in the art depending on what other components are present in the sample. Standard purification methods include electrophoretic, molecular, immunological, and chromatographic techniques, including ion exchange, hydrophobic, affinity, and reverse-phase HPLC chromatography. For example, an antibody can be purified using a standard anti-antibody column (e.g., a protein-A or protein-G column). Ultrafiltration and diafiltration techniques, in conjunction with protein concentration, are also useful. See, e.g., Scopes (1994) "Protein Purification, $3^{rd}$ edition," Springer-Verlag, New York City, N.Y. The degree of purification necessary will vary depending on the desired use. In some instances, no purification of the expressed antibody or fragments thereof will be necessary.

Methods for determining the yield or purity of a purified antibody or fragment thereof are known in the art and include, e.g., Bradford assay, UV spectroscopy, Biuret protein assay, Lowry protein assay, amido black protein assay, high pressure liquid chromatography (HPLC), mass spectrometry (MS), and gel electrophoretic methods (e.g., using a protein stain such as Coomassie Blue or colloidal silver stain).

III.D. Modification of the Antibodies or Antigen-Binding Fragments Thereof

The antibodies or antigen-binding fragments thereof can be modified following their expression and purification. The modifications can be covalent or non-covalent modifications. Such modifications can be introduced into the antibodies or fragments by, e.g., reacting targeted amino acid residues of the polypeptide with an organic derivatizing agent that is capable of reacting with selected side chains or terminal residues. Suitable sites for modification can be chosen using any of a variety of criteria including, e.g., structural analysis or amino acid sequence analysis of the antibodies or fragments.

In some aspects, the antibodies or antigen-binding fragments thereof can be conjugated to a heterologous moiety. The heterologous moiety can be, e.g., a heterologous polypeptide, a therapeutic agent (e.g., a toxin or a drug), or a detectable label such as, but not limited to, a radioactive label, an enzymatic label, a fluorescent label, a heavy metal label, a luminescent label, or an affinity tag such as biotin or streptavidin. Suitable heterologous polypeptides include, e.g., an antigenic tag (FLAG ( (SEQ ID NO: 241)
(FLAG DYKDDDDK), ), polyhistidine (6-His;

(SEQ ID NO: 142)
(6-His; HHHHHH, hemagglutinin (HA;

(SEQ ID NO: 242)
(HA; YPYDVPDYA),

), glutathione-S-transferase (GST), or maltose-binding protein (MBP)) for use in purifying the antibodies or fragments. Heterologous polypeptides also include polypeptides (e.g., enzymes) that are useful as diagnostic or detectable markers, for example, luciferase, a fluorescent protein (e.g., green fluorescent protein (GFP)), or chloramphenicol acetyl transferase (CAT). Suitable radioactive labels include, e.g., $^{32}P$ $^{33}P$, $^{14}C$, $^{125}I$, $^{131}I$, $^{35}S$, and $^{3}H$. Suitable fluorescent labels include, without limitation, fluorescein, fluorescein isothiocyanate (FITC), green fluorescent protein (GFP), DyLight™ 488, phycoerythrin (PE), propidium iodide (PI), PerCP, PE-Alexa Fluor® 700, Cy5, allophycocyanin, and Cy7. Luminescent labels include, e.g., any of a variety of luminescent lanthanide (e.g., europium or terbium) chelates. For example, suitable europium chelates include the europium chelate of diethylene triamine pentaacetic acid (DTPA) or tetraazacyclododecane-1,4,7,10-tetraacetic acid (DOTA). Enzymatic labels include, e.g., alkaline phosphatase, CAT, luciferase, and horseradish peroxidase.

Two proteins (e.g., an antibody and a heterologous moiety) can be cross-linked using any of a number of known chemical cross linkers. Examples of such cross linkers are those which link two amino acid residues via a linkage that includes a "hindered" disulfide bond. In these linkages, a disulfide bond within the cross-linking unit is protected (by hindering groups on either side of the disulfide bond) from reduction by the action, for example, of reduced glutathione or the enzyme disulfide reductase. One suitable reagent, 4-succinimidyloxycarbonyl-α-methyl-α(2-pyridyldithio) toluene (SMPT), forms such a linkage between two proteins utilizing a terminal lysine on one of the proteins and a terminal cysteine on the other. Heterobifunctional reagents that cross-link by a different coupling moiety on each protein can also be used. Other useful cross-linkers include, without limitation, reagents which link two amino groups (e.g., N-5-azido-2-nitrobenzoyloxysuccinimide), two sulfhydryl groups (e.g., 1,4-bis-maleimidobutane), an amino group and a sulfhydryl group (e.g., m-maleimidobenzoyl-N-hydroxysuccinimide ester), an amino group and a carboxyl group (e.g., 4-[p-azidosalicylamido]butylamine), and an amino group and a guanidinium group that is present in the side chain of arginine (e.g., p-azidophenyl glyoxal monohydrate).

In some aspects, a radioactive label can be directly conjugated to the amino acid backbone of the antibody. Alternatively, the radioactive label can be included as part of a larger molecule (e.g., $^{125}I$ in meta-[$^{125}I$]iodophenyl-N-hydroxysuccinimide ([$^{125}I$]mIPNHS) which binds to free amino groups to form meta-iodophenyl (mIP) derivatives of relevant proteins (see, e.g., Rogers et al. (1997) *J Nucl Med* 38:1221-1229) or chelate (e.g., to DOTA or DTPA) which is in turn bound to the protein backbone. Methods of conjugating the radioactive labels or larger molecules/chelates containing them to the antibodies or antigen-binding fragments described herein are known in the art. Such methods involve incubating the proteins with the radioactive label under conditions (e.g., pH, salt concentration, and/or temperature) that facilitate binding of the radioactive label or chelate to the protein (see, e.g., U.S. Pat. No. 6,001,329).

Methods for conjugating a fluorescent label (sometimes referred to as a "fluorophore") to a protein (e.g., an antibody) are known in the art of protein chemistry. For example, fluorophores can be conjugated to free amino groups (e.g., of lysines) or sulfhydryl groups (e.g., cysteines) of proteins using succinimidyl (NHS) ester or tetrafluorophenyl (TFP) ester moieties attached to the fluorophores. In some aspects, the fluorophores can be conjugated to a heterobifunctional cross-linker moiety such as sulfo-SMCC. Suitable conjugation methods involve incubating an antibody protein, or fragment thereof, with the fluorophore under conditions that facilitate binding of the fluorophore to the protein. See, e.g., Welch and Redvanly (2003) "Handbook of Radiopharmaceuticals: Radiochemistry and Applications," John Wiley and Sons (ISBN 0471495603).

In some aspects, the antibodies or fragments can be modified, e.g., with a moiety that improves the stabilization and/or retention of the antibodies in circulation, e.g., in blood, serum, or other tissues. For example, the antibody or fragment can be PEGylated as described in, e.g., Lee et al. (1999) *Bioconjug Chem* 10(6): 973-8; Kinstler et al. (2002) *Advanced Drug Deliveries Reviews* 54:477-485; and Roberts et al. (2002) *Advanced Drug Delivery Reviews* 54:459-476 or HESylated (Fresenius Kabi, Germany; see, e.g., Pavisid et al. (2010) *Int J Pharm* 387(1-2):110-119). The stabilization moiety can improve the stability, or retention of, the antibody (or fragment) by at least 1.5 (e.g., at least 2, 5, 10, 15, 20, 25, 30, 40, or 50 or more) fold.

In some aspects, the antibodies or antigen-binding fragments thereof described herein can be glycosylated. In some aspects, an antibody or antigen-binding fragment thereof described herein can be subjected to enzymatic or chemical treatment, or produced from a cell, such that the antibody or fragment has reduced or absent glycosylation. Methods for producing antibodies with reduced glycosylation are known in the art and described in, e.g., U.S. Pat. No. 6,933,368; Wright et al. (1991) *EMBO J* 10(10):2717-2723; and Co et al. (1993) *Mol Immunol* 30:1361.

EXAMPLES

Example 1: Generation of Antibodies

Seventeen monoclonal antibodies specific to human CCR8 were generated against an N-terminal fragment of CCR8.

Antibody Phage Panning, Cloning and Transfection

Recombinant proteins expressing either the N-terminal extracellular domain of human or cynomolgus CCR8 fused to a 6×His tag followed by mouse IgG2a-Fc (CCR8-Fc) were cloned into mammalian expression vectors (SEQ ID NOs: 173 and 174, respectively; Table 4). For the Human protein, the free cysteine as position 25 was mutated to a serine to prevent disulfide bonding. The resulting secreted proteins were expressed by transfection in CHO cells and were purified using Protein A and used as antigen for phage panning using Fab display library. For panning, the purified protein was couple to M280 Tosyl beads or to ELISA plate and panning done using standard methods. Successive rounds of panning were performed on Human CCR8-ECD-Fc or in alternating rounds with cynomolgus CCR8-ECD-Fc, with unbound phage being removed by washing each round. The DNA from the resulting bound phage pool was isolated and the heavy and light chain sequences were cloned into a mammalian expression vector. Individual transformed colonies were grown separately in wells of a 96-well bacterial culture plate and the DNA was purified using Qiagen Turbo Miniprep Kit. The 96-well DNA mini-libraries were used to transfect CHO cells in the same 96 well format and the secreted antibody supernatants were harvested after three days incubation at 37° C., 7% $CO_2$ incubator.

Development of Anti-CCR8-1

The parental antibody, anti-CCR8-parental-1, was developed by phage panning as outlined above on the human CCR8 N-terminal protein and had an affinity of 1 nM on the 293T-Human CCR8 cell line. To improve affinity, a library was created in Vaccinia Virus where the CDR3 of the heavy chain was randomized. A library of 12,000 CDR3 variants was created in vaccinia. Upon overnight infection with the heavy chain CDR3 library (one clone per cell) and the parental light chain virus construct, full-length human IgG antibody is expressed on the cell surface (reference). Infected A431 cells were incubated with the human CCR8-N-terminal protein at a final concentration of 0.1 µg/ml, washed and stained with anti-Fc-Dylight649 to detect CCR8 protein binding and anti-Hu-Fab-FITC to detect antibody expression on the cell surface. Two thousand cells with high antibody expression and high CCR8 binding were sorted and the virus was amplified. DNA was extracted from the virus pool and the new heavy chain V genes were cloned into the mammalian cell expression vector containing a signal sequence and the human IgG1 constant domain (resulting in full length IgG1) and co-transfected along with the parental light chain in CHO cells for clone evaluation as outlined above. The anti-CCR8-1 antibody (comprising a variable heavy chain having the amino acid sequence set forth in SEQ ID NO: 41 and a variable light chain having the amino acid sequence set forth in SEQ ID NO: 43) was found to have three amino acid mutations in the CDR3 as compared to the parental heavy chain and an affinity of 0.4 nM on the 293T-Human CCR8 cell line. The anti-CCR8-1 antibody was found to bind huCC8-ECD-Fc but not CyCCR8-ECD-Fc (FIG. 1A), and the antibody preferentially bound 293T

TABLE 4

CCR8-ECD-Fc Sequences (signal peptide; CCR8 extracellular domain; 6X His tag and linker; and mouse IgG2a-Fc)

| | |
|---|---|
| Human CCR8-Fc | MGWSCIILFLVATATGAHSMDYTLDLSVTTVTDYYYPDIFSSPSDAELIQTNGK HHHHHHSGGGGSEPRGPTIKPCPPCKCPAPNLLGGPSVFIFPPKIKDVLMISLS PIVTCVVVDVSEDDPDVQISWFVNNVEVHTAQTQTHREDYNSTLRVVSALPIQH QDWMSGKEFKCKVNNKDLPAPIERTISKPKGSVRAPQVYVLPPPEEEMTKKQVT LTCMVTDFMPEDIYVEWTNNGKTELNYKNTEPVLDSDGSYFMYSKLRVEKKNWV ERNSYSCSVVHEGLHNHHTTKSFSRTPGK (SEQ ID NO: 173) |
| Cynomolgus CCR8-Fc | MGWSCIILFLVATATGAHSMDYTLDPSMTTMTDYYYPDSLSSPSDGELIQRNDK HHHHHHSGGGGSEPRGPTIKPCPPCKCPAPNLLGGPSVFIFPPKIKDVLMISLS PIVTCVVVDVSEDDPDVQISWFVNNVEVHTAQTQTHREDYNSTLRVVSALPIQH QDWMSGKEFKCKVNNKDLPAPIERTISKPKGSVRAPQVYVLPPPEEEMTKKQVT LTCMVTDFMPEDIYVEWTNNGKTELNYKNTEPVLDSDGSYFMYSKLRVEKKNWV ERNSYSCSVVHEGLHNHHTTKSFSRTPGK (SEQ ID NO: 174) |

Flow Cytometry of CHO Supernatants 293T cells expressing human CCR8, cynomolgus CCR8, mouse CCR8 and human CCR2 were harvested using Accutase® and 100,000 cells were dispensed to each well of a 96 well v-bottom plate. In some instances, the native human CCR8 expressing cell line Hut78 was also tested. The mini-library CHO supernatants were then added at a 1:2 final dilution to each cell type and allowed to incubate at 4° C. for 1 hour. After pelleting, the cells were incubated with anti-human-Fc-biotin followed by streptavidin-APC or with anti-human-Fc-APC at 4° C. for 30 minutes. After washing and fixation, the cells were run on the FACS Canto II with propidium iodide for live/dead discrimination. The live cells were analyzed and clones that showed specific binding to CCR8 (human and/or cynomologus) but not CCR2 were sent for DNA sequencing and further testing.

cells expressing HuCCR8 but not cyno CCR8, human CCR2, or mouse CCR8 (FIG. 1).

Development of Anti-CCR8-1-1, Anti-CCR8-1-2, Anti-CCR8-2-3, Anti-CCR8-1-4, and Anti-CCR8-1-5

The heavy chain of the parental antibody (anti-CCR8-parental-1) was cloned into Vaccinia Virus to facilitate light chain shuffle panning with Vaccinex's Vaccinia Display human IgG libraries. Briefly, 6×10[8] BHK cells were infected with the heavy chain form the anti-CCR8-parental-1 antibody (H23188) and a pool of lambda light chains from naïve sources. After two days incubation at 37° C., 7% $CO_2$, the supernatant was harvested and the vaccinia virus particles expressing a library of human IgG on their surface were pelleted by centrifugation. The pellet was resuspended and incubated with the purified Human CCR8-Fc protein coupled to M280 Tosyl beads. The unbound virus was washed away and the bound virus was amplified for subsequent rounds. After performing two rounds on human CCR8-Fc protein followed by two rounds on cyno CCR8-Fc protein, the DNA from the bound pool was extracted and the new light chains cloned into a mammalian expression vector for CHO transfection along with the parental heavy chain and flow cytometry analysis as detailed above. The anti-CCR8-1-1, anti-CCR8-1-2, anti-CCR8-2-3, anti-CCR8-1-4, and anti-CCR8-1-5 antibodies were found to bind huCC8-ECD-Fc at a higher specificity than CyCCR8-ECD-Fc (FIGS. 1C, 1E, 1G, 1H, and 1K, respectively), and each antibody preferentially bound 293T cells expressing HuCCR8 over cyno CCR8, human CCR2, and mouse CCR8 (FIGS. 1D, 1F, 1H, 1J, and 1K, respectively).

Figure 2A:
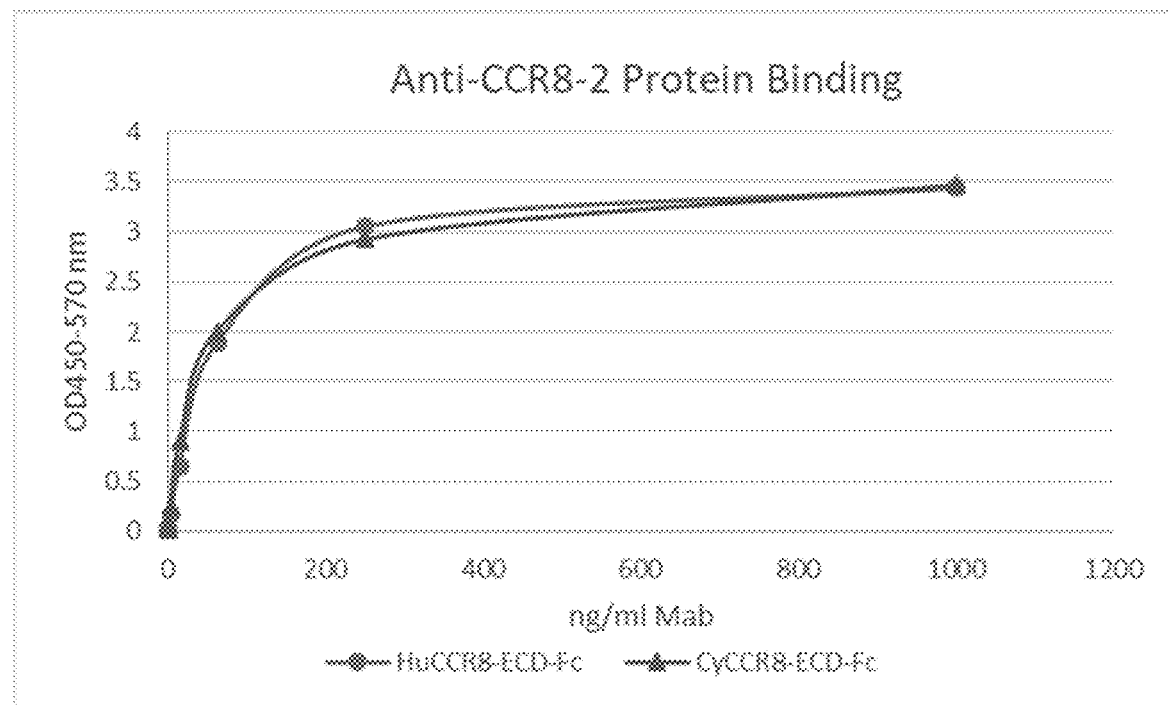
FIGS. 2A-2R are graphical representations of binding to human CCR8 (HuCCR8-ECD-Fc) or cyno CCR8 (CyCCR8-ECD-Fc) as measured by fluorescent absorbance (FIGS. 2A, 2C, 2E, 2G, 2I, 2K, 2M, 2O, 2Q, 2S, and 2U) and the relative binding over a secondary antibody to 293T cells expressing human CCR8, cyno CCR8, human CCR2, mouse CCR8, and negative control 293T cells (as indicated.
Figure 2B:
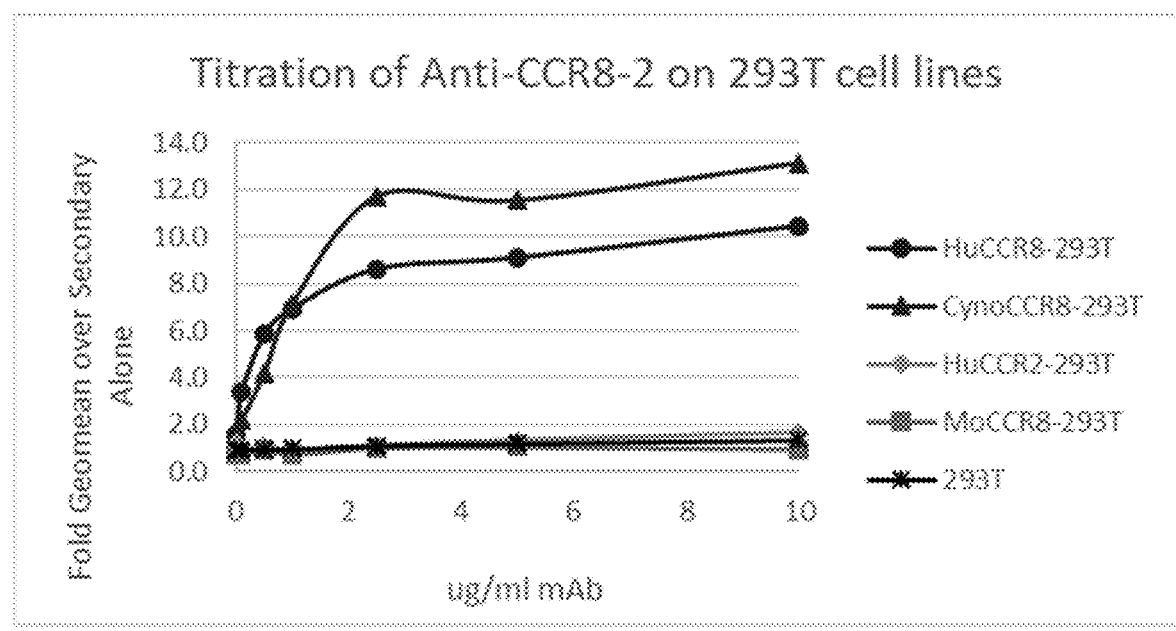
Figure 2C:
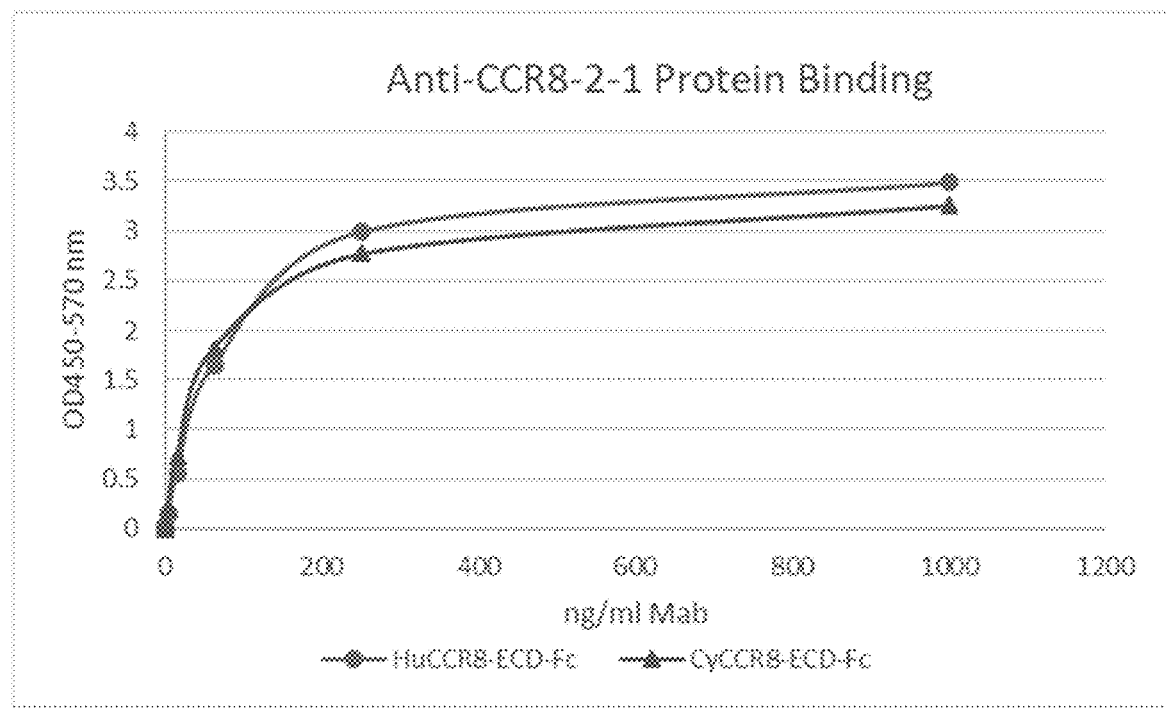
Figure 2D:
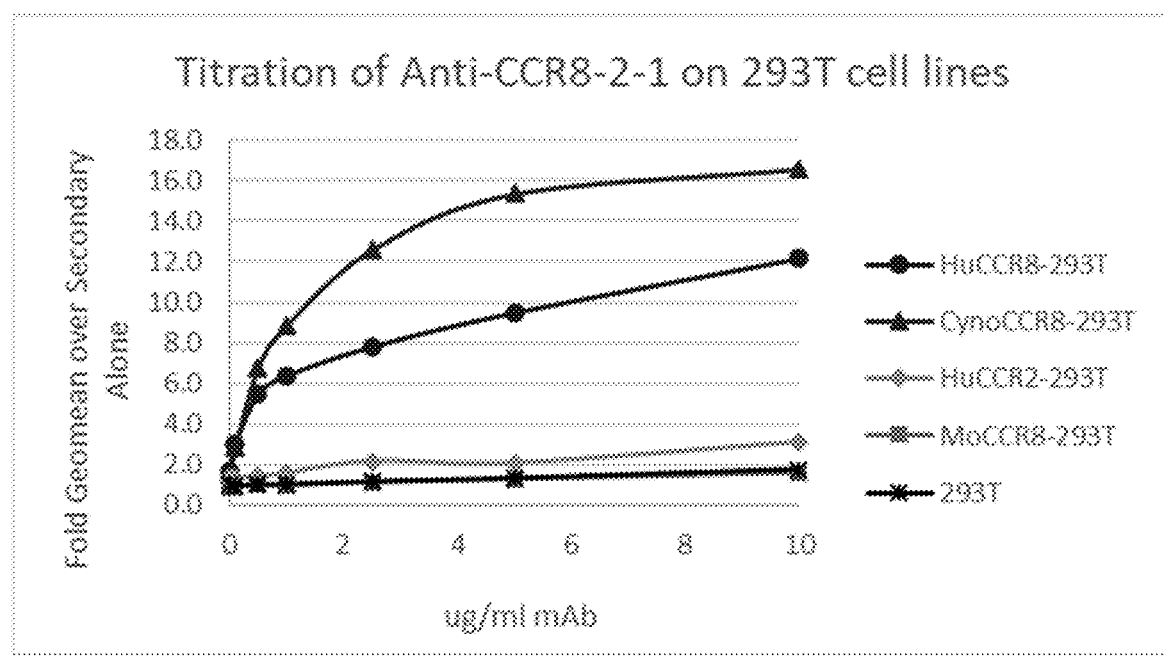
Figure 2E:
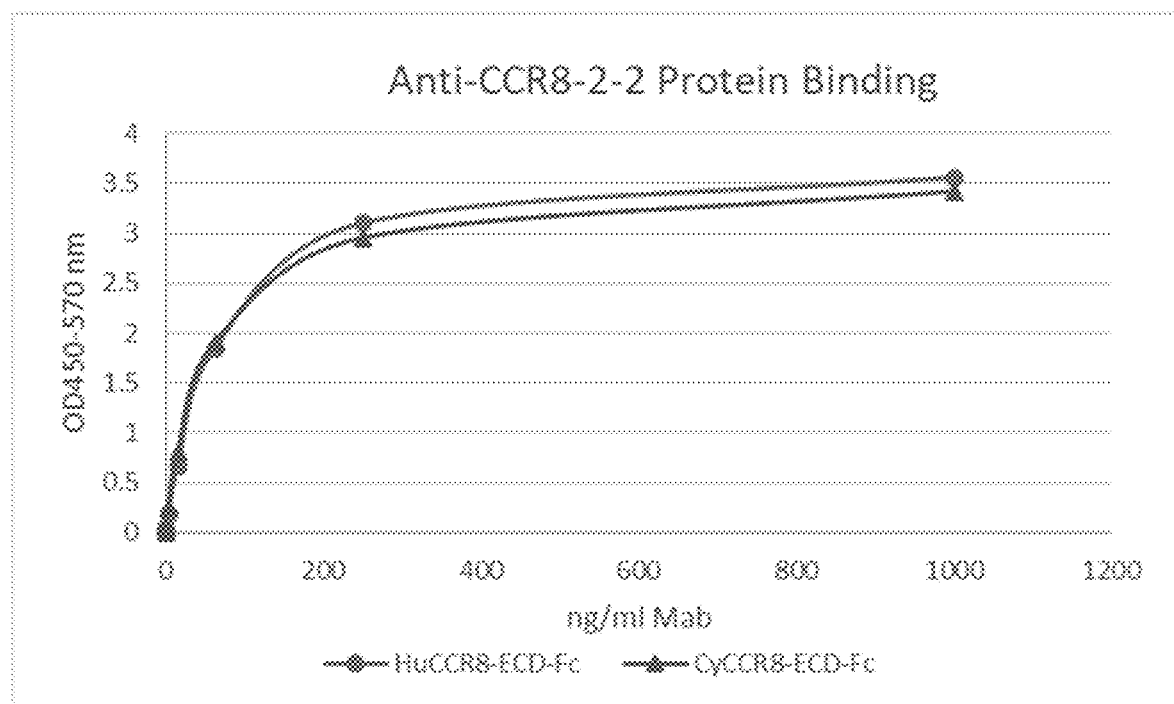
Figure 2F:
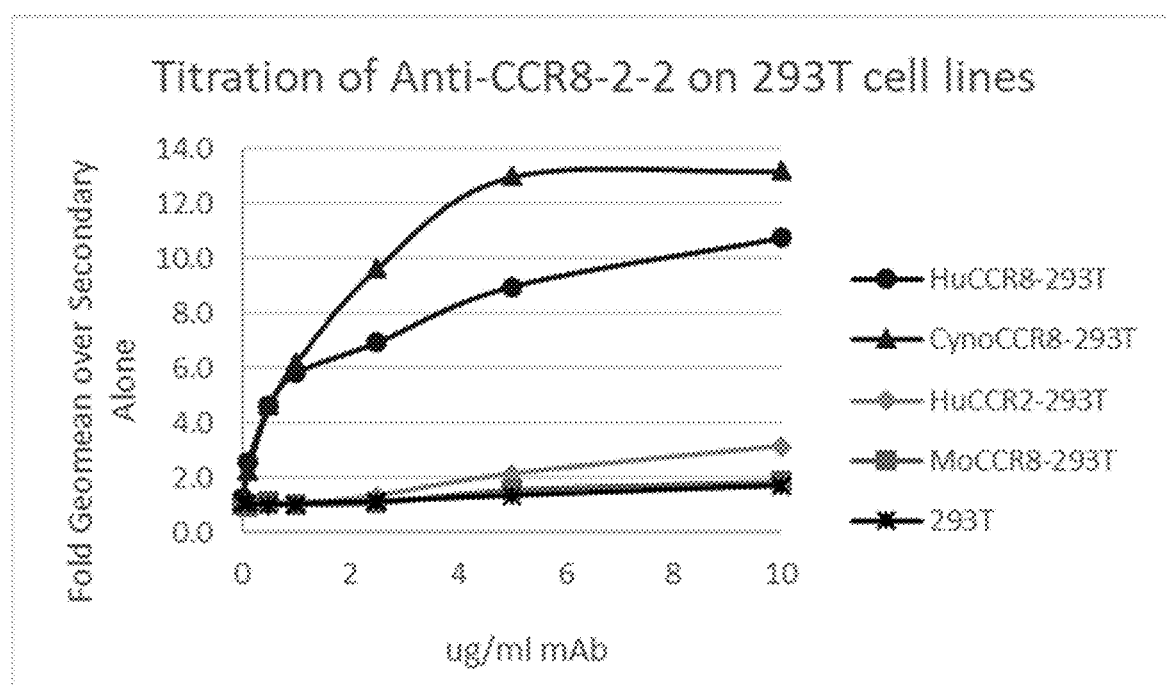
Figure 2G:
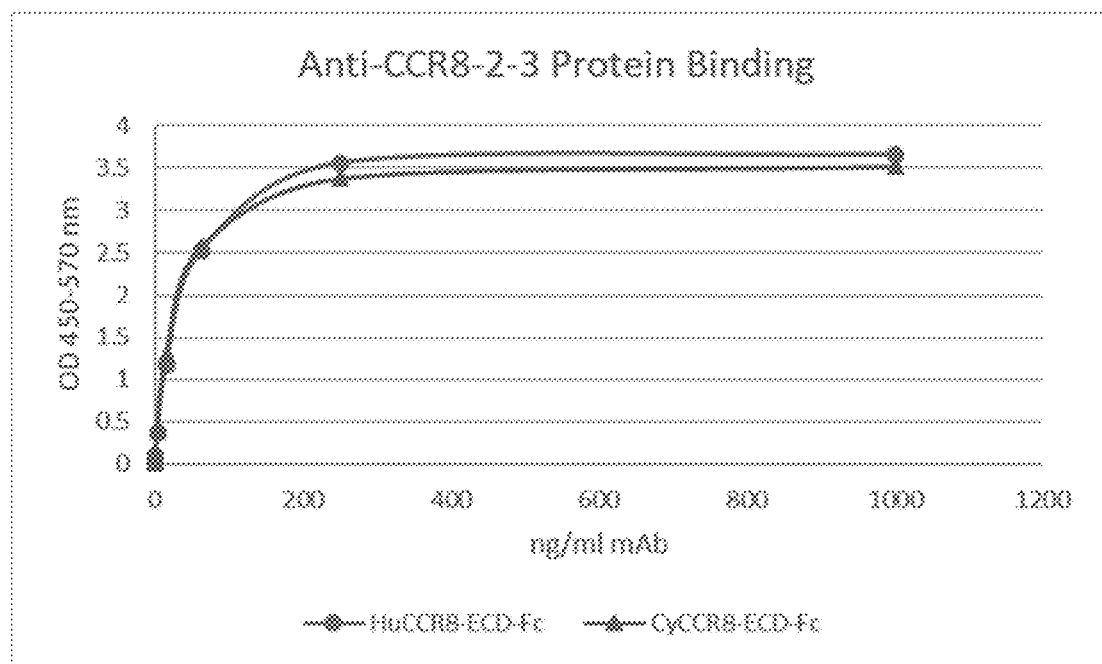
Figure 2H:
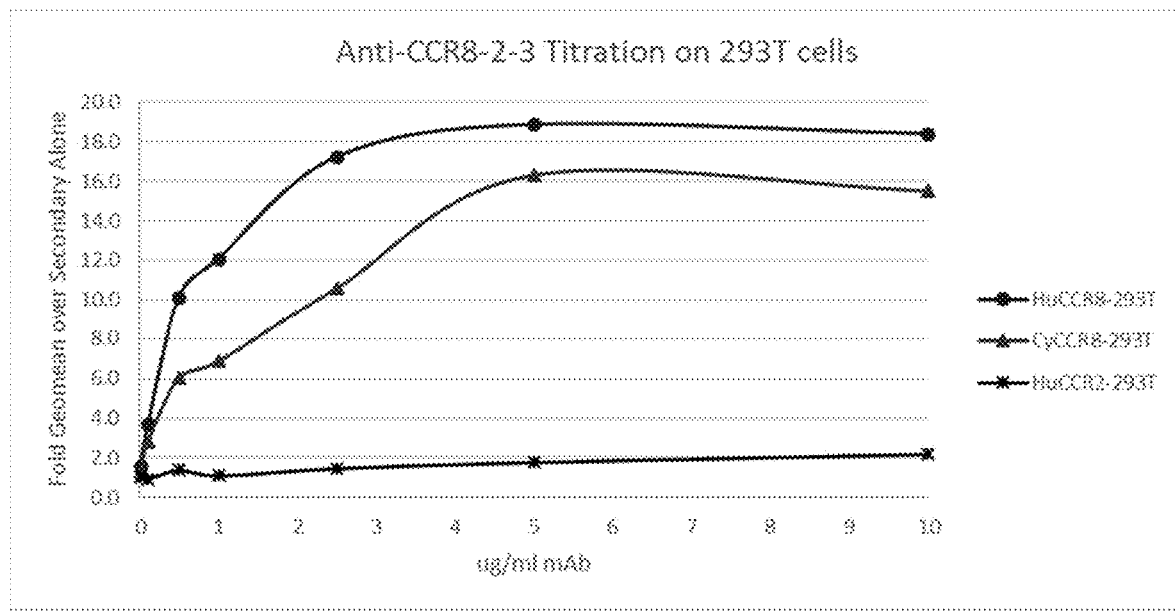
Figure 2I:
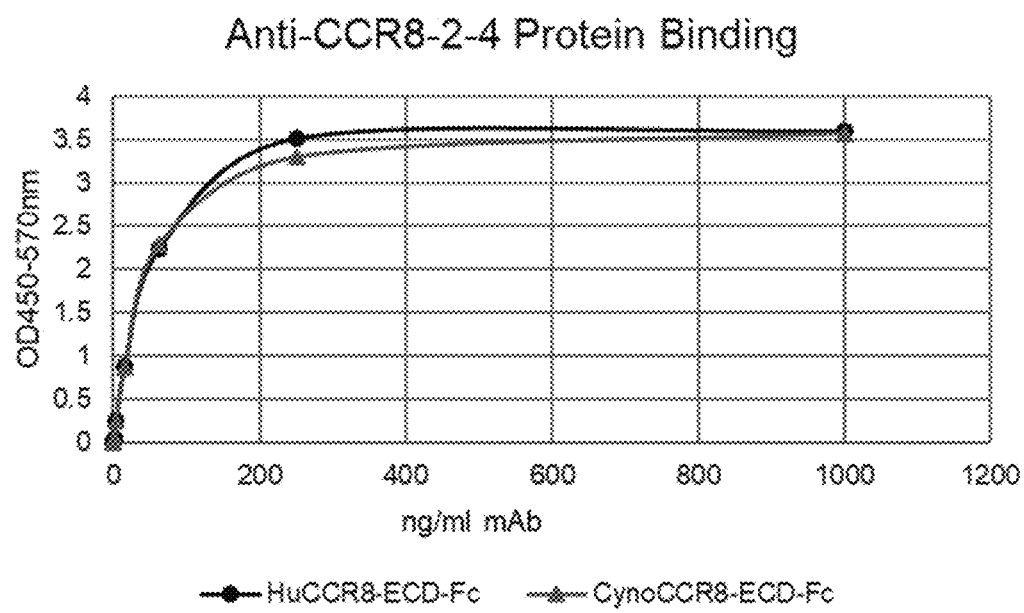
Figure 2J:
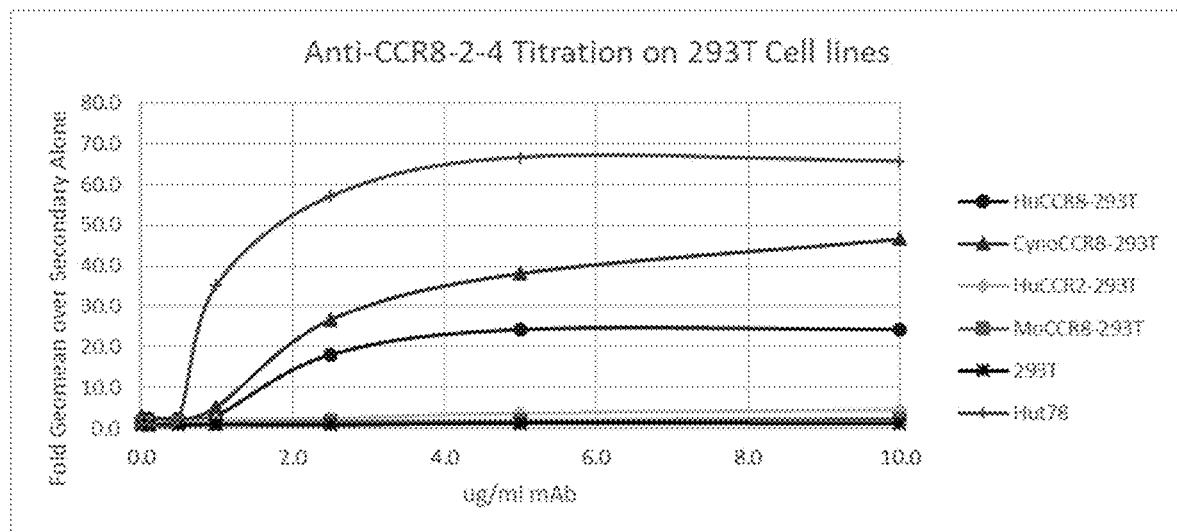
Figure 2K:
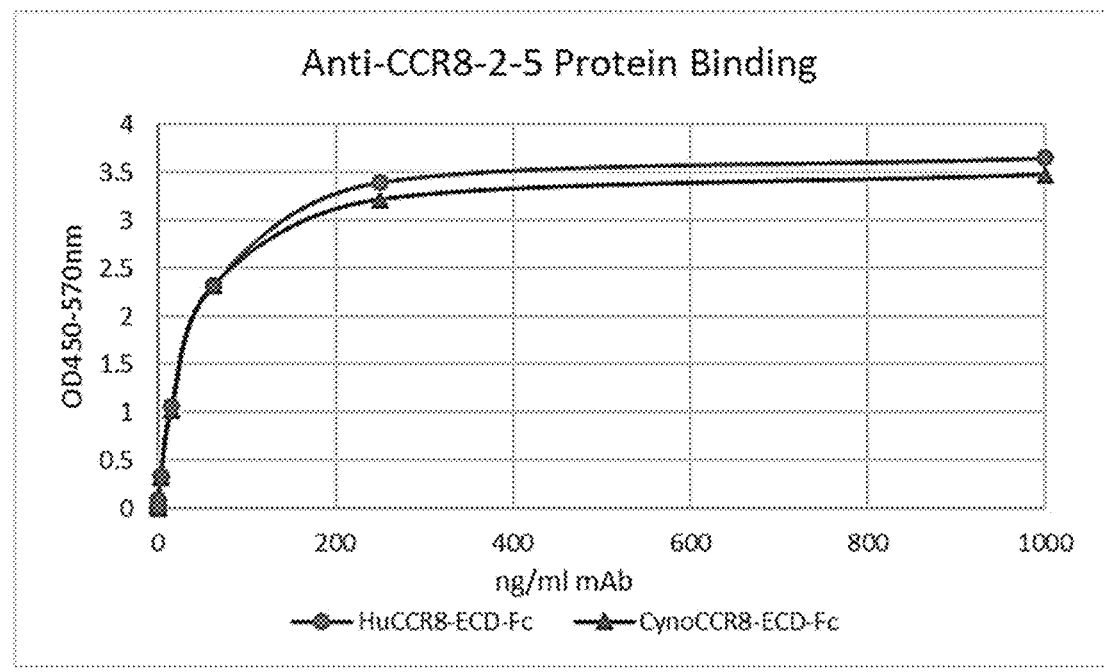
Figure 2L:
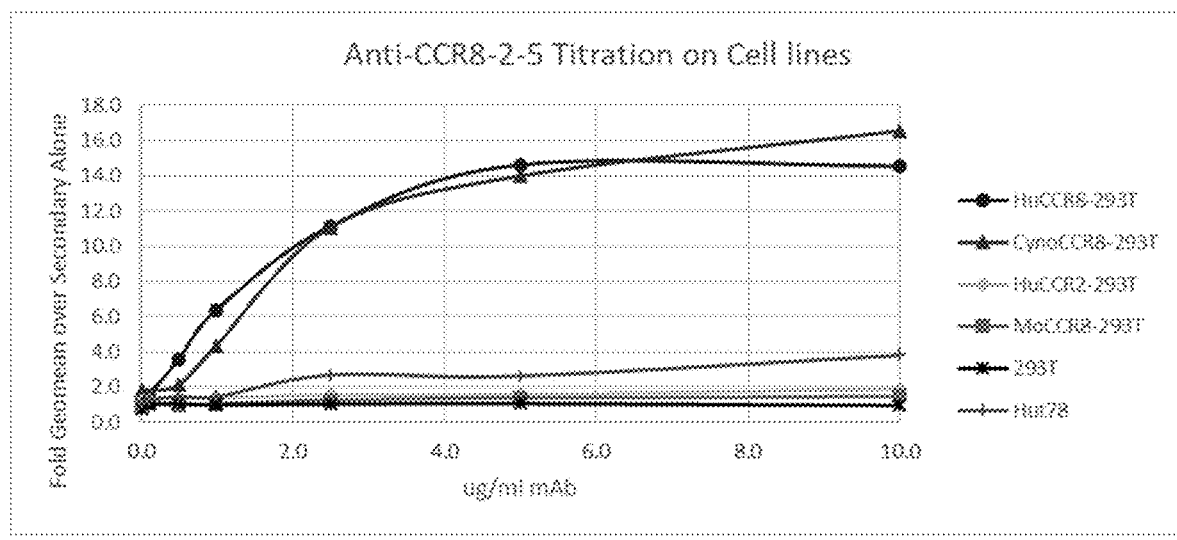
Figure 2M:
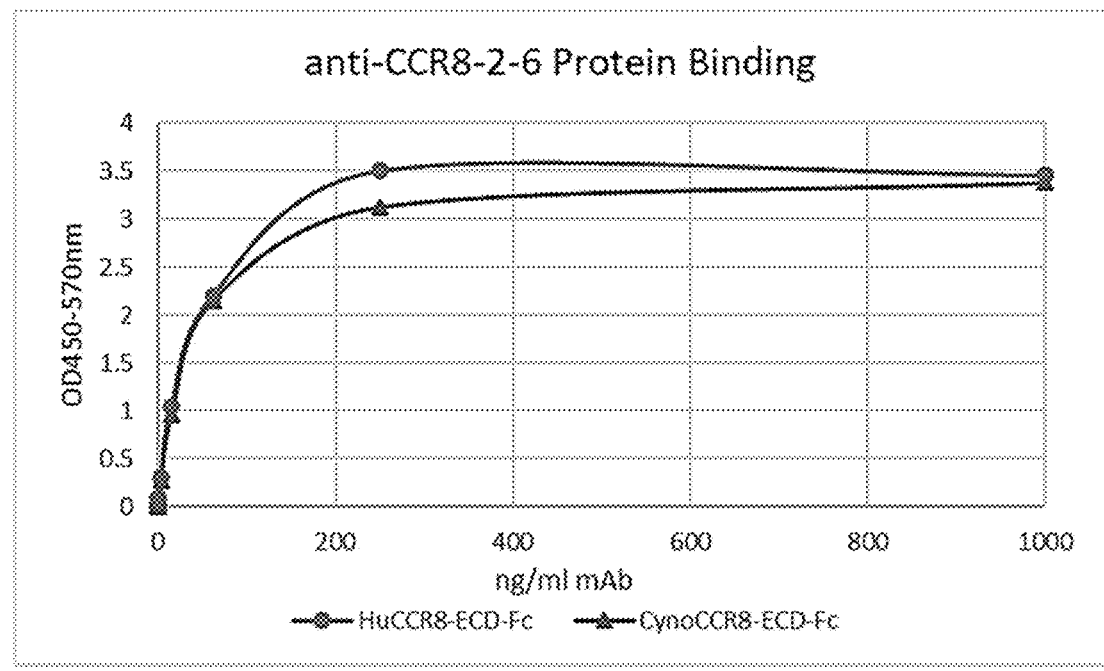
Figure 2N:
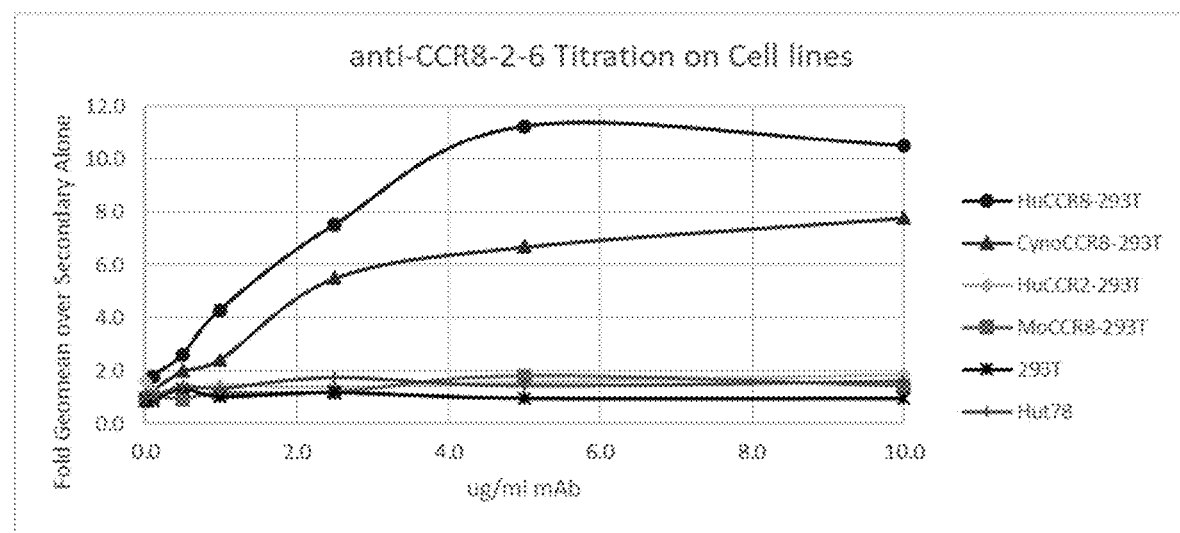
Figure 2O:
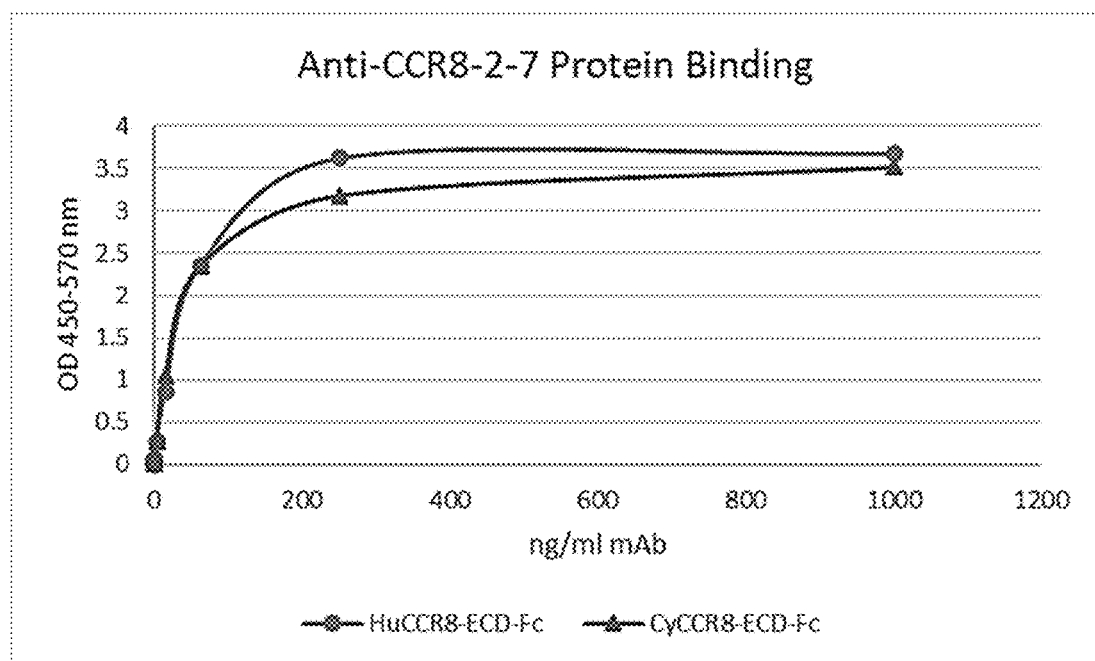
Figure 2P:
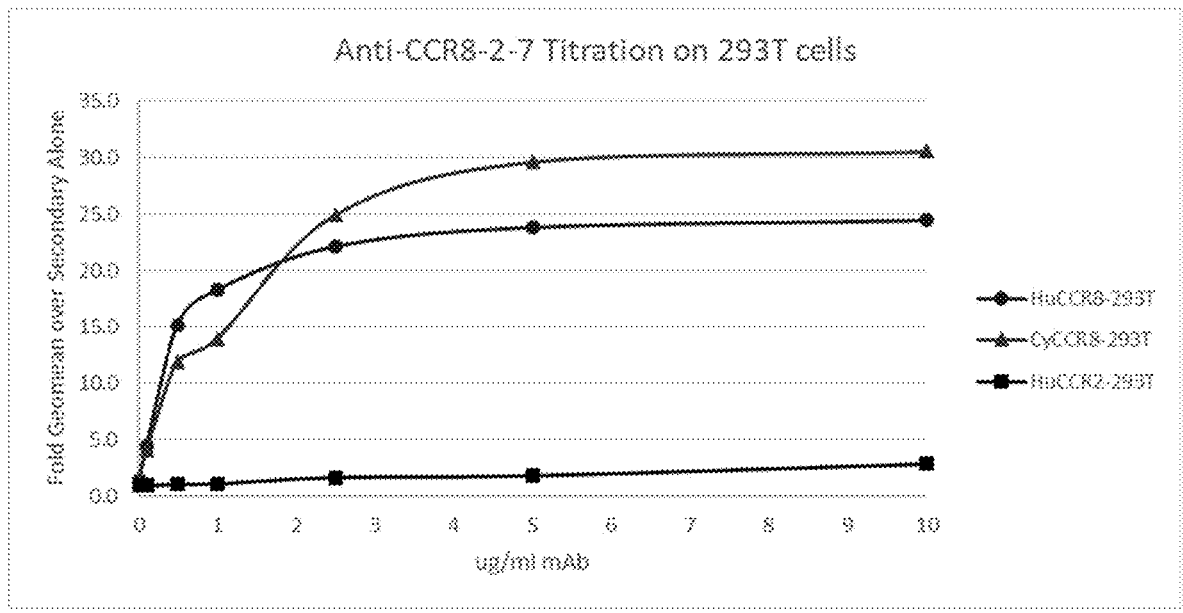
Figure 2Q:
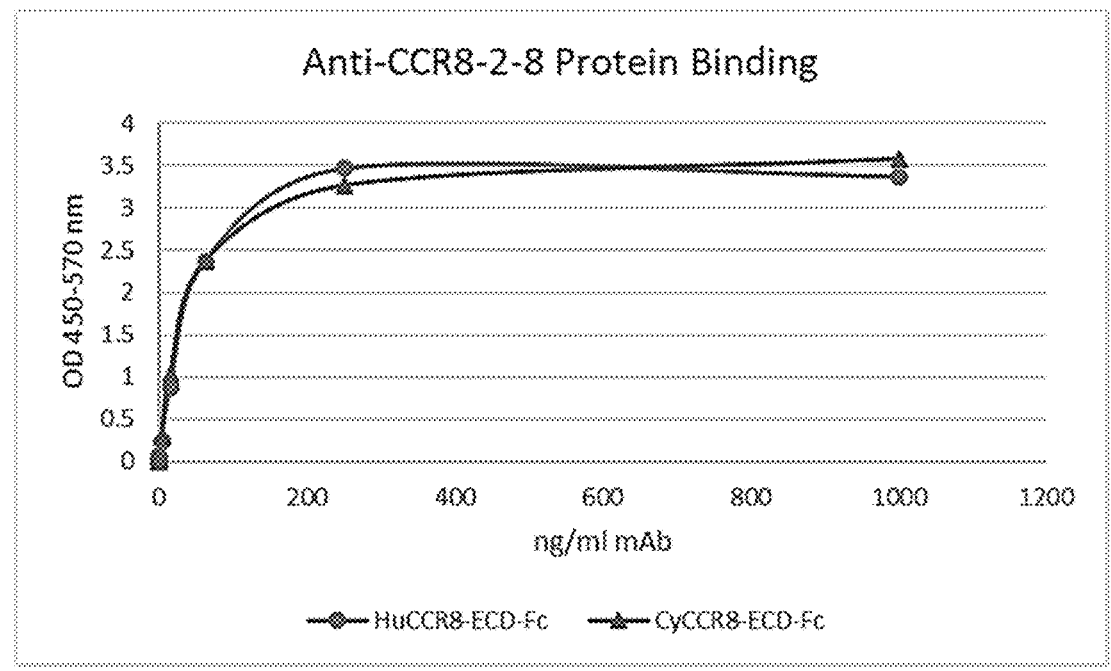
Figure 2R:
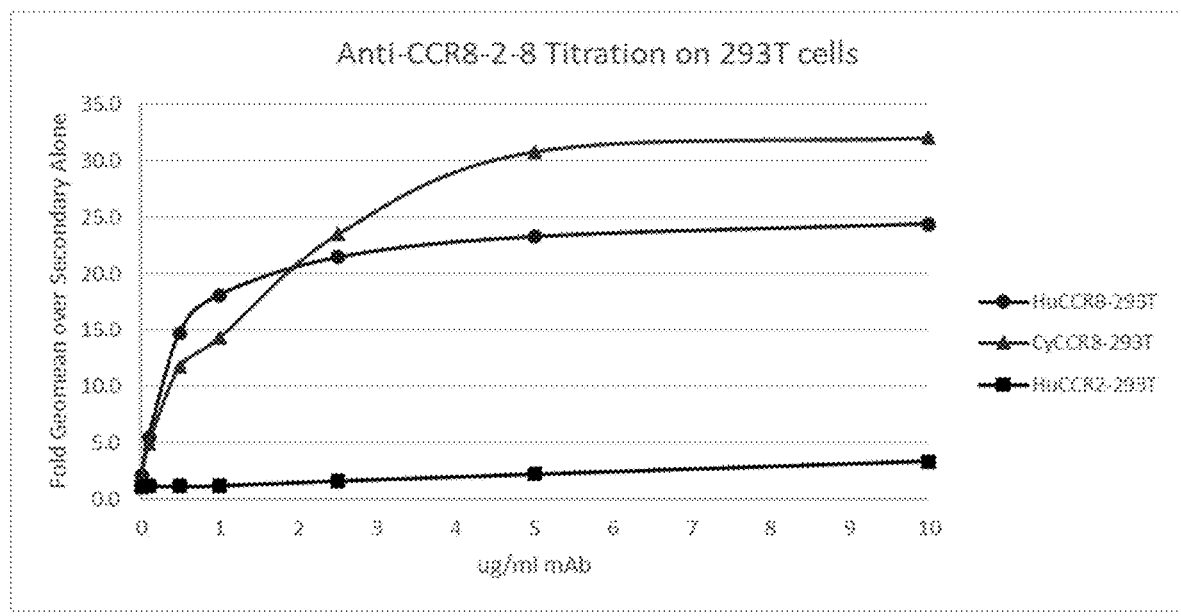
Figure 2S:
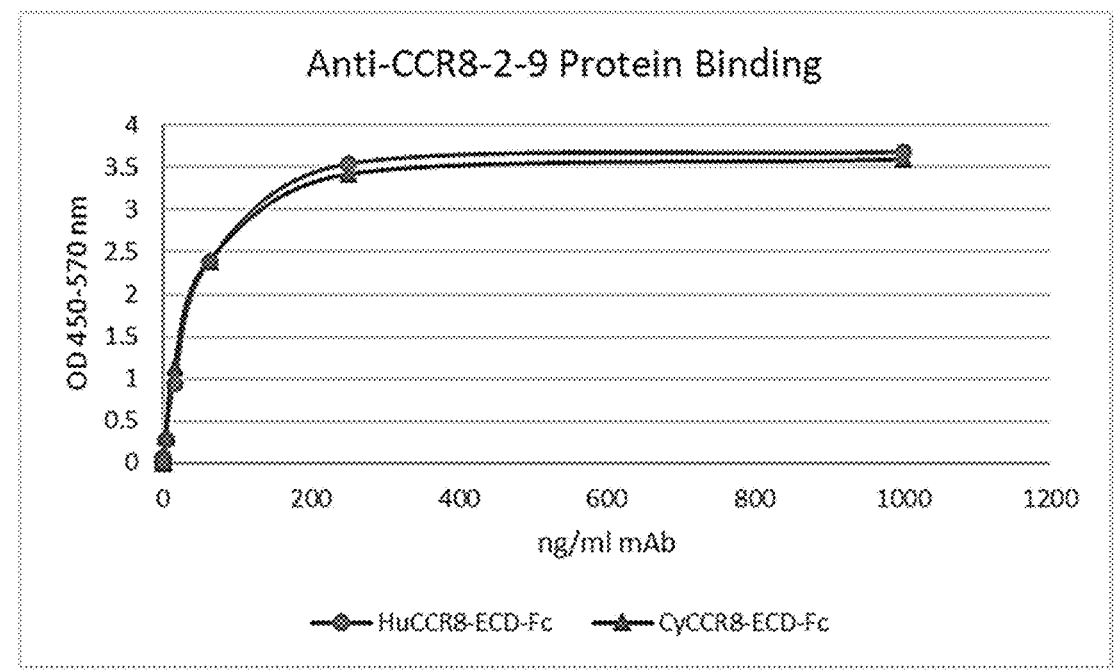
Figure 2T:
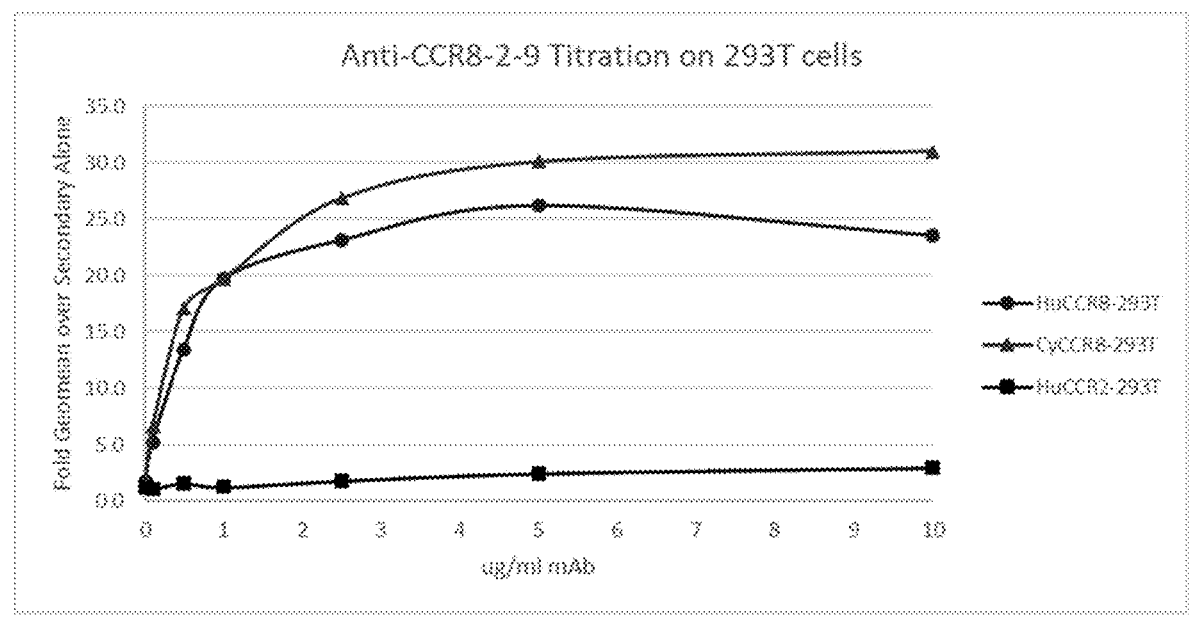
Figure 2U:
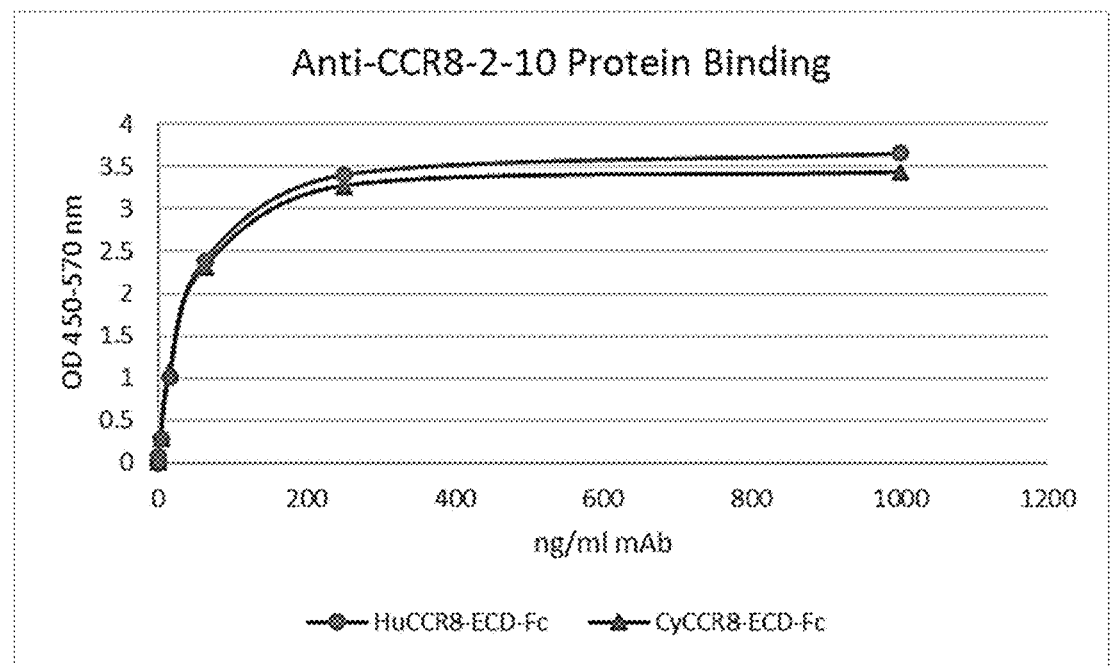
Figure 2V:
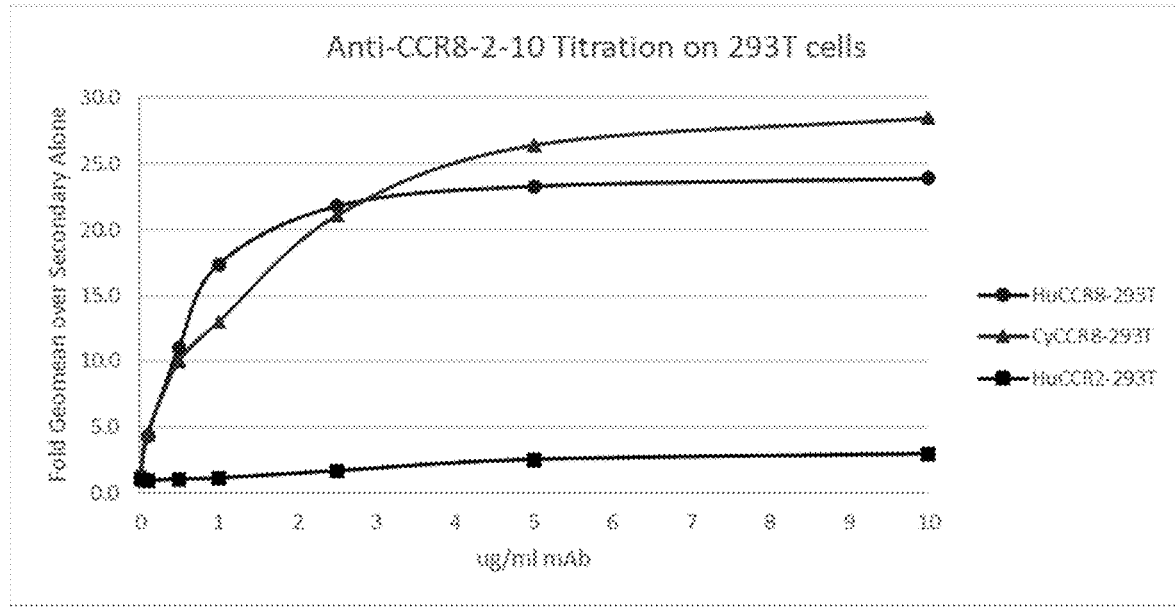

CCR8-2 and anti-CCR8-2-1 antibodies showed binding to both human and cyno CCR8 protein (FIGS. 2C and 2E) and cells expressing both human and cyno CCR8 (FIGS. 2D and 2F).

Development of Anti-CCR8-2-2

The heavy chain of the parental antibody, anti-CCR8-parental-2, was cloned into Vaccinia Virus to facilitate light chain shuffle panning with Vaccinia Display human IgG libraries. Briefly, $6 \times 10^8$ BHK cells were infected with the heavy chain form the anti-CCR8-parental-2 antibody (H23407) and a pool of lambda light chains from naïve sources. After two days incubation at 37° C., 7% $CO_2$, the supernatant was harvested and the vaccinia virus particles expressing a library of human IgG on their surface were

TABLE 5

Anti-CCR8 Antibodies

| Antibody Source | Mab Number | Heavy Chain (SEQ ID NO) | Light Chain | Affinity for 293T- Hu CCR8 cells (nM) | Affinity for 293T- CyCCR8 cells (nM) | Binding to HuCCR8- Fc protein | Binding to CyCCR8- Fc protein |
|---|---|---|---|---|---|---|---|
| Parental | anti-CCR8-parental-1 | H23188 | L1037 | 1.06 | >50 | ++++ | − |
| HCDR3 randomization | Anti-CCR8-1 | 41 | 43 | 0.41 | >50 | +++ | − |
| VL Shuffle | Anti-CCR8-1-1 | 101 | 103 | 1.01 | 22.1 | +++ | + |
| VL Shuffle | Anti-CCR8-1-2 | 111 | 113 | 1.06 | >50 | +++ | + |
| VL Shuffle | Anti-CCR8-1-3 | 121 | 123 | 1.38 | >50 | +++ | + |
| VL Shuffle | Anti-CCR8-1-4 | 131 | 133 | 0.28 | 35.9 | +++ | + |
| VL Shuffle | Anti-CCR8-1-5 | 141 | 143 | 1.36 | 48.6 | +++ | + |

Development of Anti-CCR8-2 and Anti-CCR8-2-1

The parental antibody (anti-CCR8-parental-2) was developed by phage panning as outlined above with two rounds on the Human protein followed by two rounds on the cynomolgus N-terminal protein. It was found to bind to both the human and the cynomolgus CCR8 cell lines, with affinities of 19.9 nM and 11.1 nM respectively. To improve affinity, a library was created in phage where the CDR1 and CDR2 of the heavy chain were randomized. This library was panned one round on the Cyno-CCR8-ECD-Fc protein followed by two consecutive rounds on the Human-CCR8-ECD-Fc protein. Individual phage clones were processed in a 96 well format and analyzed by phage ELISA on both the human and the cynomolgus proteins as well as negative antigens. Clones that were specific for CCR8 were sent for sequencing and cloned into mammalian expression vectors for further characterization. The anti-CCR8-2 antibody had an improved affinity of 0.4 nM on 293T-HuCCR8 cells and 0.9 nM on 293T-Cyno CCR8 cells derived from two amino acid mutations each in CDR1 and CDR2. Both the antipelleted by centrifugation. The pellet was resuspended and incubated with the purified cynomolgus CCR8-Fc protein coupled to M280 Tosyl beads. The unbound virus was washed away and the bound virus was amplified for subsequent rounds. After performing two rounds on cynomolgus CCR8-Fc protein, the bound pool was sorted for human/cyno cross-binders with 0.1 µg/ml biotin-cynomolgus CCR8-Fc and 0.1 µg/ml human CCR8-Fc protein. The highest binders to both proteins were collected, amplified and the DNA was extracted for cloning into a mammalian expression vector for CHO transfection and flow cytometry analysis as detailed above. The light chains that showed the best binding to 293T-CCR8 cell lines were cross-paired with the heavy chain from the anti-CCR8-2 antibody (H23727) to check for synergistic improvement in affinity. The anti-CCR8-2-2 antibody exhibited improved cross-reactive binding to human CCR8 as compared to the parental (FIGS. 2E-2F).

TABLE 6

Anti-CCR8 Antibodies

| Antibody Source | Mab Number | Heavy Chain (SEQ ID NO) | Light Chain (SEQ ID NO) | Affinity for 293T-HuCCR8 cells (nM) | Affinity for 293T-CyCCR8 cells (nM) | Binding to HuCCR8-Fc protein | Binding to CyCCR8-Fc protein |
|---|---|---|---|---|---|---|---|
| Parental | Anti-CCR8-Parental-2 | H23407 | L1032 | 19.9 | 11.1 | ++++ | ++++ |
| HCDR1/HCDR2 randomization | Anti-CCR8-2 | 11 | 13 | 0.41 | 0.94 | +++ | +++ |
| HCDR1/HCDR2 randomization | Anti-CCR8-2-1 | 51 | 53 | 0.54 | 1.09 | +++ | +++ |
| HCDR1/HCDR2 randomization & VL Shuffle | Anti-CCR8-2-2 | 161 | 163 | 0.8 | 1.6 | +++ | +++ |

Development of Anti-CCR8-2-3 and Anti-CCR8-2-4

The parental antibody, anti-CCR8-parental-3, was developed by phage panning as outlined above with two rounds on the Human protein followed by two rounds on the cynomolgus N-terminal protein. It was found to have binding to the human CCR8 cell lines, with an affinity of 6.8 nM. To improve affinity, a library was created in phage where the CDR3 of the heavy chain was randomized. This library was panned one round on the Cyno-CCR8-ECD-Fc protein followed by one round on the Human-CCR8-ECD-Fc protein. The DNA from the bound pool was extracted and cloned into a mammalian expression vector for CHO transfection and flow cytometry analysis as detailed above. Both the anti-CCR8-2-3 and the anti-CCR8-2-4 antibodies showed cross-reactive binding to both the human and cyno CCR8 cell lines (FIGS. 2G-2J).

Development of Anti-CCR8-2-5 and Anti-CCR8-2-6

A library of CDR3 variants for the heavy chain of the anti-CCR8-parental-3 antibody was also made in vaccinia virus. The library was sorted for human/cyno cross-binders with 1 µg/ml biotin-cynomolgus CCR8-Fc and 1 µg/ml human CCR8-Fc protein. The highest binders to both proteins were collected, amplified and the DNA was extracted for cloning into a mammalian expression vector for CHO transfection and flow cytometry analysis as detailed above. Both the anti-CCR8-2-5 and the anti-CCR8-2-6 antibodies showed cross-reactive binding to both the human and cyno CCR8 cell lines (FIGS. 2K-2N).

Development of Anti-CCR8-2-7, Anti-CCR8-2-8, Anti-CCR8-2-9, and Anti-CCR8-2-10

The heavy chain of the anti-CCR8-parental-3 antibody was cloned into Vaccinia Virus to facilitate light chain shuffle panning with Vaccinex's Vaccinia Display human IgG libraries. Briefly, $6 \times 10^8$ BHK cells were infected with the heavy chain from the anti-CCR8-parental-3 antibody (H23373) and a pool of lambda light chains from naïve sources. After two days incubation at 37° C., 7% C02, the supernatant was harvested and the vaccinia virus particles expressing a library of human IgG on their surface were pelleted by centrifugation. The pellet was resuspended and incubated with the purified cynomolgus CCR8-Fc protein coupled to M280 Tosyl beads. The unbound virus was washed away and the bound virus was amplified for subsequent rounds. After performing two rounds on cynomologous CCR8-Fc protein, the bound pool was sorted for human/cyno cross-binders with 0.1 µg/ml biotin-cynomolgus CCR8-Fc and 0.1 µg/ml Human CCR8-Fc protein. The highest binders to both proteins were collected, amplified and the DNA was extracted for cloning into a mammalian expression vector for CHO transfection and flow cytometry analysis as detailed above. The light chains that showed the best binding to 293T-CCR8 cell lines were cross-paired with the heavy chain from the anti-CCR8-2-3 antibody (H23499), and other heavy chains developed through the phage heavy chain CDR3 efforts in order to check for synergistic improvement in affinity. The anti-CCR8-2-7, anti-CCR8-2-8, anti-CCR8-2-9, and anti-CCR8-2-10 antibodies all showed enhanced binding to both human and cynomolgus CCR8 cell lines over the anti-CCR8-parental-3 antibody (FIGS. 2O-2V).

TABLE 7

Anti-CCR8 Antibodies

| Antibody Source | Mab Number | Heavy Chain (SEQ ID NO) | Light Chain (SEQ ID NO) | Affinity for 293T-HuCCR8 cells (nM) | Affinity for 293T-CyCCR8 cells (nM) | Binding to HuCCR8-Fc protein | Binding to CyCCR8-Fc protein |
|---|---|---|---|---|---|---|---|
| Parental | Anti-CCR8-parental 3 | H23373 | L1032 | 6.8 | >50 | ++++ | ++++ |
| HCDR3 randomization | Anti-CCR8-2-3 | 91 | 93 | 2.5 | 3.9 | ++++ | ++++ |
| HCDR3 randomization | Anti-CCR8-2-4 | 21 | 23 | 0.96 | 2.4 | ++++ | ++++ |

TABLE 7-continued

Anti-CCR8 Antibodies

| Antibody Source | Mab Number | Heavy Chain (SEQ ID NO) | Light Chain (SEQ ID NO) | Affinity for 293T-HuCCR8 cells (nM) | Affinity for 293T-CyCCR8 cells (nM) | Binding to HuCCR8-Fc protein | Binding to CyCCR8-Fc protein |
|---|---|---|---|---|---|---|---|
| HCDR3 randomization | Anti-CCR8-2-5 | 21 | 23 | 2.9 | 5.2 | +++ | +++ |
| HCDR3 randomization | Anti-CCR8-2-6 | 151 | 153 | 1.5 | 4.5 | +++ | +++ |
| HCDR3 randomization & VL Shuffle | Anti-CCR8-2-7 | 31 | 33 | 1.3 | 3.5 | ++++ | +++ |
| HCDR3 randomization & VL Shuffle | Anti-CCR8-2-8 | 71 | 73 | 1.5 | 2.5 | ++++ | +++ |
| HCDR3 randomization & VL Shuffle | Anti-CCR8-2-9 | 61 | 63 | 1.5 | 3.2 | ++++ | ++++ |
| HCDR3 randomization & VL Shuffle | Anti-CCR8-2-10 | 81 | 83 | 2.4 | 3.9 | +++ | +++ |

Example 2: Antibodies Bind CCR8

Of the 17 antibodies, two were selected for further characterization: anti-CCR8-1, comprising a variable heavy chain having the amino acid sequence set forth in SEQ ID NO. 41 and the variable variable light chain having the amino acid sequence set forth in SEQ ID NO: 43; and anti-CCR8-2, comprising a variable heavy chain having the amino acid sequence set forth in SEQ ID NO: 11 and a variable light chain having the amino acid sequence set forth in SEQ ID NO: 13.

Figure 3A:
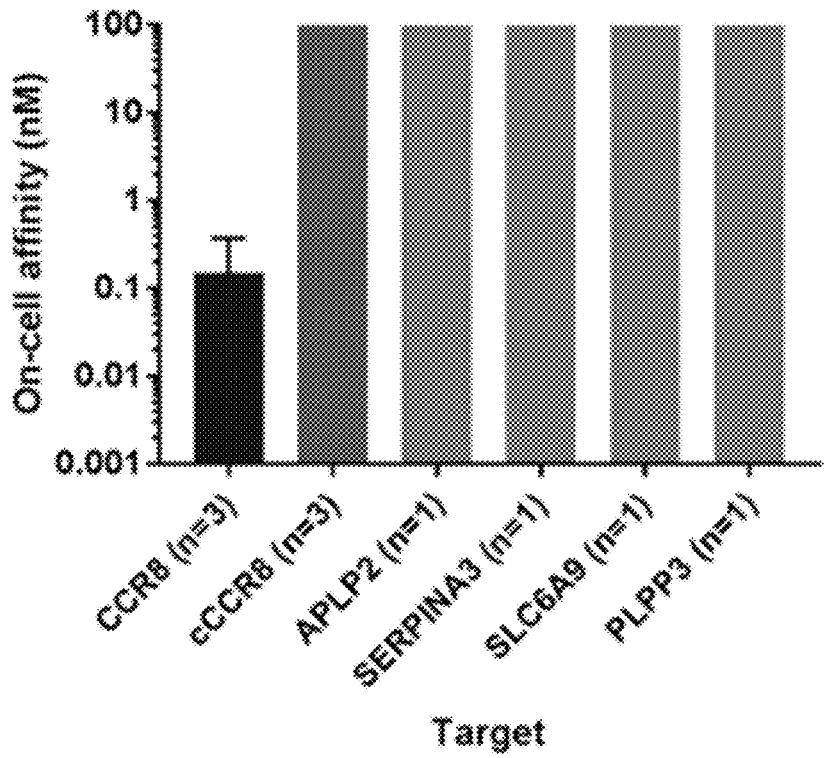
FIGS. 3A-3B are bar graphs illustrating the on-cell affinity ($K_D$) for anti-CCR8-1 antibody (FIG. 3A) or anti-CCR8-2 antibody (FIG. 3B) to human CCR8, cyno CCR8, and various negative controls (amyloid precursor-like protein 2 (APLP2), alpha 1-antichymotrypsin (SERPINA3), solute carrier family 6 member 9 (SLC6A9), and phospholipid phosphatase 3 (PLPP3)).
Figure 3B:
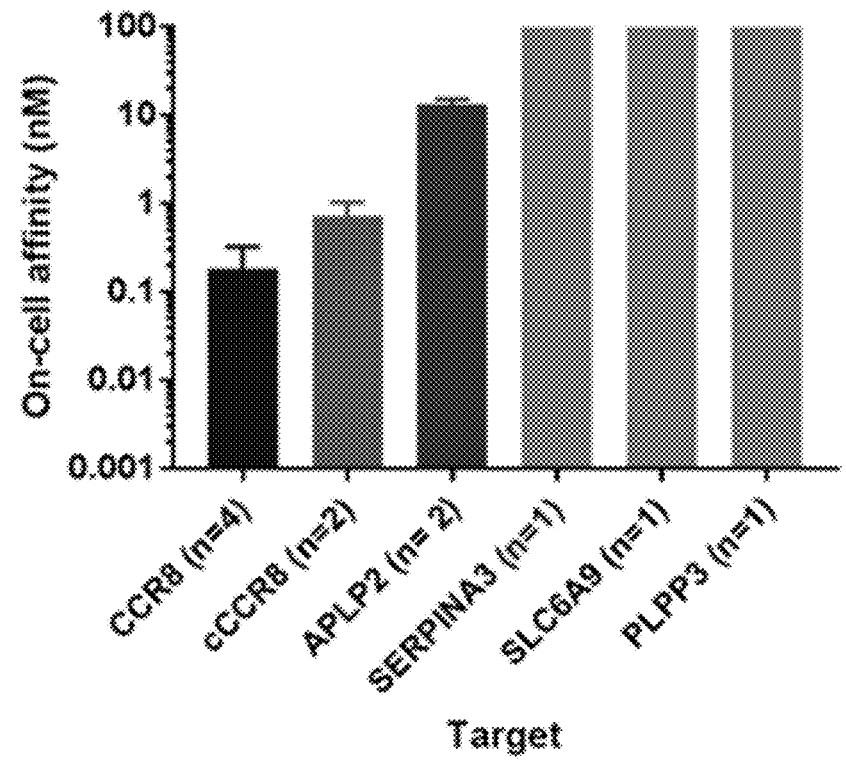

To test whether CCR8 antibodies bound to cell-expressed human or cynomolgus monkey CCR8, 293T and Raji cells were infected with lentivirus for either human or cynomolgus monkey CCR8. Cell lines expressing CCR8 constructs were incubated with CCR8 antibodies in a dose-dependent manner at 4° C. for 30 min, unbound CCR8 antibodies as removed by washing and bound CCR8 antibodies were detected using a fluorescently-conjugated anti-human secondary antibody at 4° C. for 30 min. The results showed that both anti-CCR8-1 (FIG. 3A) and anti-CCR8-2 (FIG. 3B) bound to the human CCR8 cell lines, while anti-CCR8-2 (FIG. 3B) bound to the cynomolgus monkey CCR8 cell line.

Example 3: Antibodies Bind to CCR8+ Tumor Tregs

Figure 4A:
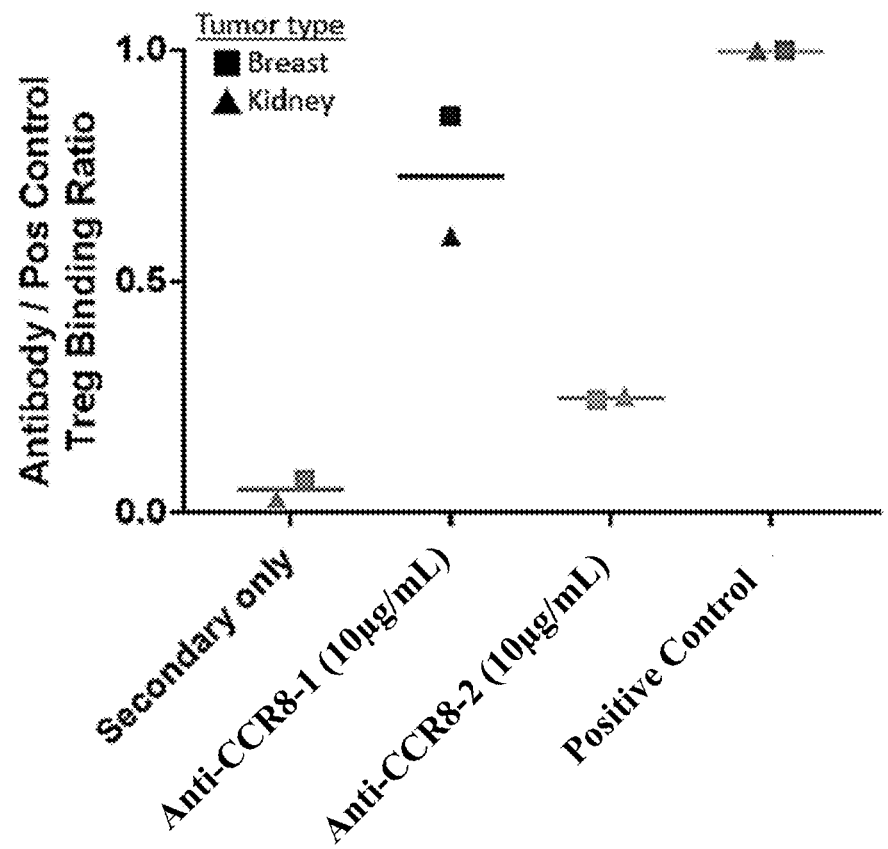
FIG. 4A is a graphical representation showing binding of anti-CCR8-1 and anti-CCR8-2 antibodies to isolated tumor-infiltrating leukocytes (TILs) from breast and kidney tumor samples, square and triangle, respectively.
Figure 4B:
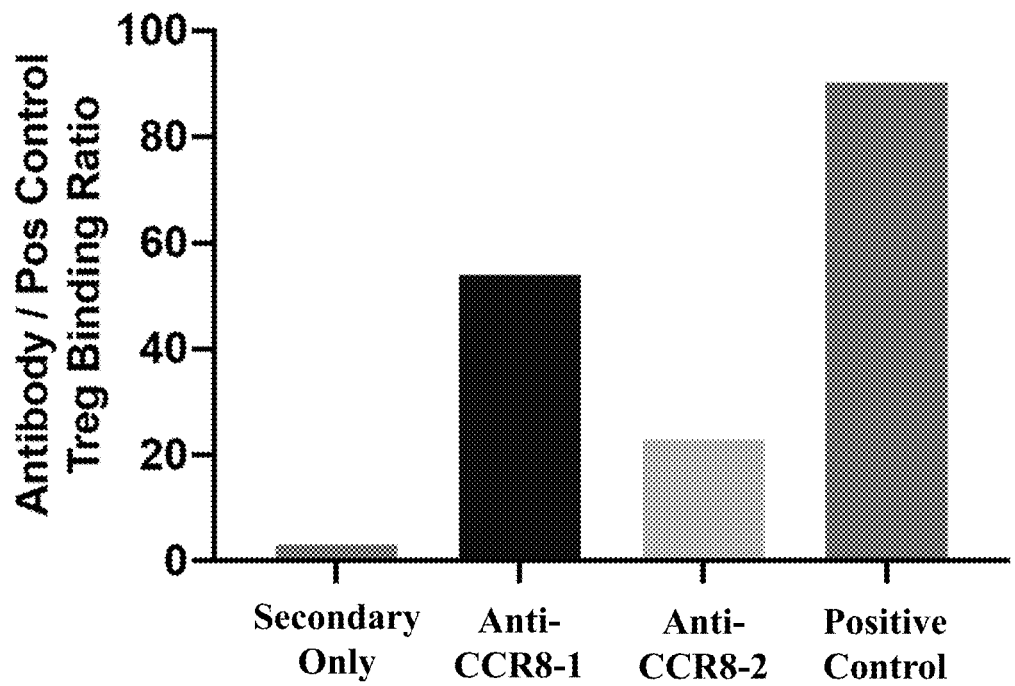
FIG. 4B is a graphical representation showing relative binding of an isotype control, anti-CCR8-1, anti-CCR8-2, and a positive control anti-CCR8 antibody to isolated regulatory T cells ($T_{reg}$ cells) from renal cell carcinoma samples, as indicated.

To test whether CCR8 antibodies bound to CCR8+ tumor Tregs, tumor-infiltrating leukocytes (TILs) were isolated from freshly-resected tumors and plated in 96-well plates. TILs were incubated with a fluorescently-tagged antibody panel (CD3, CD4, FOXP3) to identify tumor Tregs at 4° C. Additionally, CCR8 antibodies were incubated with TILs at a single concentration at 4° C. for 30 min, unbound CCR8 antibodies as removed by washing and bound CCR8 antibodies were detected using a fluorescently-conjugated anti-human secondary antibody at 4° C. for 30 min. The results showed that both anti-CCR8-1 and anti-CCR8-2 bound to the CCR8+ tumor Tregs (FIG. 4A-4B).

Example 4: Antibodies Induce ADCC Signaling in ADCC Reporter Bioassay

Figure 5:
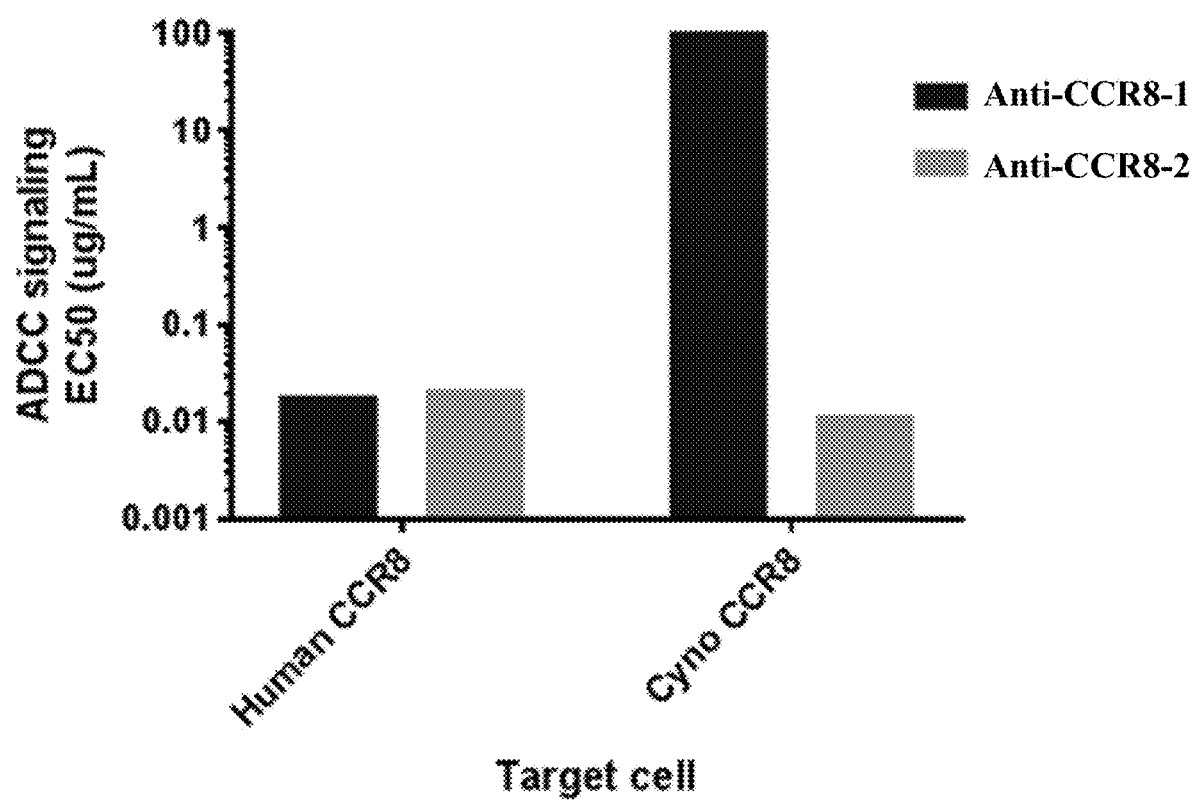
FIG. 5 is a bar graph illustrating ADCC signaling in 293T cells with forced expression of either human or cynomolgus monkey (cyno) CCR8 following contact with either anti-CCR8-1 and anti-CCR8-2 antibodies, as indicated.

To test whether CCR8 antibodies induced ADCC signaling, CCR8 antibodies were incubated with 293T cells with forced expression of either human or cynomolgus monkey CCR8 in a dose-dependent manner in 96-well plates for 6 hours at 37° C. according to manufacturer's instructions. CD16 Jurkat antibody-dependent cellular cytotoxicity (ADCC) reporter cells were co-cultured with target cells complexed with CCR8 antibodies. Upon completion of experiment, ADCC signaling was determined by a bioluminescent readout on the CD16 Jurkat ADCC reporter cells. The results showed that both anti-CCR8-1 and anti-CCR8-2 induced ADCC signaling using the human CCR8 cell line as targets, while anti-CCR8-2 also induced ADCC signaling using the cynomolgus monkey CCR8 cell line (FIG. 5).

Figure 6A:
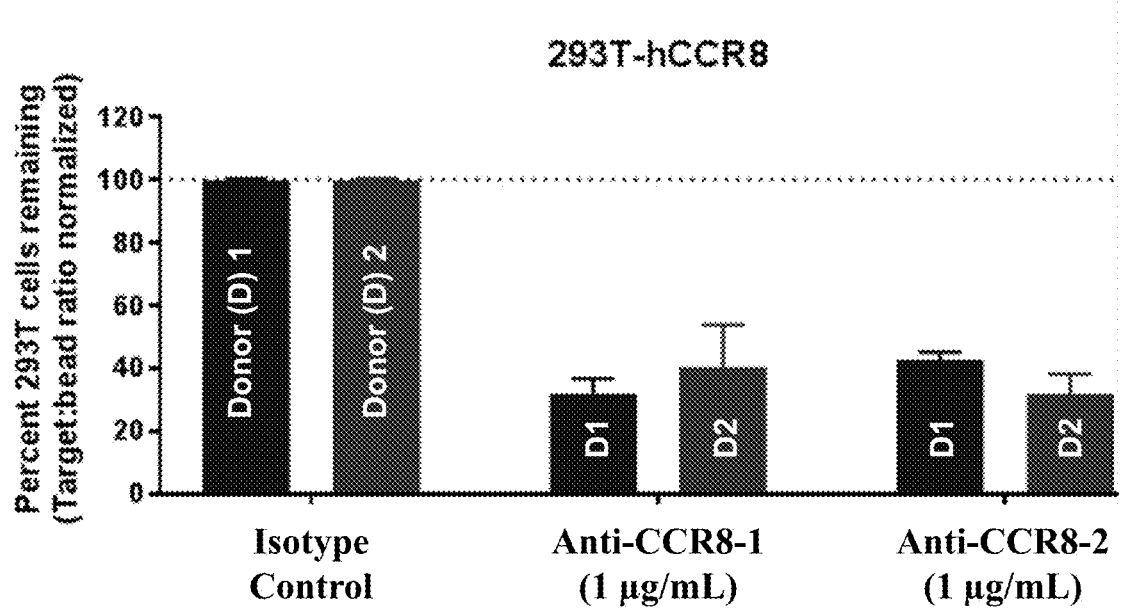
FIGS. 6A-6B are bar graphs illustrating ADCC as evidenced by the percent of 293T cells, expressing human CCR8 (FIG. 6A) or cyno CCR8 (FIG. 6B), remaining following contact with either an anti-CCR8-1 or an anti-CCR8-2 antibody, as indicated, in samples from two donors (D1 and D2).
Figure 6B:
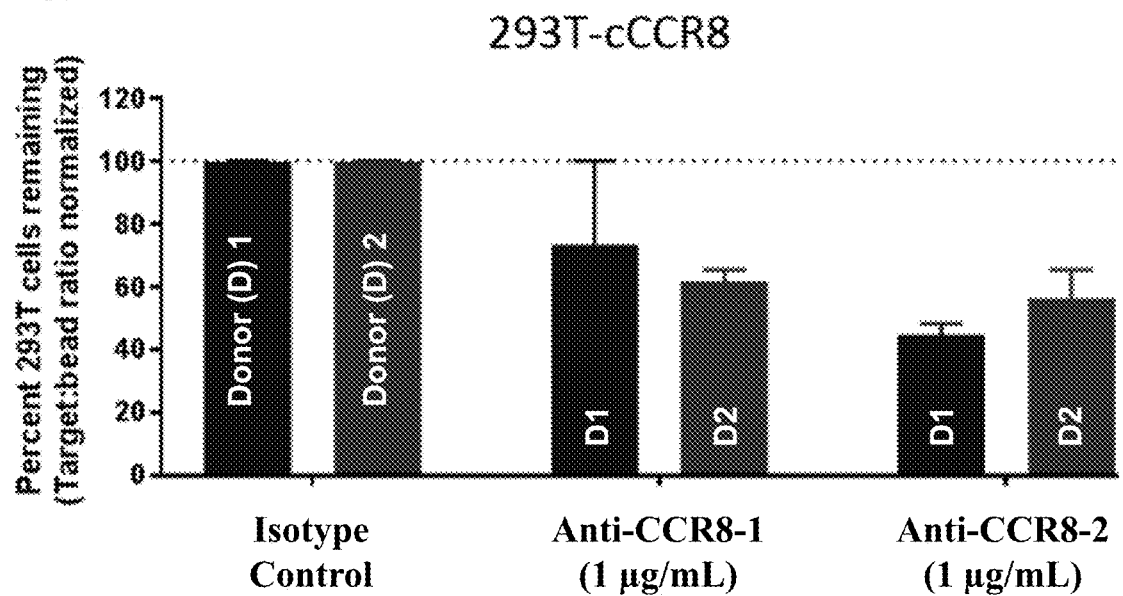

Example 5: Antibodies Induce ADCC of Cells with Forced Expression of Human and Cynomolgus Monkey CCR8 Using PBMCs as Effector Cells To test whether CCR8 antibodies induced ADCC of CCR8+ cells, CCR8 antibodies were incubated with 293T or Raji target cells with forced expression human CCR8 and labeled with CellTrace Violet in a dose-dependent manner in 96-well plates. PBMCs were co-cultured with target cells complexed with CCR8 antibodies overnight at 37° C. Upon completion of the experiment, the number of CCR8+ target cells was assessed by Flow Cytometry. The results showed that both anti-CCR8-1 and anti-CCR8-2 induced ADCC of the human CCR8 cell lines (FIG. 6A), while anti-CCR8-2 also induced ADCC of the cynomolgus monkey CCR8 cell line (FIG. 6B).

Figure 7A:
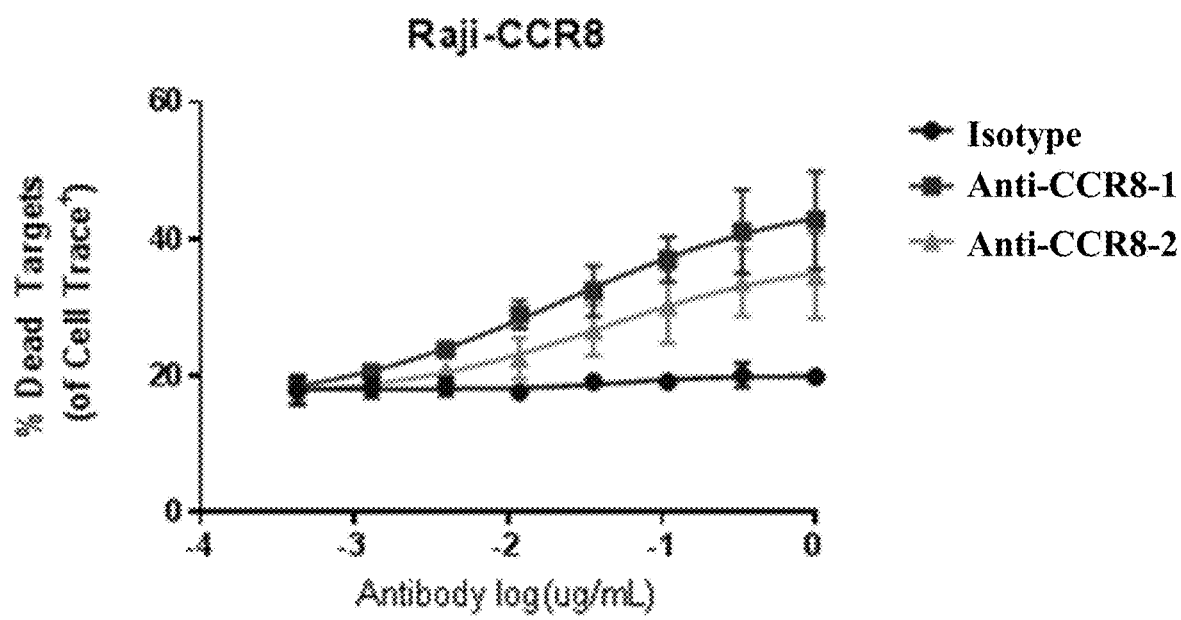
FIGS. 7A-7B are line graphs illustrating the percent of dead target Raji cells expressing either human CCR8 (FIG. 7A) or empty vector (EV.
Figure 7B:
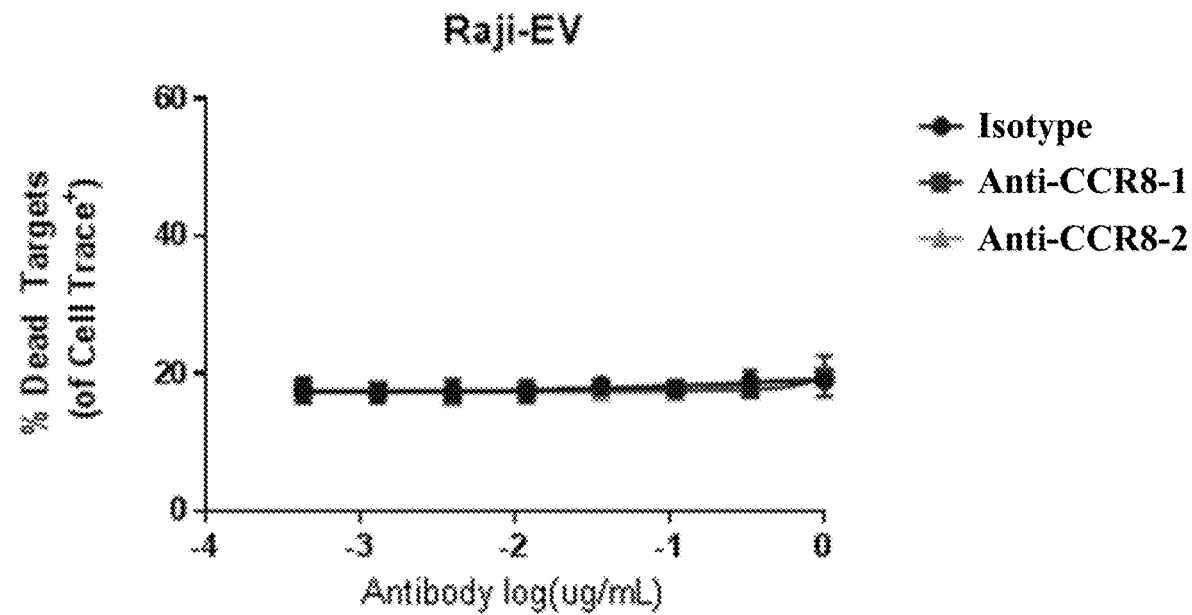

Example 6: Antibodies Induce ADCC of Cells with Forced Expression of Human CCR8 Using NK Cells as Effector Cells To test whether CCR8 antibodies induced ADCC of CCR8+ cells, CCR8 antibodies were incubated with Raji target cells with forced expression human CCR8 and labeled with CellTrace Violet in a dose-dependent manner in 96-well plates. NK cells were co-cultured with target cells complexed with CCR8 antibodies for 4 hours at 37° C. Upon completion of the experiment, the number of CCR8+ target cells was assessed by Flow Cytometry. The results showed that both anti-CCR8-1 and anti-CCR8-2 induced ADCC of the human CCR8 cell line (FIGS. 7A-7B).

Example 7: Antibodies Modulate NK Cell Activation Markers in Co-Culture Assay with Cells with Forced Expression of Human CCR8 and Kill Cells Expressing CCR8

Figure 8A:
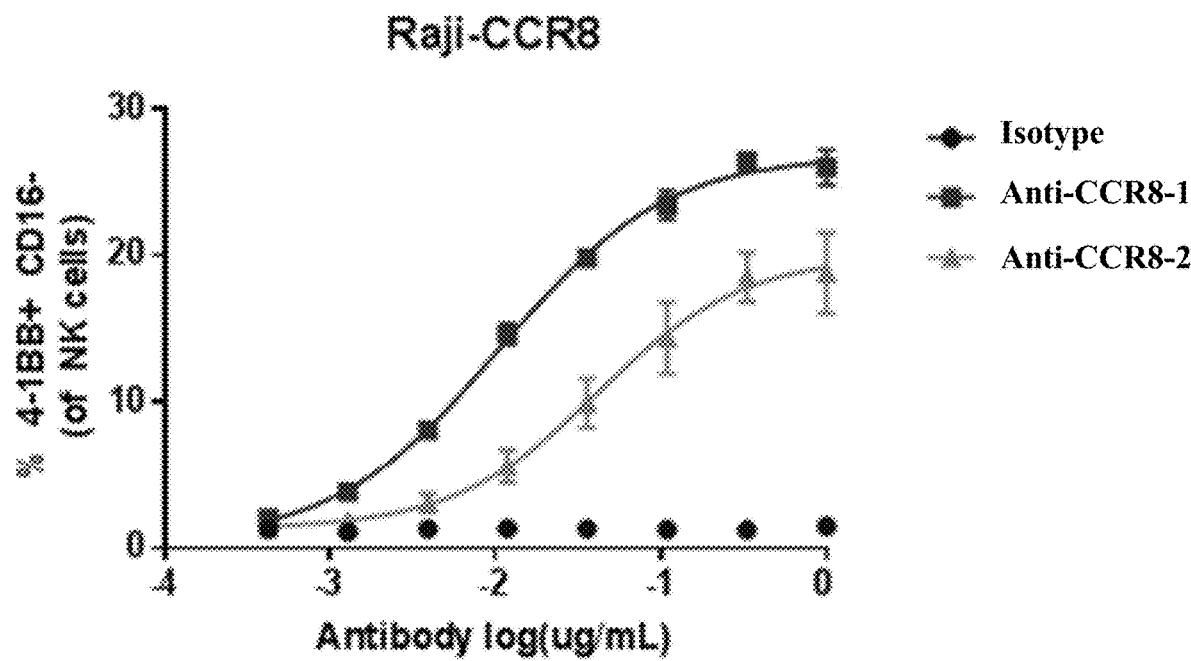
FIG. 8A is a line graph illustrating the percent of 4-1BB$^+$/CD16$^-$ cells (NK cells) in culture with Raji cells forced to express CCR8, following contacting the culture with either an anti-CCR8-1 or an anti-CCR8-2 antibody, as indicated.
Figure 8B:
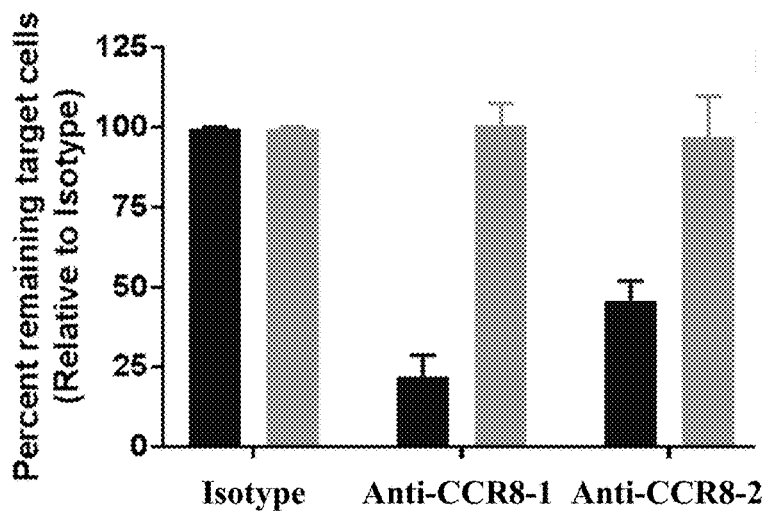
FIG. 8B is a bar graph illustrating the number of Raji cells expressing the CCR8 surface target (black bars) after exposure to either the anti-CCR8-1 antibody or the anti-CCR8-2 antibody relative to an isotype control.
Figure 8C:
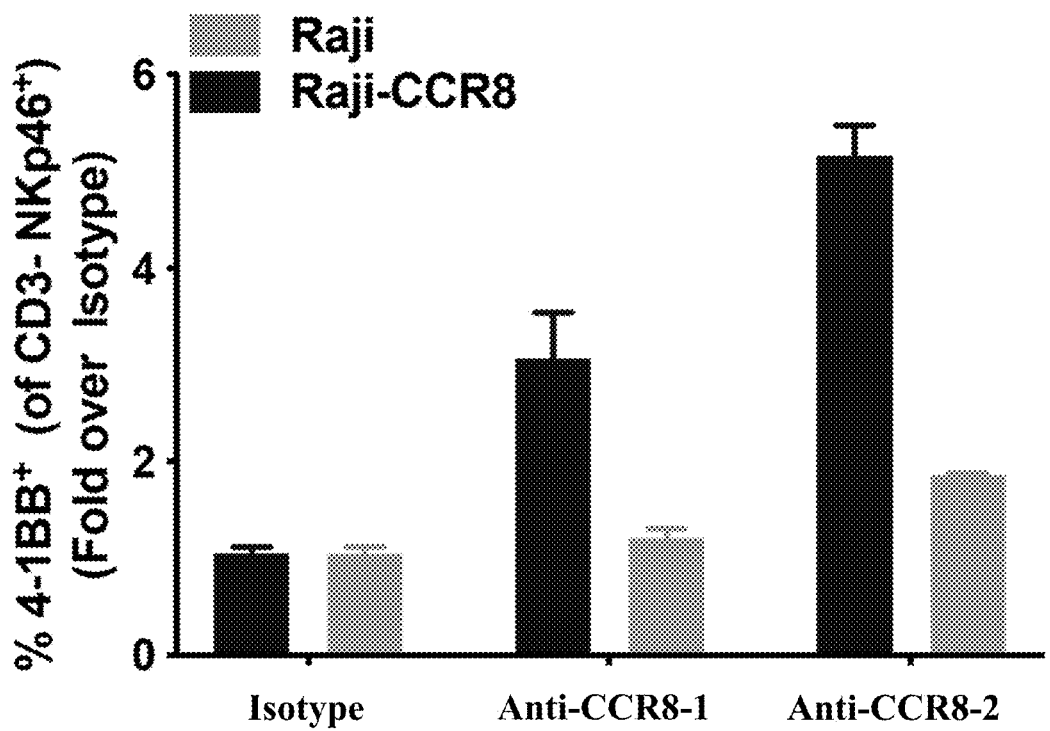
FIG. 8C is a bar graph illustrating the level of 4-1BB expression (relative to isotype controls) on CD3$^-$ NKp46+NK cells in culture with Raji cells forced to express CCR8 (left bars). Control Raji cells not expressing the CCR8 surface target are represented by right bars (FIGS. 8B-8C).

To test whether CCR8 antibodies modulated activation markers of NK cells, CCR8 antibodies were incubated with Raji target cells with forced expression human CCR8 and labeled with CellTrace Violet in a dose-dependent manner in 96-well plates. NK cells were co-cultured with target cells complexed with CCR8 antibodies overnight at 37° C. Upon completion of the experiment, the number of CCR8$^+$ target cells was assessed by Flow Cytometry measuring 4-1BB, ICAM-1 and CD16 expression on the cell surface of NK cells. The results showed that both anti-CCR8-1 and anti-CCR8-2 induced upregulation of 4-1BB and ICAM-1 on the cell surface while CD16 was down-regulated on the cell surface of NK cells (FIG. 8A, FIG. 8C).

To test whether CCR8 antibodies killed cells expressing CCR8, antibodies were incubated with both Raji cells and Raji target cells with forced expression human CCR8 ("Raji-CCR8 cells") and labeled with CellTrace Violet in a dose-dependent manner in 96-well plates. Upon completion of the experiment, the number of CCR8$^+$ target cells was assessed by Flow Cytometry measuring the number of CellTrace Violet positive cells remaining. The results showed that both anti-CCR8-1 and anti-CCR8-2 killed the Raji-CCR8 cells and did not kill the Raji cells without CCR8 (FIG. 8B).

Figure 9:
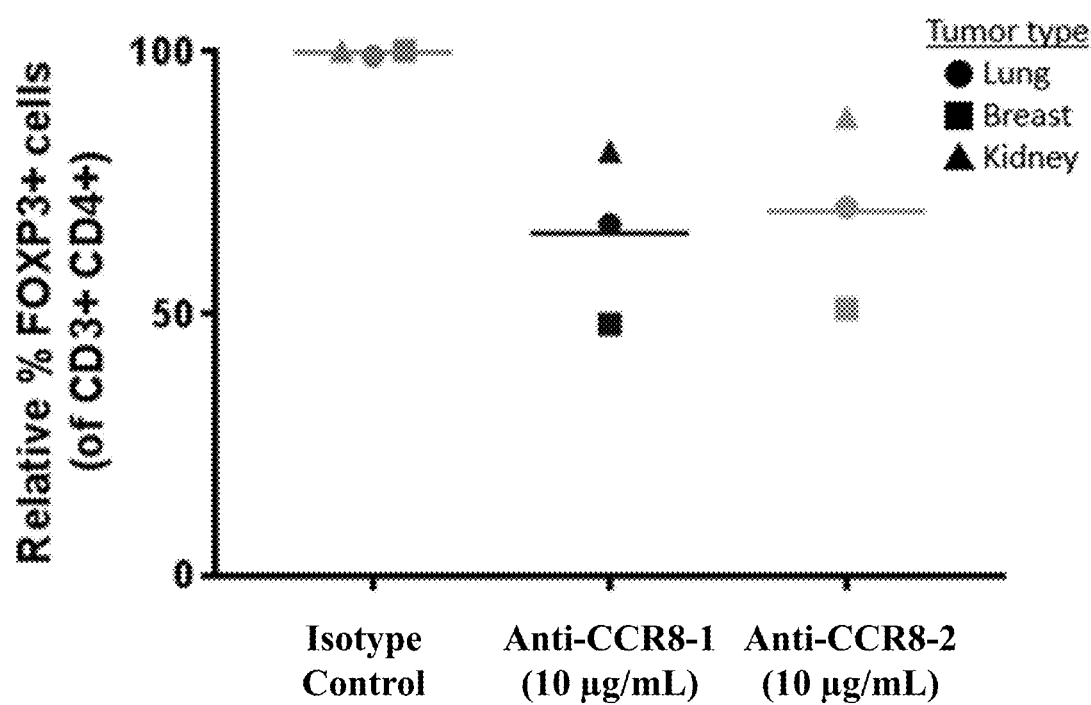
FIG. 9 is a graphical representation of the relative number (%) of FOXP3$^+$ cells of total CD3$^+$/CD4$^+$ TILs isolated from freshly resected human tumors and incubated with either an anti-CCR8-1 or an anti-CCR8-2 antibody, as indicated.

Example 8: Antibodies Induce ADCC of Tumor Tregs Using NK Cells as Effector Cells To test whether CCR8 antibodies induced ADCC of CCR8$^+$ tumor Tregs, TILs were isolated from freshly-resected human tumors and incubated with CCR8 antibodies. NK cells were co-cultured with TIL: antibody complexes in 96-well plates overnight at 37° C. Upon completion of the experiment, the number of tumor Tregs was assessed by Flow Cytometry. The results showed that both anti-CCR8-1 and anti-CCR8-2 induced killing of the human tumor Tregs (FIG. 9A).

Example 9: Antibodies Induce Internalization of CCR8 in Cells with Forced Expression of Human CCR8

Figure 10:
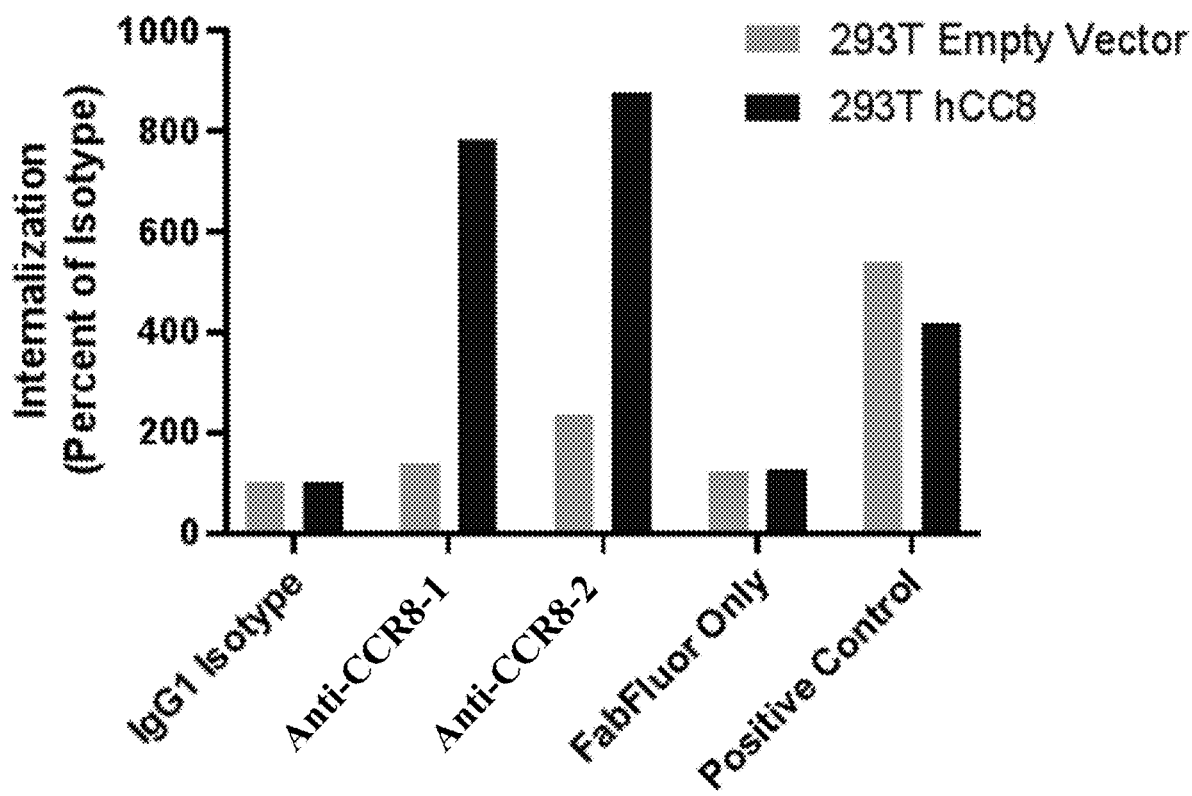
FIG. 10 is a bar graph illustrating the internalization of CCR8 in 293T cells with forced expression of human CCR8 or empty vector.

To test whether CCR8 antibodies induced CCR8-IgG complex internalization, CCR8 antibodies were incubated with pH sensitive FabFluor reagent to generate a CCR8 internalization reporter antibody. This antibody conjugate was used to treat 293T cells with forced expression of human CCR8 for 30 min at 37° C. During antibody incubation on the 293T cells, antibodies bind to CCR8 and induce internalization into an acidic endosome, eliciting a fluorescent signal from the conjugated FabFluor reagent. Upon completion of experiment, fluorescent signal can be analyzed by flow cytometry and compared between antibody conjugates. The results showed that both anti-CCR8-1 and anti-CCR8-2 induced CCR8 internalization using the human CCR8 cell line as targets (FIG. 10).

Example 10: Retrogenix Antibody Binding Experiment

To identify targets of CCR8 antibodies, CCR8 antibodies were incubated with cells forced to express about 4,500 cell surface proteins in a fixed or live state. Anti-CCR8-1 was demonstrated to bind to only CCR8 while anti-CCR8-2 also bound to amyloid precursor-like protein 2 (APLP2), but at a significantly lower concentration (data not shown).

Example 11: Characterization of Anti-CCR8 Antibody Epitopes

Figure 11:
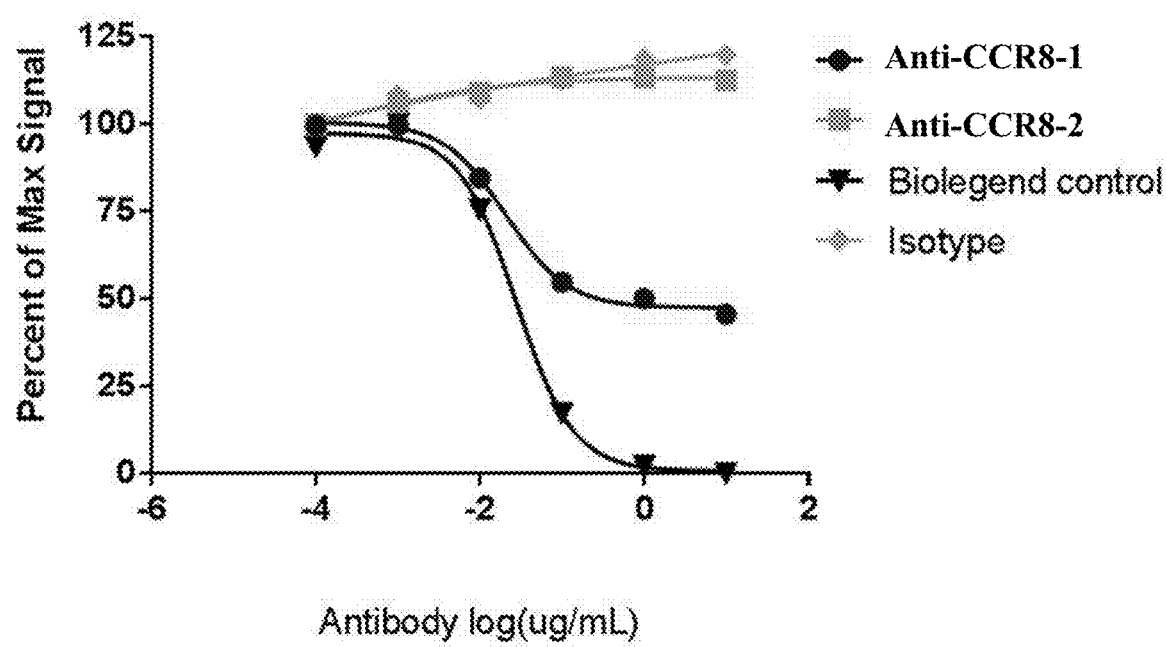
FIG. 11 is a line graph illustrating competitive binding of a monoclonal antibody that binds human CCR8 (purchased from BIOLEGEND®; catalog number 360603) and either the anti-CCR8-1 antibody or the anti-CCR8-2 antibody as measured by flow cytometry.

To characterize the binding cite of the CCR8 antibodies, CCR8 antibodies were incubated with Raji-CCR8 cells in a dose-dependent manner in 96-well plates at 4° C. for 30 min. Unbound CCR8 antibodies were washed away and the cells were incubated with a fluorescently-conjugated human monoclonal anti-CCR8 antibody (commercially available) at a single concentration for 30 min at 37° C. Upon completion of the experiment, the binding of the commercially available monoclonal CCR8 antibody was assessed by Flow Cytometry. The results showed that anti-CCR8-1 partially blocked the commercially available monoclonal CCR8 antibody from binding to cells while anti-CCR8-2 did not (FIG. 11).

Example 12: Afucosylated CCR8 Antibodies Show Enhanced ADCC Activity

Figure 12A:
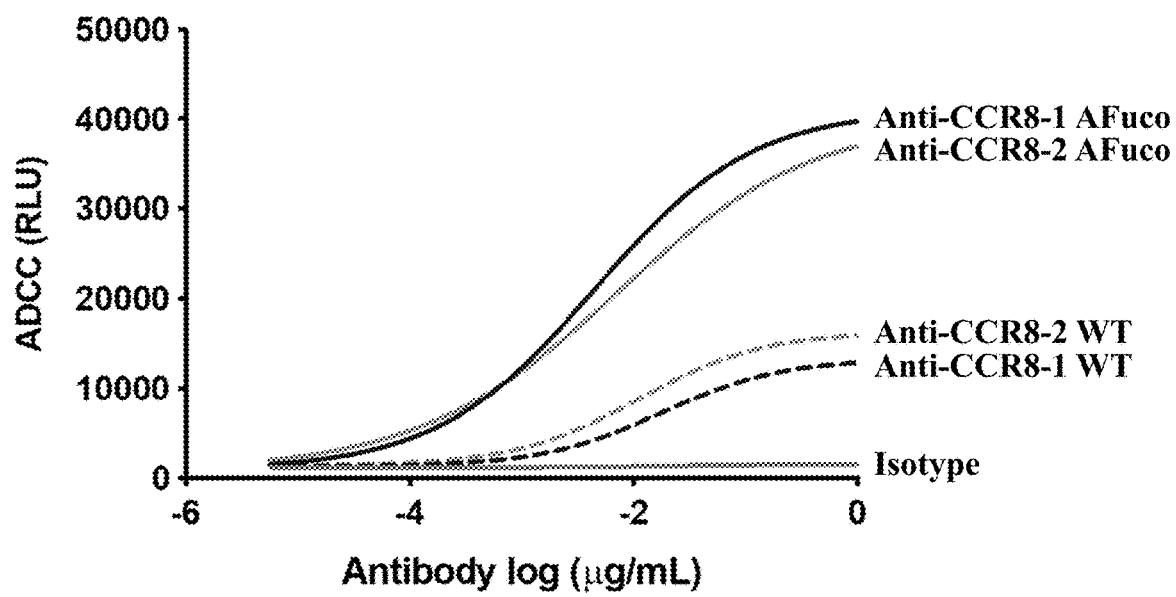
FIGS. 12A-12B are line graphs showing the ADCC activity relative to antibody concentration in CD16VV (FIG. 12A) or CD16FF (FIG. 12B) Jurkat ADCC reporter cells following incubation with increasing concentrations of the anti-CCR8-1 wild-type antibody, an afucosylated anti-CCR8-1 antibody, the anti-CCR8-2 wild-type antibody, an afucosylated anti-CCR8-2 antibody, and an isotype control, as indicated.
Figure 12B:
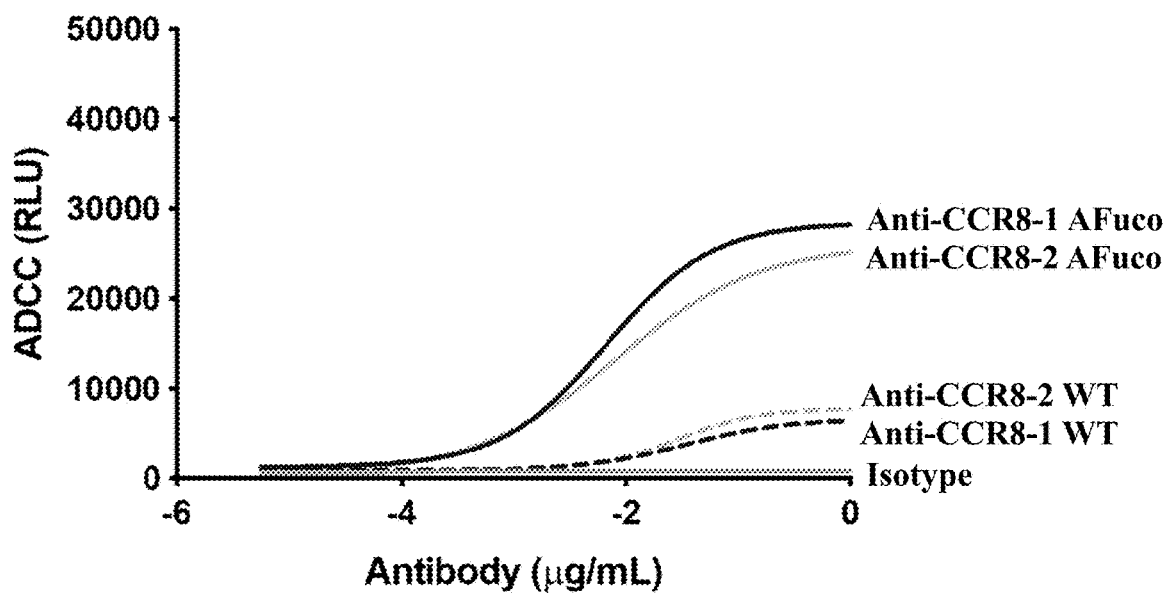

Anti-CCR8-1 was further optimized to remove fucose sugar units from the (IgG1) Fc region of the antibody. To test induction of ADCC signaling, CCR8 antibodies were incubated with 293T cells with forced expression of human CCR8 in a dose-dependent manner in 96-well plates for 6 h at 37° C. according to manufacturer's instructions. Either CD16VV or CD16FF Jurkat ADCC reporter cells were co-cultured with target cells complexed with CCR8 antibodies. Upon completion of experiment, ADCC signaling was determined by a bioluminescent readout on the CD16 Jurkat ADCC reporter cells. The results showed that both anti-CCR8-1 and anti-CCR8-2 induced ADCC signaling using the human CCR8 cell line as targets, while anti-CCR8-2 also induced ADCC signaling using the cynomolgus monkey CCR8 cell line (FIGS. 12A-12B). Increased activity was observed with high and low affinity allelic polymorphisms.

Example 12: Antibodies Bind Tumor Tregs and Induce ADCC

Figure 13B:
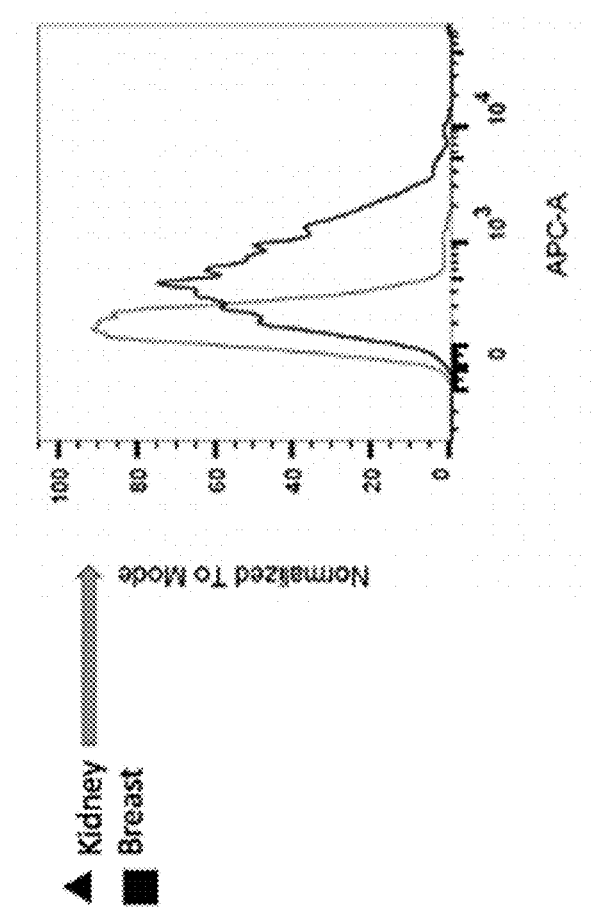
FIGS. 13A-13B are graphical representations illustrating binding of the anti-CCR8-1 antibody to tumor Tregs. Tregs were identified using flow cytometry in TIL isolated from tumors as CD3+/FoxP3+. Binding of anti-CCR8-1 antibody was measured on the gated cells from kidney and breast tumors using an APC-conjugated secondary antibody.
Figure 13A:
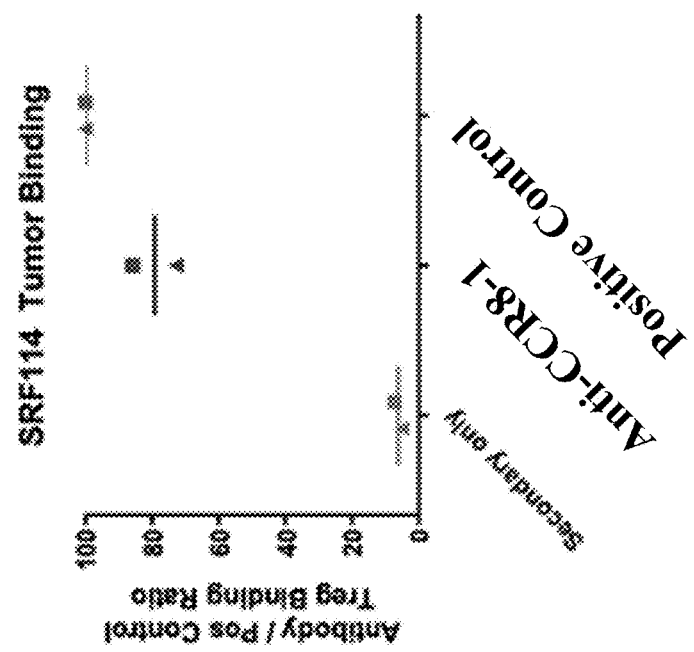
Figure 13C:
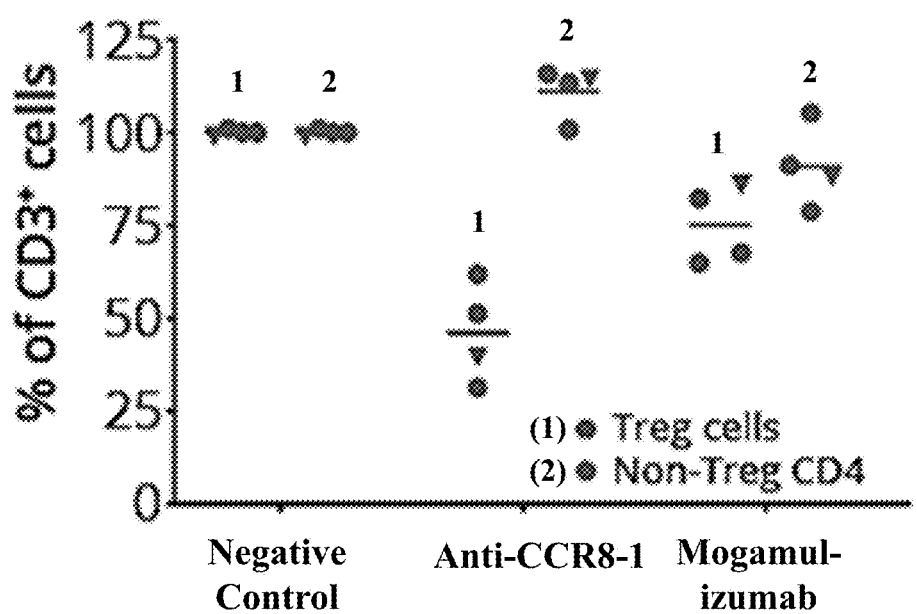
FIG. 13C is a scatter plot showing the percent of CD3$^+$ isolated TIL cells from tumors incubated with allogenic natural killer (NK) cells and contacted with control antibody, anti-CCR8-1 antibody, or a positive control antibody. For each antibody condition, the grouping on the left side is the percentage of CD3+ cells that are FoxP3− cells (e.g., non-Tregs), while the grouping on the right side is the normalized percentage of CD3+ cells that are FoxP3+ cells (e.g., Tregs).

To test whether CCR8 antibodies bind tumor Tregs and induce ADCC, tumor infiltrating lymphocytes (TILs) were isolated from fresh kidney and breast tumor resections and incubated with the anti-CCR8-1 antibody. Anti-CCR8-1 antibody binding was measured using a PE-conjugated anti-human IgG antibody (FIG. 13A), and a commercially purchased purified anti-human CD213a1 (IL-13-Rα1) antibody was used as a positive control (Biolegend catalog number 360404). As shown in FIG. 13A, triangles represent TIL from kidney tumors and circles represent TIL from breast tumors. All data were acquired by flow cytometry.

In a follow-up experiment, isolated TILs from fresh kidney and breast tumor resections were incubated with allogenic NK cells and the anti-CCR8-1 antibody, mogamulizumab, or isotype control for 24 hours. The percentage of CD3+ cells that were either Tregs (FoxP3+) or other lymphocytes (FoxP3−) was measured using flow cytometry. In the presence of NK cells, the anti-CCR8-1 antibody resulted in a significant loss of Tregs while not effecting the non-Treg population.

Collectively, these data show that the anti-CCR8-1 antibody binds tumor Tregs and causes NK cell mediated ADCC.

TABLE 8

| SEQ ID NO: | Sequence |
|---|---|
| 1 | VQLVESGGGLVQPGRSLRLSCAASGFTFDDYAMHWVRQAPGKGLEWVSGISWNSGSIGYADSVKGRFTISRDNSKNSLYLQMNSLRAEDTALYYCARGRESYRVSLRFDYWGQGTLVTVSS |
| 3 | QSVLTQPPSVSAAPGQKVTISCSGSSSNIGNNYVSWYQQLPGTAPKLLIYDNNKRPSGIPDRFSGSKSGTSATLGITGLQTGDEADYYCGTWDSSLSAWVFGGGTKLT |
| 5 | DYAMH |
| 6 | GISWNSGSIGYADSVKG |
| 7 | GRESYRVSLRFDY |
| 8 | SGSSSNIGNNYVS |
| 9 | DNNKRPS |
| 10 | GTWDSSLSAWV |
| 11 | EVQLLESGGGLVQPGGSLRLSCAAGGFTFSAYTMNWVRQAPGKGLEWVSAISASGGRTYYADSVKGRFTISRDNSKNTLYLQMNSLRAEDTAVYYCARRFARGWFDPWGQGTLVTVSS |
| 13 | QSVLTQPPSVSAAPGQKVTISCSGSSSNIGNNYVSWYQQLPGTAPKLLIYDNNKRPSGIPDRFSGSKSGTSATLGITGLQTGDEADYYCGTWDSSLSAWVFGGGTKLT |
| 15 | AYTMN |
| 16 | AISASGGRTYYADSVKG |
| 17 | RFARGWFDP |
| 18 | SGSSSNIGNNYVS |
| 19 | DNNKRPS |
| 20 | GTWDSSLSAWV |
| 21 | EVQLVESGGGLVQPGRSLRLSCAASGFTFDDYAMHWVRQAPGKGLEWVSGISWNSGSIGYADSVKGRFTISRDNSKNSLYLQMNSLRAEDTALYYCARGRKSYRVSLRFDYWGQGTLVTVSS |
| 23 | QSVLTQPPSVSAAPGQKVTISCSGSSSNIGNNYVSWYQQLPGTAPKLLIYDNNKRPSGIPDRFSGSKSGTSATLGITGLQTGDEADYYCGTWDSSLSAWVFGGGTKLT |
| 25 | DYAMH |
| 26 | GISWNSGSIGYADSVKG |
| 27 | GRKSYRVSLRFDY |
| 28 | SGSSSNIGNNYVS |
| 29 | DNNKRPS |
| 30 | GTWDSSLSAWV |
| 31 | EVQLVESGGGLVQPGRSLRLSCAASGFTFDDYAMHWVRQAPGKGLEWVSGISWNSGSIGYADSVKGRFTISRDNSKNSLYLQMNSLRAEDTALYYCARGRDSYRKSLRFDYWGQGTLVTVSS |
| 33 | QSVLTQPPSVSGAPGQRVTISCTGSGSNIGNNYVSWYQQLPGTAPKMLIYDNTRRPSGIPDRFSGSKSDTSATLGITGLQTGDEADYYCGAWDSSLRMWVFGGGTKLTVL |
| 35 | DYAMH |
| 36 | GISWNSGSIGYADSVKG |
| 37 | GRDSYRKSLRFDY |
| 38 | TGSGSNIGNNYVS |
| 39 | DNTRRPS |

TABLE 8-continued

Sequences

| SEQ ID NO: | Sequence |
|---|---|
| 40 | GAWDSSLRMWV |
| 41 | QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARAVRNRFRFDYWGQGTLVTVSS |
| 42 | |
| 43 | QSALTQPASVSGSPGQSITISCTGTSSDVGSYNLVSWYQQHPGKAPKLMIYEVSKRPSGVSNRFSGSKSGNTASLTISGLQAEDEADYYCSSYAGSSTFVVFGGGTKLTVL |
| 45 | SYYMH |
| 46 | IINPSGGSTSYAQKFQG |
| 47 | AVRNRFRFDY |
| 48 | TGTSSDVGSYNLVS |
| 49 | EVSKRPS |
| 50 | SSYAGSSTFVV |
| 51 | EVQLLESGGGLVQPGGSLRLSCAARGFIFSGYTMLWVRQAPGKGLEWVSAITASGGRTYYADSVKGRFTISRDNSKNTLYLQMNSLRAEDTAVYYCARRFARGWFDPWGQGTLVTVSS |
| 53 | QSVLTQPPSVSAAPGQKVTISCSGSSSNIGNNYVSWYQQLPGTAPKLLIYDNNKRPSGIPDRFSGSKSGTSATLGITGLQTGDEADYYCGTWDSSLSAWVFGGGTKLT |
| 55 | GYTML |
| 56 | AITASGGRTYYADSVKG |
| 57 | RFARGWFDP |
| 58 | SGSSSNIGNNYVS |
| 59 | DNNKRPS |
| 60 | GTWDSSLSAWV |
| 61 | EVQLVESGGGLVQPGRSLRLSCAASGFTFDDYAMHWVRQAPGKGLEWVSGISWNSGSIGYADSVKGRFTISRDNSKNSLYLQMNSLRAEDTALYYCARGRKSYRDSLRFDYWGQGTLVTVSS |
| 63 | QSVLTQPPSVSGAPGQRVTISCTGSGSNIGNNYVSWYQQLPGTAPKMLIYDNTRRPSGIPDRFSGSKSDTSATLGITGLQTGDEADYYCGAWDSSLRMWVFGGGTKLTVL |
| 65 | DYAMH |
| 66 | GISWNSGSIGYADSVKG |
| 67 | GRKSYRDSLRFDY |
| 68 | TGSGSNIGNNYVS |
| 69 | DNTRRPS |
| 70 | GAWDSSLRMWV |
| 71 | EVQLVESGGGLVQPGRSLRLSCAASGFTFDDYAMHWVRQAPGKGLEWVSGISWNSGSIGYADSVKGRFTISRDNSKNSLYLQMNSLRAEDTALYYCARGRRSYRDSLRFDYWGQGTLVTVSS |
| 73 | QSVLTQPPSVSGAPGQRVTISCTGSGSNIGNNYVSWYQQLPGTAPKMLIYDNTRRPSGIPDRFSGSKSDTSATLGITGLQTGDEADYYCGAWDSSLRMWVFGGGTKLTVL |
| 75 | DYAMH |
| 76 | GISWNSGSIGYADSVKG |
| 77 | GRRSYRDSLRFDY |
| 78 | TGSGSNIGNNYVS |
| 79 | DNTRRPS |

TABLE 8-continued

Sequences

| SEQ ID NO: | Sequence |
|---|---|
| 80 | GAWDSSLRMWV |
| 81 | EVQLVESGGGLVQPGRSLRLSCAASGFTFDDYAMHWVRQAPGKGLEWVSGISWNSGSIGYAD SVKGRFTISRDNSKNSLYLQMNSLRAEDTALYYCARGRKSYRDSLRFDYWGQGTLVTVSS |
| 83 | QSVLTQPPSVSAAPGQKVTISCSGTSSNIGKNFVSWYQQLPGTAPKLLIYDDNKRPSGIPDRFSGS KSATSATLGITGLQTGDADYYCGTWDSSLSAWVFGGGTKLTVL |
| 85 | DYAMH |
| 86 | GISWNSGSIGYADSVKG |
| 87 | GRKSYRDSLRFDY |
| 88 | SGTSSNIGKNFVS |
| 89 | DDNKRPS |
| 90 | GTWDSSLSAWV |
| 91 | EVQLVESGGGLVQPGRSLRLSCAASGFTFDDYAMHWVRQAPGKGLEWVSGISWNSGSIGYAD SVKGRFTISRDNSKNSLYLQMNSLRAEDTALYYCARGRKSYRDSLRFDYWGQGTLVTVSS |
| 93 | QSVLTQPPSVSAAPGQKVTISCSGSSSNIGNNYVSWYQQLPGTAPKLLIYDNNKRPSGIPDRFSGS KSGTSATLGITGLQTGDEADYYCGTWDSSLSAWVFGGGTKLT |
| 95 | DYAMH |
| 96 | GISWNSGSIGYADSVKG |
| 97 | GRKSYRDSLRFDY |
| 98 | SGSSSNIGNNYVS |
| 99 | DNNKRPS |
| 100 | GTWDSSLSAWV |
| 101 | QVQLVQSGAEVKKPGASVKVSCKASGYTFTSYYMHWVRQAPGQGLEWMGIINPSGGSTSYAQ KFQGRVTMTRDTSTSTVYMELSSLRSEDTAVYYCARGVGNGFRFDYWGQGTLVT |
| 103 | QSALTQPPSVSGSPGQSITISCTGTSSDVGTYNLVSWYQQHPGNAPKLMIYEVTKRPSGVSNRFS GSKSGNTATLTISGLQAEDEADYHCSSYAGSITHVVFGGGTKLTVL |
| 105 | SYYMH |
| 106 | IINPSGGSTSYAQKFQG |
| 107 | GVGNGFRFDY |
| 108 | TGTSSDVGTYNLVS |
| 109 | EVTKRPS |
| 110 | SSYAGSITHVV |
| 111 | QVQLVQSGAEVKKPGASVKVSCKASGYTFTSYYMHWVRQAPGQGLEWMGIINPSGGSTSYAQ KFQGRVTMTRDTSTSTVYMELSSLRSEDTAVYYCARGVGNGFRFDYWGQGTLVT |
| 113 | QSALTQPASVSGSPGQSITISCTGTSGDVGSYSLVSWYQHHPSRAPKLIIYEVNKRPSGVSDRFSG SKSGNTASLTITGLQAEDEAHYFCSSYTGNINLPVVFGGGTKLTVL |
| 115 | SYYMH |
| 116 | IINPSGGSTSYAQKFQG |
| 117 | GVGNGFRFDY |
| 118 | TGTSGDVGSYSLVS |
| 119 | EVNKRPS |
| 120 | SSYTGNINLPVV |

TABLE 8-continued

Sequences

| SEQ ID NO: | Sequence |
|---|---|
| 121 | QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARGVGNGFRFDYWGQGTLVT |
| 123 | QSALTQPPSVSGSPGQSITISCSGTSSDVGIYNLVSWYQQHPGKAPKLIIYEVIKRPSGISNRFSGFKSGNTASLTISGLQAEDEADYYCSSYAGPVTYVVFGGGTKLTVL |
| 125 | SYYMH |
| 126 | IINPSGGSTSYAQKFQG |
| 127 | GVGNGFRFDY |
| 128 | SGTSSDVGIYNLVS |
| 129 | EVIKRPS |
| 130 | SSYAGPVTYVV |
| 131 | QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARGVGNGFRFDYWGQGTLVT |
| 133 | QSALTQPASVSGSPGQSITISCSGTSSNIGKYNLVSWYQQHPGEAPTLLIYEATKRPSGVSNRFSGSKSGNTASLTISGLQAEDEADYICSSYAGSRVFVVFGGGTKLTVL |
| 135 | SYYMH |
| 136 | IINPSGGSTSYAQKFQG |
| 137 | GVGNGFRFDY |
| 138 | SGTSSNIGKYNLVS |
| 139 | EATKRPS |
| 140 | SSYAGSRVFVV |
| 141 | QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARGVGNGFRFDYWGQGTLVT |
| 143 | QSALTQPPSVSGSPGQSITISCSGTSSDVGSYNLVSWYQQEPGKAPKLIIYEVNKRPSGVSNRFSGSKSGNTASLTISGLQAEDEADYHCSSYAGSSTYVVFGGGTKLTVL |
| 145 | SYYMH |
| 146 | IINPSGGSTSYAQKFQG |
| 147 | GVGNGFRFDY |
| 148 | SGTSSDVGSYNLVS |
| 149 | EVNKRPS |
| 150 | SSYAGSSTYVV |
| 151 | EVQLVESGGGLVQPGRSLRLSCAASGFTFDDYAMHWVRQAPGKGLEWVSGISWNSGSIGYADSVKGRFTISRDNSKNSLYLQMNSLRAEDTALYYCARGRVSYRESLRFDYWGQGTLVT |
| 153 | QSVLTQPPSVSAAPGQKVTISCSGSSSNIGNNYVSWYQQLPGTAPKLLIYDNNKRPSGIPDRFSGSKSGTSATLGITGLQTGDEADYYCGTWDSSLSAWVFGGGTKLT |
| 155 | DYAMH |
| 156 | GISWNSGSIGYADSVKG |
| 157 | GRVSYRESLRFDY |
| 158 | SGSSSNIGNNYVS |
| 159 | DNNKRPS |
| 160 | GTWDSSLSAWV |

TABLE 8-continued

Sequences

| SEQ ID NO: | Sequence |
|---|---|
| 161 | EVQLLESGGGLVQPGGSLRLSCAAGGFTFSAYTMNWVRQAPGKGLEWVSAISASGGRTYYAD SVKGRFTISRDNSKNTLYLQMNSLRAEDTAVYYCARRFARGWFDPWGQGTLVT |
| 163 | QSVLTQPPSVSAAPGQRVTISCSGSTSNIGNHYVSWYQQLPRAVPKLVIYDNDKRPSGISDRFSG SRSGTSATLDISGLQAGDEADYYCATWDYSLTAVVFGGGTKLTVL |
| 165 | AYTMN |
| 166 | AISASGGRTYYADSVKG |
| 167 | RFARGWFDP |
| 168 | SGSTSNIGNHYVS |
| 169 | DNDKRPS |
| 170 | ATWDYSLTAVV |
| 171 | MDYTLDLSVTTVTDYYYPDIFSSPCDAELIQTNGKLLLAVFYCLLFVFSLLGNSLVILVLVVCKK LRSIT DVYLLNLALSDLLFVFSFPFQTYYLLDQWVFGTVMCKVVSGFYYIGFYSSMFFITLMSVDRYLA VVHAVY ALKVRTIRMGTTLCLAVWLTAIMATIPLLVFYQVASEDGVLQCYSFYNQQTLKWKIFTNFKMNI LGLLIP FTIFMFCYIKILHQLKRCQNHNKTKAIRLVLIVVIASLLFWVPFNVVLFTSLHSMHILDGCSISQ QLTY ATHVTEIISFTHCCVNPVIYAFVGEKFKKHLSEIFQKSCSQIFNYLGRQMPRESCEKSSSCQQHSS RSSS VDYIL |
| 172 | MDYTLDLSVTTVTDYYYPDIFSSPCDAELIQTNGK |
| 173 | MGWSCIILFLVATATGAHSMDYTLDLSVTTVTDYYYPDIFSSPSDAELIQTNGKHHHHHHSGGG GSEPRG PTIKPCPPCKCPAPNLLGGPSVFIFPPKIKDVLMISLSPIVTCVVVDVSEDDPDVQISWFVNNVEV HTAQ TQTHREDYNSTLRVVSALPIQHQDWMSGKEFKCKVNNKDLPAPIERTISKPKGSVRAPQVYVLP PPEEEM TKKQVTLTCMVTDFMPEDIYVEWTNNGKTELNYKNTEPVLDSDGSYFMYSKLRVEKKNWVE RNSYSCSVV HEGLHNHHTTKSFSRTPGK |
| 174 | MGWSCIILFLVATATGAHSMDYTLDPSMTTMTDYYYPDSLSSPSDGELIQRNDKHHHHHHSGG GGSEPRG PTIKPCPPCKCPAPNLLGGPSVFIFPPKIKDVLMISLSPIVTCVVVDVSEDDPDVQISWFVNNVEV HTAQ TQTHREDYNSTLRVVSALPIQHQDWMSGKEFKCKVNNKDLPAPIERTISKPKGSVRAPQVYVLP PPEEEM TKKQVTLTCMVTDFMPEDIYVEWTNNGKTELNYKNTEPVLDSDGSYFMYSKLRVEKKNWVE RNSYSCSVV HEGLHNHHTTKSFSRTPGK |
| 175 | MGWSCIILFLVATATGAHS |

What is claimed:

1. An antibody or an antigen-binding portion thereof that specifically binds to one or more amino acids within the N-terminal extracellular domain of human CCR8, wherein the antibody or antigen-binding portion thereof comprises:

(a) a VH CDR1 comprising the amino acid sequence set forth in SEQ ID NO: 45, a VH CDR2 comprising the amino acid sequence set forth in SEQ ID NO: 46, a VH CDR3 comprising the amino acid sequence set forth in SEQ ID NO: 47, a VL CDR1 comprising the amino acid sequence set forth in SEQ ID NO: 48, a VL CDR2 comprising the amino acid sequence set forth in SEQ ID NO: 49, and a VL CDR3 comprising the amino acid sequence set forth in SEQ ID NO: 50;

(b) a VH CDR1 comprising the amino acid sequence set forth in SEQ ID NO: 105, a VH CDR2 comprising the amino acid sequence set forth in SEQ ID NO: 106, a VH CDR3 comprising the amino acid sequence set forth in SEQ ID NO: 107, a VL CDR1 comprising the amino acid sequence set forth in SEQ ID NO: 108, a VL CDR2 comprising the amino acid sequence set forth in SEQ ID NO: 109, and a VL CDR3 comprising the amino acid sequence set forth in SEQ ID NO: 110;

(c) a VH CDR1 comprising the amino acid sequence set forth in SEQ ID NO: 115, a VH CDR2 comprising the amino acid sequence set forth in SEQ ID NO: 116, a VH CDR3 comprising the amino acid sequence set forth in SEQ ID NO: 117, a VL CDR1 comprising the amino acid sequence set forth in SEQ ID NO: 118, a VL CDR2 comprising the amino acid sequence set forth in SEQ ID NO: 119, and a VL CDR3 comprising the amino acid sequence set forth in SEQ ID NO: 120;

(d) a VH CDR1 comprising the amino acid sequence set forth in SEQ ID NO: 135, a VH CDR2 comprising the amino acid sequence set forth in SEQ ID NO: 136, a VH CDR3 comprising the amino acid sequence set forth in SEQ ID NO: 137, a VL CDR1 comprising the amino acid sequence set forth in SEQ ID NO: 138, a VL CDR2 comprising the amino acid sequence set forth in SEQ ID NO: 139, and a VL CDR3 comprising the amino acid sequence set forth in SEQ ID NO: 140;

(e) a VH CDR1 comprising the amino acid sequence set forth in SEQ ID NO: 145, a VH CDR2 comprising the amino acid sequence set forth in SEQ ID NO: 146, a VH CDR3 comprising the amino acid sequence set forth in SEQ ID NO: 147, a VL CDR1 comprising the amino acid sequence set forth in SEQ ID NO: 148, a VL CDR2 comprising the amino acid sequence set forth in SEQ ID NO: 149, and a VL CDR3 comprising the amino acid sequence set forth in SEQ ID NO: 150;

(f) a VH CDR1 comprising the amino acid sequence set forth in SEQ ID NO: 5, a VH CDR2 comprising the amino acid sequence set forth in SEQ ID NO: 6, a VH CDR3 comprising the amino acid sequence set forth in SEQ ID NO: 7, a VL CDR1 comprising the amino acid sequence set forth in SEQ ID NO: 8, a VL CDR2 comprising the amino acid sequence set forth in SEQ ID NO: 9, and a VL CDR3 comprising the amino acid sequence set forth in SEQ ID NO: 10;

(g) a VH CDR1 comprising the amino acid sequence set forth in SEQ ID NO: 15, a VH CDR2 comprising the amino acid sequence set forth in SEQ ID NO: 16, a VH CDR3 comprising the amino acid sequence set forth in SEQ ID NO: 17, a VL CDR1 comprising the amino acid sequence set forth in SEQ ID NO: 18, a VL CDR2 comprising the amino acid sequence set forth in SEQ ID NO: 19, and a VL CDR3 comprising the amino acid sequence set forth in SEQ ID NO: 20;

(h) a VH CDR1 comprising the amino acid sequence set forth in SEQ ID NO: 25, a VH CDR2 comprising the amino acid sequence set forth in SEQ ID NO: 26, a VH CDR3 comprising the amino acid sequence set forth in SEQ ID NO: 27, a VL CDR1 comprising the amino acid sequence set forth in SEQ ID NO: 28, a VL CDR2 comprising the amino acid sequence set forth in SEQ ID NO: 29, and a VL CDR3 comprising the amino acid sequence set forth in SEQ ID NO: 30;

(i) a VH CDR1 comprising the amino acid sequence set forth in SEQ ID NO: 35, a VH CDR2 comprising the amino acid sequence set forth in SEQ ID NO: 36, a VH CDR3 comprising the amino acid sequence set forth in SEQ ID NO: 37, a VL CDR1 comprising the amino acid sequence set forth in SEQ ID NO: 38, a VL CDR2 comprising the amino acid sequence set forth in SEQ ID NO: 39, and a VL CDR3 comprising the amino acid sequence set forth in SEQ ID NO: 40;

(j) a VH CDR1 comprising the amino acid sequence set forth in SEQ ID NO: 55, a VH CDR2 comprising the amino acid sequence set forth in SEQ ID NO: 56, a VH CDR3 comprising the amino acid sequence set forth in SEQ ID NO: 57, a VL CDR1 comprising the amino acid sequence set forth in SEQ ID NO: 58, a VL CDR2 comprising the amino acid sequence set forth in SEQ ID NO: 59, and a VL CDR3 comprising the amino acid sequence set forth in SEQ ID NO: 60;

(k) a VH CDR1 comprising the amino acid sequence set forth in SEQ ID NO: 65, a VH CDR2 comprising the amino acid sequence set forth in SEQ ID NO: 66, a VH CDR3 comprising the amino acid sequence set forth in SEQ ID NO: 67, a VL CDR1 comprising the amino acid sequence set forth in SEQ ID NO: 68, a VL CDR2 comprising the amino acid sequence set forth in SEQ ID NO: 69, and a VL CDR3 comprising the amino acid sequence set forth in SEQ ID NO: 70;

(l) a VH CDR1 comprising the amino acid sequence set forth in SEQ ID NO: 75, a VH CDR2 comprising the amino acid sequence set forth in SEQ ID NO: 76, a VH CDR3 comprising the amino acid sequence set forth in SEQ ID NO: 77, a VL CDR1 comprising the amino acid sequence set forth in SEQ ID NO: 78, a VL CDR2 comprising the amino acid sequence set forth in SEQ ID NO: 79, and a VL CDR3 comprising the amino acid sequence set forth in SEQ ID NO: 80;

(m) a VH CDR1 comprising the amino acid sequence set forth in SEQ ID NO: 85, a VH CDR2 comprising the amino acid sequence set forth in SEQ ID NO: 86, a VH CDR3 comprising the amino acid sequence set forth in SEQ ID NO: 87, a VL CDR1 comprising the amino acid sequence set forth in SEQ ID NO: 88, a VL CDR2 comprising the amino acid sequence set forth in SEQ ID NO: 89, and a VL CDR3 comprising the amino acid sequence set forth in SEQ ID NO: 90;

(n) a VH CDR1 comprising the amino acid sequence set forth in SEQ ID NO: 95, a VH CDR2 comprising the amino acid sequence set forth in SEQ ID NO: 96, a VH CDR3 comprising the amino acid sequence set forth in SEQ ID NO: 97, a VL CDR1 comprising the amino acid sequence set forth in SEQ ID NO: 98, a VL CDR2 comprising the amino acid sequence set forth in SEQ ID NO: 99, and a VL CDR3 comprising the amino acid sequence set forth in SEQ ID NO: 100;

(o) a VH CDR1 comprising the amino acid sequence set forth in SEQ ID NO: 125, a VH CDR2 comprising the amino acid sequence set forth in SEQ ID NO: 126, a VH CDR3 comprising the amino acid sequence set forth in SEQ ID NO: 127, a VL CDR1 comprising the amino acid sequence set forth in SEQ ID NO: 128, a VL CDR2 comprising the amino acid sequence set forth in SEQ ID NO: 129, and a VL CDR3 comprising the amino acid sequence set forth in SEQ ID NO: 130;

(p) a VH CDR1 comprising the amino acid sequence set forth in SEQ ID NO: 155, a VH CDR2 comprising the amino acid sequence set forth in SEQ ID NO: 156, a VH CDR3 comprising the amino acid sequence set forth in SEQ ID NO: 157, a VL CDR1 comprising the amino acid sequence set forth in SEQ ID NO: 158, a VL CDR2 comprising the amino acid sequence set forth in SEQ ID NO: 159, and a VL CDR3 comprising the amino acid sequence set forth in SEQ ID NO: 160; or q) a VH CDR1 comprising the amino acid sequence set forth in SEQ ID NO: 165, a VH CDR2 comprising the amino acid sequence set forth in SEQ ID NO: 166, a VH CDR3 comprising the amino acid sequence set forth in SEQ ID NO: 167, a VL CDR1 comprising the amino acid sequence set forth in SEQ ID NO: 168, a VL CDR2 comprising the amino acid sequence set forth in SEQ ID NO: 169, and a VL CDR3 comprising the amino acid sequence set forth in SEQ ID NO: 170.

2. The antibody, or antigen-binding portion thereof, of claim 1, which is capable of:
   (a) enhancing an immune response to a tumor;
   (b) reducing, depleting, or killing tumor infiltrating regulatory T ("Treg") cells;
   (c) inducing internalization of CCR8 in tumor infiltrating regulatory T ("Treg") cells;
   (d) activating NK cells;
   (e) inducing NK cell mediated killing of tumor infiltrating regulatory T ("Treg") cells;
   (f) binding to cynomolgus monkey ("cyno") CCR8;
   (g) binding to human CCR8 with $K_D$ of 10 nM or less as measured by a binding assay utilizing surface plasmon resonance (SPR) analysis;
   (h) inducing antibody-dependent cellular cytotoxicity (ADCC) in a subject following administration of the anti-CCR8 antibody;
   (i) inducing upregulation of 4-1BB, ICAM-1, or both 4-1BB and ICAM-1 on the surface of NK cells;
   (j) inducing down-regulation of CD16 on the surface of NK cells in the subject; or
   (k) any combination thereof.

3. The antibody or antigen-binding portion thereof claim 1, which comprises:
   (a) a VH chain comprising the amino acid sequence set forth in SEQ ID NO: 41 and a VL chain comprising the amino acid sequence set forth in SEQ ID NO: 43;
   (b) a VH chain comprising the amino acid sequence set forth in SEQ ID NO: 101 and a VL chain comprising the amino acid sequence set forth in SEQ ID NO: 103;
   (c) a VH chain comprising the amino acid sequence set forth in SEQ ID NO: 111 and a VL chain comprising the amino acid sequence set forth in SEQ ID NO: 113;
   (d) a VH chain comprising the amino acid sequence set forth in SEQ ID NO: 131 and a VL chain comprising the amino acid sequence set forth in SEQ ID NO: 133;
   (e) a VH chain comprising the amino acid sequence set forth in SEQ ID NO: 141 and a VL chain comprising the amino acid sequence set forth in SEQ ID NO: 143;
   (f) a VH chain comprising the amino acid sequence set forth in SEQ ID NO: 1 and a VL chain comprising the amino acid sequence set forth in SEQ ID NO: 3;
   (g) a VH chain comprising the amino acid sequence set forth in SEQ ID NO: 11 and a VL chain comprising the amino acid sequence set forth in SEQ ID NO: 13;
   (h) a VH chain comprising the amino acid sequence set forth in SEQ ID NO: 21 and a VL chain comprising the amino acid sequence set forth in SEQ ID NO: 23;
   (i) a VH chain comprising the amino acid sequence set forth in SEQ ID NO: 31 and a VL chain comprising the amino acid sequence set forth in SEQ ID NO: 33;
   (j) a VH chain comprising the amino acid sequence set forth in SEQ ID NO: 51 and a VL chain comprising the amino acid sequence set forth in SEQ ID NO: 53;
   (k) a VH chain comprising the amino acid sequence set forth in SEQ ID NO: 61 and a VL chain comprising the amino acid sequence set forth in SEQ ID NO: 63;
   (l) a VH chain comprising the amino acid sequence set forth in SEQ ID NO: 71 and a VL chain comprising the amino acid sequence set forth in SEQ ID NO: 73;
   (m) a VH chain comprising the amino acid sequence set forth in SEQ ID NO: 81 and a VL chain comprising the amino acid sequence set forth in SEQ ID NO: 83;
   (n) a VH chain comprising the amino acid sequence set forth in SEQ ID NO: 91 and a VL chain comprising the amino acid sequence set forth in SEQ ID NO: 93;
   (o) a VH chain comprising the amino acid sequence set forth in SEQ ID NO: 121 and a VL chain comprising the amino acid sequence set forth in SEQ ID NO: 123;
   (p) a VH chain comprising the amino acid sequence set forth in SEQ ID NO: 151 and a VL chain comprising the amino acid sequence set forth in SEQ ID NO: 153; or
   (q) a VH chain comprising the amino acid sequence set forth in SEQ ID NO: 161 and a VL chain comprising the amino acid sequence set forth in SEQ ID NO: 163.

4. The antibody or antigen-binding portion thereof of claim 1, which is a humanized antibody; or a chimeric antibody.

5. The antibody or antigen-binding portion thereof of claim 1, which comprises a single-chain variable fragment (scFv) of an antibody.

6. The antibody or antigen-binding portion thereof of claim 1, which is a bispecific antibody, a bispecific T cell engager (BiTE), a multispecific antibody, a biparatopic antibody, an immunoconjugate, an antibody drug conjugate, or any combination thereof.

7. A bispecific antibody or a multispecific antibody comprising the antibody or antigen-binding portion thereof of claim 1.

8. A BiTe comprising the antibody or antigen-binding portion thereof of claim 1.

9. A biparatopic antibody comprising the antibody or antigen-binding portion thereof of claim 1.

10. The antibody or antigen-binding portion thereof of claim 6, wherein the bispecific antibody, the BiTe, the multispecific antibody, or the biparatopic antibody comprises (i) a first VH domain, comprising a first VH CDR1, a first VH CDR2, and a first VH CDR3; (ii) a first VL domain, comprising a first VL CDR1, a first VL CDR2, and a first VL CDR3; (iii) a second VH domain, comprising a second VH CDR1, a second VH CDR2, and a second VH CDR3; and (iv) a second VL domain, comprising a second VL CDR1, a second VL CDR2, and a second VL CDR3; wherein
   (a) the first VH CDR1 comprises the amino acid sequence set forth in SEQ ID NOs: 45, the first VH CDR2 comprises the amino acid sequence set forth in SEQ ID NO: 46, the first VH CDR3 comprises the amino acid sequence set forth in SEQ ID NO: 47, the first VL CDR1 comprises the amino acid sequence set forth in SEQ ID NO: 48, the first VL CDR2 comprises the amino acid sequence set forth in SEQ ID NO: 49, and the first VL CDR3 comprises the amino acid sequence set forth in SEQ ID NO: 50;
   (b) the first VH CDR1 comprises the amino acid sequence set forth in SEQ ID NO: 105, the first VH CDR2 comprises the amino acid sequence set forth in SEQ ID NO: 106, the first VH CDR3 comprises the amino acid sequence set forth in SEQ ID NO: 107, the first VL CDR1 comprises the amino acid sequence set forth in SEQ ID NO: 108, the first VL CDR2 comprises the amino acid sequence set forth in SEQ ID NO: 109, and the first VL CDR3 comprises the amino acid sequence set forth in SEQ ID NO: 110;

(c) the first VH CDR1 comprises the amino acid sequence set forth in SEQ ID NO: 115, the first VH CDR2 comprises the amino acid sequence set forth in SEQ ID NO: 116, the first VH CDR3 comprises the amino acid sequence set forth in SEQ ID NO: 117, the first VL CDR1 comprises the amino acid sequence set forth in SEQ ID NO: 118, the first VL CDR2 comprises the amino acid sequence set forth in SEQ ID NO: 119, and the first VL CDR3 comprises the amino acid sequence set forth in SEQ ID NO: 120;

(d) the first VH CDR1 comprises the amino acid sequence set forth in SEQ ID NO: 135, the first VH CDR2 comprises the amino acid sequence set forth in SEQ ID NO: 136, the first VH CDR3 comprises the amino acid sequence set forth in SEQ ID NO: 137, the first VL CDR1 comprises the amino acid sequence set forth in SEQ ID NO: 138, the first VL CDR2 comprises the amino acid sequence set forth in SEQ ID NO: 139, and the first VL CDR3 comprises the amino acid sequence set forth in SEQ ID NO: 140; or (e) the first VH CDR1 comprises the amino acid sequence set forth in SEQ ID NO: 145, the first VH CDR2 comprises the amino acid sequence set forth in SEQ ID NO: 146, the first VH CDR3 comprises the amino acid sequence set forth in SEQ ID NO: 147, the first VL CDR1 comprises the amino acid sequence set forth in SEQ ID NO: 148, the first VL CDR2 comprises the amino acid sequence set forth in SEQ ID NO: 149, and the first VL CDR3 comprises the amino acid sequence set forth in SEQ ID NO: 150;

and wherein:

(f) the second VH CDR1 comprises the amino acid sequence set forth in SEQ ID NOs: 5, the second VH CDR2 comprises the amino acid sequence set forth in SEQ ID NO: 6, the second VH CDR3 comprises the amino acid sequence set forth in SEQ ID NO: 7, the second VL CDR1 comprises the amino acid sequence set forth in SEQ ID NO: 8, the second VL CDR2 comprises the amino acid sequence set forth in SEQ ID NO: 9, and the second VL CDR3 comprises the amino acid sequence set forth in SEQ ID NO: 10;

(g) the second VH CDR1 comprises the amino acid sequence set forth in SEQ ID NO: 15, the second VH CDR2 comprises the amino acid sequence set forth in SEQ ID NO: 15, the second VH CDR3 comprises the amino acid sequence set forth in SEQ ID NO: 15, the second VL CDR1 comprises the amino acid sequence set forth in SEQ ID NO: 18, the second VL CDR2 comprises the amino acid sequence set forth in SEQ ID NO: 19, and the second VL CDR3 comprises the amino acid sequence set forth in SEQ ID NO: 20;

(h) the second VH CDR1 comprises the amino acid sequence set forth in SEQ ID NO: 25, the second VH CDR2 comprises the amino acid sequence set forth in SEQ ID NO: 26, the second VH CDR3 comprises the amino acid sequence set forth in SEQ ID NO: 27, the second VL CDR1 comprises the amino acid sequence set forth in SEQ ID NO: 28, the second VL CDR2 comprises the amino acid sequence set forth in SEQ ID NO: 29, and the second VL CDR3 comprises the amino acid sequence set forth in SEQ ID NO: 30;

(i) the second VH CDR1 comprises the amino acid sequence set forth in SEQ ID NO: 35, the second VH CDR2 comprises the amino acid sequence set forth in SEQ ID NO: 36, the second VH CDR3 comprises the amino acid sequence set forth in SEQ ID NO: 37, the second VL CDR1 comprises the amino acid sequence set forth in SEQ ID NO: 38, the second VL CDR2 comprises the amino acid sequence set forth in SEQ ID NO: 39, and the second VL CDR3 comprises the amino acid sequence set forth in SEQ ID NO: 40;

(j) the second VH CDR1 comprises the amino acid sequence set forth in SEQ ID NO: 55, the second VH CDR2 comprises the amino acid sequence set forth in SEQ ID NO: 56, the second VH CDR3 comprises the amino acid sequence set forth in SEQ ID NO: 57, the second VL CDR1 comprises the amino acid sequence set forth in SEQ ID NO: 58, the second VL CDR2 comprises the amino acid sequence set forth in SEQ ID NO: 59, and the second VL CDR3 comprises the amino acid sequence set forth in SEQ ID NO: 60;

(k) the second VH CDR1 comprises the amino acid sequence set forth in SEQ ID NO: 65, the second VH CDR2 comprises the amino acid sequence set forth in SEQ ID NO: 66, the second VH CDR3 comprises the amino acid sequence set forth in SEQ ID NO: 67, the second VL CDR1 comprises the amino acid sequence set forth in SEQ ID NO: 68, the second VL CDR2 comprises the amino acid sequence set forth in SEQ ID NO: 69, and the second VL CDR3 comprises the amino acid sequence set forth in SEQ ID NO: 70;

(l) the second VH CDR1 comprises the amino acid sequence set forth in SEQ ID NO: 75, the second VH CDR2 comprises the amino acid sequence set forth in SEQ ID NO: 76, the second VH CDR3 comprises the amino acid sequence set forth in SEQ ID NO: 77, the second VL CDR1 comprises the amino acid sequence set forth in SEQ ID NO: 78, the second VL CDR2 comprises the amino acid sequence set forth in SEQ ID NO: 79, and the second VL CDR3 comprises the amino acid sequence set forth in SEQ ID NO: 80;

(m) the second VH CDR1 comprises the amino acid sequence set forth in SEQ ID NO: 85, the second VH CDR2 comprises the amino acid sequence set forth in SEQ ID NO: 86, the second VH CDR3 comprises the amino acid sequence set forth in SEQ ID NO: 87, the second VL CDR1 comprises the amino acid sequence set forth in SEQ ID NO: 88, the second VL CDR2 comprises the amino acid sequence set forth in SEQ ID NO: 89, and the second VL CDR3 comprises the amino acid sequence set forth in SEQ ID NO: 90;

(n) the second VH CDR1 comprises the amino acid sequence set forth in SEQ ID NO: 95, the second VH CDR2 comprises the amino acid sequence set forth in SEQ ID NO: 96, the second VH CDR3 comprises the amino acid sequence set forth in SEQ ID NO: 97, the second VL CDR1 comprises the amino acid sequence set forth in SEQ ID NO: 98, the second VL CDR2 comprises the amino acid sequence set forth in SEQ ID NO: 99, and the second VL CDR3 comprises the amino acid sequence set forth in SEQ ID NO: 100;

(o) the second VH CDR1 comprises the amino acid sequence set forth in SEQ ID NO: 125, the second VH CDR2 comprises the amino acid sequence set forth in SEQ ID NO: 126, the second VH CDR3 comprises the amino acid sequence set forth in SEQ ID NO: 127, the second VL CDR1 comprises the amino acid sequence set forth in SEQ ID NO: 128, the second VL CDR2 comprises the amino acid sequence set forth in SEQ ID NO: 129, and the second VL CDR3 comprises the amino acid sequence set forth in SEQ ID NO: 130;

(p) the second VH CDR1 comprises the amino acid sequence set forth in SEQ ID NO: 155, the second VH CDR2 comprises the amino acid sequence set forth in SEQ ID NO: 156, the second VH CDR3 comprises the amino acid sequence set forth in SEQ ID NO: 157, the second VL CDR1 comprises the amino acid sequence set forth in SEQ ID NO: 158, the second VL CDR2 comprises the amino acid sequence set forth in SEQ ID NO: 159, and the second VL CDR3 comprises the amino acid sequence set forth in SEQ ID NO: 160; or (q) the second VH CDR1 comprises the amino acid sequence set forth in SEQ ID NO: 165, the second VH CDR2 comprises the amino acid sequence set forth in SEQ ID NO: 166, the second VH CDR3 comprises the amino acid sequence set forth in SEQ ID NO: 167, the second VL CDR1 comprises the amino acid sequence set forth in SEQ ID NO: 168, the second VL CDR2 comprises the amino acid sequence set forth in SEQ ID NO: 169, and the second VL CDR3 comprises the amino acid sequence set forth in SEQ ID NO: 170.

11. An immunoconjugate comprising the antibody or antigen-binding portion thereof of claim 1.

12. The immunoconjugate of claim 11, which is an antibody-drug conjugate.

13. A chimeric antigen receptor (CAR) comprising the antibody or antigen-binding portion thereof of claim 1.

14. A T cell receptor (TCR) comprising the antibody or antigen-binding portion of claim 1.

15. A nucleic acid molecule or a set of nucleic acid molecules encoding the antibody or antigen-binding portion thereof of claim 1.

16. A pharmaceutical composition comprising the antibody or antigen-binding portion thereof of claim 1, and a pharmaceutically acceptable carrier.

17. A method of treating a tumor in a subject in need thereof, comprising administering to the subject the antibody or an antigen-binding portion thereof of claim 1.

18. The antibody or antigen-binding portion thereof of claim 1 which is afucosylated.

19. An antibody or antigen-binding portion thereof that specifically binds to CCR8, wherein the antibody or antigen-binding portion thereof comprises heavy chain CDR1, CDR2, and CDR3 sequences set forth in SEQ ID NOs: 45, 46, and 47, respectively, and light chain CDR1, CDR2, and CDR3 sequences set forth in SEQ ID NOs: 48, 49, and 50.

20. An antibody or antigen-binding portion thereof that specifically binds to CCR8, wherein the antibody or antigen-binding portion thereof comprises a heavy chain variable region comprising an amino acid sequence as set forth in SEQ ID NO: 41 and a light chain variable region comprising the amino acid sequence as set forth in SEQ ID NO: 43.

* * * * *